United States Patent
Shen et al.

(10) Patent No.: US 10,174,037 B2
(45) Date of Patent: Jan. 8, 2019

(54) DIHYDROPYRAZOLOPYRIMIDINONE COMPOUNDS AS PDE2 INHIBITORS

(71) Applicants: Merck Sharp & Dohme Corp., Rahway, NJ (US); MSD R & D (China) Co., LTD., Shanghai (CN)

(72) Inventors: Dong-Ming Shen, Edison, NJ (US); Michael P. Dwyer, Scotch Plains, NJ (US); Christopher J. Sinz, South San Francisco, CA (US); Deping Wang, Furlong, PA (US); Shawn J. Stachel, Perkasie, PA (US); Daniel V. Paone, Lansdale, PA (US); Ashley Forster, Harleysville, PA (US); Richard Berger, Harleysville, PA (US); Yili Chen, Hillsborough, NJ (US); Yimin Qian, Plainsboro, NJ (US); Shimin Xu, Beijing (CN); Chunmei Hu, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/576,351

(22) PCT Filed: May 31, 2016

(86) PCT No.: PCT/US2016/034928
§ 371 (c)(1),
(2) Date: Nov. 22, 2017

(87) PCT Pub. No.: WO2016/196417
PCT Pub. Date: Dec. 8, 2016

(65) Prior Publication Data
US 2018/0148453 A1    May 31, 2018

(30) Foreign Application Priority Data

Jun. 4, 2015    (WO) ................ PCT/CN2015/080784

(51) Int. Cl.
| | | |
|---|---|---|
| C07D 487/04 | (2006.01) |
| A61P 25/28 | (2006.01) |
| A61P 25/22 | (2006.01) |
| A61P 25/18 | (2006.01) |
| A61P 25/16 | (2006.01) |
| A61P 25/06 | (2006.01) |

(52) U.S. Cl.
CPC ............ C07D 487/04 (2013.01); A61P 25/06 (2018.01); A61P 25/16 (2018.01); A61P 25/18 (2018.01); A61P 25/22 (2018.01); A61P 25/28 (2018.01)

(58) Field of Classification Search
CPC .................................................. C07D 487/04
See application file for complete search history.

(56) References Cited

U.S. PATENT DOCUMENTS

| 3,211,731 A | 10/1965 | Schmidt et al. |
| 5,202,328 A | 4/1993 | de Laszlo et al. |
| 6,573,263 B2 | 6/2003 | Niewohner et al. |
| 8,598,155 B2 | 12/2013 | Helal et al. |
| 8,680,116 B2 | 3/2014 | DeLeon et al. |
| 2004/0241706 A1* | 12/2004 | Shah ...................... C07H 21/04 435/6.14 |
| 2007/0135457 A1 | 6/2007 | Beyer et al. |
| 2012/0214791 A1 | 8/2012 | Helal et al. |
| 2013/0018063 A1 | 1/2013 | Li et al. |

FOREIGN PATENT DOCUMENTS

| CN | 1697661 | 3/2003 |
| EP | 1097706 A1 | 5/2001 |
| EP | 1097707 A1 | 5/2001 |

(Continued)

OTHER PUBLICATIONS

Smirnova et al. (Khimiya Geterotsiklicheskikh Soedinenii (1992), (2), 219-24). Abstract.*

(Continued)

*Primary Examiner* — Bruck Kifle
(74) *Attorney, Agent, or Firm* — Sylvia A. Ayler; John C. Todaro

(57) ABSTRACT

The present invention is directed to dihydropyrazolopyrimidinone compounds of formula (I) which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis, Parkinson's disease, Parkinson's disease dementia (PDD), or Huntington's disease, and those associated with striatal hypofunction or basal ganglia dysfunction.

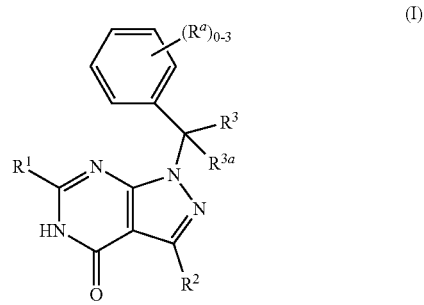

19 Claims, No Drawings

(56) References Cited

FOREIGN PATENT DOCUMENTS

| WO | 2000021926 | 4/2000 |
|---|---|---|
| WO | 2002074312 A1 | 9/2002 |
| WO | WO2005041957 | 10/2004 |
| WO | 2004099210 | 11/2004 |
| WO | WO2005061497 | 7/2005 |
| WO | WO2006024640 | 3/2006 |
| WO | WO2006072615 | 7/2006 |
| WO | WO2009016498 | 2/2009 |
| WO | WO2010136493 | 12/2010 |
| WO | 2011011312 A1 | 1/2011 |
| WO | WO2012114222 | 8/2012 |
| WO | WO2013034758 | 9/2012 |
| WO | WO2013034761 | 9/2012 |
| WO | WO2012168817 | 12/2012 |
| WO | WO201300924 | 1/2013 |
| WO | WO2013034755 | 3/2013 |
| WO | WO2013098373 | 7/2013 |
| WO | 2013161913 | 10/2013 |
| WO | WO2014010732 | 1/2014 |
| WO | WO2014019979 | 2/2014 |
| WO | WO2014135507 | 9/2014 |
| WO | WO2014139983 | 9/2014 |
| WO | WO2015012328 | 1/2015 |
| WO | WO2015060368 | 4/2015 |
| WO | WO2005063723 | 7/2017 |

OTHER PUBLICATIONS

Ahlstrom et al., Inactivation of Atrial Natriuretic Factor-Stimulated, Biochemical Pharmacology, 2000, 1133-1139, 59.
Arulomozhi et al., Migraine: Current Therapeutic Targets and Future Avenues, Current Vascular Pharmacology, 2006, 117-128, 4.
Beavo et al., Cyclic GMP as Substrate and Regulator of Cyclic Nucleotide Phosphodiesterases (PDEs), Rev. Physio Biochem Pharm, 1999, 67-104, 135.
Bernard et al., PDE2 Is a Novel Target for Attenuating Tumor Formation in a Mouse Model of UVB-Induced Skin Carcinogenesis, Plos One, 2014, 1-8, 9.
Boess et al., Inhibition of phosphodiesterase 2 increases neuronal cGMP, synaptic plasticity and memory, Neuropharmacology, 2004, 1081-92, 47.
Brandon et al., Potential CNS Applications for, Annual Reports in Medicinal Chemistry, 2007, 3-11, 42.
Bubb et al., Inhibition of Phosphodiesterase 2 Augments cGMP and, Circulation, 2014, 496-507, 268.
Cote et al., Comparative Involvement of Cyclic Nucleotide, Endocrinology, 1999, 3594-3601, 140.
Demaria et al., Highlights of the Year in JACC 2013, j. aMER. cOLL. cARD, 2014, 570-602, 63, (6).
Dickinson et al., Activation of cGMP-stimulated phosphodiesterase by nitroprusside limits, Biochem J., 1997, 371-377, 323.
Ding et al., Protective effects of phosphodiesterase 2 inhibitor on depression- and -Anxiety-Like Behaviors: Involvement of antioxidant and anti-apotoic Mechanisms, Behaviorual Brain Research, 2014, 150-158, 268.
Domek-Lopacinska et al., The Effect of Selective Inhibition of Cyclic GMP Hydrolyzing Phosphodiesterases 2 and 5 on Learning and Memory Processes and Nitric Oxide Synthase Activity, Brain Research, 2008, 68-77, 1216.
Ducrot et al., CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.
Duran et al., The NO cascade, eNOS Location, and Microvascular Permeability, Cardiovascular Research, 2010, 254-261, 87.
Favot et al., VEGF-Induced HUVEC Migration and Proliferation, Schattauer GmbH Stuttgart, 2003, 3443-343, 90.
Gergega et al., Systematic Effect of Benzo-Annelation on Oxo-Hydroxy Tautomerism of Heterocyclic, J. Phys. Chem A., 2007, 4934-4943, 111.

Giuliano et al., Correction to Tautomerism in 4-Hydroxypyrimidine, S-Methyl-2-thiouracil, and 2-Thiouracil, The Journal of Physical Chemistry A, 2011, 8178-8179, 115.
Giuliano et al., Tautomerism in 4-Hydroxypyrimidine, S-Methyl-2-thiouracil, and 2-Thiouracil, J. Phys. Chem. A, 2010, 12725-12730, 114.
Haynes et al., Erythro-9-(2-Hydroxy-3-Nonyl) Adenine Inhibits Cyclic-3',5' Guanosine Monophosphate-Stimulated Phosphodiesterase to Reverse Hypoxic Pulmonary Vasoconstriction in the Perfused Rat Lung, The J. of Pharmacology, 1996, 752-757, 276.
Herring et al., NO-cGMP Pathway Increases the Hyperpolarisation-Activated Current ,I, and Heart Rate During Adrenergic Stimulation, Cardiovascular Research, 2001, 446-453, 52.
Hiramoto et al., Role of Phosphodiesterase 2 in Growth and Invasion of HUman Maligant Melanoma, Cellular Signaling, 2014, 1807-1817, 26.
Huang et al., A Fluroescence Polarization Assay for Cyclic Nucleotide Phosphodiesterases, J. of Biomolecular Screening, 2002, pp. 215-222, 7.
Jorgensen et al., Selective Inhibitors of PDE2, PDE9, and PDE10: Modulators of Activity of the Central Nervous System, Annual Reports in Medicinal Chemistry, 2013, pp. 37-55, 48.
Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.
Kheifets et al., Structure and Amide-Amide Tautomerism of 4-Hydroxypyrimidines. Determination of the Tautomeric Composition by 13C NMR Spectroscopy, Russ. J. of Organic Chemistry, 2000, 1373-1387, 36, 9.
Lai et al., Carbonecarbon bond-forming reactions of a-carbonyl carbocations: explorationCarbonecarbon bond-forming reactions of a-carbonyl carbocations: exploration of a reversed-polarity equivalent of enolate chemistry, Tetrahedron, 2011, pp. 7586-7592, 67.
Lebel et al., Copper-Carbene Complexes as Catalysts in the Synthesis of Functionalized Styrenes and Aliphatic Alkenes; J. Org. Chem., 2007, 144-149, 72.
Li et al., Synthesis of α-Trifluoromethyl Ketones via the Cu-Catalyzed Trifluoromethylation of Silyl Enol Ethers Using an Electrophilic Trifuloromethylating Agent, J. Org Chem, 2014, 5145-5152, 79.
Lieberman et al., Effectiveness of Antipsychotic Drugs in Patients with Chronic Schizophrenia, New England J. of Medicine, Sep. 22, 2005, pp. 1209-1223, 353, US.
Lopez et al., Solution and solid state (CPMAS) NMR Studies of the Tautomerism of Six-Membered Heterocyclic Compounds Related to 2-Pyridones, Spectroscopy, 2000, pp. 121-126, 14.
Markwalder, Synthesis and Biological Evaluation of 1-Aryl-4,5-dihydro-1H-pyrazolo[3,4-d] pyrimidin-4-one Inhibitors of Cyclin-Dependent Kinases, J. Med. Chem, 2004, 5894-5911, 47.
Masood et al., Anxiolytic Effects of Phosphodiesterase-2 Inhibitors Associated with Increased cGMP Signaling, J. of Pharmacology, 2009, 690-699, 331.
Masood et al., Reversal of Oxidative Stress-Induced Anxiety by Inhibition of Phosphodiesterase-2 in Mice, J. of Pharmacology and Experimental Therapeutics, 2008, 369-379, 326.
Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.
Morita et al., Characterization of Phosphodiesterase 2A in Human Malignant Melanoma PMP Cells, Oncology Reports, 2013, 1275-1284, 29.
Netherton et al., Vascular Endothelial Cell Cyclic Nucleotide phosphodiesterases and Regulated Cell Migration: IMplications in Angiogenesis, Molecular Pharmacology, 2005, 263-272, 67.
P. C. Tfelt-Hansen et al., One Hundred Years of Migraine Research: Major Clinical and, Headache, 2011, 752-778, 51.
Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone

(56) References Cited

OTHER PUBLICATIONS

Phosphodiesterase 4 (PDE4) Inhibitors into Selective PDE2 Inhibitors, Biorganic & Medicinal Chemistry Letters, 2013, 3438-3442, 23.
Plummer et al., Discovery of potent selective bioavailable phosphodiesterase, Bioorganic & Medicinal Chemistry Letters, 2013, 3443-3447, 23.
Reierson et al., Repeated antidepressant therapy increases cyclic GMP signaling, Neurosci Letter, 2009, 149-153, 466 (3).
Rivet-Bastide et al., cGMP-stimulated Cyclic Nucleotide Phosphodiesterase Regulates the Basal, J. Clin. Invest, 1997, 2710-2718, 99.
Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.
Sanchez et al., Gas-Phase Tautomeric Equilibrium of 4-Hydroxypyrimidine, J. Am. Chem Soc., 2007, 6287-6290, 129.
Savai et al., Targeting Cancer with Phosphodiesterase Inhibitors, Expert Opinion, 2010, 117-131, 19.
Surapisitchat et al., Differential Regulation of Endothelial Cell Permeability by cGMP via Phosphodiesterases 2 and 3, Circulation Research, 2007, 811-818, 101.
Suvrana et al., Hydrolysis of N-Methyl-D-aspartate Receptor-Stimulated cAMP, J. of Pharmacology, 2002, 249-256, 302.
Van Staveren et al., The effects of phosphodiesterase inhibition on cyclic GMP and cyclic, Brain Research, 2001, 275-286, 888.
Vandecasteele, Cyclic GMP regulation of the L-type Ca2+ channel current, J. of Physiology, 2001, 329-340, 533.
Velardez et al., Role of Phosphodiesterase and Protein Kinase G on Nitric Oxide-Induced Inhibition of Prolactin Relase from the Rat Anterior Pituitary, Europe J. of Endocrinology, 2000, 279-284, 143.
Wakabayashi et al., Involvement of Phosphodiesterase Isozymes in Osteoblastic, J. of Bone and Mineral Research, 2002, 249-253, 17.
Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.
Schmidt et al., "Heilmittelchemische Studien in der Heterocyclischen Reihe. 25. Mitteilung. Pyrazolo-Pyrimidine III Paraxanthin, Theobromin und Tehophyllin-Analoga der Pyrazolo[3,4,-d] Pyrimidin Reithe", Helvetica Chimica ACTA, vol. 42, No. 1, Jan. 1, 1959, p. 349-359, XP055510876.

* cited by examiner

DIHYDROPYRAZOLOPYRIMIDINONE COMPOUNDS AS PDE2 INHIBITORS

CROSS REFERENCE TO RELATED APPLICATIONS

This application is the National Stage of International Application No. PCT/US2016/034928 filed on May 31, 2016, which claims the benefit under International Application PCT/CN2015/080784 filed on Jun. 4, 2015.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic receptors associated with cyclic adenosine monophosphate (cAMP). These ubiquitous secondary messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these secondary messengers, known as 3', 5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et al., Brain Res., 888, 275 (2001) and J. O'Donnell, et al., J. Pharm. Exp. Ther., 302, 249 (2002)); prolactin and aldosterone secretion (M. O. Velardez, et al., Eur. J. Endo., 143, 279 (2000) and N. Gallo-Payet, et al., Endo., 140, 3594 (1999)); bone cell differentiation, growth, and bone resorption (C. Allardt-Lamberg, et al., Biochem. Pharm., 59, 1133 (2000) and S. Wakabayashi, et al., J. Bone, Miner. Res., 17, 249 (2002); immunological response (M. D. Houslay, et al., Cell. Signal., 8, 97 (1996); vascular angiogenesis (T. Keravis, et al., J. Vasc. Res., 37, 235 (2000); inflammatory cell transit (S. L. Wolda, et al., J. Histochem. Cytochem., 47, 895 (1999); cardiac contraction (R. Fischmeister, et al., J. Clin. Invest., 99, 2710 (1997), P. Donzeau-Gouge, et al., J. Physiol., 533, 329 (2001), and D. J. Paterson, et Al., Card. Res., 52, 446 (2001); platelet aggregation (R. J. Haslam, et Al., Biochem. J., 323, 371 (1997); female sexual arousal disorder (C. P. Wayman, et al., EP Patent Publications EP10977707 and EP1097706); osteoarthritis pain (M. Plummer et. al., Bioorganic & Medicinal Chemistry Letters, 23(11), 3438-3442 and 3443-3447(2013)); malignant melanoma (H. Morita, et al., Oncology Reports, 29, 1275-1284, 2013; Hiramoto, et al., Cell. Signal., 26(9), 1807-1817, 2014; and J. J. Bernard, et al., PloS ONE 9(10): e109862, 2014); heart failure (A. N. DeMaria, et al., J. Amer. Coll. Card. 63 (6), 570-602, 2014); pulmonary hypertension (K. J, Bubb, et al., Circulation, 130, 496-508, 2014); depression and anxiety (L. Ding, et al., Behav. Brain Res. 268, 150-158, 2014); and hypoxic pulmonary vasoconstriction (J. Haynes, et. al., J. Pharm. Exp. Ther., 276, 752 (1996). See also US2007135457, WO00/21926, U.S. Pat. No. 3,211,731, WO2015060368, and J. Markwalder, et al., J. Med. Chem. 2004, 47, 5894-5911.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7): 1081-92, 2004). PDE2A inhibition was also shown to improve cognitive deficits that develop in aging and Alzheimer's disease (Domek-Lopacinska and Strosznajder, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors*, Annual Reports in Medicinal Chemistry 42: 4-5, 2007 (compound BAY 60-7550 was reported to have significant potency at other PDE isoforms, had high clearance and limited brain penetration). See also Jorgenson, et al, Annual Reports in Medicinal Chemistry 48: 37-55, 2013. "Selective Inhibitors of PDE2, PDE9, and PDE10: Modulators of Activity of the Central Nervous System".

PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Lett., 466(3):149-53, 2009). See also Ducrot et al., CoMFA and CoMSIA 3D-quantitative structure-activity relationship model on benzodiazepine derivatives, inhibitors of phosphodiesterase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. Nos. 6,573,263; 8,598,155, and 8,680,116; WO2015012328; WO2014139983; WO2014019979; WO2014010732; WO2013000924; WO2012114222; WO2006072615; WO2005063723; M. Plummer et al., Bioorg Med Chem Lett 23(11), 3438, 2013; and M. Plummer et al., Bioorg Med Chem Lett 23(11), 3443, 2013.

An increase in vascular permeability has been shown to be attributable to increased activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al., *Differential Regulation of Endothelial Cell Permeability by cGMP via Phosphodiesterase 2 and 3*, Circulation Research, 2007; 101, pgs.: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating diseases or disorders associated with PDE2 such as Alzheimer's disease, cognitive impairment associated with schizophrenia, depression, migraines, Parkinson's disease, Parkinson's disease dementia (PDD) and the like continues to exist. Inhibitors of PDE2 are not only believed to be useful in treating schizophrenia but also a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to dihydropyrazolopyrimidinone compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

DETAILED DESCRIPTION OF THE INVENTION

The present invention is directed to dihydropyrazolopyrimidinone compounds of formula I:

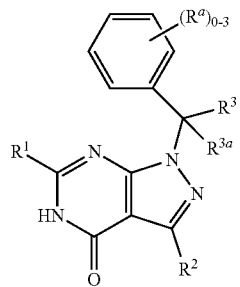

or a pharmaceutically acceptable salt thereof, wherein:

$R^1$ represents OH, $OC_{1-6}$alkyl, $NR_2$, said alkyl optionally substituted with 1 to 3 groups of $R^a$, R represents hydrogen, or $C_{1-6}$alkyl, or two R groups can be combined with the nitrogen to which they are attached to form a $C_{3-6}$ heterocycloalkyl, said alkyl and heterocycloalkyl optionally substituted with 1 to 2 groups of halogen, or $C_{1-6}$alkyl;

$R^2$ represents halo, $C_{1-6}$alkyl, $(CH_2)_nOR$, $C_{1-4}$haloalkyl, C(O)OR, $(CH_2)_nC_{4-10}$heterocyclyl, $O-(CH_2)_nC_{4-10}$heterocyclyl, $C(O)NH(CH_2CF_3)$, $C(O)NR_2$, $NR_2$, $NHSO_2R$, C(O)R, C(O)—N-linked morpholinyl, $NHC(O)CH_3$, $(CH_2)_nC(CF_3)OH$, $CH(CH_3)CH_2OH$, $CF_2CH_2OH$, said alkyl and heterocyclyl optionally substituted with 1 to 3 groups of $R^a$, $R^3$ and $R^{3a}$ independently represent hydrogen, $C_{1-6}$alkyl, $C_{2-6}$alkenyl, or $C_{3-6}$ cycloalkyl, or $R^3$ and $R^{3a}$ can combine with the carbon atom to which they are attached to form a $C_{3-6}$cycloalkyl, said alkyl and cycloalkyl optionally substituted with 1 to 3 groups of $R^a$, $R^a$ is selected from the group consisting of halo, CN, $C_{1-6}$alkyl, $(CH_2)_nOR$, $(CH_2)_nC_{1-4}$haloalkyl, $O-C_{1-4}$haloalkyl, $SCF_3$, $SF_5$, $C_{6-10}$aryl, $-O(CH_2)_nN(R)_2$, $(CHR)_n N(R)_2$, $NHC(O)CH_3$, $OCH_2C_{6-10}$aryl, and $C_{3-6}$cycloalkyl, said cycloalkyl optionally substituted with 1 to 3 groups of $C_{1-6}$alkyl and $C_{1-4}$haloalkyl;

n represents 0, 1, 2, 3, or 4.

An embodiment of the invention of formula I is realized when $R^1$ is OH.

An embodiment of the invention of formula I is realized when $R^1$ is $OC_{1-6}$alkyl. A subembodiment of this aspect of the invention is realized when $R^1$ is $OCH_3$ or $OCH_2CH_3$.

Another embodiment of the invention of formula I is realized when $R^1$ is $NR_2$ wherein R independently represents hydrogen, or optionally substituted $C_{1-6}$alkyl. A subembodiment of this aspect of the invention is realized when $R^1$ is $NR_2$ selected from the group consisting of $N(CH_3)_2$, $NH_2$, and $NHCH_3$. Another subembodiment of this aspect of the invention is realized when $R^1$ is $N(CH_3)_2$. Another subembodiment of this aspect of the invention is realized when $R^1$ is $NH_2$. Another subembodiment of this aspect of the invention is realized when $R^1$ is $NHCH_3$. Still another subembodiment of this aspect of the invention is realized when $R^1$ is $NR_2$ and the two R groups combine with the nitrogen to which they are attached to form a $C_{3-6}$ heterocycloalkyl selected from the group consisting of optionally substituted piperidinyl, pyrrolidinyl, and azetidinyl.

Another embodiment of the invention of formula I is realized when $R^2$ is optionally substituted $C_{1-6}$alkyl selected from $CH_2OH$, $CH_2CH_2OH$, $CH_2F$, $CH_3$, $CF_3$, $CH_2CF_3$, $CHF_2$, $CH_2CN$, $(CH_2)_2F$, $CH_2OCH_2$phenyl, $CH_2OCH_3$, $CF_2CF_3$, and $CH(CH_3)CH_2OH$. A subembodiment of this aspect of the invention is realized when $R^2$ is $CH_2OH$. A subembodiment of this aspect of the invention is realized when $R^2$ is $CH_2CH_2OH$. A subembodiment of this aspect of the invention is realized when $R^2$ is $CH_2F$. A subembodiment of this aspect of the invention is realized when $R^2$ is $CHF_2$. A subembodiment of this aspect of the invention is realized when $R^2$ is $CF_3$. A subembodiment of this aspect of the invention is realized when $R^2$ is $CH_3$. A subembodiment of this aspect of the invention is realized when $R^2$ is $CH_2CF_3$.

Still another embodiment of the invention is realized when $R^3$ and $R^{3a}$ both represent hydrogen.

Another embodiment of the invention is realized when $R^3$ and $R^{3a}$ independently represent hydrogen, $CH_3$, $CH(CH_3)_2$, $CH_2CH_3$, $C(CH_3)_3$, $CH_2CF_3$, cyclopropyl, cyclobutyl, cyclopentyl and cyclohexyl. A subembodiment of this aspect of the invention is realized when one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, cyclopropyl, cyclobutyl, cyclopentyl and cyclohexyl. Another subembodiment of this aspect of the invention is realized when one of $R^3$ and $R^{3a}$ is hydrogen and the other is $CH_3$. Another subembodiment of this aspect of the invention is realized when one of $R^3$ and $R^{3a}$ is hydrogen and the other is $CH(CH_3)_2$. Another subembodiment of this aspect of the invention is realized when one of $R^3$ and $R^{3a}$ is hydrogen and the other is $CH_2CH_3$. Another subembodiment of this aspect of the invention is realized when one of $R^3$ and $R^{3a}$ is hydrogen and the other is optionally substituted cyclopropyl.

Another embodiment of the invention is realized when $R^3$ and $R^{3a}$ can combine with the carbon atom to which they are attached to form an optionally substituted $C_{3-6}$cycloalkyl selected from cyclopropyl, cyclobutyl, cyclopentyl and cyclohexyl. A subembodiment of this aspect of the invention is realized when $R^3$ and $R^{3a}$ combine to form an optionally substituted cyclopropyl.

Another embodiment of the invention of formula I is realized when $R^a$ is selected from OH, halo, $(CH_2)_nCH_3$, $CH(CH_3)_2$, $C(CH_3)_3$, $(CH_2)_nOCH_3$, $OCH(CH_3)_2$, $CH_2F$, $CHF_2$, $(CH_2)_nCF_3$, $CF_2CH_3$, $OCHF_2$, $OCF_3$, $SCF_3$, $SF_5$, $CH_2NH_2$, $(CH_2)_nN(CH_3)_2$, $CF_2CF_3$, cyclobutyl, cyclopropyl, phenyl, naphthyl, pyrimidinyl, pyridyl, said groups where appropriate, optionally substituted with one to three groups of $R^b$.

Another embodiment of the invention of formula I is realized when the $R^a$ on the phenyl ring of formula I is selected from fluorine, chlorine, bromine, $CH_3$, $CH(CH_3)_2$, $C(CH_3)_3$, $(CH_2)_nOCH_3$, $OCH(CH_3)_2$, $CF_2CH_3$, $CF_2CF_3$, $CH_2F$, $CHF_2$, $CF_3$, $OCHF_2$, $OCF_3$, $SF_5$, cyclopropyl.

Another embodiment of the invention of formula I is realized when n is 0. Another embodiment of the invention of formula I is realized when n is 1. Another embodiment of the invention of formula I is realized when n is 2. Another embodiment of the invention of formula I is realized when n is 3. Still another embodiment of the invention of formula I is realized when n of $R^a$ is 0-1, 0-2, or 0-3.

Still another embodiment of the invention of the compounds of formula I are represented by structural formula Ia:

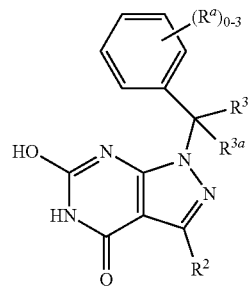

or a pharmaceutically acceptable salt thereof wherein $R^2$, $R^3$, $R^{3a}$ and $R^a$ are as originally described.

An aspect of the invention of formula Ia is realized when $R^2$ is optionally substituted $C_{1-6}$alkyl selected from $CH_2OH$, $CH_2CH_2OH$, $CH_2F$, $CH_3$, $CF_3$, $CH_2CF_3$, $CHF_2$, $CH_2CN$, $(CH_2)_2F$, $CH_2OCH_2$phenyl, $CH_2OCH_3$, $CF_2CF_3$, and $CH(CH_3)CH_2OH$. A subembodiment of this aspect of the invention of formula Ia is realized when $R^2$ is $CH_2OH$. A subembodiment of this aspect of the invention of formula Ia is realized when $R^2$ is $CH_2F$. A subembodiment of this aspect of the invention of formula Ia is realized when $R^2$ is $CHF_2$. A subembodiment of this aspect of the invention is realized when $R^2$ is $CF_3$. A subembodiment of this aspect of the invention of formula Ia is realized when $R^2$ is $CH_3$.

Another aspect of the invention of formula Ia is realized when $R^3$ and $R^{3a}$ independently represents hydrogen, $CH_3$, $CH(CH_3)_2$, $CH_2CH_3$, $C(CH_3)_3$, $CF_3$, $CH_2CF_3$, cyclopropyl, cyclobutyl, cyclopentyl and cyclohexyl. A subembodiment of this aspect of the invention of formula Ia is realized when one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, cyclopropyl, cyclobutyl, cyclopentyl and cyclohexyl. Another subembodiment of this aspect of the invention of formula Ia is realized when one of $R^3$ and $R^{3a}$ is hydrogen and the other is $CH_3$. Another subembodiment of this aspect of the invention of formula Ia is realized when one of $R^3$ and $R^{3a}$ is hydrogen and the other is $CH(CH_3)_2$. Another subembodiment of this aspect of the invention of formula Ia is realized when one of $R^3$ and $R^{3a}$ is hydrogen and the other is optionally substituted cyclopropyl.

Still another embodiment of the invention of formula Ia is realized when $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl. A subembodiment of this aspect of the invention of formula Ia is realized when $R^3$ and $R^{3a}$ combine to form an optionally substituted cyclopropyl.

Yet another embodiment of the invention of formula Ia is realized when the $R^a$ on the phenyl ring of formula Ia is selected from chlorine, fluorine, $CH_3$, $CH(CH_3)_2$, $C(CH_3)_3$, $(CH_2)_nOCH_3$, $OCH(CH_3)_2$, $CF_2CH_3$, $CF_2CF_3$, $CH_2F$, $CHF_2$, $CF_3$, $OCHF_2$, $OCF_3$, $SF_5$, and cyclopropyl.

Another embodiment of the invention of formula Ia is realized when $R^2$ is $CH_2OH$, $CH_2F$, $CHF_2$, $CF_3$, or $CH_3$, one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, and cyclopropyl, $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl, and the $R^a$ on the phenyl ring of formula Ia is selected from chlorine, fluorine, $CH_3$, $CH(CH_3)_2$, $C(CH_3)_3$, $(CH_2)_nOCH_3$, $OCH(CH_3)_2$, $CF_2CH_3$, $CF_2CF_3$, $CH_2F$, $CHF_2$, $CF_3$, $OCHF_2$, $OCF_3$, $SF_5$, and cyclopropyl.

Still another embodiment of the invention is realized when it is represented by structural formula Ib:

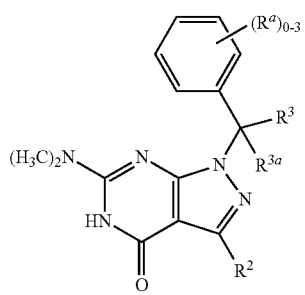

Ib or a pharmaceutically acceptable salt thereof wherein $R^2$, $R^3$, $R^{3a}$ and $R^a$ are as originally described.

An aspect of the invention of formula Ib is realized when $R^2$ is optionally substituted $C_{1-6}$alkyl selected from $CH_2OH$, $CH_2CH_2OH$, $CH_2F$, $CH_3$, $CF_3$, $CH_2CF_3$, $CHF_2$, $CH_2CN$, $(CH_2)_2F$, $CH_2OCH_2phenyl$, $CH_2OCH_3$, $CF_2CF_3$, and $CH(CH_3)CH_2OH$. A subembodiment of this aspect of the invention of formula Ib is realized when $R^2$ is $CH_2OH$. A subembodiment of this aspect of the invention of formula Ib is realized when $R^2$ is $CH_2CH_2OH$. A subembodiment of this aspect of the invention of formula Ib is realized when $R^2$ is $CH_2F$. A subembodiment of this aspect of the invention is realized when $R^2$ is $CHF_2$. A subembodiment of this aspect of the invention is realized when $R^2$ is $CF_3$. A subembodiment of this aspect of the invention of formula Ib is realized when $R^2$ is $CH_3$.

Another aspect of the invention of formula Ib is realized when $R^3$ and $R^{3a}$ independently represents hydrogen, $CH_3$, $CH(CH_3)_2$, $CH_2CH_3$, $C(CH_3)_3$, $CH_2CF_3$, cyclopropyl, cyclobutyl, cyclopentyl and cyclohexyl. A subembodiment of this aspect of the invention of formula Ib is realized when one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, cyclopropyl, cyclobutyl, cyclopentyl and cyclohexyl. Another subembodiment of this aspect of the invention of formula Ib is realized when one of $R^3$ and $R^{3a}$ is hydrogen and the other is $CH_3$. Another subembodiment of this aspect of the invention of formula Ib is realized when one of $R^3$ and $R^{3a}$ is hydrogen and the other is $CH(CH_3)_2$. Another subembodiment of this aspect of the invention of formula Ib is realized when one of $R^3$ and $R^{3a}$ is hydrogen and the other is optionally substituted cyclopropyl.

Still another embodiment of the invention of formula Ib is realized when $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl. A subembodiment of this aspect of the invention of formula Ib is realized when $R^3$ and $R^{3a}$ combine to form an optionally substituted cyclopropyl.

Yet another embodiment of the invention of formula Ib is realized when the $R^a$ on the phenyl ring of formula Ib is selected from chlorine, fluorine, $CH_3$, $CH(CH_3)_2$, $C(CH_3)_3$, $(CH_2)_nOCH_3$, $OC(CH_3)_2$, $OCH(CH_3)_2$, $CF_2CH_3$, $CH_2F$, $CHF_2$, $CF_3$, $OCHF_2$, $OCF_3$, $SF_5$, and cyclopropyl.

Another embodiment of the invention of formula Ib is realized when $R^2$ is $CH_2OH$, $CH_2F$, $CHF_2$ or $CH_3$, one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, and cyclopropyl, $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl, and the $R^a$ on the phenyl ring of formula Ib is selected from chlorine, fluorine, $CH_3$, $CH(CH_3)_2$, $C(CH_3)_3$, $(CH_2)_nOCH_3$, $OC(CH_3)_2$, $CH(CH_3)F_2$, $CF_2CF_3$, $CH_2F$, $CHF_2$, $CF_3$, $OCHF_2$, $OCF_3$, $SF_5$, and cyclopropyl.

The invention is also directed to a method for the treatment of central nervous system disorders associated with phosphodiesterase 2 (PDE2) using the compounds of Formula I. More specifically, the present invention relates to the use of such compounds for treating neurological and psychiatric disorders, such as schizophrenia, psychosis, Alzheimer's, cognitive impairment, anxiety, depression, migraines, Parkinson's disease, Parkinson's disease dementia (PDD), or Huntington's disease, and those associated with striatal hypofunction or basal ganglia dysfunction using the compounds of formula I.

Examples of compounds of the invention can be found throughout the specification.

The invention also encompasses pharmaceutical compositions containing a compound of formula I, and methods for treatment or prevention of phosphodiesterase mediated diseases using compounds of formula I.

Where a variable occurs more than once in any formula of the invention, or in a substituent thereof, the individual occurrences of that variable are independent of each other, unless otherwise specified. Also, combinations of substituents/or variables are permissible only if such combinations result in stable compounds and valency is permissible.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydroisobenzofuranyl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo. The term "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$.

It should be appreciated by anyone skilled in the art that the compounds of this invention can exist in several tautomeric forms as shown below:

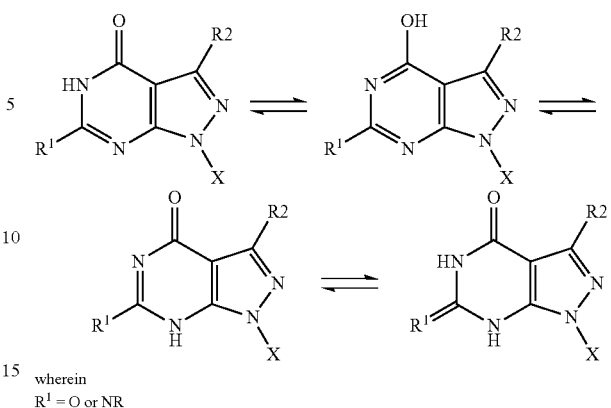

wherein
$R^1$ = O or NR

Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I, Ia and Ib and they are intended to represent all possible tautomeric forms for these compounds without regard to what actually is the predominant tautomeric form in existence for a particular compound.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

The compounds of the present invention may contain one or more stereogenic centers and can thus occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of the compound bound to PDE2 enzyme, crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates and the like. "Hydrate" is a solvate wherein the solvent molecule is $H_2O$.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulas I, Ia, and Ib. For example, isotopic forms of hydrogen (H), including protium ($^1H$) and deuterium ($^2H$); isotopic forms of carbon, including $^{11}C$; and isotopic forms of fluorine, including $^{18}F$. Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. While $^{12}C$ and $^{19}F$ are the predominant isotopes of carbon and fluorine found in nature, enriching for $^{11}C$ or $^{18}F$ may afford advantages, particularly for use in imaging via positron emission tomography (PET). In general, one of ordinary skill in the art would appreciate that a preferred substance for potential use as a PET imaging agent would effectively inhibit the PDE2 enzyme with a Ki value less than or about 0.5 nM, where compounds tested are comprised of naturally occurring isotopes. Such preferred substances, when enriched with $^{11}C$ or $^{18}F$, may be therefore be useful as PET imaging agents. Isotopically enriched compounds within generic formulas I, Ia, and Ib can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:

Ac=acetyl
ACN=acetonitrile
AcO=acetate
BOC=t-butyloxycarbonyl
CBZ=carbobenzoxy
CDI=carbonyldiimidazole
DCC=1,3-dicyclohexylcarbodiimide
DCE=1,2-dichloroethane
DCM=dichloromethane
DI=de-ionized
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt
EtOAc or EA=ethyl acetate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOAt=1-Hydroxy-7-azabenzotriazole
HOBt=1-hydroxybenzotriazole
HRMS=high resolution mass spectrometry
IBCF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=metachloroperbenzoic acid
MMPP=magnesium monoperoxyphthlate hexahydrate
Ms=methanesulfonyl=mesyl
MsO=methanesulfonate=mesylate
MTBE=Methyl t-butyl ether
NBS=N-bromosuccinimide
NMM=4-methylmorpholine
NMP=N-methylpyrrolidinone
NMR=Nuclear magnetic resonance
PCC=pyridinium chlorochromate
PDC=pyridinium dichromate
Ph=phenyl
PPTS=pyridinium p-toluene sulfonate
pTSA=p-toluene sulfonic acid
PyH.Br$_3$=pyridine hydrobromide perbromide
r.t./RT=room temperature
rac.=racemic
T3P=2,4,6-Tripropyl-1,3,5,2,4,6-trioxatriphosphinane 2,4,6-trioxide
TBAF=tetrabutylammonium fluoride
TFA=trifluoroacetic acid TfO=trifluoromethanesulfonate=triflate
THF=tetrahydrofuran
TLC=thin layer chromatography
TMSCl=trimethylsilyl chloride All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 function or activity in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

"Treating" or "treatment of" a disease state includes: 1 inhibiting the disease state, i.e., arresting the development of the disease state or its clinical symptoms; 2) or relieving the disease state, i.e., causing temporary or permanent regression of the disease state or its clinical symptoms.

The invention is also directed to use of the compounds to prevent the disease state.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Parkinson's disease dementia (PDD), Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, cannabis, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Parkinson's disease dementia (PDD), Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with post-partum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder, mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, Parkinson's disease dementia (PDD), drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemiballism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder, learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment 0 See Savai, et al, *Targeting cancer with phosphodiesterase inhibitors*, Expert Opin.

Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-inducedHUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB-Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, AChEi's such as (Aricept (donepezil)) and Exelon (rivastigmine) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an antidepressant or antianxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical antidepressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

In another specific embodiment, compounds of the present invention may be suitable as PET imaging agents. An aspect of the invention is realized when the PET imaging compounds of the instant invention are those that effectively inhibit the PDE2 enzyme with a Ki value less than or about 0.5 nM. Another aspect of the invention is realized when the compounds of the invention are enriched with $^{11}C$ or $^{18}F$. Still another aspect of the invention is realized when the compounds of Examples 1 through 316 are enriched with $^{11}C$ or $^{18}F$. Yet another aspect of the invention is realized when Examples 62, 64, 65, 67, 69, 73, 76, 77, 78, 79, 81, 85, 87, 88, 89, 91, 93, 94, 95, 96, 97, 99, 101, 103, 107, 108, 111, 113, 115, 116, 117, 118, 119, 120, 121, 122, 126, 128, 130, 132, 133, 134, 137, 138, 139, 140, 142, 143, 145, 147, 149, 150, 163, 164, 167, 169, 171, 173, 175, 176, 177, 179, 181, 182, 183, 184, 185, 186, 187, 188, 189, 191, 192, 193, 195, 196, 198, 200, 202, 205, 206, 207, 209, 211, 214, 214, 216, 217, 218, 219, 220, 221, 222, 224, 225, 226, and 289 are enriched with $^{11}C$ or $^{18}F$.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below and can be found in further detail in U.S. Pat. No. 7,144,913, which is incorporated by reference herein in its entirety. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. The compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood.

The representative examples of the compounds of the invention are illustrated in the following non-limiting schemes and Examples.

General

Starting materials used were obtained from commercial sources or prepared in other examples, unless otherwisely noted.

The progress of reactions was often monitored by TLC or LC-MS. The LC-MS was recorded using one of the following methods.

Method A: XBridge C18: 4.6×50 mm, 3.5 um, 1.0 uL injection, 1.50 mL/min flow rate, 90-900 amu scan range, 190-400 nm UV range, 10-95% (over 2.2 min) gradient with MeCN and water (5 μM $NH_4HCO_3$), hold 1 min; 3.6 minute total run time.

Method B: Supelco Ascentis Express C18, 3×50 mm, 2.7 um column. 2.0 uL injection, 1.25 ml/min flow rate, 170-900 amu scan range, 200-400 nm UV range, 10-99% (over 2.0 min) gradient with MeCN (0.05% TFA) and water (0.05%); 3 minute total run time.

Method C: Supelco Ascentis Express C18, 3×100 mm, 2.7 um column. 2.0 uL injection, 1.00 ml/min flow rate, 170-900 amu scan range, 200-400 nm UV range, 10-99% (over 4.0 min) gradient with MeCN (0.05% TFA) and water (0.05%); 5 minute total run time.

Method D: Waters Acquity UPLC, HSS C18 1.8 um, 2.1×50 mm, MeCN and water with 0.1% trifluoroacetic acid, 1 mL/min flow rate, gradient 5%-100% MeCN over 1.4 min.

Method E: Waters Acquity UPLC, HSS C18 1.8 um, 2.1×50 mm, MeCN and water with 0.1% formic acid, 1 mL/min flow rate, gradient 5%-100% MeCN over 1.4 min.

Method F: Shimadzu: 3.0×50 mm, 2.2 um, 1.0 uL injection, 1.00 mL/min flow rate, 90-900 amu scan range, 190-400 nm UV range, 5-100% (over 2.2 min) gradient with MeCN (0.05% TFA) and water (0.05% TFA), hold 1 min; 3.6 minute total run time.

Method G: Titan C18: 2.1×50 mm, 1.9 um, 1.0 uL injection, 0.80 mL/min flow rate, 90-900 amu scan range, 190-400 nm UV range, 5-100% (over 2.1 min) gradient with MeCN (0.05% TFA) and water (0.05% TFA), hold 0.5 min; 3.0 minute total run time.

Method H: ZORBAX Eclipse Plus C18: 3.0×50 mm, 1.8 um, 1.0 uL injection, 1.00 mL/min flow rate, 90-900 amu scan range, 190-400 nm UV range, 5-100% (over 2.1 min) gradient with MeCN (0.1% FA) and water (0.1% FA), hold 0.5 min; 3.0 minute total run time.

NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

The methods used for the preparation of the compounds of this invention are illustrated by the following schemes. Unless specified otherwise, all starting materials used are commercially available.

Scheme 1.

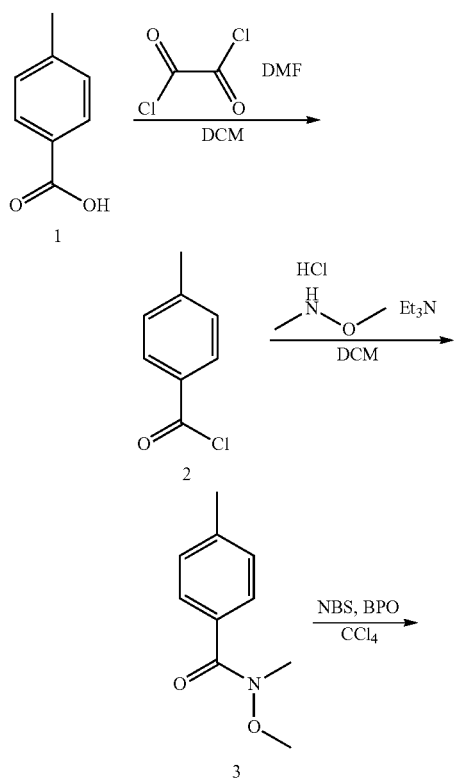

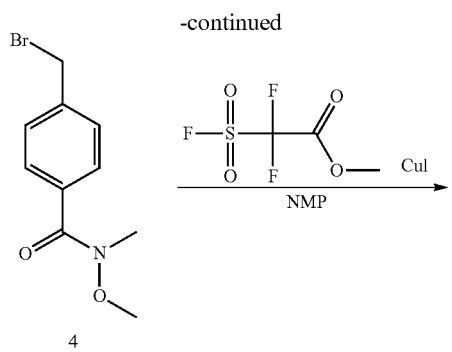

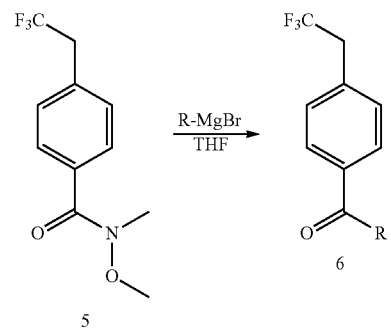

Scheme 1 illustrates a synthetic procedure for the preparation of ketones such as 6 from acid precursors such as 1. Treatment of acid 1 with oxalyl chloride will afford the intermediate acid chloride 2 which can be exposed to N,O-dimethyl hydroxylamine in the presence of base to furnish amide 3. Benzylic bromination with n-bromosuccinimide and benzoyl peroxide (BPO) followed by trifluoromethylation should afford compound 5. Treatment with a Grignard reagent will furnish ketone 6.

Scheme 2.

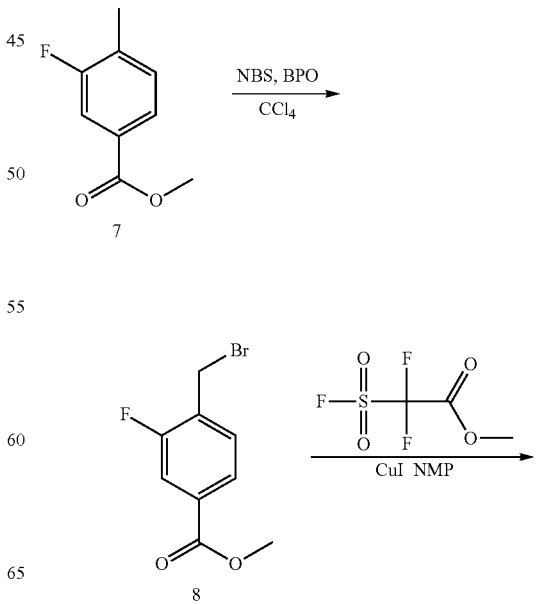

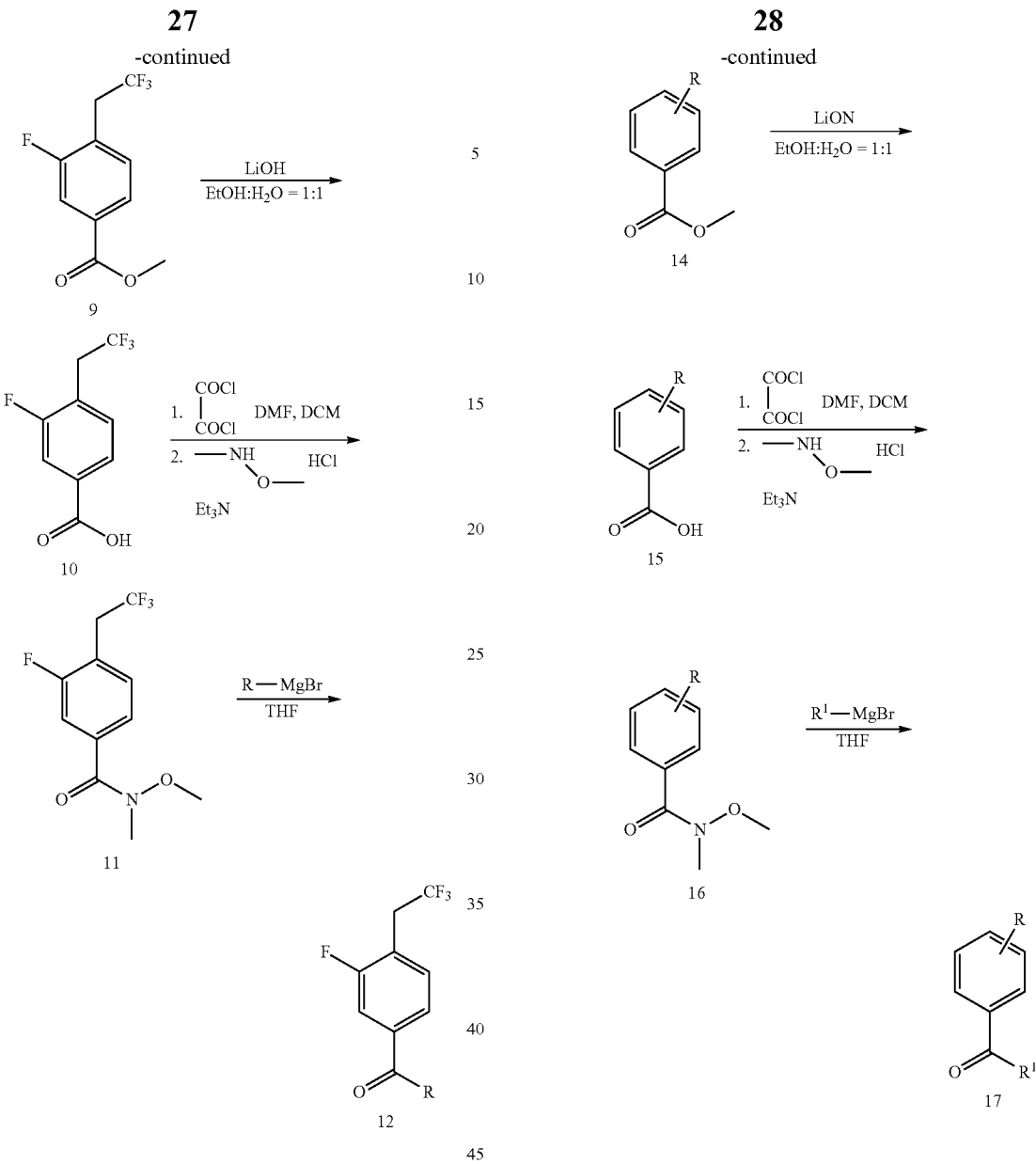

Scheme 2 illustrates a synthetic sequence for the preparation of ketones such as 12 from ester precursors such as 7. Benzylic bromination with N-bromosuccinimide followed by trifluoromethylation in the presence of a copper salt will afford 9. Treatment with lithium hydroxide will afford the intermediate acid which can be exposed to oxalyl chloride and N,O-dimethyl hydroxylamine in the presence of base to afford amide 11. Reaction of 11 in the presence of a Grignard reagent will furnish ketone 12.

Scheme 3 illustrates a synthetic sequence for the preparation of ketones such as 17 from aryl bromide precursors such as 13. Palladium-mediated carbonylation of 13 in the presence of methanol will afford ester 14 which may be hydrolyzed in the presence of lithium hydroxide to afford acid 15. Acid 15 can be converted to amide 16 via the acid chloride followed by Grignard treatment to furnish ketone 17.

Scheme 3.

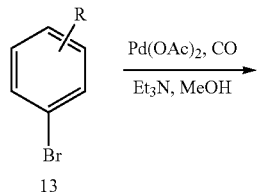

Scheme 4.

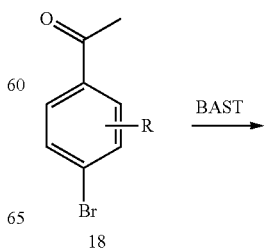

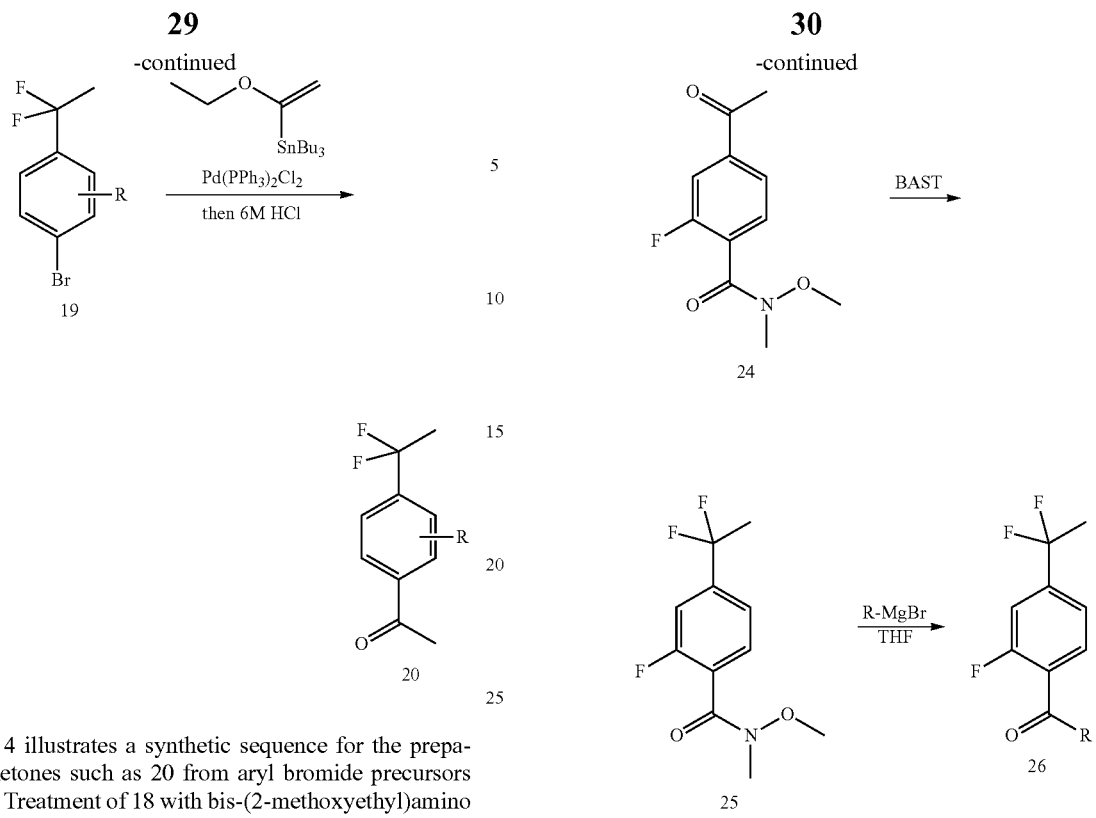

Scheme 4 illustrates a synthetic sequence for the preparation of ketones such as 20 from aryl bromide precursors such as 18. Treatment of 18 with bis-(2-methoxyethyl)amino sulfur trifluoride (BAST) will furnish the intermediate difluoro analog 19 which can be treated with a vinyl stannane and a palladium catalyst followed by acidic hydrolysis to furnish acetophenone 20.

Scheme 5 illustrates a synthetic sequence for the preparation of ketones such as 26 from aryl carboxylic acid precursors such as 21. Treatment of 21 with oxalyl chloride will furnish acid chloride 22 which in presence of an amine and base should furnish amide 23. Heck coupling in the presence of an enol ether followed by acid treatment will afford acetophenone 24. BAST treatment of 24 will furnish the intermediate difluoroethyl adduct 25, which after Grignard addition, provides ketone 26.

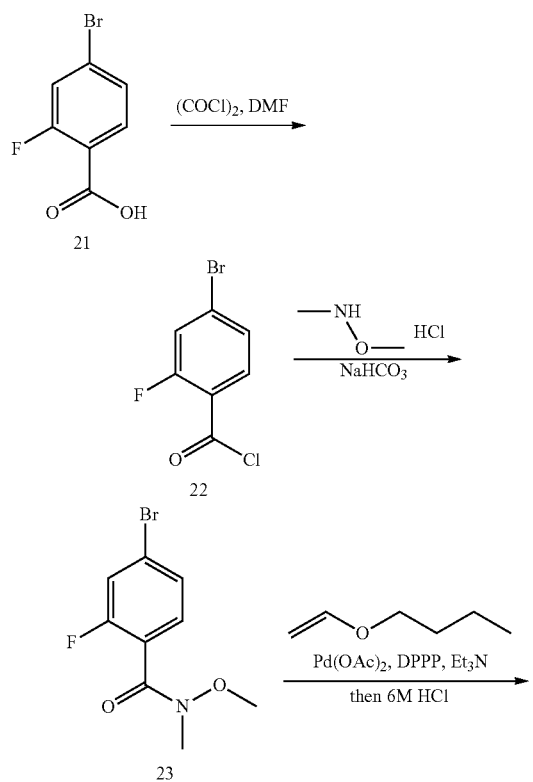

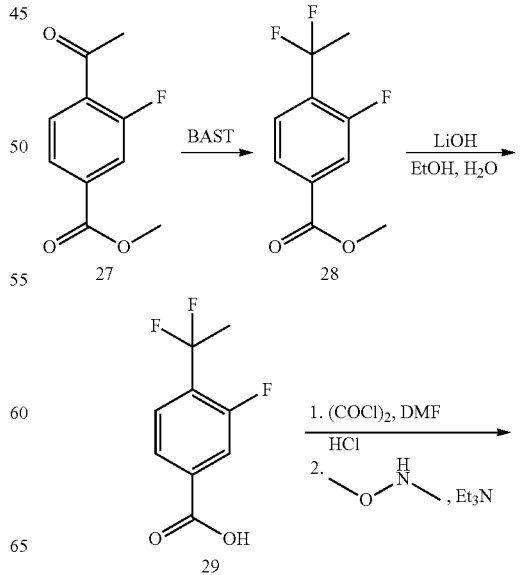

31
-continued

32
-continued

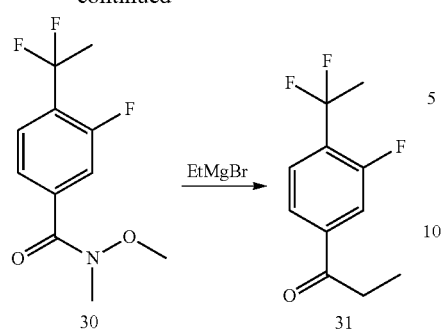

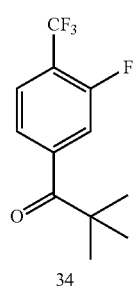

Scheme 6 illustrates a synthetic sequence for the preparation of ketone 31 from ester 27. BAST treatment of 27 should furnish ester 28 which can be hydrolyzed to afford acid 29. Two-step conversion to amide 30 can be accomplished via the intermediate acid chloride. Treatment of 30 with ethyl magnesium bromide will afford ketone 31.

Scheme 8 illustrates a synthetic sequence for the preparation of ketone 34 from aldehyde 32. Grignard addition to aldehyde 32 should afford the intermediate secondary alcohol 33 which can be treated under Swern oxidation conditions to furnish ketone 34.

Scheme 7.

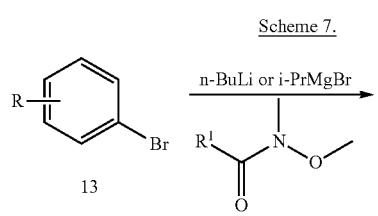

Scheme 9.

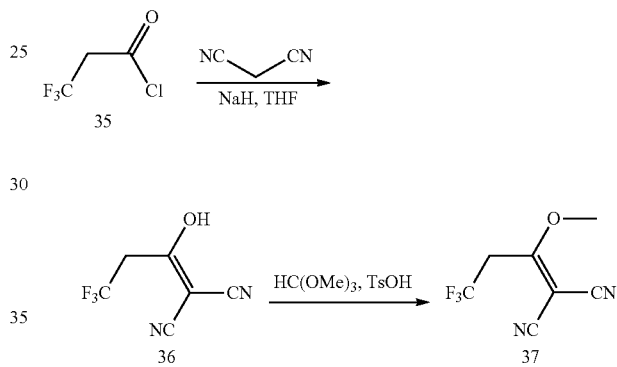

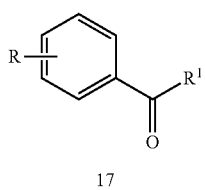

Scheme 9 illustrates a synthetic sequence for the preparation of alkylidene 37 from acid chloride 35. Treatment of acid chloride 35 with the anion derived from malononitrile and sodium hydride should afford 36 which can be exposed to trimethyl orthoformate in the presence of acid to furnish alkylidene 37.

Scheme 7 illustrates a synthetic sequence for the preparation of ketone 17 from bromide 13. Halogen-metal exchange on 13 with either n-butyllithium or isopropylmagnesium bromide followed by quenching with a Weinreb amide will furnish ketone 17.

Scheme 10.

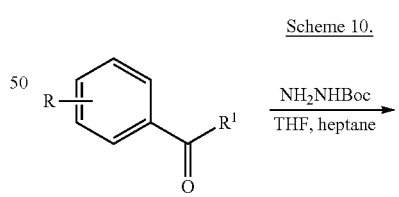

Scheme 8.

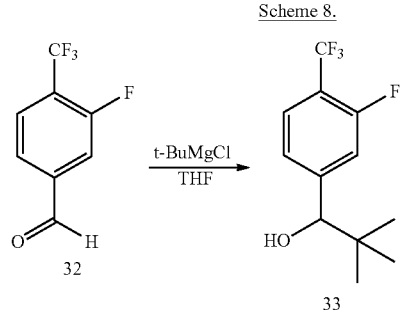

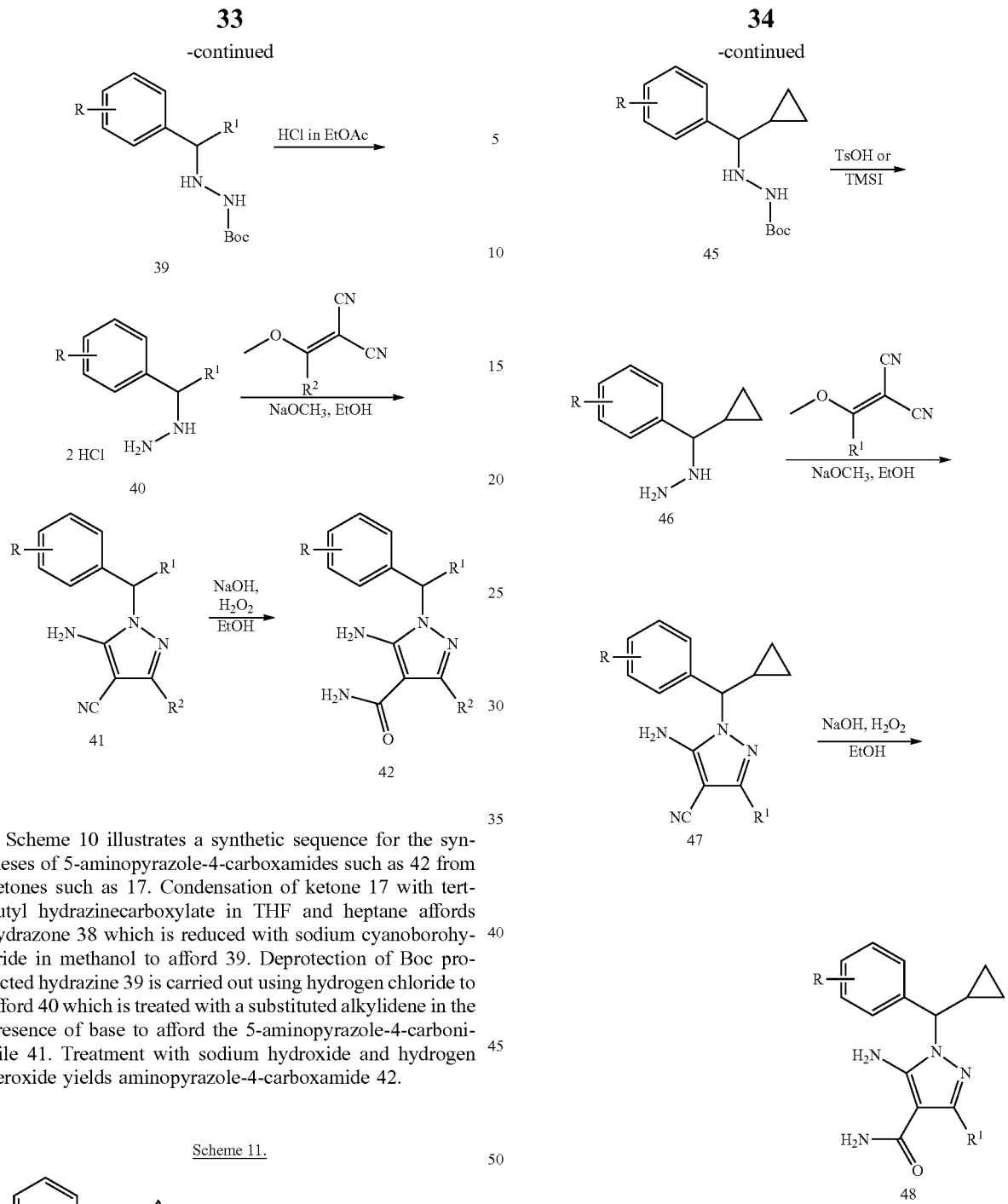

Scheme 10 illustrates a synthetic sequence for the syntheses of 5-aminopyrazole-4-carboxamides such as 42 from ketones such as 17. Condensation of ketone 17 with tert-butyl hydrazinecarboxylate in THF and heptane affords hydrazone 38 which is reduced with sodium cyanoborohydride in methanol to afford 39. Deprotection of Boc protected hydrazine 39 is carried out using hydrogen chloride to afford 40 which is treated with a substituted alkylidene in the presence of base to afford the 5-aminopyrazole-4-carbonitrile 41. Treatment with sodium hydroxide and hydrogen peroxide yields aminopyrazole-4-carboxamide 42.

Scheme 11 illustrates a synthetic sequence for the syntheses of cyclopropane-substituted 5-aminopyrazole-4-carboxamides such as 48 from ketones such as 43. Starting with ketone 43, condensation with tert-butyl hydrazinecarboxylate will afford hydrazone 44 which can be reduced with sodium cyanoborohydride to afford 45. Deprotection of Boc protected hydrazine 45 can be carried out with either p-toluenesulfonic acid or trimethylsilyliodide to furnish 46. Cyclization of 46 with a substituted alkylidene will yield 47 which can be hydrolyzed under basic conditions to aminopyrazole-4-carboxamide 48.

Scheme 12.

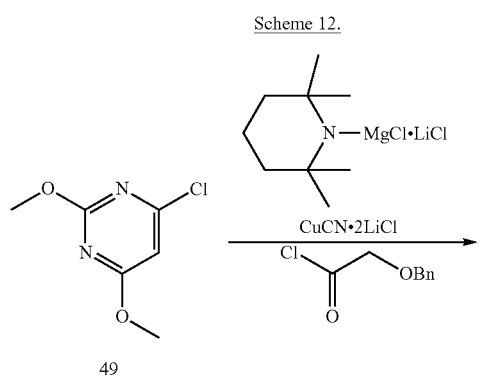

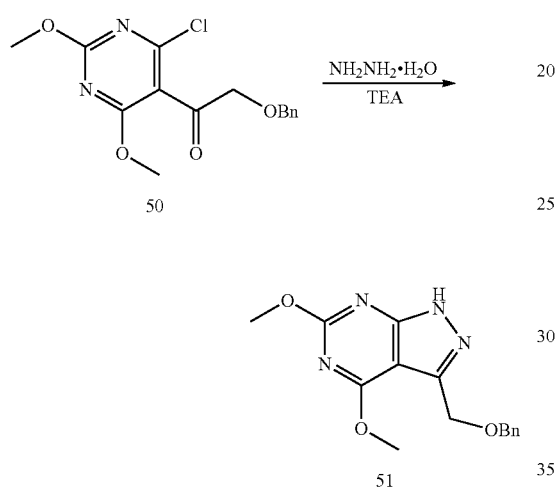

Scheme 12 illustrates a synthetic sequence for the preparation of pyrazolopyrimidine 51 from dimethoxy pyrimidine 49. Treatment of 49 under metallation conditions in the presence of copper salts with quenching by an acid chloride will afford ketone 50. Cyclization with hydrazine monohydrate in the presence of base will furnish pyrazolopyrimidine 51.

Scheme 13.

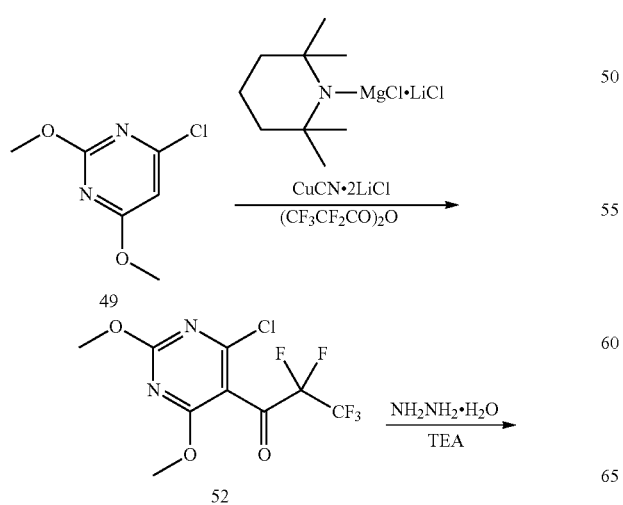

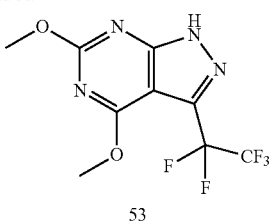

Scheme 13 illustrates a synthetic sequence for the preparation of pyrazolopyrimidine 53 bearing a pentafluoroethyl sidechain from dimethoxy pyrimidine 49. Treatment of 49 under metallation conditions in the presence of copper salts with quenching by a perfluorinated anhydride will afford ketone 52. Cyclization with hydrazine monohydrate in the presence of base will furnish pyrazolopyrimidine 53.

Scheme 14.

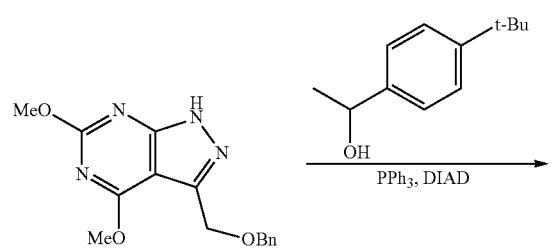

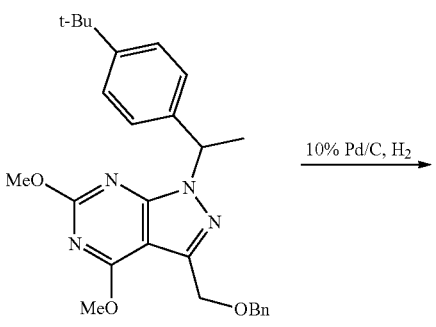

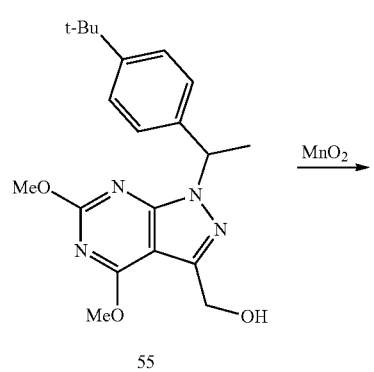

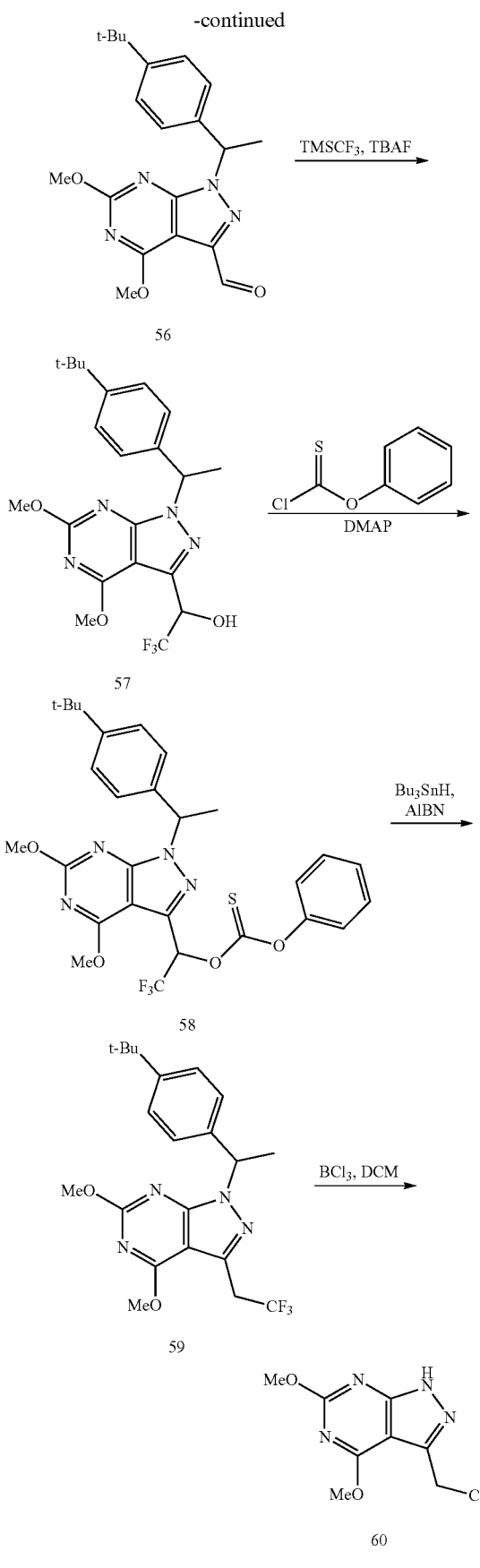

Scheme 14 illustrates a synthetic sequence for the syntheses of the trifluoroethyl-substituted pyrazolopyrimidine 60 from pyrazolopyrimidine 51. Mitsunobu coupling of a secondary alcohol with 51 will afford 54 which can be treated under hydrogenolysis conditions to yield 55. Oxidation of 55 will afford 56 followed by fluoride promoted $CF_3$ addition will furnish 57. Conversion of alcohol 57 to the thiocarbonate derivative 58 followed by radical deoxygenation with tributyltin hydride will afford 59. Deprotection with boron trichloride ($BCl_3$) will furnish pyrazolopyrimidine 60.

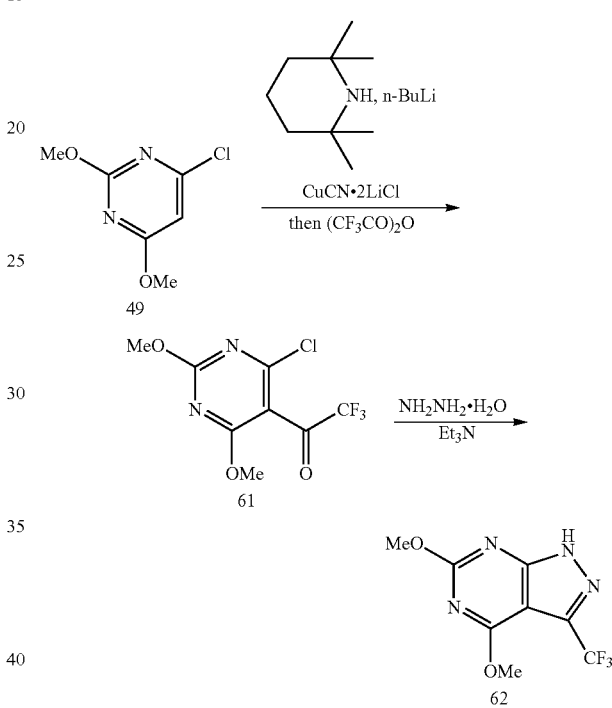

Scheme 15 illustrates a synthetic sequence for the preparation of pyrazolopyrimidine 62 bearing a trifluoromethyl sidechain from dimethoxy pyrimidine 49. Treatment of 49 with lithium tetramethylpiperidide in the presence of copper salts with quenching by trifluoroacetic anhydride will afford ketone 61. Cyclization with hydrazine monohydrate in the presence of base will furnish pyrazolopyrimidine 62.

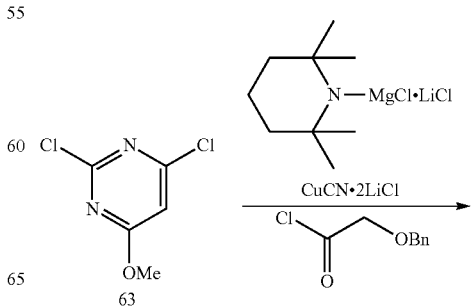

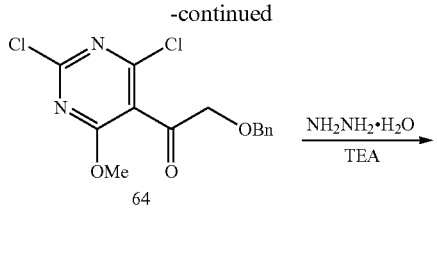

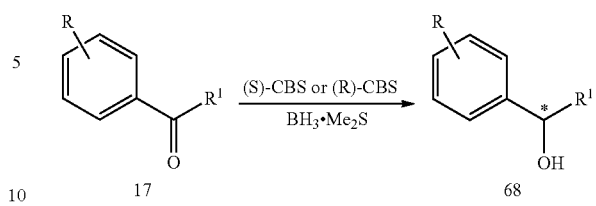

Scheme 19.

Scheme 19 illustrates a synthetic sequence for the preparation of enantioenriched alcohols such as 68 using either (S)-2-methyl-CBS-oxazaborolidine or (R)-2-methyl-CBS-oxazaborolidine (*J. Chem. Soc., Chem. Commun.* 1983, 8, 469) in the presence of borane on ketone precursors such as 17.

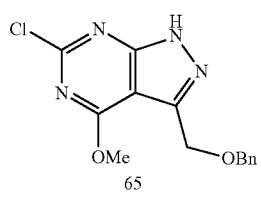

Scheme 16 illustrates a synthetic sequence for the preparation of pyrazolopyrimidine 65 from dichloro pyrimidine 63. Treatment of 63 under metallation conditions in the presence of copper salts with quenching by an acid chloride will afford ketone 64. Cyclization with hydrazine monohydrate in the presence of base will furnish pyrazolopyrimidine 65.

Scheme 17.

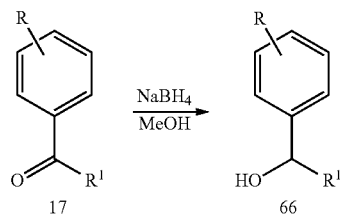

Scheme 17 illustrates a synthetic sequence for the preparation of alcohols such as 66 from ketone precursors such as 17 using a reducing agent such as sodium borohydride.

Scheme 18.

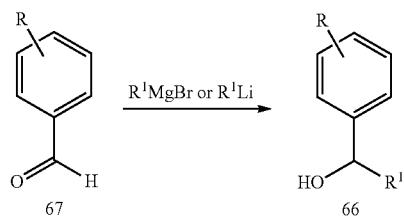

Scheme 18 illustrates a synthetic sequence for the preparation of alcohols such as 66 by reacting aldehyde precursors such as 67 with either a Grignard or organolithium reagent.

Scheme 20.

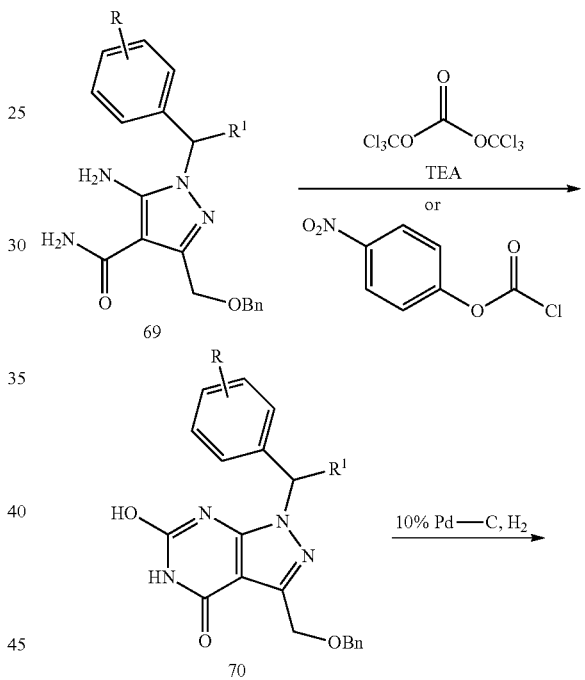

Scheme 20 illustrates a synthetic sequence for the preparation of methanol containing pyrazolopyrimidinones such as 71 from 5-aminopyrazole-4-carboxamides such as 69. Treatment of 69 with triphosgene in the presence of triethyl amine or p-nitrophenyl chloroformate will afford 70 which can be treated under hydrogenolysis conditions to afford pyrazolopyrimidinone 71.

Scheme 21.

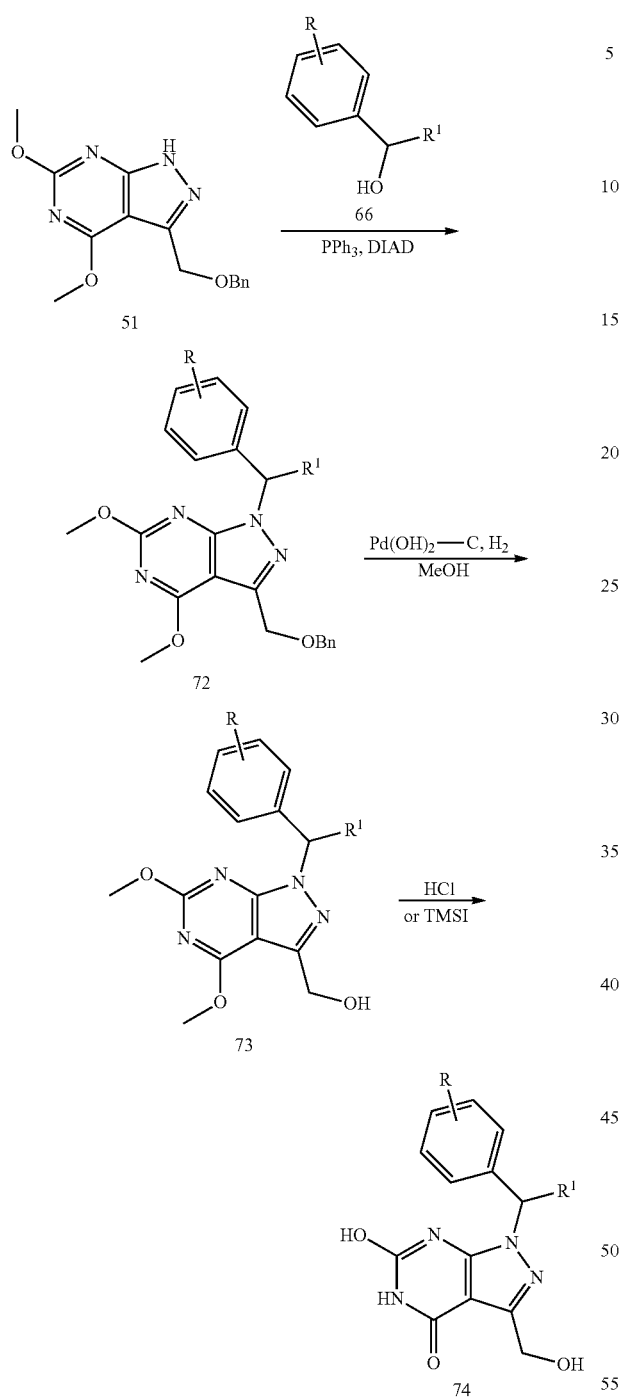

Scheme 22.

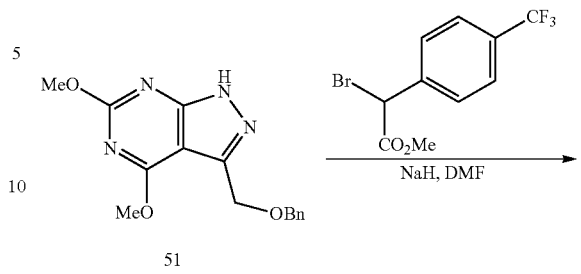

Scheme 21 illustrates a synthetic sequence for the preparation of hydroxymethyl containing pyrazolopyrimidinones such as 74 from the dimethoxypyrazolopyrimidine 51. Mitsunobu coupling of alcohol 66 with 51 will yield 72 which can be subjected to hydrogenolysis conditions to furnish alcohol 73. Deprotection of 73 can be achieved with either hydrochloric acid or trimethylsilyliodide to afford pyrazolopyrimidinone 74.

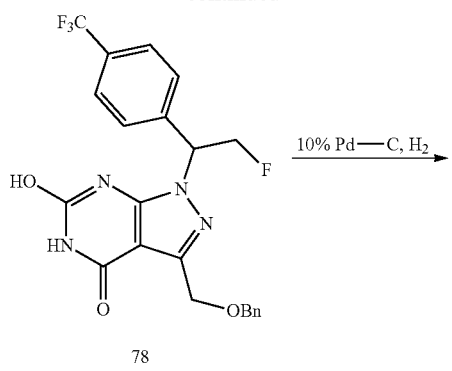

78

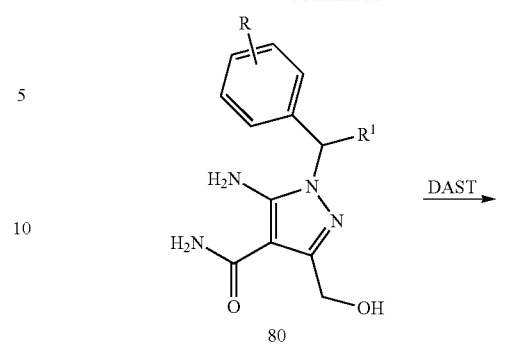

80

81

82

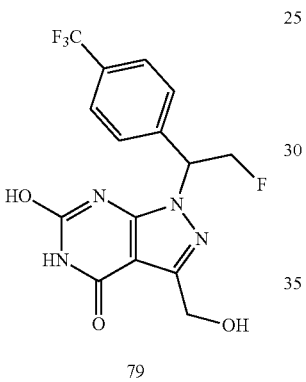

79

Scheme 22 illustrates a synthetic sequence for the preparation of methanol containing pyrazolopyrimidinones such as 79 from the dimethoxypyrazolopyrimidine 51. Treatment of 51 with a secondary bromide under basic conditions will afford ester 75 which can be reduced with sodium borohydride to afford alcohol 76. DAST treatment of 76 will afford primary fluoride 77 which can be deprotected by treatment with TMSI followed by hydrogenolysis to furnish pyrazolopyrimidinone 79.

Scheme 23 illustrates a synthetic sequence for the preparation of primary fluoride containing pyrazolopyrimidinones such as 82 from 5-aminopyrazole-4-carboxamides such as 69. Treatment of 69 with hydrogen and a palladium catalyst will afford 80 which can be treated with DAST to yield primary fluoride 81. Treatment with either ethyl chloroformate in dioxane or triphosgene in the presence of triethyl amine will furnish pyrazolopyrimidinone 82.

Scheme 23.

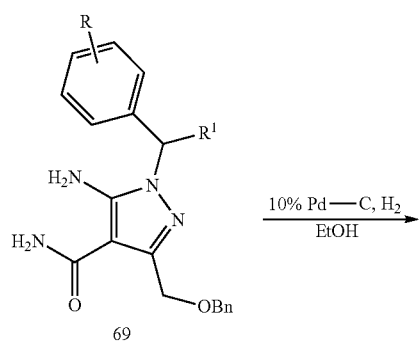

69

Scheme 24.

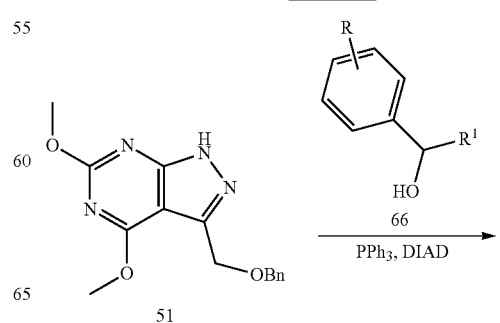

51

Scheme 25.

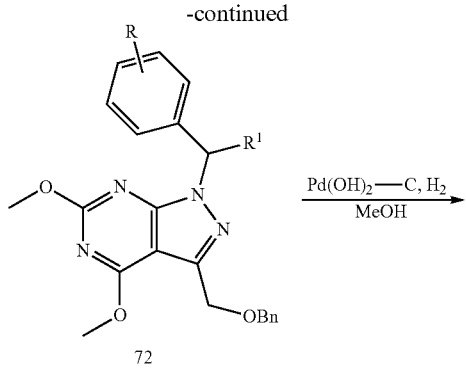

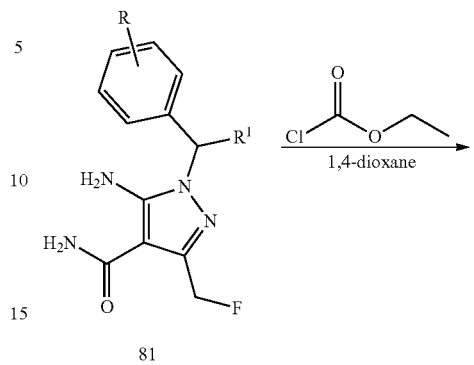

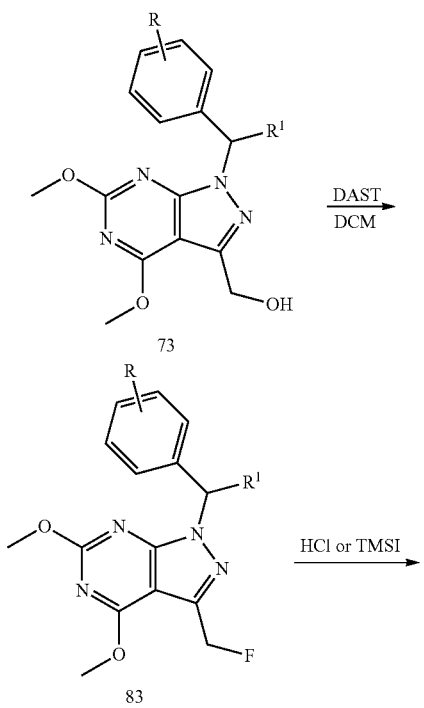

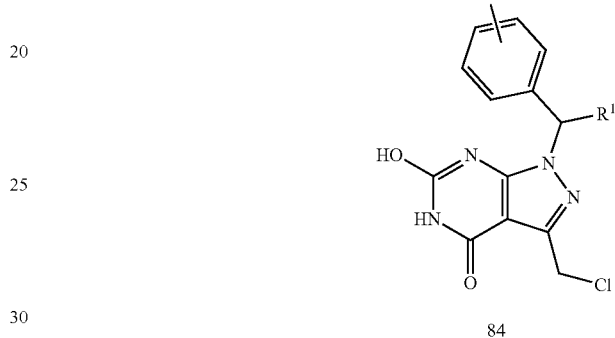

Scheme 25 illustrates a synthetic sequence for the preparation of primary chloride containing pyrazolopyrimidinones such as 84 from 5-aminopyrazole-4-carboxamide such as 81 by treatment with ethyl chloroformate in dioxane.

Scheme 26.

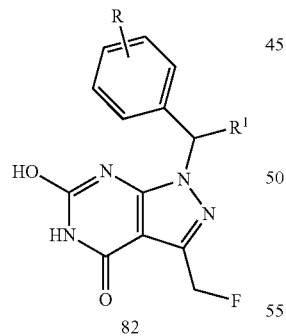

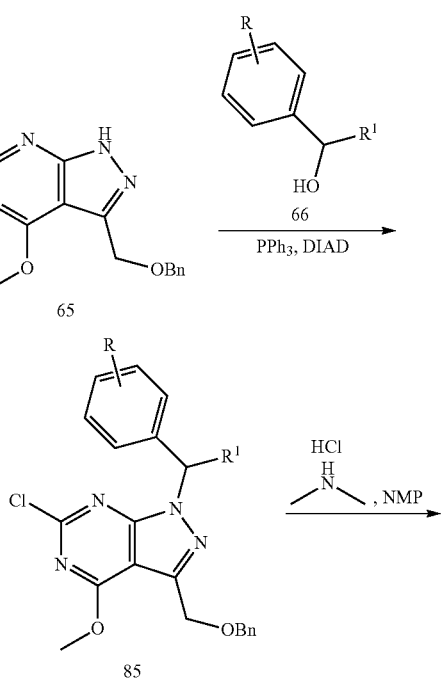

Scheme 24 illustrates a synthetic sequence for the preparation of primary fluoride containing pyrazolopyrimidinones such as 82 from the dimethoxypyrazolopyrimidine 51. Mitsunobu coupling of alcohol 66 with 51 will yield 72, which can be subjected to hydrogenolysis conditions to furnish alcohol 73. Treatment of 72 with DAST should afford primary fluoride 84 which can exposed to either hydrochloric acid or trimethylsilyliodide to afford pyrazolopyrimidinone 82.

47
-continued

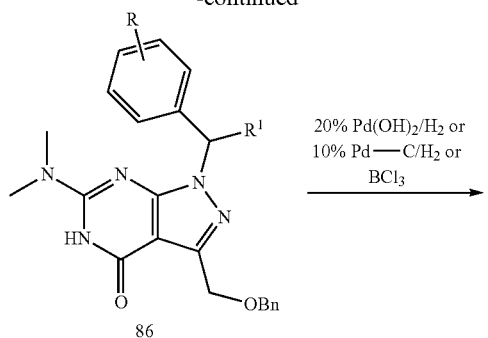

86

48
-continued

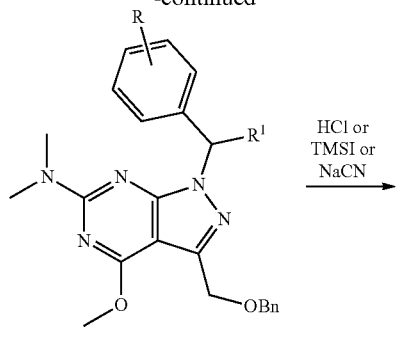

88

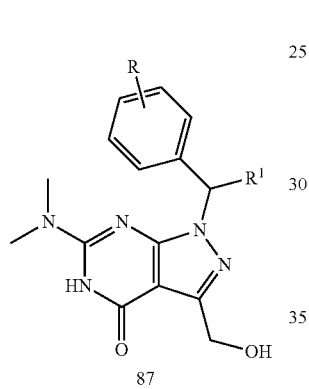

87

Scheme 26 illustrates a synthetic sequence for the preparation of dimethylamino-bearing pyrazolopyrimidinones such as 87 from chloro pyrazolopyrimidine 65. Mitsunobu coupling of alcohol 66 with 65 should yield 85 which can be subjected to dimethylamine hydrochloride to furnish pyrimidinone 86. Treatment of 86 under standard hydrogenolysis conditions with a palladium catalyst and hydrogen or boron trichloride will furnish dimethyl amino pyrazolopyrimidinone 87.

Scheme 27.

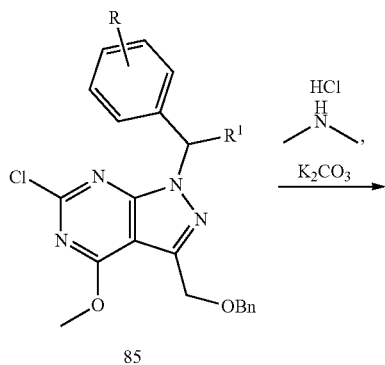

85

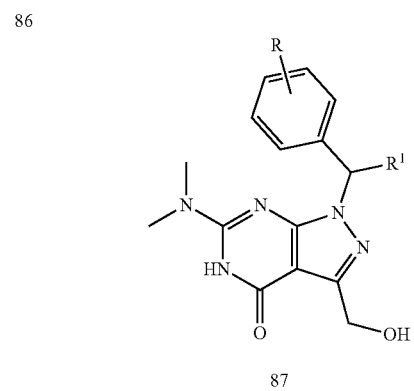

86

87

Scheme 27 illustrates a synthetic sequence for the preparation of dimethylamino-bearing pyrazolopyrimidinones such as 87 from pyrazolopyrimidine 85. Treatment of 85 with dimethylamine hydrochloride in the presence of potassium carbonate should furnish 88 which can be treated with either hydrochloric acid, trimethylsilyliodide, or sodium cyanide to afford pyrimidinone 86. Treatment of 86 under standard hydrogenolysis conditions with a palladium catalyst and hydrogen or boron trichloride will furnish dimethyl amino pyrazolopyrimidinone 87.

Scheme 28.

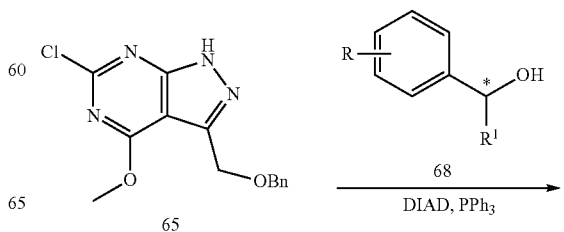

65

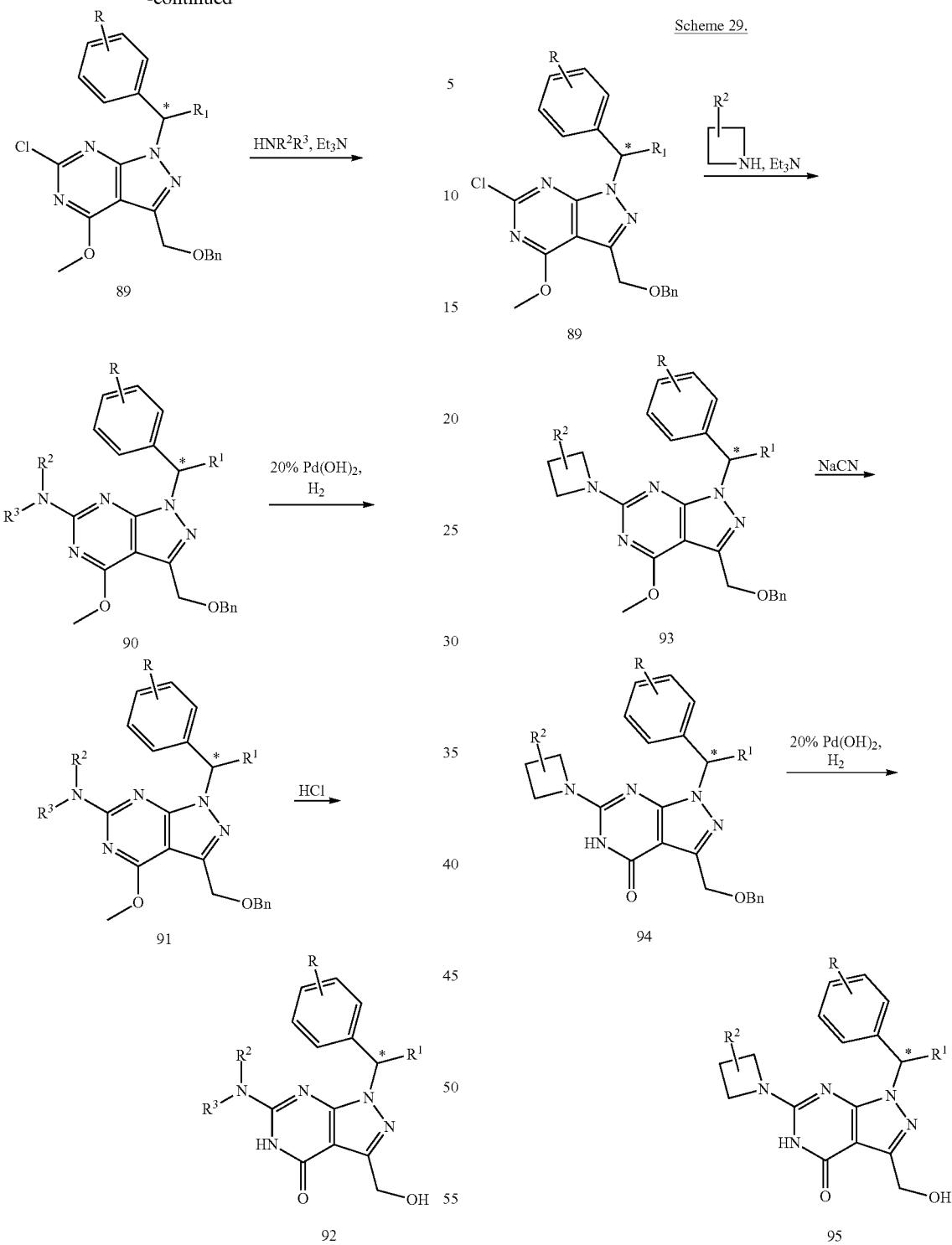

Scheme 28 illustrates a synthetic sequence for the preparation of non-racemic pyrazolopyrimidinones such as 92 from pyrazolopyrimidine 65. Mitsunobu coupling of chiral alcohol 68 with 65 should afford 89 which can be treated with an amine in the presence of triethylamine to afford 90. Hydrogenolysis using 20% Pd(OH)$_2$ in the presence of hydrogen should afford pyrimidinone 91 which upon treatment with HCl will furnish pyrazolopyrimidinone 92.

Scheme 29 illustrates a synthetic sequence for the preparation of non-racemic, azetidine-containing pyrazolopyrimidinones such as 95 from pyrazolopyrimidine 89. Treatment of 89 with a substituted azetidine in the presence of triethylamine to should afford 93 which can be exposed to sodium cyanide to furnish 94. Hydrogenolysis using 20% Pd(OH)$_2$ in the presence of hydrogen should afford azetidine-bearing pyrazolopyrimidinone 95.

Scheme 30.

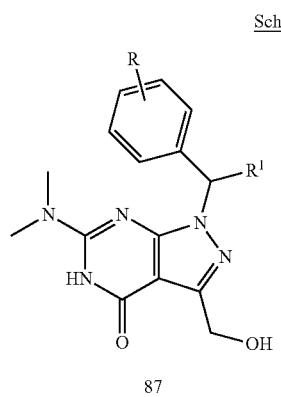

87

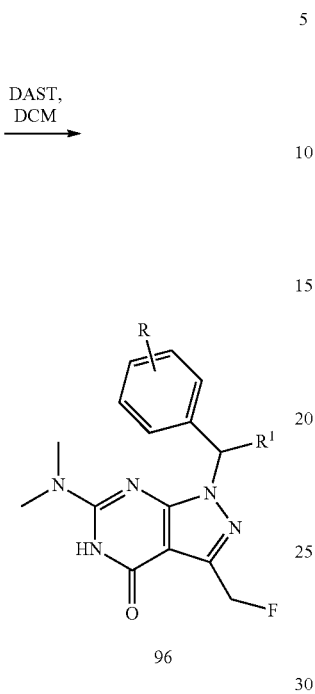

96

Scheme 30 illustrates a synthetic sequence for the preparation primary fluoride-containing pyrazolopyrimidinones such as 96 from pyrazolopyrimidinone 87 by treatment with DAST.

Scheme 31.

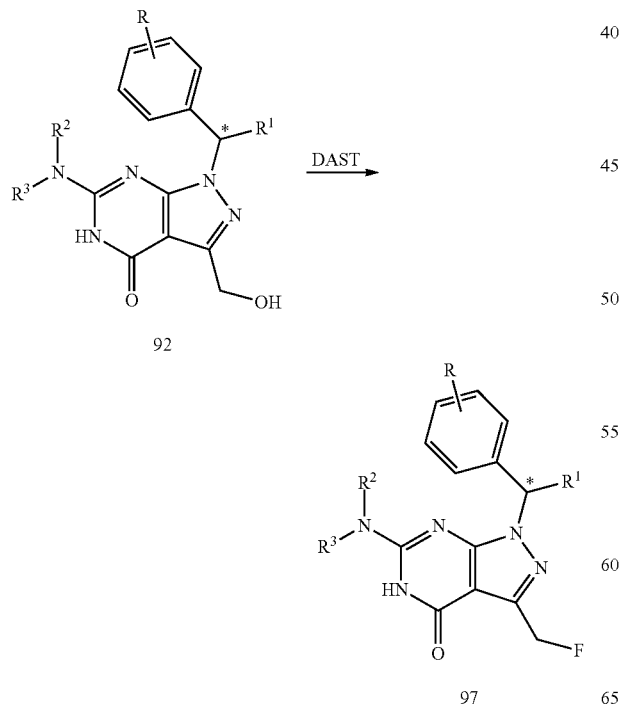

92

97

Scheme 31 illustrates a synthetic sequence for the preparation of enantioenriched primary fluoride-containing pyrazolopyrimidinones such as 97 from the pyrazolopyrimidinone precursor 92 by treatment with DAST.

Scheme 32.

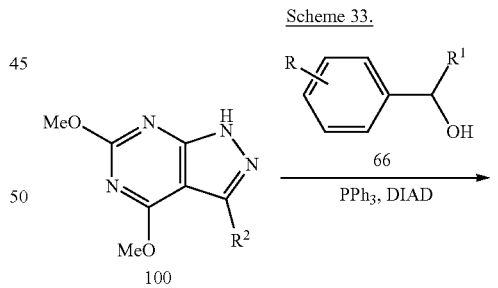

98

99

Scheme 32 illustrates a synthetic sequence for the preparation of trifluoroethyl containing pyrazolopyrimidinones such as 99 from trifluoroethyl-substituted 5-aminopyrazole-4-carboxamides such as 98. Treatment of 98 with triphosgene in the presence of triethyl amine or ethyl chloroformate in dioxane will furnish pyrazolopyrimidinone 99.

Scheme 33.

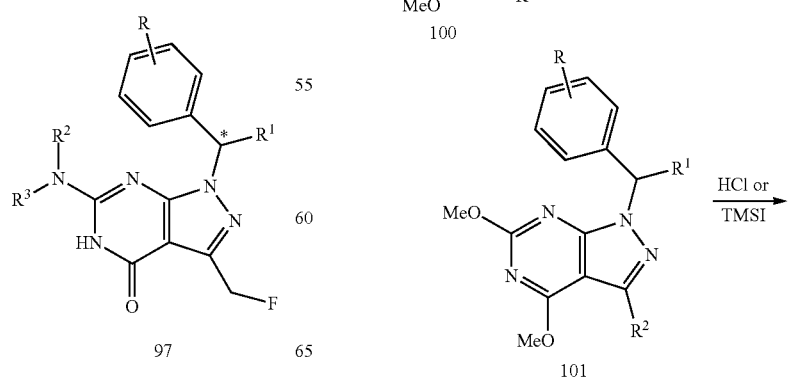

100

101

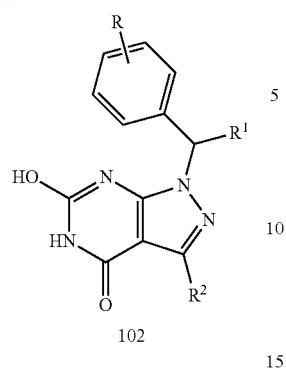

102

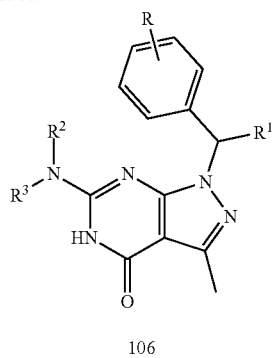

106

Scheme 33 illustrates a synthetic sequence for the preparation of pyrazolopyrimidinones such as 102 from pyrazolopyrimidine 100. Mitsunobu coupling of alcohol 66 with 100 should afford 101, followed by treatment with HCl or TMSI to furnish pyrazolopyrimidinone 102.

Scheme 34 illustrates a synthetic sequence for the preparation of C3 methyl-containing pyrazolopyrimidinones such as 106 from methyl-substituted 5-aminopyrazole-4-carboxamides such as 103. Treatment of 103 with urea at high temperature should afford 104 which can be treated under chlorination conditions to furnish chloride 105. Treatment of 105 with an amine in the presence of triethyl amine will furnish pyrazolopyrimidinone 106.

Scheme 34.

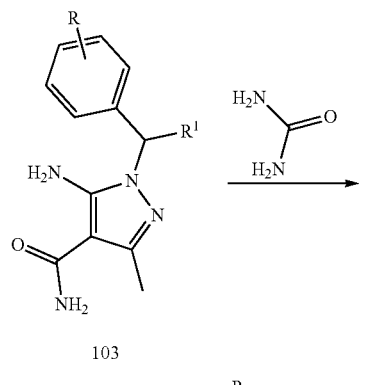

103

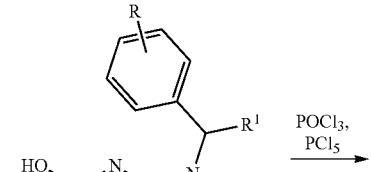

104

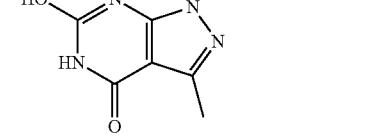

105

Scheme 35.

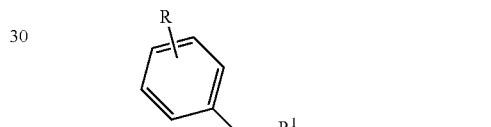

72

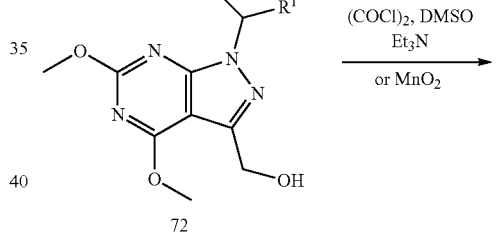

107

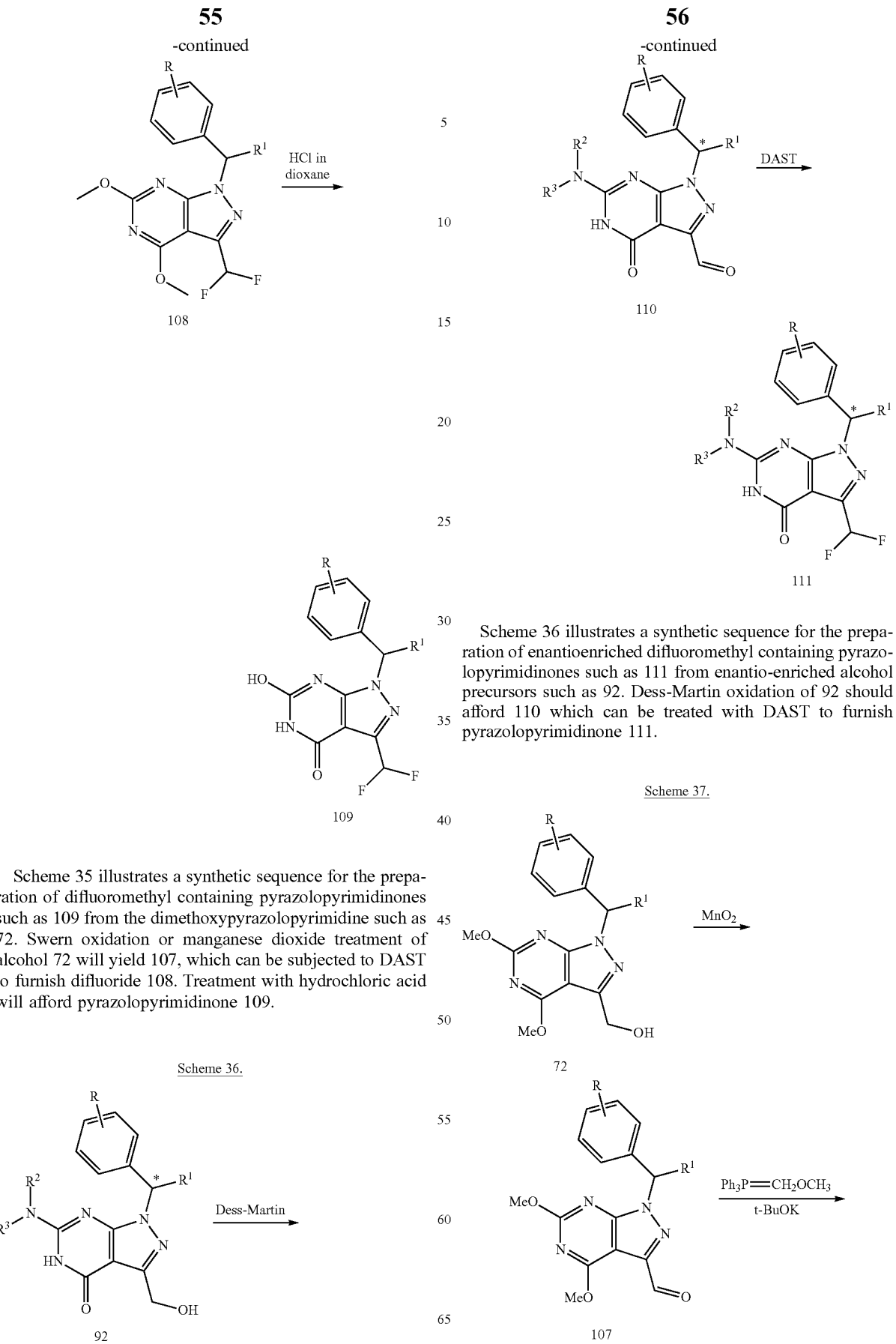

Scheme 36 illustrates a synthetic sequence for the preparation of enantioenriched difluoromethyl containing pyrazolopyrimidinones such as 111 from enantio-enriched alcohol precursors such as 92. Dess-Martin oxidation of 92 should afford 110 which can be treated with DAST to furnish pyrazolopyrimidinone 111.

Scheme 35 illustrates a synthetic sequence for the preparation of difluoromethyl containing pyrazolopyrimidinones such as 109 from the dimethoxypyrazolopyrimidine such as 72. Swern oxidation or manganese dioxide treatment of alcohol 72 will yield 107, which can be subjected to DAST to furnish difluoride 108. Treatment with hydrochloric acid will afford pyrazolopyrimidinone 109.

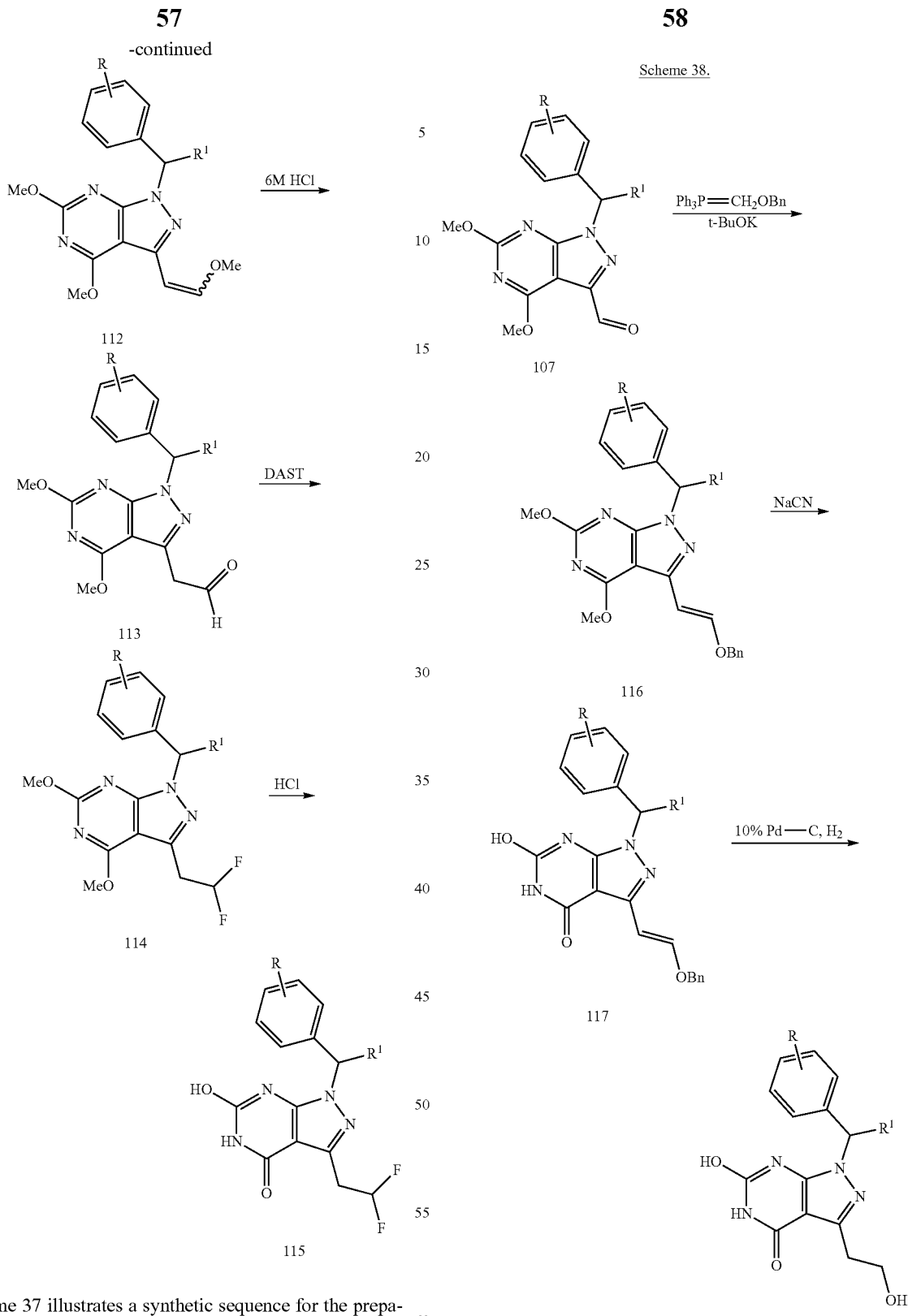

Scheme 37 illustrates a synthetic sequence for the preparation of difluoroethyl containing pyrazolopyrimidinones such as 115 from alcohol precursors such as 72. Oxidation of alcohol 72 using manganese dioxide should afford 107 which can be homologated to enol ether 112 using a Wittig reaction. Hydrolysis of 112 with hydrochloric acid followed by treatment of aldehyde 113 with DAST will furnish difluoroethyl derivative 114. HCl treatment of 114 will yield pyrazolopyrimidinone 115.

Scheme 38 illustrates a synthetic sequence for the preparation of ethanol containing pyrazolopyrimidinones such as 118 from aldehyde precursors such as 107. Wittig reaction on 107 will afford 116 which can be treated with sodium cyanide to furnish 117. Treatment with 10% palladium on carbon in the presence of hydrogen will afford pyrazolopyrimidinone 118.

Scheme 39.

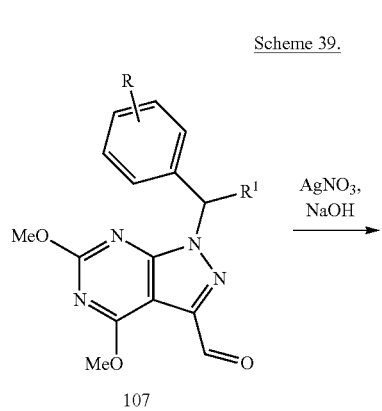

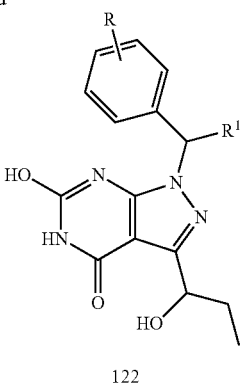

Scheme 39 illustrates a synthetic sequence for the preparation of substituted methanol pyrazolopyrimidinones such as 122 from aldehyde precursors such as 107. Treatment of 107 with silver nitrate in the presence of sodium hydroxide will afford acid 119 which upon treatment with thionyl chloride in methanol will furnish ester 120. Reductive alkylation of 120 should yield 121 which upon treatment with TMSI will afford pyrazolopyrimidinone 122.

Scheme 40.

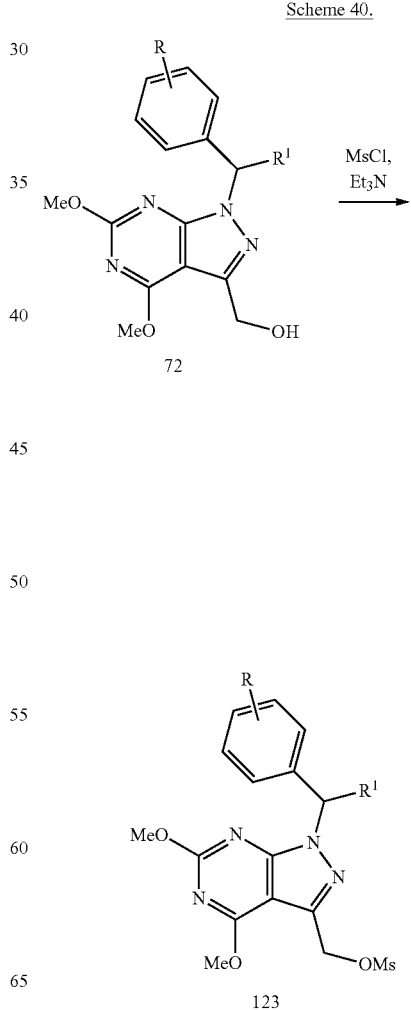

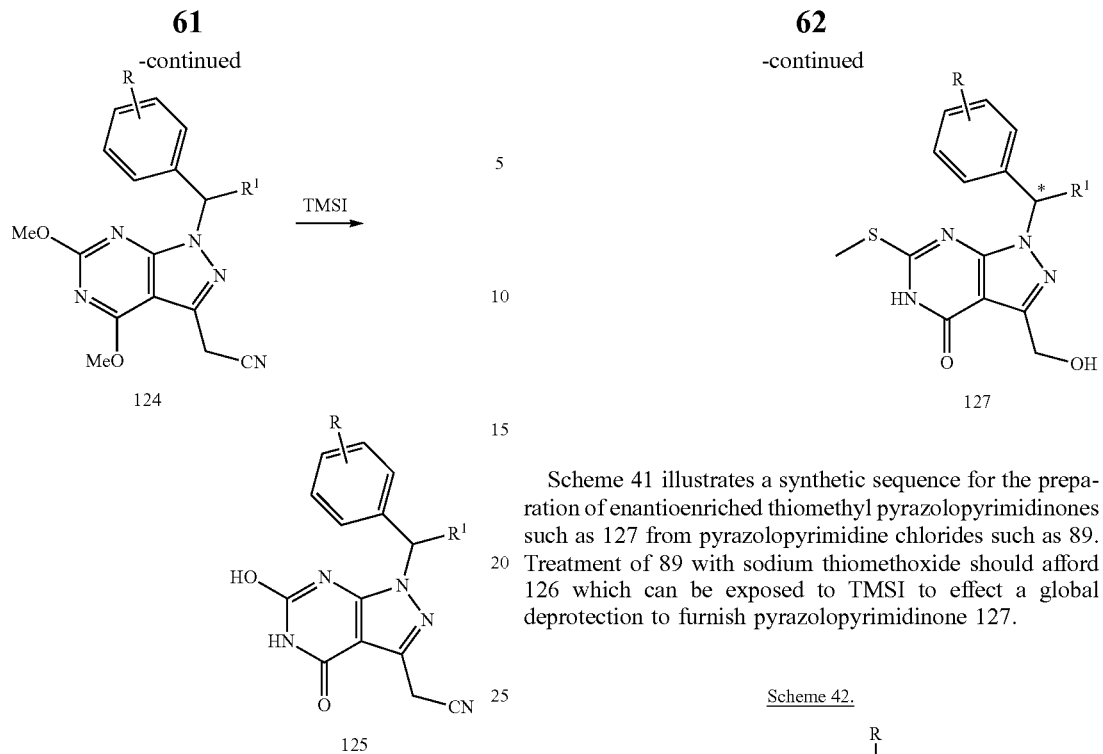

Scheme 40 illustrates a synthetic sequence for the preparation of acetonitrile-substituted pyrazolopyrimidinones such as 125 from alcohol precursors such as 72. Treatment of 72 with methanesulfonyl chloride in the presence of base will afford mesylate 123 which can be treated with sodium cyanide in the presence of 18-crown-6 to furnish nitrile 124. Deprotection of 124 can be achieved with TMSI to yield pyrazolopyrimidinone 125.

Scheme 41 illustrates a synthetic sequence for the preparation of enantioenriched thiomethyl pyrazolopyrimidinones such as 127 from pyrazolopyrimidine chlorides such as 89. Treatment of 89 with sodium thiomethoxide should afford 126 which can be exposed to TMSI to effect a global deprotection to furnish pyrazolopyrimidinone 127.

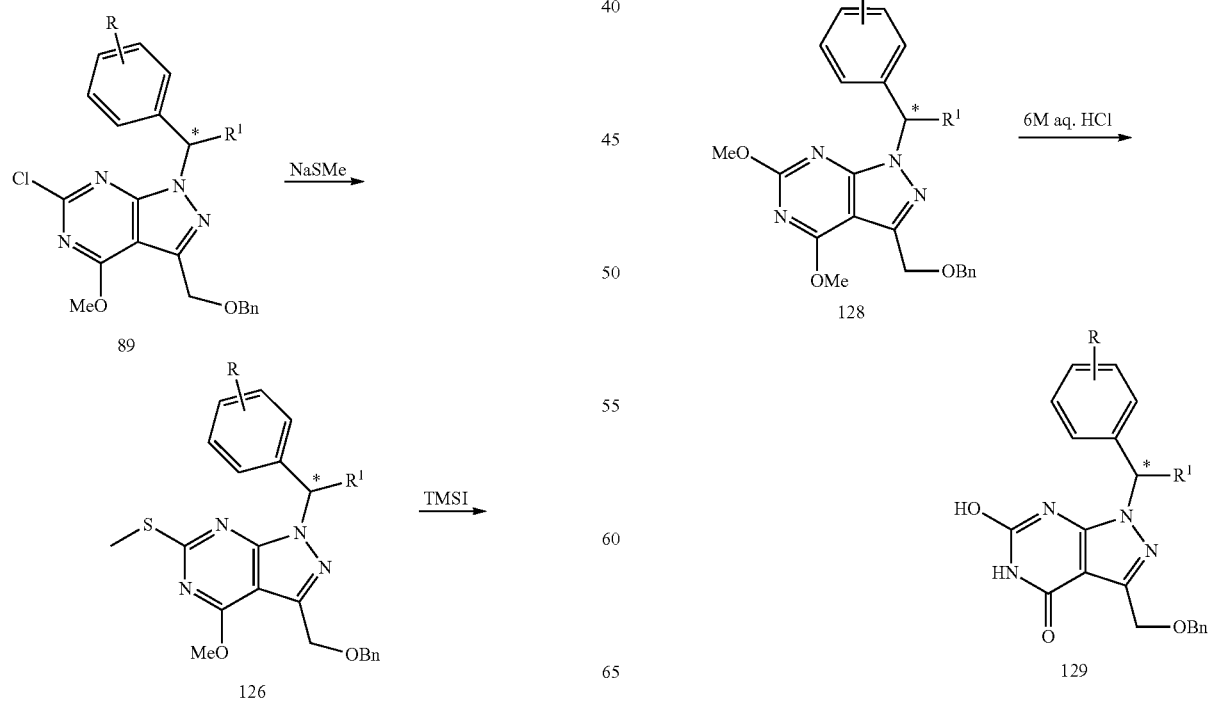

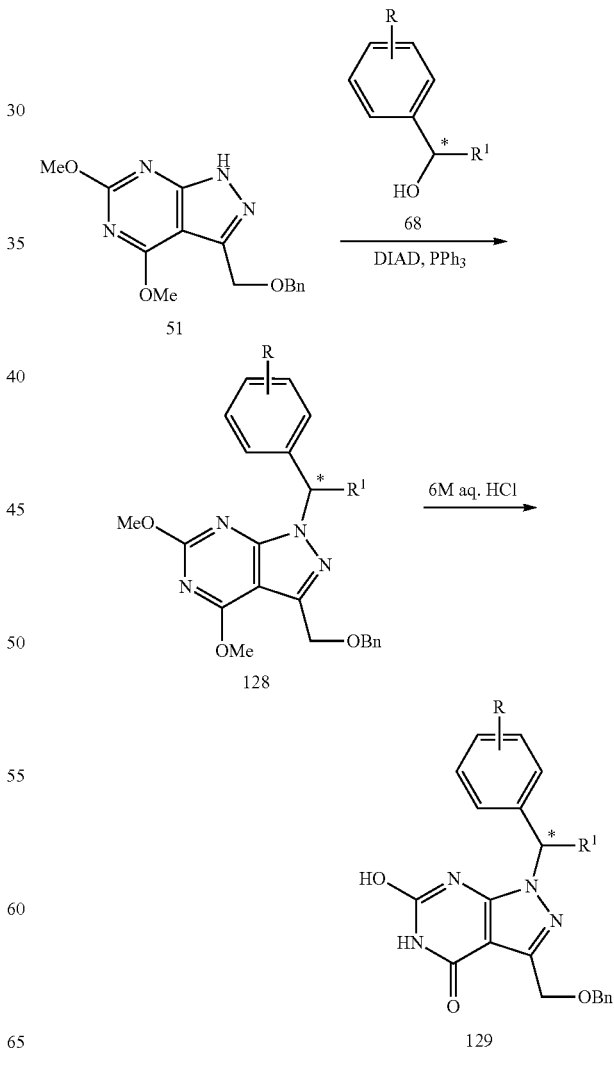

Scheme 42 illustrates a synthetic sequence for the preparation of enantioenriched pyrazolopyrimidinones such as 129 from pyrazolopyrimidine 51. Mitsunobu coupling of enantioenriched alcohol 68 with 51 will afford 128, which can be treated with an aqueous solution of HCl to furnish pyrazolopyrimidinone 129.

Scheme 43 illustrates a synthetic sequence for the preparation of enantioenriched pyrazolopyrimidinones such as 132 from dimethoxy pyrazolopyrimidine 128. Benzyl group deprotection of 128 can be achieved under hydrogenolysis conditions to afford 130 which can be subjected to sodium hydride in the presence of methyl iodide to yield methoxy intermediate 131. Treatment of 131 with aqueous solution of HCl will furnish pyrazolopyrimidinone 132.

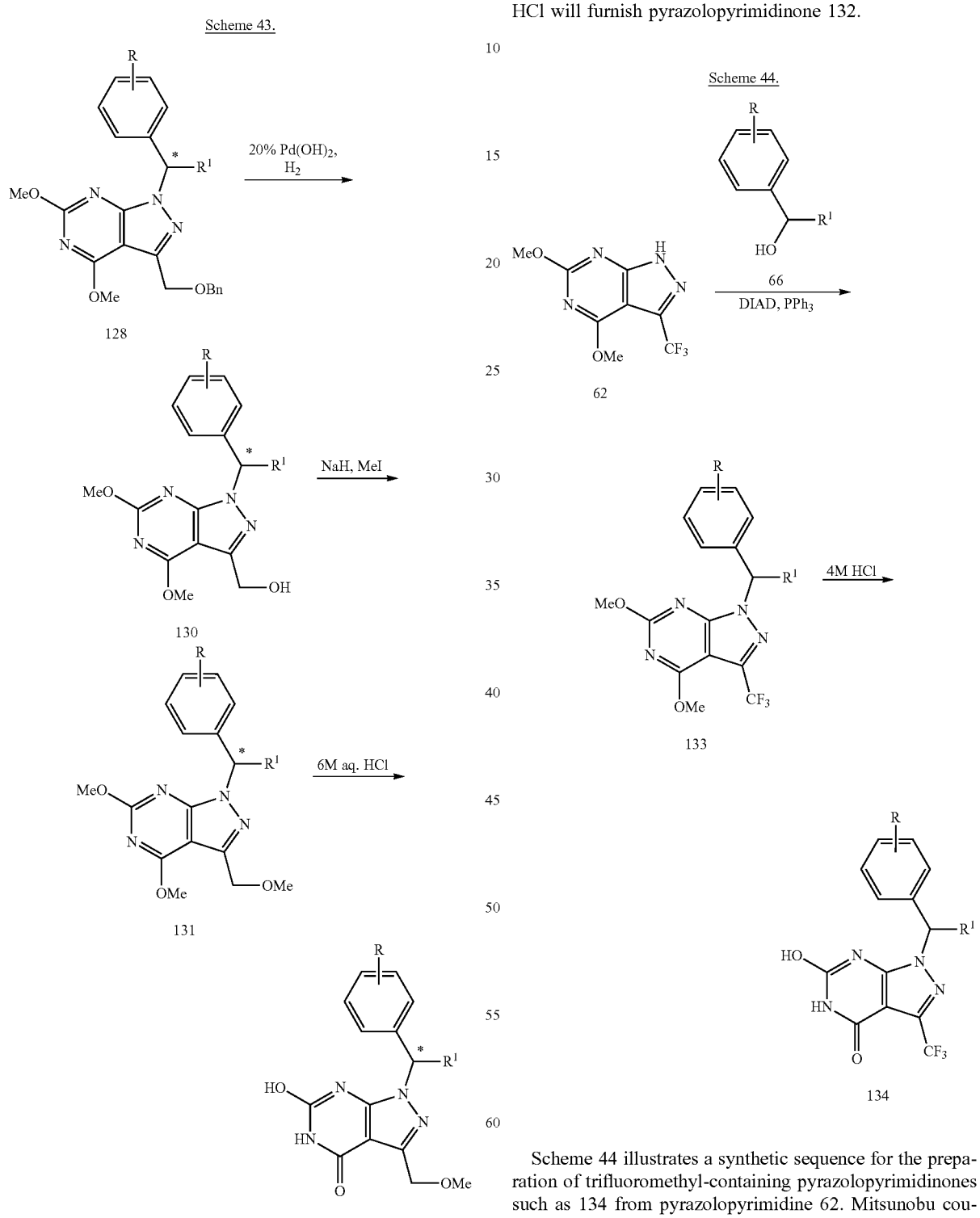

Scheme 44 illustrates a synthetic sequence for the preparation of trifluoromethyl-containing pyrazolopyrimidinones such as 134 from pyrazolopyrimidine 62. Mitsunobu coupling of alcohol 66 with 62 will afford 133, which can be treated with a solution of HCl to furnish pyrazolopyrimidinone 134.

Scheme 45.

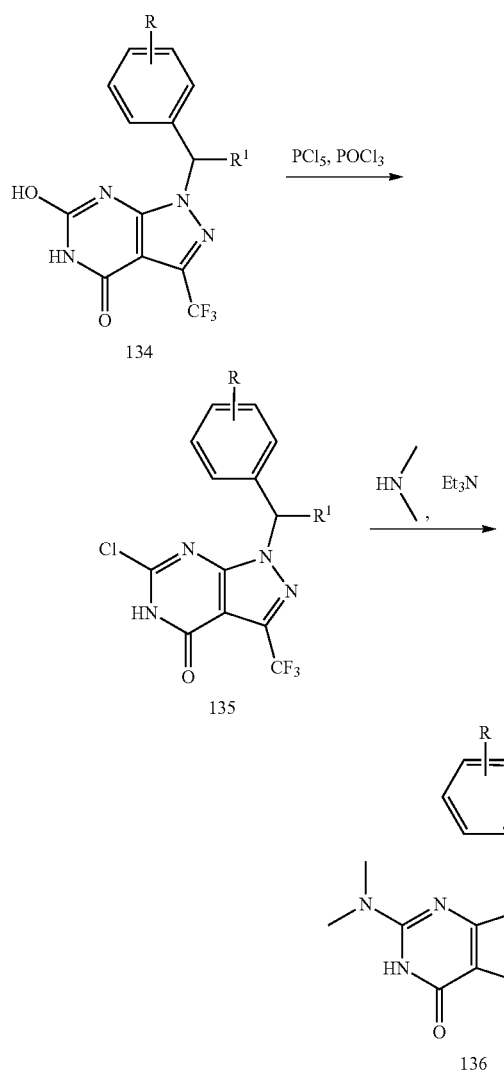

Scheme 45 illustrates a synthetic sequence for the preparation of trifluoromethyl-containing pyrazolopyrimidinones such as 136 from pyrazolopyrimidine 134. Chlorination of 134 followed by treatment with dimethyl amine in the presence of base to furnish pyrazolopyrimidinone 136.

Scheme 46.

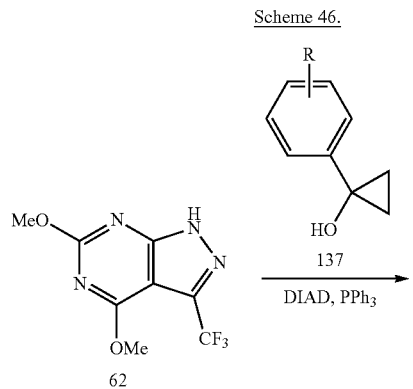

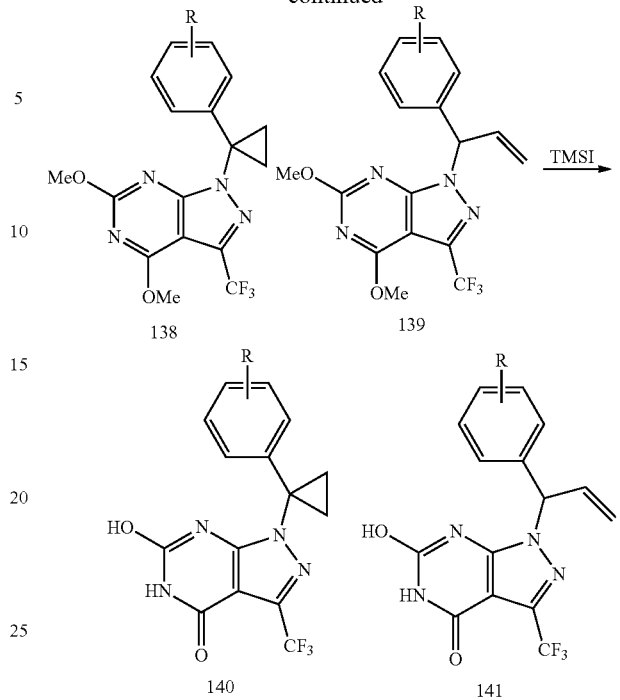

Scheme 46 illustrates a synthetic sequence for the preparation of trifluoromethyl-containing pyrazolopyrimidinones such as 140 and 141 from pyrazolopyrimidine 62. Mitsunobu coupling of alcohol 66 with cyclopropanol 137 will afford a mixture of 138 and 139, which can be treated with TMSI to furnish pyrazolopyrimidinones 140 and 141.

Scheme 47.

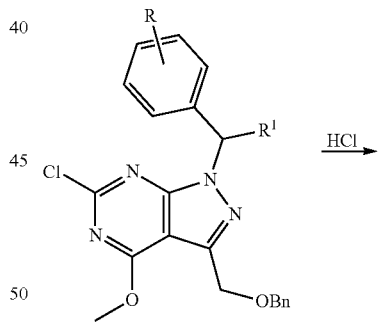

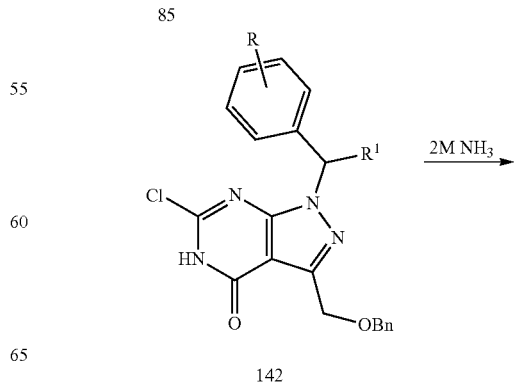

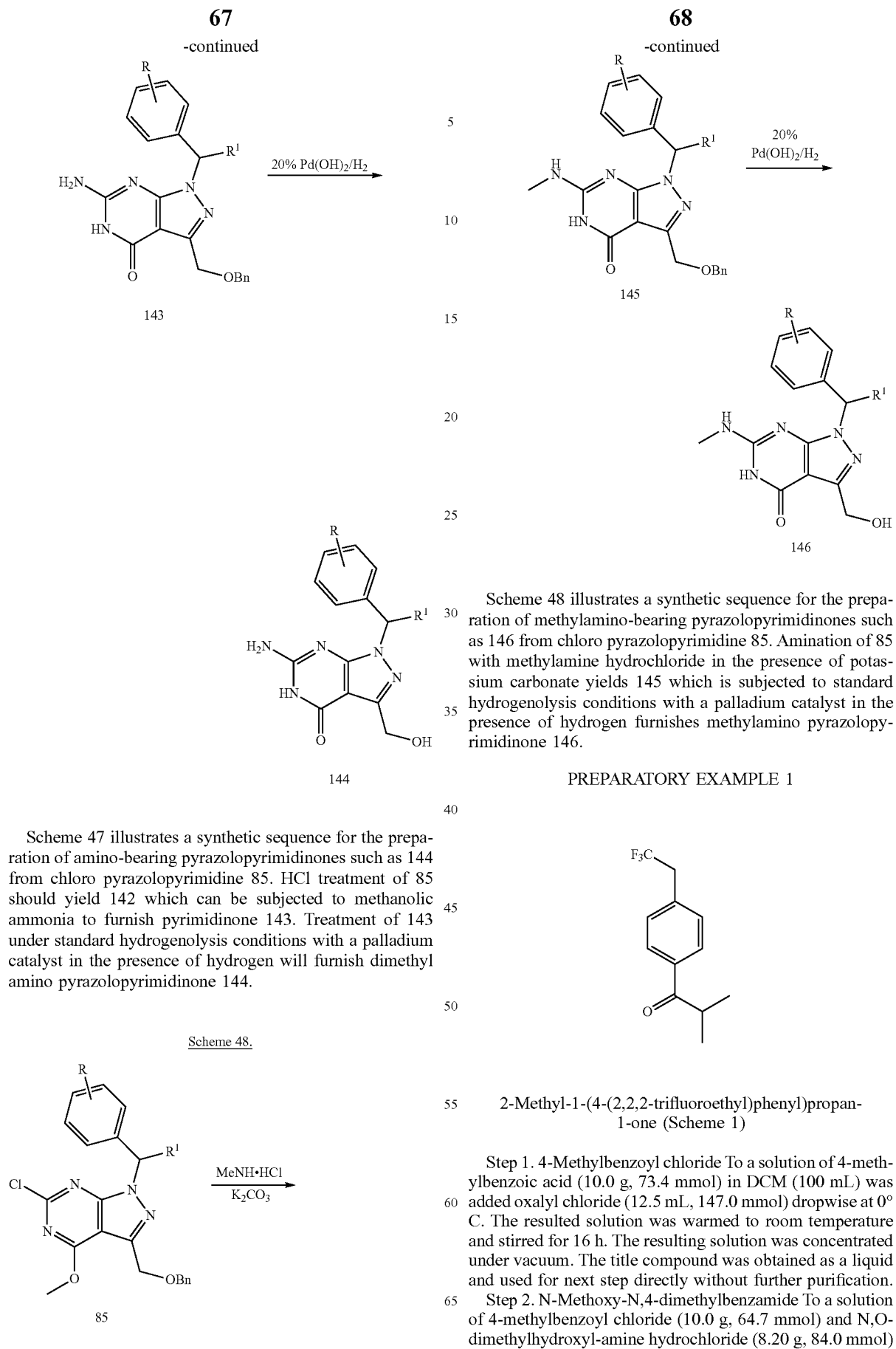

Scheme 47 illustrates a synthetic sequence for the preparation of amino-bearing pyrazolopyrimidinones such as 144 from chloro pyrazolopyrimidine 85. HCl treatment of 85 should yield 142 which can be subjected to methanolic ammonia to furnish pyrimidinone 143. Treatment of 143 under standard hydrogenolysis conditions with a palladium catalyst in the presence of hydrogen will furnish dimethyl amino pyrazolopyrimidinone 144.

Scheme 48 illustrates a synthetic sequence for the preparation of methylamino-bearing pyrazolopyrimidinones such as 146 from chloro pyrazolopyrimidine 85. Amination of 85 with methylamine hydrochloride in the presence of potassium carbonate yields 145 which is subjected to standard hydrogenolysis conditions with a palladium catalyst in the presence of hydrogen furnishes methylamino pyrazolopyrimidinone 146.

PREPARATORY EXAMPLE 1

2-Methyl-1-(4-(2,2,2-trifluoroethyl)phenyl)propan-1-one (Scheme 1)

Step 1. 4-Methylbenzoyl chloride To a solution of 4-methylbenzoic acid (10.0 g, 73.4 mmol) in DCM (100 mL) was added oxalyl chloride (12.5 mL, 147.0 mmol) dropwise at 0° C. The resulted solution was warmed to room temperature and stirred for 16 h. The resulting solution was concentrated under vacuum. The title compound was obtained as a liquid and used for next step directly without further purification.

Step 2. N-Methoxy-N,4-dimethylbenzamide To a solution of 4-methylbenzoyl chloride (10.0 g, 64.7 mmol) and N,O-dimethylhydroxyl-amine hydrochloride (8.20 g, 84.0 mmol)

in DCM (100 ml) was added triethylamine (27 mL, 194.0 mmol) dropwise at 0° C. The resulting mixture was warmed to room temperature and stirred for 2 h. The reaction mixture was quenched with water (50 mL) and extracted with ethyl acetate (3×50 mL). The combined organic layers were washed with brine (100 mL), dried over anhydrous sodium sulfate, filtered, and concentrated under reduced pressure. The residue was purified by silica gel column chromatography (0-33% ethyl acetate in hexanes) as eluent to afford the title compound as an oil. $^1$H NMR (300 MHz, CDCl$_3$) δ: 7.59 (d, J=8.4 Hz, 2H), 7.19 (d, J=8.4 Hz, 2H), 3.58 (s, 3H), 3.34 (s, 3H), 2.34 (s, 3H).

Step 3. 4-(Bromomethyl)-N-methoxy-N-methylbenzamide To a solution of NBS (7.75 g, 43.5 mmol) and benzoyl peroxide (0.53 g, 2.2 mmol) in CCl$_4$ (20 mL) was added N-methoxy-N,4-dimethylbenzamide (7.80 g, 43.5 mmol) at RT. The resulting mixture was heated to reflux, stirred for 16 h, and was cooled down to room temperature. The mixture was diluted with water (100 mL) and extracted with dichloromethane (3×100 mL). The combined organic layers were washed with brine (300 mL), dried over sodium sulfate, filtered, and concentrated under vacuum. The residue was purified by silica gel column chromatography (50% EtOAc in petroleum ether) to afford the title compound as an oil. MS=258.0, 259.9 (+ESI).

Step 4. N-methoxy-N-methyl-4-(2,2,2-trifluoroethyl)benzamide To a solution of 4-(bromomethyl)-N-methoxy-N-methylbenzamide (5.0 g, 19.4 mmol) and methyl 2,2-difluoro-2-(fluorosulfonyl)acetate (7.44 g, 38.7 mmol) in NMP (10 mL) at RT under N$_2$ was added copper(I) iodide (0.74 g, 3.9 mmol). The resulting mixture was heated to 80° C., stirred for 16 h, and was cooled down to room temperature. The mixture was diluted with water (50 mL) and extracted with EtOAc (3×50 mL). The combined organic layers were washed with brine (1×100 mL), dried over sodium sulfate, filtered, and concentrated under vacuum. The residue was purified by silica gel column chromatography (50% EtOAc in petroleum ether) to afford the title compound as an oil. $^1$H NMR (300 MHz, CDCl$_3$) δ: 7.68 (d, J=8.1 Hz, 2H), 7.34 (d, J=8.1 Hz, 2H), 3.60 (s, 3H), 3.41 (q, J=10.8 Hz, 2H), 3.67 (s, 3H).

Step 5: 2-Methyl-1-(4-(2,2,2-trifluoroethyl)phenyl)propan-1-one: To a solution of N-methoxy-N-methyl-4-(2,2,2-trifluoroethyl)benzamide (0.80 g, 3.24 mmol) in THF (8 mL) at 0° C. was added isopropylmagnesium bromide (1 M in THF, 6.47 mL, 6.47 mmol) dropwise with stirring. The resulting solution was warmed to room temperature and was stirred for 16 h. Water (40 mL) was added and the mixture was extracted with diethyl ether (3×30 mL). The combined organic fractions were washed with brine (1×100 mL), dried over Na$_2$SO$_4$, filtered, and concentrated under reduced pressure. The residue was purified by silica gel column chromatography (50% EtOAc in petroleum ether) to afford the title compound as an oil. $^1$H NMR (300 MHz, CDCl$_3$) δ: 7.95 (d, J=8.4 Hz, 2H), 7.41 (d, J=8.4 Hz, 2H), 3.59-3.38 (m, 3H), 1.22 (d, J=6.9 Hz, 6H).

TABLE 1

The following compounds in Table 1 were prepared using procedures similar to those described in Preparatory Example 1 using appropriate starting materials.

| Prep Ex No. | Structure | IUPAC Name | $^1$H NMR |
|---|---|---|---|
| 2 | 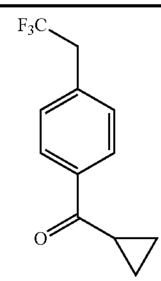 | cyclopropyl(4-(2,2,2-trifluoroethyl)phenyl)methanone | $^1$H NMR (300 MHz, CDCl$_3$) δ: 8.01 (d, J = 8.1 Hz, 2H), 7.52 (d, J = 8.1 Hz, 2H), 3.55 (q, J = 10.8 Hz, 2H), 2.71-2.62 (m, 1H), 1.30-1.20 (m, 2H), 1.11-1.01 (m, 2H). |
| 3 | 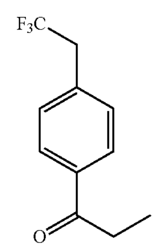 | 1-(4-(2,2,2-trifluoroethyl)phenyl)propan-1-one | $^1$H NMR (300 MHz, CDCl$_3$) δ: 7.96 (d, J = 8.0 Hz, 2H), 7.40 (d, J = 8.0 Hz, 2H), 3.43 (q, J = 11.2 Hz, 2H), 3.00 (q, J = 7.2 Hz, 2H), 1.25 (t, J = 7.2 Hz, 3H). |

PREPARATORY EXAMPLE 4

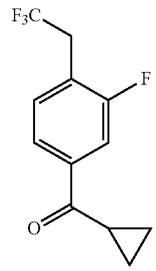

Cyclopropyl(3-fluoro-4-(2,2,2-trifluoroethyl)phenyl)methanone (Scheme 2)

Step 1. Methyl 4-(bromomethyl)-3-fluorobenzoate The title compound was prepared using procedures similar to those described in step 3 of Preparatory Example 1 using methyl 3-fluoro-4-methylbenzoate to afford the title compound as an oil. $^1$H NMR (300 MHz, CDCl$_3$) δ: 7.89-7.70 (m, 3H), 4.75 (s, 2H), 3.88 (s, 3H).

Step 2. Methyl 3-fluoro-4-(2,2,2-trifluoroethyl)benzoate The title compound was prepared using procedures similar to those described in step 4 of Preparatory Example 1 using methyl 4-(bromomethyl)-3-fluorobenzoate to afford the title compound as a liquid. MS=236.0 (+EI)

Step 3. 3-Fluoro-4-(2,2,2-trifluoroethyl)benzoic acid To a mixture of methyl 3-fluoro-4-(2,2,2-trifluoroethyl)benzoate (3.00 g, 12.7 mmol) in EtOH and water (1:1, 5 mL) at RT was added LiOH (1.52 g, 63.5 mmol). The reaction mixture was stirred for 1 h at 60° C. The resulting mixture was cooled to room temperature and diluted with water (10 mL). The pH of the solution was adjusted to ~3-4 by addition of 3 M HCl and the resulting mixture was extracted with EtOAc (3×50 mL). The combined organic layers was washed with water (1×40 mL), brine (3×20 mL), and dried over Na$_2$SO$_4$. The organic layer was filtered and concentrated under reduced pressure to afford the title compound as a solid which was used in the next step directly without purification. MS=220.9 (−ESI).

Step 4. 3-Fluoro-N-methoxy-N-methyl-4-(2,2,2-trifluoroethyl)benzamide

The title compound was prepared using procedures similar to those described in step 1 and step 2 of Preparatory Example 1 using 3-fluoro-4-(2,2,2-trifluoroethyl)benzoic acid to afford the title compound as a liquid. MS=265.9 (+ESI).

Step 5. Cyclopropyl(3-fluoro-4-(2,2,2-trifluoroethyl)phenyl)methanone The title compound was prepared using procedures similar to those described in step 5 of Preparatory Example 1 using 3-fluoro-N-methoxy-N-methyl-4-(2,2,2-trifluoroethyl)benzamide to afford the title compound as a liquid. MS=246.0 (+EI).

TABLE 2

The following compounds were prepared using procedures similar to those described in Preparatory Example 4 using appropriate starting materials.

| Prep Ex No. | Structure | IUPAC Name | GC-MS or $^1$H NMR |
|---|---|---|---|
| 5 | F$_3$C, F, O (structure) | 1-(3-fluoro-4-(2,2,2-trifluoroethyl)phenyl)propan-1-one | MS (+EI) m/z = 234.1. |

TABLE 2-continued

The following compounds were prepared using procedures similar to those described in Preparatory Example 4 using appropriate starting materials.

| Prep Ex No. | Structure | IUPAC Name | GC-MS or $^1$H NMR |
|---|---|---|---|
| 6 | F$_3$C, F, O (structure) | 1-(3-fluoro-4-(2,2,2-trifluoroethyl)phenyl)ethanone | $^1$H NMR (300 MHz, CDCl$_3$) δ: 7.85-7.60 (m, 3H), 3.83 (q, J = 11.2 Hz, 2H), 2.60 (s, 3H). |

PREPARATORY EXAMPLE 7

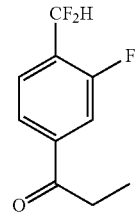

1-(4-(Difluoromethyl)-3-fluorophenyl)propan-1-one (Scheme 3)

Step 1. Methyl 4-(difluoromethyl)-3-fluorobenzoate A mixture of 4-bromo-1-(difluoromethyl)-2-fluorobenzene (2.0 g, 8.9 mmol), Pd(OAc)$_2$ (0.40 g, 1.8 mmol), TEA (7.43 mL, 53.3 mmol) and dppf (0.99 g, 1.8 mmol) in DMF (60 mL) and MeOH (20 mL) was stirred at 110° C. under carbon monoxide (5 atm) for 16 h. After cooling to room temperature, the resulting mixture was filtered and the filtrate was concentrated under vacuum. The residue was purified by silica gel column chromatography (0-30% ethyl acetate in petroleum ether) to afford the title compound as an oil. MS=203.9 (+EI).

Step 2. 4-(Difluoromethyl)-3-fluorobenzoic acid The title compound was prepared using procedures similar to those described in step 3 of Preparatory Example 4 using methyl 4-(difluoromethyl)-3-fluorobenzoate to afford the title compound as an oil. $^1$H NMR (300 MHz, CDCl$_3$) δ: 13.30 (br s, 1H), 7.90 (d, J=8.1 Hz, 1H), 7.83-7.76 (m, 2H), 7.30 (t, J=54.0 Hz, 1H).

Step 3. 4-(Difluoromethyl)-3-fluoro-N-methoxy-N-methylbenzamide The title compound was prepared using procedures similar to those described in step 1 to step 2 of Preparatory Example 1 using 4-(difluoromethyl)-3-fluorobenzoic acid to afford an oil. MS=234.0 (+ESI).

Step 4. 1-(4-(Difluoromethyl)-3-fluorophenyl)propan-1-one The title compound was prepared using procedures similar to those described in step 5 of Preparatory Example 1 using 4-(difluoromethyl)-3-fluoro-N-methoxy-N-methylbenzamide to afford an oil. $^1$H NMR (400 MHz, CDCl$_3$) δ: 7.82 (d, J=8.0 Hz, 1H), 7.72-7.69 (m, 2H), 6.92 (t, J=54.8 Hz, 1H), 3.04-2.98 (m, 2H), 1.24 (t, J=7.2 Hz, 3H).

TABLE 3

The following compounds were prepared using procedures similar to those described in Preparatory Example 7 using appropriate starting materials.

| Prep Ex No. | Structure | IUPAC Name | GCMS or ¹H NMR |
|---|---|---|---|
| 8 | 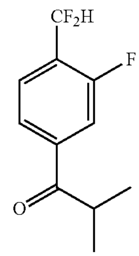 | 1-(4-(difluoromethyl)-3-fluorophenyl)-2-methylpropan-1-one | ¹H NMR (300 MHz, CDCl₃) δ: 7.82 (d, J = 8.1 Hz, 1H), 7.74-7.69 (m, 2H), 6.93 (t, J = 54.6 Hz, 1H), 3.55-3.45 (m, 1H), 1.24 (d, J = 7.2 Hz, 6H). |
| 9 | 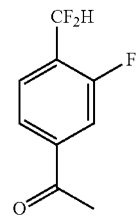 | 1-(4-(difluoromethyl)-3-fluorophenyl)ethanone | ¹H NMR (400 MHz, CDCl₃) δ: 7.82 (d, J = 8.0 Hz, 1H), 7.74-7.69 (m, 2H), 6.92 (t, J = 54.6 Hz, 1H), 2.63 (s, 3H). |
| 10 | 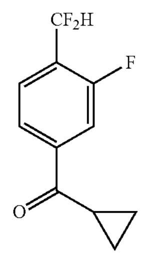 [SMILES: O=C(c1ccc(C(F)F)c(F)c1)C1CC1] | cyclopropyl(4-(difluoromethyl)-3-fluorophenyl)methanone | ¹H NMR (300 MHz, CDCl₃) δ: 7.82 (d, J = 8.0 Hz, 1H), 7.75-7.70 (m, 2H), 6.93 (t, J = 54.9 Hz, 1H), 2.66-2.58 (m, 1H), 1.32-1.26 (m, 2H), 1.15-1.09 (m, 2H). |
| 11 | 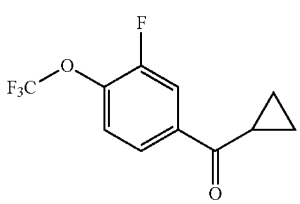 [SMILES: O=C(c1ccc(OC(F)(F)F)c(F)c1)C1CC1] | cyclopropyl(3-fluoro-4-(trifluoromethoxy)phenyl)methanone | ¹H NMR (400 MHz, CDCl₃) δ: 7.88-7.85 (m, 2H), 7.46-7.42 (m, 1H), 2.65-2.59 (m, 1H), 1.28-1.34 (m, 2H), 1.19-1.12 (m, 2H). |
| 12 | 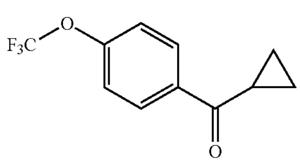 [SMILES: O=C(c1ccc(OC(F)(F)F)cc1)C1CC1] | cyclopropyl(4-(trifluoromethoxy)phenyl)methanone | ¹H NMR (300 MHz, CDCl₃) δ: 8.07 (d, J = 8.1 Hz, 2H), 7.30 (d, J = 8.1 Hz, 2H), 2.68-2.59 (m, 1H), 1.29-1.24 (m, 2H), 1.15-1.06 (m, 2H). |
| 13 | 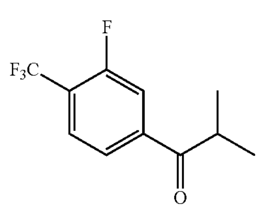 [SMILES: CC(C)C(=O)c1ccc(C(F)(F)F)c(F)c1] | 1-(3-fluoro-4-(trifluoromethyl)phenyl)-2-methylpropan-1-one | ¹H NMR (300 MHz, CDCl₃) δ: 7.82-7.70 (m, 3H), 3.55-3.42 (m, 1H), 1.24 (d, J = 6.6 Hz, 6H). |
| 14 | 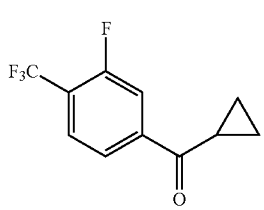 [SMILES: O=C(c1ccc(C(F)(F)F)c(F)c1)C1CC1] | cyclopropyl(3-fluoro-4-(trifluoromethyl)phenyl)methanone | ¹H NMR (400 MHz, CDCl₃) δ: 7.90 (d, J = 8.0 Hz, 1H), 7.82 (d, J = 10.8 Hz, 1H), 7.78-7.74 (m, 1H), 2.67-2.60 (m, 1H), 1.35-1.29 (m, 2H), 1.19-1.12 (m, 2H). |

TABLE 3-continued

The following compounds were prepared using procedures similar to those described in Preparatory Example 7 using appropriate starting materials.

| Prep Ex No. | Structure | IUPAC Name | GCMS or $^1$H NMR |
|---|---|---|---|
| 15 | ![structure] | 1-(3-fluoro-4-(trifluoromethoxy)phenyl)-2-methylpropan-1-one | $^1$H NMR (400 MHz, CDCl$_3$) δ: 7.84-7.78 (m, 2H), 7.45-7.41 (m, 1H), 3.53-3.46 (m, 1H), 1.25 (d, J = 6.8 Hz, 6H). |

PREPARATORY EXAMPLE 16

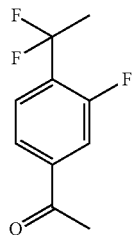

1-(4-(1,1-Difluoroethyl)-3-fluorophenyl)ethanone (Scheme 4)

Step 1. 4-Bromo-1-(1,1-difluoroethyl)-2-fluorobenzene 1-(4-Bromo-2-fluorophenyl)ethanone (1.00 g, 4.6 mmol) was added in portions to bis-(2-methoxyethyl)amino sulfur trifluoride (BAST) (17.0 mL, 92.0 mmol) at 0° C. with stirring. The resulting mixture was heated to 50° C. stirred for 16 h at 50° C. The reaction mixture was cooled to room temperature, quenched with water (40 mL), and extracted with DCM (3×35 mL). The combined organic layers were washed with brine (35 mL), dried over sodium sulfate, filtered, and concentrated under vacuum. The residue was purified by silica gel column chromatography (100% petroleum ether) to afford the title compound as an oil. MS=237.8, 239.8 (+EI).

Step 2. 1-(4-(1,1-Difluoroethyl)-3-fluorophenyl)ethanone To a solution of 4-bromo-1-(1,1-difluoroethyl)-2-fluorobenzene (0.90 g, 3.8 mmol) in toluene (3 mL) was added tributyl(1-ethoxyvinyl)stannane (1.63 g, 4.5 mmol) and Pd(PPh$_3$)$_2$Cl$_2$ (0.26 g, 0.4 mmol) at room temperature. The mixture was purged with nitrogen 3 times and was heated to 120° C. and stirred for 3 h. The mixture was cooled to RT and filtered thru a pad of Celite™ washing the filter cake with ethyl acetate (20 mL). The resulting organic layer was diluted with a sat. aq. KF solution (30 mL) and the layers were separated. The aqueous layer was extracted with ethyl acetate (3×10 mL) and the organic layers were combined. The organic layer was dried over Na$_2$SO$_4$, filtered, and concentrated under vacuum. The residue was dissolved in THF (10 mL) and a 6 M aq. HCl solution (10 mL) was added dropwise at RT. The reaction solution was stirred at RT for 1 h whereupon water (20 mL) was added and the mixture was extracted with ethyl acetate (3×50 mL). The combined organic layers were dried over anhydrous Na$_2$SO$_4$, filtered, and concentrated under vacuum to afford the title compound as an oil which was used in the next step without purification. MS=201.9 (+EI).

TABLE 4

The following compounds were prepared using procedures similar to those described in Preparatory Example 16 using appropriate starting materials.

| Prep Ex No. | Structure | IUPAC Name | GC-MS (+EI) |
|---|---|---|---|
| 17 | ![structure] | 1-(4-(1,1-difluoro-ethyl)-2-fluorophenyl)ethanone | 203.0 |
| 18 | ![structure] | 1-(4-(1,1-difluoroethyl)phenyl)ethanone | 184.0 |

PREPARATORY EXAMPLE 19

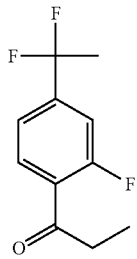

1-(4-(1,1-Difluoroethyl)-2-fluorophenyl)propan-1-one (Scheme 5)

Step 1. 4-Bromo-2-fluorobenzoyl chloride The title compound was prepared using procedures similar to those described in step 1 of Preparatory Example 1 using 4-bromo-2-fluorobenzoic acid and oxalyl chloride to afford an oil which was used in the next step directly without purification.

Step 2. 4-Bromo-2-fluoro-N-methoxy-N-methylbenzamide The title compound was prepared using procedures similar to those described in step 2 of Preparatory Example 1 using 4-bromo-2-fluorobenzoyl chloride to afford an oil. MS=262.1, 264.0 (+ESI).

Step 3. 4-Acetyl-2-fluoro-N-methoxy-N-methylbenzamide Diacetoxypalladium (0.017 g, 0.08 mmol), 1,3-bis(diphenylphosphino)propane (0.063 g, 0.15 mmol), 1-(vinyloxy)butane (2.29 g, 23 mmol) and triethylamine (2.6 mL, 19.1 mmol) were added to a solution of 4-bromo-2-fluoro-N-methoxy-N-methylbenzamide (2.0 g, 7.6 mmol) in ethylene glycol (8 mL) at RT. The mixture was purged with nitrogen three times and was heated to 145° C. and stirred for 3 h under nitrogen. The mixture was cooled to RT, diluted with brine (50 mL), and extracted with DCM (3×50 mL). The combined organic layers were dried over $Na_2SO_4$, filtered, and concentrated under vacuum. The residue was dissolved in THF (2 mL) at RT whereupon a 6 M aqueous solution of HCl (2 mL) was added and the mixture was stirred for 2 h. The resulting mixture was diluted with brine (50 mL) and extracted with DCM (3×50 mL). The combined organic layers were dried over $Na_2SO_4$, filtered, and concentrated under reduced pressure. The residue was purified by silica gel column chromatography (5% of ethyl acetate in petroleum ether) to afford the title compound as an oil. MS=226.0 (+ESI).

Step 4. 4-(1,1-Difluoroethyl)-2-fluoro-N-methoxy-N-methylbenzamide The title compound was prepared using procedures similar to those described in step 1 of Preparatory Example 16 using 4-acetyl-2-fluoro-N-methoxy-N-methylbenzamide to afford an oil. MS=248.0 (+ESI).

Step 5. 1-(4-(1,1-Difluoroethyl)-2-fluorophenyl)propan-1-one The title compound was prepared using procedures similar to those described in step 5 of Preparatory Example 1 using 4-(1,1-difluoroethyl)-2-fluoro-N-methoxy-N-methylbenzamide and EtMgBr to afford an oil. MS=216.0 (+EI).

PREPARATORY EXAMPLE 20

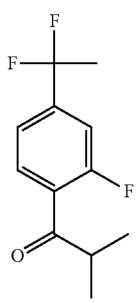

1-(4-(1,1-Difluoroethenyl)-2-fluorophenyl)-2-methylpropan-1-one (Scheme 5)

The title compound was prepared using procedures similar to those described in step 5 of Preparatory Example 1 using 4-(1,1-difluoroethyl)-2-fluoro-N-methoxy-N-methylbenzamide and isopropylmagnesium bromide to afford an oil. $^1$H NMR (400 MHz, CDCl$_3$) δ: 7.41-7.28 (m, 3H), 3.42-3.36 (m, 1H), 1.93 (t, J=19.2 Hz, 3H), 1.22 (d, J=7.2 Hz, 6H).

PREPARATORY EXAMPLE 21

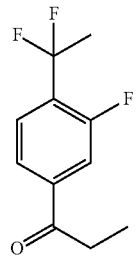

1-(4-(1,1-Difluoroethyl)-3-fluorophenyl)propan-1-one (Scheme 6)

Step 1. Methyl 4-(1,1-difluoroethyl)-3-fluorobenzoate The title compound was prepared using procedures similar to those described in step 1 of Preparatory Example 14 using methyl 4-acetyl-3-fluorobenzoate to afford an oil. $^1$H NMR (400 MHz, CDCl$_3$) δ: 7.89 (d, J=8.4 Hz, 1H), 7.80 (d, J=10.8 Hz, 1H). 7.67-7.43 (m, 1H), 3.97 (s, 3H), 2.03 (td, J=18.4 Hz, 0.8 Hz, 3H).

Step 2. 4-(1,1-Difluoroethyl)-3-fluorobenzoic acid The title compound was prepared using procedures similar to those described in step 3 of Example 4 using methyl 4-(1,1-difluoroethyl)-3-fluorobenzoate to afford an oil. MS=202.9 (−ESI).

Step 3. 4-(1,1-Difluoroethyl)-3-fluoro-N-methoxy-N-methylbenzamide The title compound was prepared using procedures similar to those described in step 1 to step 2 of Preparatory Example 1 using 4-(1,1-difluoroethyl)-3-fluorobenzoic acid to afford an oil. MS=248.0 (+ESI).

Step 4. 1-(4-(1,1-Difluoroethyl)-3-fluorophenyl)propan-1-one The title compound was prepared using procedures similar to those described in step 5 of Preparatory Example 1 using 4-(1,1-difluoroethyl)-3-fluoro-N-methoxy-N-methylbenzamide and ethyl magnesium bromide to afford an oil. MS=216.0 (+EI).

TABLE 5

The following compounds were prepared using procedures similar to those described in Preparatory Examples 20 and 21 using appropriate starting materials.

| Prep Ex No. | Structure | IUPAC Name | GCMS or $^1$H NMR |
|---|---|---|---|
| 22 | 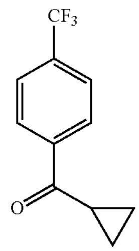 [SMILES: O=C(c1ccc(C(F)(F)F)cc1)C1CC1] | cyclopropyl(4-(difluoromethyl)phenyl)methanone | $^1$H NMR (400 MHz, DMSO-d$_6$) δ: 8 17 (d, J = 8.0 Hz, 2H), 7.54 (d, J = 8.0 Hz, 2H), 7.15 (t, J = 55.6 Hz, 1H), 2.94-2.91 (m, 1H), 1.30-1.20 (m, 2H), 1.11-1.02 (m, 2H). |
| 23 | 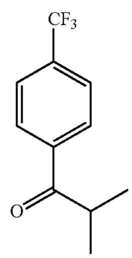 | 1-(4-(difluoromethyl)phenyl)-2-methylpropan-1-one | $^1$H NMR (400 MHz, DMSO-d$_6$) δ: 8.09 (d, J = 8.4 Hz, 2H), 7.73 (d, J = 8.4 Hz, 2H), 7.13 (t, J = 55.6 Hz, 1H), 3.73-3.64 (m, 1H), 1.11 (d, J = 7.2 Hz, 6H). |
| 24 | 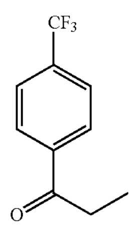 | 1-(4-(difluoromethyl)phenyl)propan-1-one | $^1$H NMR (300 MHz, DMSO-d$_6$) δ: 8.09 (d J = 8.4 Hz, 2H), 7.72 (d, J = 8.4 Hz, 2H), 7.13 (t, J = 55.6 Hz, 1H), 3.09 (q, J = 7.2 Hz, 2H), 1.10 (t, J = 7.2 Hz, 3H). |
| 25 | 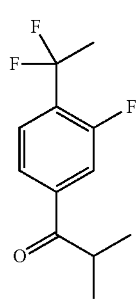 | 1-(4-(1,1-difluoroethyl)-3-fluorophenyl)-2-methylpropan-1-one | MS (+EI) m/z = 230.1. |

PREPARATORY EXAMPLE 26

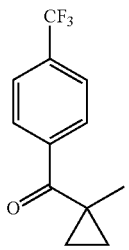 [SMILES: CC1(C(=O)c2ccc(C(F)(F)F)cc2)CC1]

(1-Methylcyclopropyl)(4-(trifluoromethyl)phenyl)
methanone (Scheme 7)

(1-Methylcyclopropyl)(4-(trifluoromethyl)phenyl)methanone To a solution of 1-bromo-4-(trifluoromethyl)benzene (2.0 g, 8.9 mmol) in THF (40 mL) was added n-butyllithium (2.5 M in hexanes, 4.3 mL, 10.7 mmol) at −78° C. under $N_2$. The solution was stirred for 1 h at −78° C. whereupon N, O-dimethyl-N-(1-methylcyclopropyl)hydroxylamine (1.23 g, 10.7 mmol) was added to the solution at −78° C. The solution was stirred an addition 1 h at −78° C., then the reaction mixture was treated with sat. aq. $NH_4Cl$ (50 mL). The mixture was warmed to RT and was extracted with DCM (3×50 mL). The combined organic layers were dried over anhydrous sodium sulfate, filtered, and concentrated under vacuum. The residue was purified by silica gel chromatography (0-20% ethyl acetate in petroleum ether) to afford the title compound as an oil. $^1$H NMR (400 MHz, $CDCl_3$) δ: 7.86 (d, J=8.0 Hz, 2H), 7.72 (d, J=8.0 Hz, 2H), 1.45 (s, 3H), 1.37-1.33 (m, 2H), 0.91-0.83 (m, 2H).

PREPARATORY EXAMPLE 27

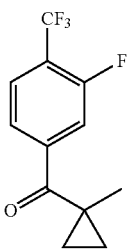

(3-Fluoro-4-(trifluoromethyl)phenyl)(1-methylcyclopropyl)methanone (Scheme 7)

To a solution of 4-bromo-2-fluoro-1-(trifluoromethyl)benzene (0.34 g, 1.4 mmol) in THF (5 mL) at −78° C. under $N_2$ was added a solution of isopropylmagnesium bromide (3 M in THF, 0.48 mL, 1.4 mmol) dropwise. The mixture was stirred for 1 h at −78° C., then a solution of N-methoxy-N, 1-dimethylcyclopropanecarboxamide (0.20 g, 1.4 mmol) in THF (2 mL) was added dropwise. The reaction mixture was warmed to room temperature gradually and was stirred for an additional 16 h. Sat. aq. $NH_4Cl$ (5 mL) was added to the mixture which was extracted then with EtOAc (3×5 mL). The combined organic layers were dried over sodium sulfate, filtered, and concentrated under vacuum. The residue was purified by silica gel column chromatography (0-10% ethyl acetate in petroleum ether) to afford the title compound as an oil. MS=246.0 (+EI).

PREPARATORY EXAMPLE 28

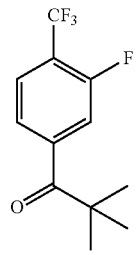 [SMILES: CC(C)(C)C(=O)c1ccc(C(F)(F)F)c(F)c1]

1-(3-Fluoro-4-(trifluoromethyl)phenyl)-2,2-dimethylpropan-1-one (Scheme 8)

Step 1. 1-(3-Fluoro-4-(trifluoromethyl)phenyl)-2,2-dimethylpropan-1-ol To a solution of 3-fluoro-4-(trifluoromethyl)benzaldehyde (2.00 g, 10.4 mmol) in THF (5 mL) at −70° C. under $N_2$ was added a solution of tert-butylmagnesium chloride (1 M in THF, 20.8 mL, 20.8 mmol) dropwise. The reaction solution was warmed to room temperature gradually and was stirred for additional 16 h. Water (10 mL) was added to the mixture which was extracted with ethyl acetate (3×10 mL). The combined organic layers were dried over anhydrous sodium sulfate, filtered, and concentrated under vacuum. The residue was purified by silica gel column chromatography (10% EtOAc in petroleum ether) to afford the title compound as an oil. $^1$H NMR (400 MHz, $CDCl_3$) δ: 7.60-7.50 (m, 1H), 7.21-7.13 (m, 2H), 4.46 (s, 1H), 0.95 (s, 9H).

Step 2. 1-(3-Fluoro-4-(trifluoromethyl)phenyl)-2,2-dimethylpropan-1-one

To a solution of dimethyl sulfoxide (1.70 mL, 24.0 mmol) in DCM (20 mL) at −78° C. under $N_2$ was added oxalyl chloride (1.0 mL, 12.0 mmol) dropwise. The solution was stirred for 30 min at −78° C. whereupon a solution of 1-(3-fluoro-4-(trifluoromethyl)phenyl)-2,2-dimethylpropan-1-ol (1.50 g, 6.0 mmol) in DCM (5 mL) was added dropwise. The resulting solution was stirred for 40 min at −78° C., quenched with triethyl amine (6.7 mL, 48.0 mmol), and warmed to RT. The mixture was extracted with DCM (3×30 mL) and the combined organic layers were dried over sodium sulfate, filtered, and concentrated under vacuum. The residue was purified by silica gel column chromatography (0-20% ethyl acetate in petroleum ether) to afford the title compound as an oil. $^1$H NMR (400 MHz, $CDCl_3$) δ: 7.70-7.66 (m, 1H), 7.52-7.45 (m, 2H), 1.36 (s, 9H).

TABLE 6

The following ketones were prepared using the literature procedures listed in the table using the appropriate starting materials.

| Prep Ex No. | Structure | IUPAC Name | Literature |
|---|---|---|---|
| 29 | 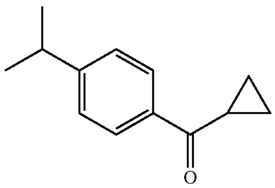 | cyclopropyl(4-isopropylphenyl)methanone | WO2006/2762 A2, 2006 |
| 30 | 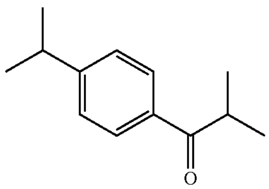 | 1-(4-isopropylphenyl)-2-methylpropan-1-one | Can. J. Chem., 1980, 58, 1198. |
| 31 | 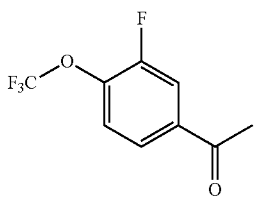 | 1-(3-fluoro-4-(trifluoromethoxy)phenyl)ethan-1-one | US2014/329796A1, 2014 |
| 32 | 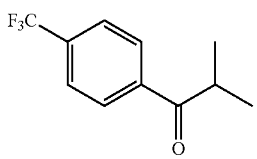 | 2-methyl-1-(4-(trifluoromethyl)phenyl)propan-1-one | Org. Lett. 2008, 10, 2067. |
| 33 | 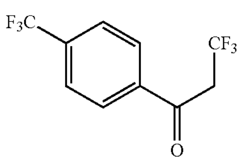 [SMILES: O=C(CC(F)(F)F)c1ccc(C(F)(F)F)cc1] | 3,3,3-trifluoro-1-(4-(trifluoromethyl)phenyl)propan-1-one | J. Org. Chem. 2014, 79, 5145. |
| 34 | 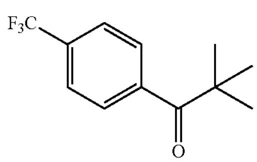 [SMILES: CC(C)(C)C(=O)c1ccc(C(F)(F)F)cc1] | 2,2-dimethyl-1-(4-(trifluoromethyl)phenyl)propan-1-one | Tetrahedron 2012, 68, 6557. |
| 35 | 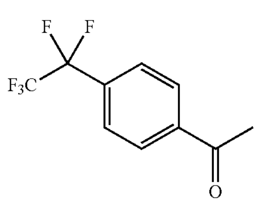 [SMILES: CC(=O)c1ccc(C(F)(F)C(F)(F)F)cc1] | 1-(4-(perfluoroethyl)phenyl)ethan-1-one | J. Am. Chem. Soc. 2013, 135, 12584. |
| 36 | 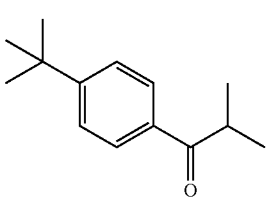 | 1-(4-(tert-butyl)phenyl)-2-methylpropan-1-one | Chem. Comm. 2012, 48, 7034. |

TABLE 6-continued

The following ketones were prepared using the literature procedures listed in the table using the appropriate starting materials.

| Prep Ex No. | Structure | IUPAC Name | Literature |
|---|---|---|---|
| 37 | 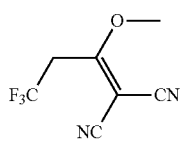 | 1-(4-(2,2,2-trifluoroethyl)phenyl)ethan-1-one | *J. Org. Chem.* 1997, 62, 7758. |

PREPARATORY EXAMPLE 38

2-(3,3,3-Trifluoro-1-methoxypropylidene)malononitrile (Scheme 9)

Step 1. 2-(3,3,3-Trifluoropropanoyl)malononitrile A solution of malononitrile (0.43 mL, 6.8 mmol) in THF (6 mL) was added over 1 h to a mixture of 60% sodium hydride (0.55 g, 13.6 mmol) in THF (7 mL) at 0° C. The mixture was stirred at 0° C. for 2 h whereupon 3,3,3-trifluoropropanoyl chloride (0.70 mL, 6.8 mmol) was added over 20 min. The mixture was warmed to RT and was stirred for 20 h. Water (10 mL) was added to the mixture and the pH value of the resulting mixture was adjusted to ~3 with 3M aqueous HCl (10 mL). The mixture was extracted with ethyl acetate (3×40 mL) and the combined organic layers were washed with water (2×50 mL) and brine (1×50 mL). The organic layer was dried over sodium sulfate, filtered, and concentrated under vacuum. The title compound was obtained as an oil and was used in the next step without purification. $^1$H NMR (300 MHz, DMSO-$d_6$) δ: 3.22 (q, J=8.4 Hz, 2H).

Step 2. 2-(3,3,3-Trifluoro-1-methoxypropylidene)malononitrile To a mixture of 2-(3,3,3-trifluoropropanoyl)malononitrile (1.0 g, 5.7 mmol) in trimethoxymethane (11.2 mL, 102 mmol) was added 4-methylbenzenesulfonic acid (0.49 g, 2.84 mmol) at RT. The mixture was heated to 110° C., stirred for 16 h, and was recooled to RT. The mixture was concentrated under reduced pressure and the resulting residue was purified by silica gel column chromatography (0-20% ethyl acetate in petroleum ether) as eluent to afford the title compound as a solid. $^1$H NMR (300 MHz, CDCl$_3$) δ: 4.35 (s, 3H), 3.47 (q, J=9.3 Hz, 2H).

TABLE 7

The following alkylidenes were prepared using the literature procedures listed in the table using the appropriate starting materials.

| Prep Ex No. | Structure | IUPAC Name | Literature |
|---|---|---|---|
| 39 | | 2-(2-(benzyloxy)-1-methoxyethylidene)malononitrile | WO2009/62118 A2, 2009 |
| 40 | 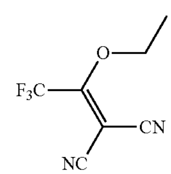 | 2-(1-ethoxy-2,2,2-trifloroethylidene)malononitrile | U.S. Pat. No. 5,294,612 A1, 1994 |
| 41 | 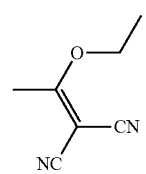 | 2-(1-ethoxyethylidene)malononitrile | *Tetrahedron* 2006, 62, 6222. |

PREPARATORY EXAMPLE 42

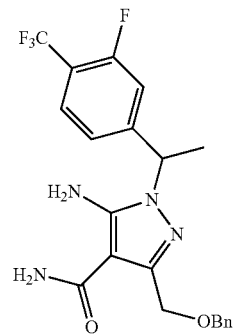 [SMILES: CC(c1ccc(C(F)(F)F)c(F)c1)n1nc(COCc2ccccc2)c(C(N)=O)c1N]

5-Amino-3-(benzyloxymethyl)-1-(1-(3-fluoro-4-(trifluoromethyl)phenyl)ethyl)-1H-pyrazole-4-carboxamide (Scheme 10)

Step 1. tert-Butyl 2-(1-(3-fluoro-4-(trifluoromethyl)phenyl)ethylidene)hydrazinecarboxylate tert-Butyl hydrazinecarboxylate (0.71 g, 5.3 mmol) and 1-(3-fluoro-4-(trifluoromethyl)phenyl)ethanone (1.10 g, 5.34 mmol) were dissolved in THF (2 mL) and heptane (6 mL). The resulting mixture was heated to 75° C., stirred 16 h, and was cooled to RT. The mixture was concentrated under reduced pressure to afford the title compound as a solid which was used in the next step directly without purification. $^1$H NMR (400 MHz, CDCl$_3$) δ: 7.81-7.79 (br s, 1H), 7.71-7.57 (m, 3H), 2.21 (s, 3H), 1.58 (s, 9H).

Step 2. tert-Butyl 2-(1-(3-fluoro-4-(trifluoromethyl)phenyl)ethyl)hydrazinecarboxylate To a solution of tert-butyl-2-(1-(3-fluoro-4-(trifluoromethyl)phenyl)ethylidene)hydrazine-carboxylate (1.7 g, 5.31 mmol) in MeOH (6 mL) and acetic acid (6 mL) at 0° C. under N$_2$ was added sodium cyanoborohydride (0.33 g, 5.3 mmol) portionwise. The resulting solution was slowly warmed to room temperature, stirred for 2 h, and was concentrated under reduced pressure. The residue was partitioned between sat. aq. sodium bicarbonate (10 mL) and dichloromethane (10 mL) and the layers were separated. The aqueous layer was extracted with dichloromethane (10 mL) and the organic layers were combined. The organic layer was dried over sodium sulfate, filtered, and concentrated under reduced pressure to afford the title compound as a solid which was used in the next step directly without purification. $^1$H NMR (300 MHz, CDCl$_3$) δ: 7.61-7.51 (m, 1H), 7.28-7.19 (m, 2H), 4.32-4.20 (m, 1H), 1.44 (s, 9H), 1.32 (d, J=6.6 Hz, 3H).

Step 3. (1-(3-Fluoro-4-(trifluoromethyl)phenyl)ethyl)hydrazine dihydrochloride To a solution of tert-butyl 2-(1-(3-fluoro-4-(trifluoromethyl)phenyl)ethyl)hydrazine-carboxylate (1.7 g, 5.3 mmol) in dichloromethane (20 mL) at 0° C. was added a saturated solution of hydrogen chloride (20 mL, 5.3 mmol) in ethyl acetate. The solution was slowly warmed to room temperature, stirred for additional 16 h at RT, and concentrated under reduced pressure. The title compound was obtained as a solid which was used in the next step directly without purification. $^1$H NMR (300 MHz, CDCl$_3$) δ: 7.88-7.78 (m, 1H), 7.60-7.50 (m, 1H), 7.48-7.39 (m, 1H), 4.31-4.27 (m, 1H), 1.34 (d, J=6.3 Hz, 3H).

Step 4. 5-Amino-3-((benzyloxy)methyl)-1-(1-(3-fluoro-4-(trifluoromethyl)phenyl)ethyl)-1H-pyrazole-4-carbonitrile To a solution of (1-(3-fluoro-4-(trifluoromethyl)phenyl)ethyl)hydrazine dihydrochloride (0.52 g, 1.78 mmol) in ethanol (15 mL) at 0° C. was added a solution of 2-(2-(benzyloxy)-1-methoxy-ethylidene)malononitrile (0.40 g, 1.8 mmol) in ethanol (4 mL) dropwise. A sodium methoxide solution (30% in methanol, 0.7 mL, 3.7 mmol) was added to the mixture which was warmed to RT and stirred for 16 h. The mixture was concentrated under reduced pressure and the residue was partitioned between ethyl acetate (10 mL) and sat. aq. sodium bicarbonate (5 mL). The layers were separated and the aqueous layer was extracted with ethyl acetate (3×5 mL). The organic layers were combined, dried over anhydrous sodium sulfate, filtered, and concentrated under reduced pressure. The residue was purified by silica gel column chromatography (0-50% ethyl acetate in petroleum ether) to afford the title compound as an oil. $^1$H NMR (300 MHz, CDCl$_3$) δ: 7.63-7.55 (m, 1H), 7.46-7.27 (m, 5H), 7.09-7.01 (m, 2H), 5.22 (q, J=7.2 Hz, 1H), 4.64 (s, 2H), 4.54 (s, 2H), 1.88 (d, J=6.9 Hz, 3H).

Step 5. 5-Amino-3-((benzyloxy)methyl)-1-(1-(3-fluoro-4-(trifluoromethyl)phenyl)ethyl)-1H-pyrazole-4-carboxamide To a solution of 5-amino-3-((benzyloxy)methyl)-1-(1-(3-fluoro-4-(trifluoromethyl)phenyl)ethyl)-1H-pyrazole-4-carbonitrile (0.37 g, 0.9 mmol) in methanol (8 mL) at 0° C. were added 2 M sodium hydroxide (0.5 mL, 0.9 mmol) followed by 30% hydrogen peroxide (0.36 mL, 3.6 mmol). The solution was warmed to room temperature and stirred for 16 h. The residue was partitioned between water (5 mL) and ethyl acetate (10 mL) and the layers were separated. The aqueous layer was extracted with ethyl acetate (5 mL). The organic layers were combined, dried over sodium sulfate, filtered, and concentrated under vacuum. The title compound was obtained as a solid which was used in the next step directly without purification. MS=437.1 (+ESI).

TABLE 8

The following compounds were prepared using procedures similar to those described in Preparatory Example 42 using appropriate starting materials.

| Prep Ex No. | Structure | IUPAC Name | Exact Mass [M + H]$^+$ |
|---|---|---|---|
| 43 | F$_3$CO, F, H$_2$N, H$_2$N, O, OBn | 5-amino-3-(benzyloxymethyl)-1-(1-(3-fluoro-4-(trifluoromethoxy)phenyl)ethyl)-1H-pyrazole-4-carboxamide | Calc'd 453.1, found 453.2 |

TABLE 8-continued

The following compounds were prepared using procedures similar to those described in Preparatory Example 42 using appropriate starting materials.

| Prep Ex No. | Structure | IUPAC Name | Exact Mass [M + H]+ |
|---|---|---|---|
| 44 | 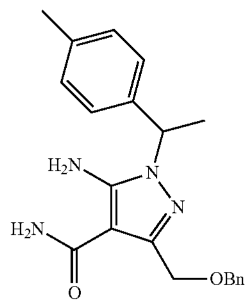 [SMILES: Cc1ccc(C(C)n2nc(COCc3ccccc3)c(C(N)=O)c2N)cc1] | 5-amino-3-(benzyloxymethyl)-1-(1-p-tolylethyl)-1H-pyrazole-4-carboxamide | Calc'd 365.2, found 365.3 |
| 45 | 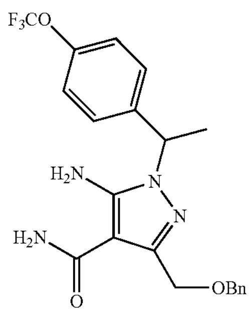 [SMILES: CC(c1ccc(OC(F)(F)F)cc1)n1nc(COCc2ccccc2)c(C(N)=O)c1N] | 5-amino-3-(benzyloxymethyl)-1-(1-(4-(trifluoromethoxy)phenyl)ethyl)-1H-pyrazole-4-carboxamide | Calc'd 435.2, found 435.1 |
| 46 | 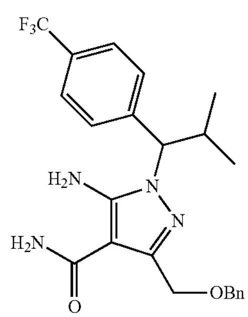 [SMILES: CC(C)C(c1ccc(C(F)(F)F)cc1)n1nc(COCc2ccccc2)c(C(N)=O)c1N] | 5-amino-3-(benzyloxymethyl)-1-(2-methyl-1-(4-(trifluoromethyl)phenyl)propyl)-1H-pyrazole-4-carboxamide | Calc'd 447.2, found 447.4 |
| 47 | 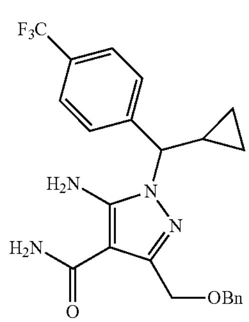 [SMILES: NC(=O)c1c(COCc2ccccc2)nn(C(c2ccc(C(F)(F)F)cc2)C2CC2)c1N] | 5-amino-3-(benzyloxymethyl)-1-(cyclopropyl(4-(trifluoromethyl)phenyl)methyl)-1H-pyrazole-4-carboxamide | Calc'd 445.2, found 445.2 |

TABLE 8-continued

The following compounds were prepared using procedures similar to those described in Preparatory Example 42 using appropriate starting materials.

| Prep Ex No. | Structure | IUPAC Name | Exact Mass [M + H]+ |
|---|---|---|---|
| 48 | 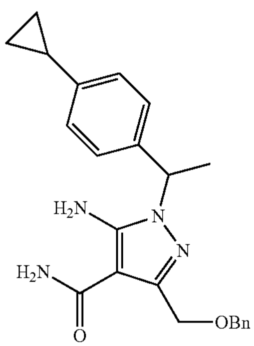 [SMILES: CC(c1ccc(C2CC2)cc1)n1nc(COCc2ccccc2)c(C(N)=O)c1N] | 5-amino-3-(benzyloxymethyl)-1-(1-(4-cyclopropylphenyl)ethyl)-1H-pyrazole-4-carboxamide | Calc'd 391.2, found 391.3 |
| 49 | 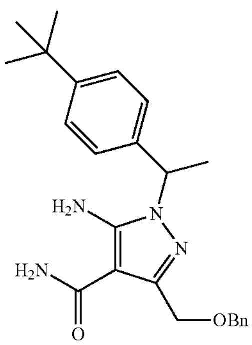 [SMILES: CC(c1ccc(C(C)(C)C)cc1)n1nc(COCc2ccccc2)c(C(N)=O)c1N] | 5-amino-3-(benzyloxymethyl)-1-(1-(4-tert-butylphenyl)ethyl)-1H-pyrazole-4-carboxamide | Calc'd 407.2, found 407.2 |
| 50 | 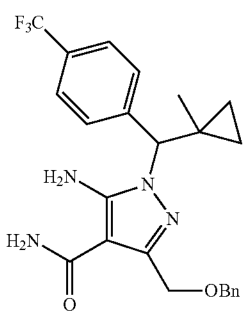 [SMILES: CC1(C(c2ccc(C(F)(F)F)cc2)n2nc(COCc3ccccc3)c(C(N)=O)c2N)CC1] | 5-amino-3-(benzyloxymethyl)-1-((1-methylcyclopropyl)(4-(trifluoromethyl)phenyl)methyl)-1H-pyrazole-4-carboxamide | Calc'd 459.1, found 459.2 |
| 51 | 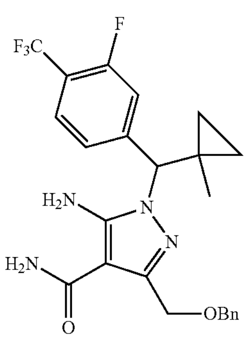 [SMILES: CC1(C(c2ccc(C(F)(F)F)c(F)c2)n2nc(COCc3ccccc3)c(C(N)=O)c2N)CC1] | 5-amino-3-(benzyloxymethyl)-1-((3-fluoro-4-(trifluoromethyl)phenyl)(1-methylcyclopropyl)methyl)-1H-pyrazole-4-carboxamide | Calc'd 477.2, found 477.4 |

TABLE 8-continued

The following compounds were prepared using procedures similar to those described in Preparatory Example 42 using appropriate starting materials.

| Prep Ex No. | Structure | IUPAC Name | Exact Mass [M + H]+ |
|---|---|---|---|
| 52 | 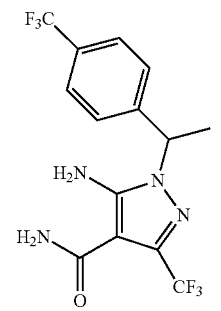 [SMILES: CC(c1ccc(C(F)(F)F)cc1)n1nc(C(F)(F)F)c(C(N)=O)c1N] | 5-amino-3-(trifluoromethyl)-1-(1-(4-(trifluoromethyl)phenyl)ethyl)-1H-pyrazole-4-carboxamide | Calc'd 367.1, found 367.2 |
| 53 | 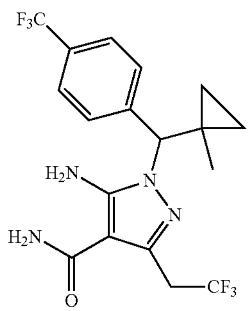 [SMILES: CC1(C(c2ccc(C(F)(F)F)cc2)n2nc(CC(F)(F)F)c(C(N)=O)c2N)CC1] | 5-amino-1-((1-methylcyclopropyl)(4-(trifluoromethyl)phenyl)methyl)-3-(2,2,2-trifluoroethyl)-1H-pyrazole-4-carboxamide | Calc'd 421.2, found 421.1 |
| 54 | 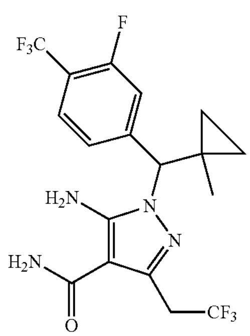 [SMILES: CC1(C(c2ccc(C(F)(F)F)c(F)c2)n2nc(CC(F)(F)F)c(C(N)=O)c2N)CC1] | 5-amino-1-((3-fluoro-4-(trifluoromethyl)phenyl)(1-methylcyclopropyl)methyl)-3-(2,2,2-trifluoroethyl)-1H-pyrazole-4-carboxamide | Calc'd 439.1, found 439.3 |
| 55 | 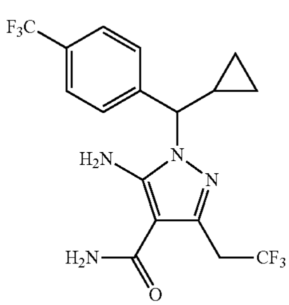 [SMILES: NC(=O)c1c(CC(F)(F)F)nn(C(c2ccc(C(F)(F)F)cc2)C2CC2)c1N] | 5-amino-1-(cyclopropyl(4-(trifluoromethyl)phenyl)methyl)-3-(2,2,2-trifluoroethyl)-1H-pyrazole-4-carboxamide | Calc'd 407.1, found 407.1 |

TABLE 8-continued

The following compounds were prepared using procedures similar to those described in Preparatory Example 42 using appropriate starting materials.

| Prep Ex No. | Structure | IUPAC Name | Exact Mass [M + H]+ |
|---|---|---|---|
| 56 | 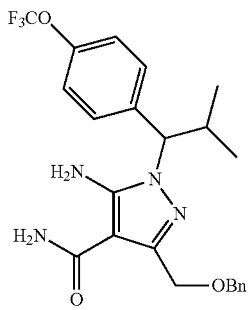 [SMILES: CC(C)C(c1ccc(OC(F)(F)F)cc1)n1nc(COCc2ccccc2)c(C(N)=O)c1N] | 5-amino-3-(benzyloxymethyl)-1-(2-methyl-1-(4-(trifluoromethoxy)phenyl)propyl)-1H-pyrazole-4-carboxamide | Calc'd 463.2, found 463.4 |
| 57 | 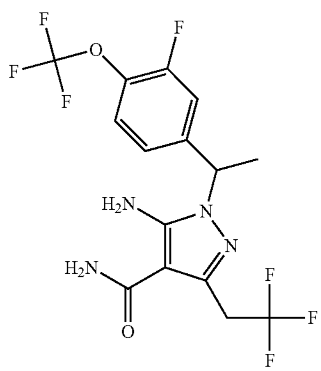 [SMILES: CC(c1ccc(OC(F)(F)F)c(F)c1)n1nc(CC(F)(F)F)c(C(N)=O)c1N] | 5-amino-1-(1-(3-fluoro-4-(trifluoromethoxy)phenyl)ethyl)-3-(2,2,2-trifluoroethyl)-1H-pyrazole-4-carboxamide | Calc'd 415.1, found 415.0 |
| 58 | 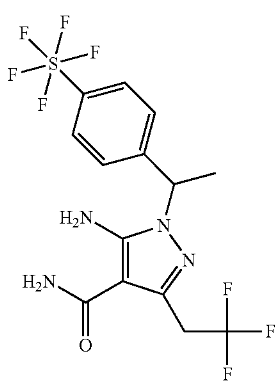 [SMILES: CC(c1ccc(S(F)(F)(F)(F)F)cc1)n1nc(CC(F)(F)F)c(C(N)=O)c1N] | 5-amino-1-(2-methyl-1-(4-(pentafluorothio)phenyl)propyl)-3-(2,2,2-trifluoroethyl)-1H-pyrazole-4-carboxamide | Calc'd 439.1, found 439.1 |
| 59 | 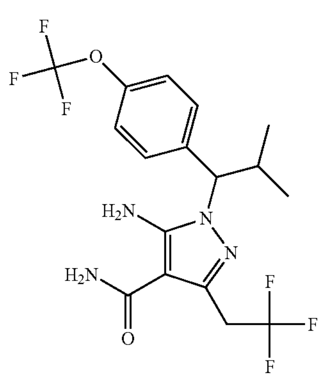 [SMILES: CC(C)C(c1ccc(OC(F)(F)F)cc1)n1nc(CC(F)(F)F)c(C(N)=O)c1N] | 5-amino-1-(2-methyl-1-(4-(trifluoromethoxy)phenyl)propyl)-3-(2,2,2-trifluoroethyl)-1H-pyrazole-4-carboxamide | Calc'd 425.1, found 425.1 |

TABLE 8-continued

The following compounds were prepared using procedures similar to those described in Preparatory Example 42 using appropriate starting materials.

| Prep Ex No. | Structure | IUPAC Name | Exact Mass [M + H]+ |
|---|---|---|---|
| 60 | 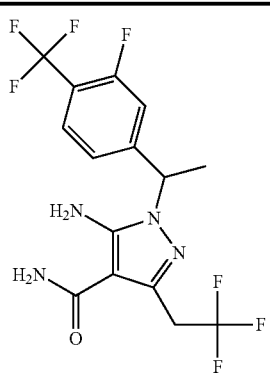 | 5-amino-1-(1-(3-fluoro-4-(trifluoromethyl)phenyl)ethyl)-3-(2,2,2-trifluoroethyl)-1H-pyrazole-4-carboxamide | Calc'd 399.1, found 399.1 |
| 61 | 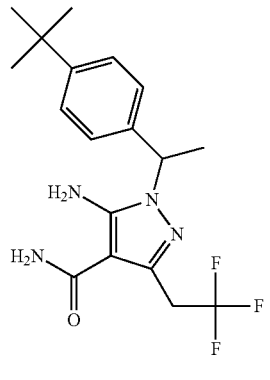 [SMILES: CC(c1ccc(C(C)(C)C)cc1)n1nc(CC(F)(F)F)c(C(N)=O)c1N] | 5-amino-1-(1-(4-tert-butylphenyl)ethyl)-3-(2,2,2-trifluoroethyl)-1H-pyrazole-4-carboxamide | Calc'd 369.2, found 369.2 |
| 62 | 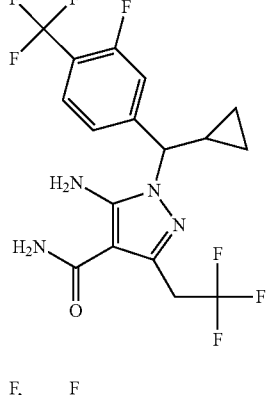 | 5-amino-1-(cyclopropyl(3-fluoro-4-(trifluoromethyl)phenyl)methyl)-3-(2,2,2-trifluoroethyl)-1H-pyrazole-4-carboxamide | Calc'd 425.1, found 425.2 |
| 63 | 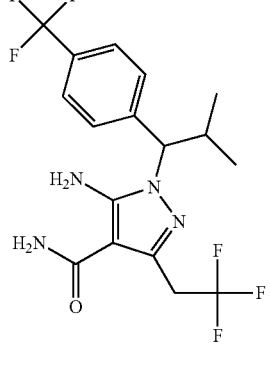 | 5-amino-1-(2-methyl-1-(4-(trifluoromethyl)phenyl)propyl)-3-(2,2,2-trifluoroethyl)-1H-pyrazole-4-carboxamide | Calc'd 409.1, found 409.3 |

TABLE 8-continued

The following compounds were prepared using procedures similar to those described in Preparatory Example 42 using appropriate starting materials.

| Prep Ex No. | Structure | IUPAC Name | Exact Mass [M + H]+ |
|---|---|---|---|
| 64 | 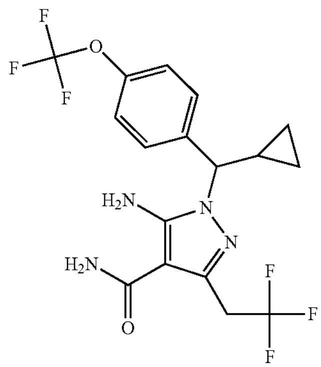 [SMILES: NC(=O)c1c(CC(F)(F)F)nn(C(c2ccc(OC(F)(F)F)cc2)C2CC2)c1N] | 5-amino-1-(cyclopropyl(4-(trifluoromethoxy)phenyl)methyl)-3-(2,2,2-trifluoroethyl)-1H-pyrazole-4-carboxamide | Calc'd 423.1, found 423.1 |
| 65 | 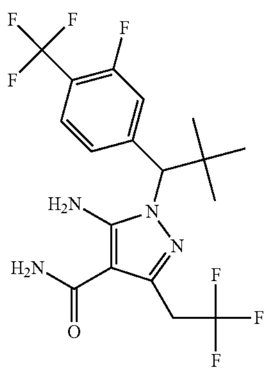 [SMILES: CC(C)(C)C(c1ccc(C(F)(F)F)c(F)c1)n1nc(CC(F)(F)F)c(C(N)=O)c1N] | 5-amino-1-(1-(3-fluoro-4-(trifluoromethyl)phenyl)-2,2-dimethylpropyl)-3-(2,2,2-trifluoroethyl)-1H-pyrazole-4-carboxamide | Calc'd 441.2, found 441.1 |
| 66 | 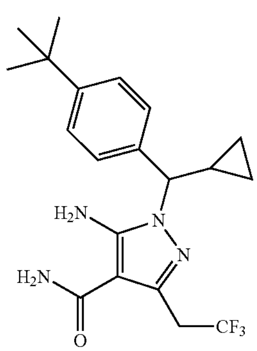 [SMILES: CC(C)(C)c1ccc(C(C2CC2)n2nc(CC(F)(F)F)c(C(N)=O)c2N)cc1] | 5-amino-1-((4-tert-butylphenyl)(cyclopropyl)methyl)-3-(2,2,2-trifluoroethyl)-1H-pyrazole-4-carboxamide | Calc'd 395.2, found 395.2 |
| 67 | 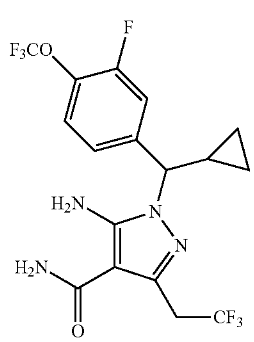 [SMILES: NC(=O)c1c(CC(F)(F)F)nn(C(c2ccc(OC(F)(F)F)c(F)c2)C2CC2)c1N] | 5-amino-1-(cyclopropyl(3-fluoro-4-(trifluoromethoxy)phenyl)methyl)-3-(2,2,2-trifluoroethyl)-1H-pyrazole-4-carboxamide | Calc'd 441.1, found 441.1 |

TABLE 8-continued

The following compounds were prepared using procedures similar to those described in Preparatory Example 42 using appropriate starting materials.

| Prep Ex No. | Structure | IUPAC Name | Exact Mass [M + H]⁺ |
|---|---|---|---|
| 68 | 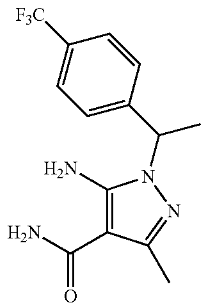 [SMILES: Cc1nn(C(C)c2ccc(C(F)(F)F)cc2)c(N)c1C(N)=O] | 5-amino-3-methyl-1-(1-(4-(trifluoromethyl)phenyl)ethyl)-1H-pyrazole-4-carboxamide | Calc'd 313.1, found 313.3 |
| 69 | 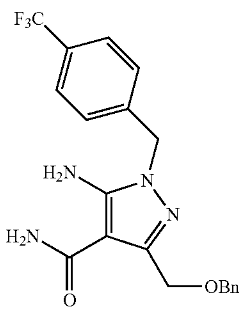 [SMILES: NC(=O)c1c(COCc2ccccc2)nn(Cc2ccc(C(F)(F)F)cc2)c1N] | 5-amino-3-((benzyloxy)methyl)-1-(4-(trifluoromethyl)benzyl)-1H-pyrazole-4-carbonitrile | Calc'd 405.4, found 405.3 |
| 70 | 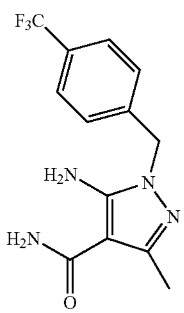 [SMILES: Cc1nn(Cc2ccc(C(F)(F)F)cc2)c(N)c1C(N)=O] | 5-amino-3-methyl-1-(4-(trifluoromethyl)benzyl)-1H-pyrazole-4-carboxamide | Calc'd 299.3, found 299.2 |

PREPARATORY EXAMPLE 71

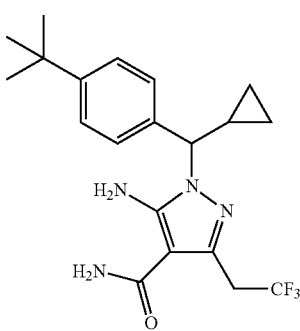 [SMILES: CC(C)(C)c1ccc(C(C2CC2)n2nc(CC(F)(F)F)c(C(N)=O)c2N)cc1]

5-Amino-1-((4-tert-butylphenyl)(cyclopropyl)methyl)-3-(2,2,2-trifluoroethyl)-1H-pyrazole-4-carboxamide (Scheme 11)

Step 1. tert-Butyl 2-((4-(tert-butyl)phenyl)(cyclopropyl)methylene)hydrazinecarboxylate The title compound was prepared using procedures similar to those described in step 1 of Preparatory Example 42 using (4-tert-butylphenyl)(cyclopropyl)methanone (*J. Org. Chem.*, 2007, 72, 144-149) to afford a solid. MS=317.2 (+ESI).

Step 2. tert-Butyl 2-((4-(tert-butyl)phenyl)(cyclopropyl)methyl)hydrazinecarboxylate The title compound was prepared using procedures similar to those described in step 2 of Preparatory Example 42 using tert-butyl2-((4-(tert-butyl)phenyl)(cyclopropyl)methylene)hydrazinecarboxylate to afford a solid. MS=319.2 (+ESI).

Step 3. ((4-tert-Butylphenyl)(cyclopropyl)methyl)hydrazine To a solution of tert-butyl 2-((4-(tert-butyl)phenyl)(cyclopropyl)methyl)hydrazinecarboxylate (100 mg, 0.3 mmol) in 1,1,1,3,3,3-hexafluoropropan-2-ol (52.8 mg, 0.3 mmol) in a microwave tube at room temperature was added 4-methylbenzenesulfonic acid (5.4 mg, 0.03 mmol). The reaction mixture was irradiated with microwave radiation for 40 min at 120° C. whereupon the solution was cooled to RT and concentrated under vacuum. The title compound was obtained as a solid and was used in the next step directly without purification. MS=219.2 (+ESI).

Step 4: 5-Amino-1-((4-(tert-butyl)phenyl)(cyclopropyl)methyl)-3-(2,2,2-trifluoroethyl)-1H-pyrazole-4-carbonitrile The title compound was prepared using procedures similar to those described in step 4 of Preparatory Example 42 using ((4-(tert-butyl)phenyl)(cyclopropyl)methyl)hydrazine to afford a solid. MS=377.1 (+ESI).

Step 5. 5-Amino-1-((4-(tert-butyl)phenyl)(cyclopropyl)methyl)-3-(2,2,2-trifluoroethyl)-1H-pyrazole-4-carboxamide The title compound was prepared using procedures similar to those described in step 5 of Preparatory Example 42 using 5-amino-1-((4-(tert-butyl)phenyl)(cyclopropyl)methyl)-3-(2,2,2-trifluoroethyl)-1H-pyrazole-4-carbonitrile to afford a solid. MS=395.1 (+ESI).

PREPARATORY EXAMPLE 72

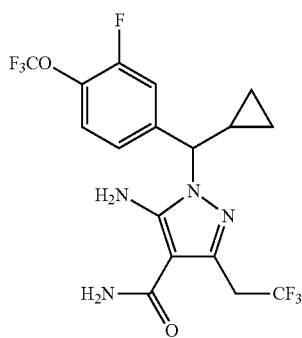 [SMILES: NC(=O)c1c(CC(F)(F)F)nn(C(c2ccc(OC(F)(F)F)c(F)c2)C2CC2)c1N]

5-Amino-1-(cyclopropyl(3-fluoro-4-(trifluoromethoxy)phenyl)methyl)-3-(2,2,2-trifluoroethyl)-1H-pyrazole-4-carboxamide (Scheme 11)

Step 1. tert-Butyl 2-(cyclopropyl(3-fluoro-4-(trifluoromethoxy)phenyl)methyl)-hydrazinecarboxylate The title compound was prepared using procedures similar to those described in steps 1 and 2 of Preparatory Example 42 using cyclopropyl (3-fluoro-4-(trifluoromethoxy)phenyl)methanone from Preparatory Example 11 to afford a solid. $^1$H NMR (300 MHz, CDCl$_3$) δ: 7.32-7.21 (m, 2H), 7.19-7.10 (m, 1H), 6.05 (br, 1H), 3.28-3.26 (m, 1H), 1.45 (s, 9H), 1.04-0.93 (m, 1H), 0.76-0.67 (m, 1H), 0.65-0.55 (m, 1H), 0.49-0.40 (m, 1H), 0.33-0.23 (m, 1H).

Step 2. (Cyclopropyl(3-fluoro-4-(trifluoromethoxy)phenyl)methyl)hydrazine To a solution of tert-butyl 2-(cyclopropyl(3-fluoro-4-(trifluoromethoxy)-phenyl)methyl)hydrazinecarboxylate (0.28 g, 0.8 mmol) in MeCN (8 mL) at RT was added iodotrimethylsilane (0.44 mL, 2.3 mmol). The mixture was stirred for 2 h whereupon sat. aq. sodium bisulfate (10 mL) was added followed by extraction with DCM (3×20 mL). The combined organic layers were washed with brine (3×20 mL), dried over sodium sulfate, filtered, and concentrated under vacuum. The title compound was obtained as a solid which was used in the next step directly without purification. MS=265.1 (+ESI).

Step 3. 5-Amino-1-(cyclopropyl(3-fluoro-4-(trifluoromethoxy)phenyl)methyl)-3-(2,2,2-trifluoroethyl)-1H-pyrazole-4-carbonitrile The title compound was prepared using procedures similar to those described in step 4 of Preparatory Example 42 using (cyclopropyl(3-fluoro-4-(trifluoromethoxy)phenyl)methyl)hydrazine as a solid. MS=423.1 (+ESI).

Step 4. 5-Amino-1-(cyclopropyl(3-fluoro-4-(trifluoromethoxy)phenyl)methyl)-3-(2,2,2-trifluoroethyl)-1H-pyrazole-4-carboxamide The title compound was prepared using procedures similar to those described in step 5 of Preparatory Example 42 using 5-amino-1-(cyclopropyl(3-fluoro-4-(trifluoromethoxy)phenyl)methyl)-3-(2,2,2-trifluoroethyl)-1H-pyrazole-4-carbonitrile as a solid. MS=441.1 (+ESI).

PREPARATORY EXAMPLE 73

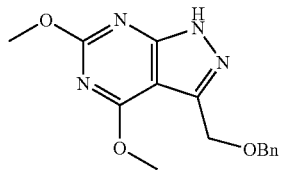 [SMILES: COc1nc(OC)c2c(COCc3ccccc3)n[nH]c2n1]

3-(Benzyloxymethyl)-4,6-dimethoxy-1H-pyrazolo[3,4-d]pyrimidine (Scheme 12)

Step 1. 2-(Benzyloxy)-1-(4-chloro-2,6-dimethoxypyrimidin-5-yl)ethanone To a solution of 4-chloro-2,6-dimethoxypyrimidine (10.0 g, 57.3 mmol) in THF (200 mL) at −20° C. under N$_2$ was added 2,2,6,6-tetramethylpiperidinylmagnesium chloride lithium chloride complex solution (1.5 M in THF, 45.8 mL, 68.7 mmol) dropwise. The reaction mixture was stirred at −20° C. for 2 h whereupon a copper(I) cyanide di(lithium chloride) complex solution (1 M in THF, 63.0 mL, 63.0 mmol) was added dropwise maintaining the temperature at −20° C. The resulting mixture was stirred at −20° C. for 30 min whereupon 2-(benzyloxy)acetyl chloride (21.2 g, 0.115 mol) was added dropwise. The reaction mixture was allowed to gradually warm to room temperature and stir for 16 h. Sat. aq. NH$_4$Cl (20 mL) was added to the mixture, and all the volatiles were removed under vacuum. The residue was diluted with water (200 mL) and extracted with EtOAc (2×200 mL). The combined organic layers were washed with brine (200 mL), dried over Na$_2$SO$_4$, filtered and concentrated under vacuum. The residue was purified by silica gel column chromatography (6% ethyl acetate in petroleum ether) to afford the title compound as an oil. MS=323.0, 325.0 (+ESI).

Step 2. 3-((Benzyloxy)methyl)-4,6-dimethoxy-1H-pyrazolo[3,4-d]pyrimidine To a mixture of 2-(benzyloxy)-1-(4-chloro-2,6-dimethoxypyrimidin-5-yl)ethanone (5.0 g, 15.5 mmol) in EtOH (15 mL) at room temperature was added TEA (2.6 mL, 18.6 mmol) dropwise. Hydrazine hydrate (0.82 mL, 17.0 mmol) was added to the mixture which was stirred for 3 h at RT. Sat. aq. NaHCO$_3$ (50 mL) was added to the reaction mixture which was extracted with EtOAc (2×50 mL). The combined organic layers were washed with water (1×50 mL), dried over Na$_2$SO$_4$, filtered, and concentrated under vacuum. The residue was purified by silica gel column chromatography (70% ethyl acetate in petroleum ether) to afford the title compound as a solid. MS=301.1 (+ESI). $^1$H NMR (300 MHz, DMSO-d$_6$) δ: 13.46 (br, 1H), 7.38-7.25 (m, 5H), 4.67 (s, 2H), 4.56 (s, 2H), 4.03 (s, 3H), 3.93 (s, 3H).

PREPARATORY EXAMPLE 74

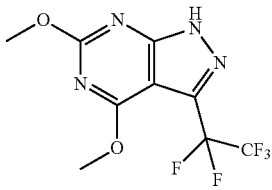 [SMILES: COc1nc(OC)c2c(C(F)(F)C(F)(F)F)n[nH]c2n1]

4,6-Dimethoxy-3-(perfluoroethyl)-1H-pyrazolo[3,4-d]pyrimidine (Scheme 13)

Step 1. 1-(4-Chloro-2,6-dimethoxypyrimidin-5-yl)-2,2,3,3,3-pentafluoropropan-1-one To a stirred solution of 4-chloro-2,6-dimethoxypyrimidine (0.50 g, 2.86 mmol) in THF (30 mL) at −30° C. under N$_2$ was added 2,2,6,6-tetramethylpiperidinylmagnesium chloride lithium chloride complex (1.5 M in THF, 1.4 mL, 2.86 mmol) dropwise. The reaction solution was stirred at −30° C. for 2 h whereupon a copper(I) cyanide di(lithium chloride) complex solution (1 M in THF, 2.86 mL, 2.86 mmol) was added dropwise. The reaction mixture was stirred for an additional 30 min at −30° C. whereupon 2,2,3,3,3-pentafluoropropanoic anhydride (1.78 g, 5.7 mmol) was added. The reaction mixture allowed to gradually warm to RT and was stirred for 16 h. The resulting mixture was quenched with sat. aq. sodium bicarbonate (50 mL), diluted with water (50 mL) and extracted with EtOAc (3×50 mL). The combined organic layers were washed with brine (1×30 mL), dried over Na$_2$SO$_4$, filtered, and concentrated under reduced pressure. The residue was purified by silica gel column chromatography (0-10% ethyl acetate in hexanes) to afford the title compound as an oil. $^1$H NMR (400 MHz, CDCl$_3$) δ: 4.11 (s, 3H), 4.10 (s, 3H).

Step 2. 4,6-Dimethoxy-3-(perfluoroethyl)-1H-pyrazolo[3,4-d]pyrimidine The title compound was prepared using procedures similar to those described in step 2 of Preparatory Example 73 using 1-(4-chloro-2,6-dimethoxypyrimidin-5-yl)-2,2,3,3,3-pentafluoropropan-1-one to afford a solid. MS=299.0 (+ESI).

PREPARATORY EXAMPLE 75

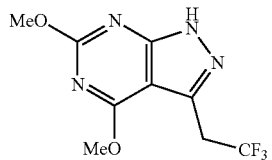

4,6-Dimethoxy-3-(2,2,2-trifluoroethyl)-1H-pyrazolo[3,4-d]pyrimidine (Scheme 14)

Step 1. 3-((Benzyloxy)methyl)-1-(1-(4-(tert-butyl)phenyl)ethyl)-4,6-dimethoxy-1H-pyrazolo[34-d]pyrimidine To a stirred mixture of 1-(4-(tert-butyl)phenyl)ethanol (0.49 g, 2.8 mmol), 3-((benzyloxy)methyl)-4,6-dimethoxy-1H-pyrazolo[3,4-d]pyrimidine (0.55 g, 1.8 mmol) from Preparative Example 73, and PPh$_3$ (1.4 g, 5.5 mmol) in toluene (2 mL) at room temperature was added DIAD (1.1 mL, 5.5 mmol) at room temperature. The reaction mixture was stirred at room temperature for 16 h whereupon the mixture was concentrated under vacuum. The residue was purified by silica gel column chromatography (0-25% ethyl acetate in petroleum ether) to afford the title compound as an oil. MS=461.3 (+ESI).

Step 2. (1-(1-(4-(tert-Butyl)phenyl)ethyl)-4,6-dimethoxy-1H-pyrazolo[3,4-d]pyrimidin-3-yl) methanol To a solution of 3-((benzyloxy)methyl)-1-(1-(4-(tert-butyl)phenyl)ethyl)-4,6-dimethoxy-1H-pyrazolo[3,4-d]pyrimidine (0.75 g, 1.6 mmol) in MeOH (6 mL) under N$_2$ was added 10% Pd/C (1.73 g, 1.63 mmol) in one portion. The resulting mixture was purged with hydrogen three times and stirred for 16 h at RT under a hydrogen balloon. The reaction mixture was purged with N$_2$, filtered thru a pad of Celite™, and the pad was washed with MeOH (3×5 mL). The filtrate was concentrated under vacuum and the residue was purified by silica gel column chromatography (0-50% ethyl acetate in petroleum ether) to afford the title compound as an oil. MS=371.1 (+ESI).

Step 3. 1-(1-(4-(tert-Butyl)phenyl)ethyl)-4,6-dimethoxy-1H-pyrazolo[3,4-d]pyrimidine-3-carbaldehyde To a solution of (1-(1-(4-(tert-butyl)phenyl)ethyl)-4,6-dimethoxy-1H-pyrazolo[3,4-d]pyrimidin-3-yl)methanol (0.18 g, 0.5 mmol) in DCE (5 mL) at rt was added manganese dioxide (0.21 g, 2.4 mmol). The mixture was heated at 50° C., stirred for 2 h, and cooled to room temperature. The mixture was filtered thru pad of Celite™ and the pad was washed with DCM (3×5 mL). The filtrate was concentrated under reduced pressure to afford the title compound as a solid. MS=369.1 (+ESI).

Step 4. 1-(1-(1-(4-(tert-Butyl)phenyl)ethyl)-4,6-dimethoxy-1H-pyrazole[3,4-d]pyrimidin-3-yl)-2,2,2-trifluoroethanol To a solution of 1-(1-(4-(tert-butyl)phenyl)ethyl)-4,6-dimethoxy-1H-pyrazolo[3,4-d]pyrimidine-3-carbaldehyde (0.17 g, 0.46 mmol) in THF (1.5 mL) at RT was added trimethyl(trifluoromethyl)silane (0.12 mL, 0.8 mmol) followed by the addition of a tetrabutylammonium fluoride solution (1.0 M in THF, 9.23 µl, 9.23 µmol). The resulting reaction solution was stirred at room temperature for 3 h whereupon the mixture was diluted with ethyl acetate (30 mL). The organic layer was washed with water (1×5 mL), brine (1×5 mL), dried over sodium sulfate, filtered, and concentrated under vacuum. The title compound was obtained as an oil and was used in the next step directly without purification. MS=439.1 (+ESI).

Step 5. O-(1-(1-(1-(4-(tert-Butyl)phenyl)ethyl)-4,6-dimethoxy-1H-pyrazolo[3,4-d] pyrimidin-3-yl)-2,2,2-trifluoroethyl)O-phenyl carbonothioate To a mixture of 1-(1-(1-(4-(tert-butyl)phenyl)ethyl)-4,6-dimethoxy-1H-pyrazolo[3,4-d]pyrimidin-3-yl)-2,2,2-trifluoroethanol (95 mg, 0.22 mmol) toluene (3 mL) at RT under N$_2$ was added O-phenyl carbonochloridothioate (56 mg, 0.33 mmol) and DMAP (53 mg, 0.433 mmol). The reaction mixture was heated to 55° C., stirred for 4 h, and cooled to room temperature. The mixture was diluted with water (10 mL) and extracted with ethyl acetate (3×10 mL). The combined organic layers were washed with brine (1×10 mL), dried over Na$_2$SO$_4$, filtered, and concentrated under vacuum. The residue was purified by silica gel column chromatography (0-15% ethyl acetate in petroleum ether) to afford the title compound as an oil. MS=575.2 (+ESI).

Step 6. 1-(1-(4-(tert-Buty)phenyl)ethyl)-4,6-dimethoxy-3-(2,2,2-trifluoroethyl)-1H-pyrazolo[3,4-d] pyrimidine To a solution of O-(1-(1-(1-(4-(tert-butyl)phenyl)ethyl)-4,6-dimethoxy-1H-pyrazolo[3,4-d] pyrimidin-3-yl)-2,2,2-trifluoroethyl)O-phenyl carbonothioate (0.350 g, 0.61 mmol) in toluene (8 mL) under N₂ at RT was added tributyltin hydride (0.71 g, 2.44 mmol) and AIBN (60 mg, 0.37 mmol). The mixture was heated to 80° C., stirred for 1.5 h, and cooled to room temperature. Water (20 mL) was added to the mixture was extracted with ethyl acetate (3×15 mL). The combined organic layers were washed with brine (1×15 mL), dried over Na₂SO₄, filtered, and concentrated under vacuum. The residue was purified by silica gel column chromatography (0-15% ethyl acetate in petroleum ether) as eluent to afford the title compound as an oil. MS=423.4 (+ESI).

Step 7. 4,6-Dimethoxy-3-(2,2,2-trifluoroethyl)-1H-pyrazolo[3,4-d]pyrimidine Boron trichloride (1 M in DCM, 9.47 mL, 9.47 mmol) was added into the solution of 1-(1-(4-(tert-butyl)phenyl)ethyl)-4,6-dimethoxy-3-(2,2,2-trifluoroethyl)-1H-pyrazolo[3,4-d]pyrimidine (0.80 g, 1.9 mmol) in DCM (5 mL) at 0° C. The reaction mixture was stirred at 0° C. for 1 h. The resulting mixture was diluted with DCM (30 mL), washed with water (10 mL), brine (10 mL), dried over sodium sulfate, filtered and concentrated. The title compound was obtained as a solid, which was used in the next step directly without further purification. MS=263.1 (+ESI).

PREPARATORY EXAMPLE 76

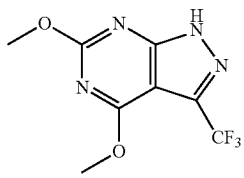 [SMILES: COc1nc(OC)c2c(C(F)(F)F)n[nH]c2n1]

4,6-Dimethoxy-3-(trifluoromethyl)-1H-pyrazolo[3,4-d]pyrimidine (Scheme 15)

Step 1. 1-(4-Chloro-2,6-dimethoxypyrimidin-5-yl)-2,2,2-trifluoroethan-1-one To a round-bottom flask charged with a stir bar under N₂ was added 2,2,6,6-tetramethylpiperidine (2.3 mL, 13.8 mmol) followed by THF (16 mL). The mixture was cooled to −50° C. whereupon a solution of n-BuLi (2.5 M in hexanes, 5.5 mL, 13.8 mmol) was added dropwise. The resulting solution was stirred for 1 hour at −50° C. whereupon a solution of 4-chloro-2,6-dimethoxypyrimidine (2 g, 11.5 mmol) in tetrahydrofuran (10 mL) dropwise. The resulting solution was stirred for an additional 2.5 h at −50° C. whereupon a solution of CuCN.2 LiCl (1M in THF, 13.8 mL, 13.8 mmol) was dropwise. The mixture was stirred for an additional 0.5 hour at −50° C. whereupon trifluoroacetic anhydride (3.2 mL, 22.9 mmol) dropwise over ~10 min. The solution was warmed to RT and stirred overnight whereupon sat. aq. NaHCO₃ (~15 mL) and EtOAc (~75 mL) were added. The organic layer was separated and the aqueous layer was extracted with EtOAc (3×75 mL). The organic layers were combined, washed with brine (1×50 mL), dried over sodium sulfate, filtered, and concentrated under reduced pressure. The residue was purified by silica gel column chromatography (0-20% ethyl acetate in hexanes) to afford the title compound as a solid. MS=270.9 (M+1).

Step 2. 4,6-Dimethoxy-3-(trifluoromethyl)-1H-pyrazolo[3,4-d]pyrimidine To a round bottom flask charged with 1-(4-chloro-2,6-dimethoxypyrimidin-5-yl)-2,2,2-trifluoroethan-1-one (2.0 g, 7.4 mmol) in EtOH (37 mL) under N₂ at rt was added Et₃N (1.2 mL, 8.9 mmol) dropwise followed by dropwise addition of hydrazine monohydrate (0.65 mL, 13.3 mmol). The resulting mixture was stirred for 3 h at rt whereupon the mixture was concentrated to dryness under reduced pressure. The resulting solid was partitioned between EtOAc (100 mL) and sat. aq. NaHCO₃ (20 mL) and the layers were separated. The aqueous layer was extracted with EtOAc (3×100 mL) and the organic layers were combined. The organic layer was washed with brine (1×75 mL), dried over Na₂SO₄, filtered, and concentrated under reduced pressure to afford the title compound as solid. MS=248.9 (M+1).

PREPARATORY EXAMPLE 77

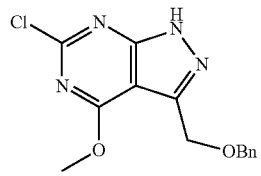 [SMILES: COc1nc(Cl)nc2[nH]nc(COCc3ccccc3)c12]

3-((Benzyloxy)methyl)-6-chloro-4-methoxy-1H-pyrazolo[3,4-d]pyrimidine (Scheme 16)

Step 1. 2-(Benzyloxy)-1-(2,4-dichloro-6-methoxypyrimidin-5-yl)ethan-1-one To a stirred solution of 2,4-dichloro-6-methoxypyrimidine (15 g, 84 mmol) in THF (200 ml) at under N₂ at −40° C. was added a solution of 2,2,6,6-tetramethylpiperidinylmagnesium chloride lithium chloride complex (1.5 M in THF, 67.0 ml, 101 mmol) dropwise. The resulting mixture was stirred for 2 h at −40° C., whereupon a solution of CuCN.2LiCl (92 ml, 92 mmol) was added dropwise. The mixture was stirred for an additional 30 minutes at −40° C., whereupon 2-(benzyloxy)acetyl chloride (26.4 mL, 168 mmol) was added dropwise. The mixture was allowed to gradually warm to RT and stir overnight. A 20% aqueous solution of NaHCO₃ (20 mL) was added to the mixture followed by water (100 mL). The mixture was extracted with EtOAc (3×400 mL) and the organic layers were combined. The organic layer was washed with brine (300 mL), dried over sodium sulfate, filtered, and concentrated under reduced pressure. The residue was purified by silica gel column chromatography (10% EtOAc in petroleum ether) to afford the title compound as an oil. MS=328.2 (+ESI).

Step 2. 3-((Benzyloxy)methyl)-6-chloro-4-methoxy-1H-pyrazolo[3,4-d]pyrimidine To a solution of 2-(benzyloxy)-1-(2,4-dichloro-6-methoxypyrimidin-5-yl)ethanone (10 g, 30.6 mmol) in toluene (190 mL) was added hydrazine monohydrate (7.41 ml, 0.15 mol) dropwise at room temperature under N₂. The mixture was stirred at RT for 30 min whereupon EtOAc (500 mL) was added and the organic layer was washed with brine (1×60 mL). The organic layer was dried over Na$_2$SO$_4$, filtered, and concentrated under reduced pressure to afford the title compound as a solid. MS=305.0 (M+H)$^+$.

PREPARATIVE EXAMPLE 78

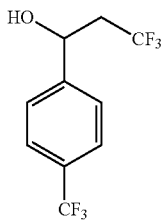

3,3,3-Trifluoro-1-(4-(trifluoromethyl)phenyl)propan-1-ol (Scheme 17)

Sodium borohydride (31.0 mg, 0.8 mmol) was added to a stirred solution of 3,3,3-trifluoro-1-(4-(trifluoromethyl)phenyl)propan-1-one (0.21 g, 0.8 mmol) (*J. Org. Chem.*, 2014, 79, 5145) in methanol (4 mL) at room temperature. The reaction mixture was stirred at RT for 2 h. The reaction solution was diluted with water (5 mL) and extracted with ethyl acetate (3×5 mL). The combined organic layers were washed with brine (2×5 mL), dried over sodium sulfate, filtered, and concentrated under vacuum. The residue was purified by silica gel column chromatography (30% ethyl acetate in petroleum ether) to afford the title compound as an oil. $^1$H NMR (400 MHz, DMSO-d$_6$) δ: 7.73 (d, J=8.0 Hz, 2H), 7.65 (d, J=8.0 Hz, 2H), 5.88 (d, J=5.2 Hz, 1H), 5.01-4.97 (m, 1H), 2.69-2.58 (m, 2H).

TABLE 9

The following compounds were prepared using the procedures similar to those described in Preparatory Example 78 using the appropriate starting materials.

| Prep Ex No. | Structure | IUPAC Name | $^1$H NMR or Exact Mass [M + H]$^+$ |
|---|---|---|---|
| 79 | 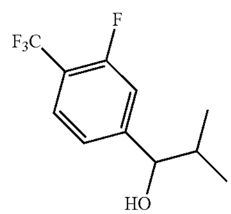 [SMILES: CC(C)C(O)c1ccc(C(F)(F)F)c(F)c1] | 1-(3-fluoro-4-(trifluoromethyl)phenyl)-2-methylpropan-1-ol | $^1$H NMR (400 MHz, CDCl$_3$) δ: 7.61-7.54 (m, 1H), 7.24-7.02 (m, 2H), 4.51 (d, J = 6.0 Hz, 1H), 1.98-1.93 (m, 1H), 0.97 (d, J = 6.8 Hz, 3H), 0.90 (d, J = 6.8 Hz, 3H). |
| 80 | 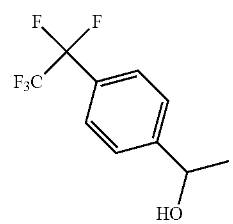 [SMILES: CC(O)c1ccc(C(F)(F)C(F)(F)F)cc1] | 1-(4-(perfluoroethyl)phenyl)ethan-1-ol | $^1$H NMR (400 MHz, CDCl$_3$) δ: 7.61 (d, J = 8.4 Hz, 2H), 7.53 (d, J = 8.4 Hz, 2H), 5.00 (q, J = 6.4 Hz, 1H), 1.54 (d, J = 6.4 Hz, 3H). |
| 81 | 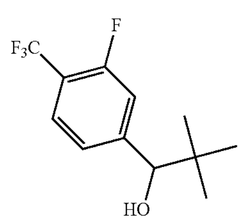 [SMILES: CC(C)(C)C(O)c1ccc(C(F)(F)F)c(F)c1] | 1-(3-fluoro-4-(trifluoromethyl)phenyl)-2,2-dimethylpropan-1-ol | $^1$H NMR (400 MHz, CDCl$_3$) δ: 7.58-7.54 (m, 1H), 7.23-7.18 (m, 2H), 4.46 (s, 1H), 0.95 (s, 9H) |
| 82 | 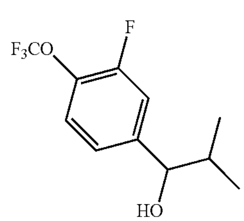 [SMILES: CC(C)C(O)c1ccc(OC(F)(F)F)c(F)c1] | 1-(3-fluoro-4-(trifluoromethoxy)phenyl)-2-methylpropan-1-ol)-one | $^1$H NMR (400 MHz, CDCl$_3$): δ 7.21-7.31 (m, 2H), 7.10-7.13 (m, 1H), 4.44 (d, J = 6.4 Hz, 1H), 1.90-1.99 (m, 1H), 0.98 (d, J = 6.8 Hz, 3H), 0.87 (d, J = 6.8 Hz, 3H). |

TABLE 9-continued

The following compounds were prepared using the procedures similar to those described in Preparatory Example 78 using the appropriate starting materials.

| Prep Ex No. | Structure | IUPAC Name | $^1$H NMR or Exact Mass [M + H]$^+$ |
|---|---|---|---|
| 83 | 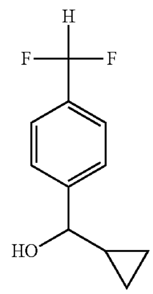 | cyclopropyl(4-(difluoromethyl)phenyl)methanol | $^1$H NMR (DMSO-d$_6$) δ: 7.60-7.50 (m, 4H), 7.00 (t, J = 55.8 Hz, 1H), 5.29 (d, J = 4.5 Hz, 1H), 4.05-4.01 (m, 1H), 1.05-0.95 (m, 1H), 0.50-0.35 (m, 4H). |
| 84 | 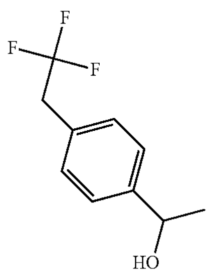 | 1-(4-(2,2,2-trifluoroethyl)phenyl)ethan-1-ol | $^1$H NMR (400 MHz, CDCl$_3$) δ: 7.39 (d, J = 8.0 Hz, 2H), 7.30 (d, J = 8.0 Hz, 2H), 4.98-4.88 (m, 1H), 3.38 (q, J = 10.8 Hz, 2H), 1.52 (d, J = 6.4 Hz, 3H). |
| 85 | 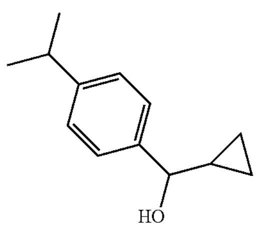 | cyclopropyl(4-isopropylphenyl)methanol | $^1$H NMR (400 MHz, CDCl$_3$) δ: 7.37 (d, J = 8.0 Hz, 2H), 7.24 (d, J = 8.0 Hz, 2H), 4.00 (d, J = 8.4 Hz, 1H), 2.96-2.90 (m, 1H), 1.27 (d, J = 6.8 Hz, 6H), 0.75-0.32 (m, 4H). |
| 86 | 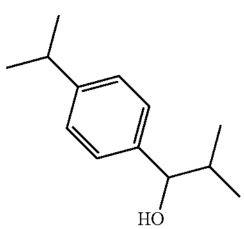 | 1-(4-isopropylphenyl)-2-methylpropan-1-ol | $^1$H NMR (400 MHz, CDCl$_3$) δ: 7.32-7.21 (m, 4H), 4.35 (d, J = 7.2 Hz, 2H), 2.95-2.85 (m, 1H), 2.02-1.95 (m, 1H), 1.28 (d, J = 6.8 Hz, 6H), 1.04 (d, J = 6.8 Hz, 3H), 0.82 (d, J = 6.8 Hz, 3H). |
| 87 | 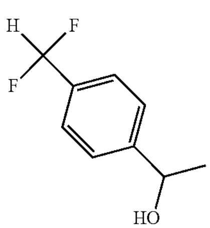 | 1-(4-(difluoromethyl)phenyl)ethan-1-ol | $^1$H NMR (300 MHz, DMSO-d$_6$) δ: 7.54-7.46 (m, 4H), 7.00 (t, J = 56.1 Hz, 1H), 5.27 (d, J = 4.5 Hz, 1H), 4.81-4.73 (m, 1H), 1.32 (d, J = 6.3 Hz, 3H). |
| 88 | 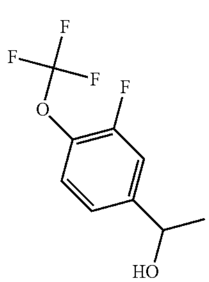 | 1-(3-fluoro-4-(trifluoromethoxy)phenyl)ethan-1-ol | $^1$H NMR (300 MHz, DMSO-d$_6$) δ 7.58-7.30 (m, 2H), 7.24 (d, J = 8.4 Hz, 1H), 5.37 (d, J = 4.4 Hz, 1H), 4.78-4.68 (m, 1H), 1.28 (d, J = 6.5 Hz, 3H). |

TABLE 9-continued

The following compounds were prepared using the procedures similar to those described in Preparatory Example 78 using the appropriate starting materials.

| Prep Ex No. | Structure | IUPAC Name | $^1$H NMR or Exact Mass [M + H]$^+$ |
|---|---|---|---|
| 89 | 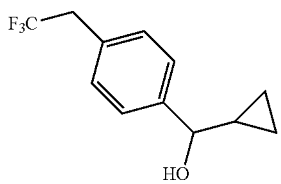 [SMILES: OC(c1ccc(CC(F)(F)F)cc1)C1CC1] | cylclopropyl(4-(2,2,2-trifluoroethyl)phenyl)methanol | $^1$H NMR (300 MHz, CDCl$_3$) δ: 7.42 (d, J = 7.8 Hz, 2H), 7.29 (d, J = 8.1 Hz, 2H), 4.15-4.02 (m, 1H), 4.01 (d, J = 8.4 Hz, 1H), 3.36 (q, J = 10.9 Hz, 2H), 1.33-1.08 (m, 1H), 0.72-0.32 (m, 4H). |
| 90 | 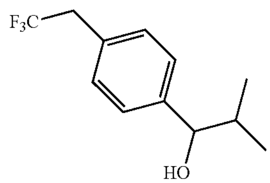 [SMILES: CC(C)C(O)c1ccc(CC(F)(F)F)cc1] | 2-methyl-1-(4-(2,2,2-trifluoroethyl)phenyl)propan-1-ol | $^1$H NMR (300 MHz, CDCl$_3$) δ: 7.32-7.13 (m, 4H), 4.38 (d, J = 6.6 Hz, 1H), 3.38 (q, J = 10.8 Hz, 2H), 1.00 (d, J = 6.6 Hz, 3H), 0.82 (d, J = 6.6 Hz, 3H) |
| 91 | 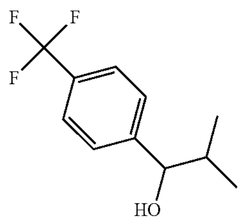 | 1-(4-(difluoromethyl)phenyl)-2-methylpropan-1-ol | $^1$H NMR (300 MHz, DMSO-d$_6$) δ: 7.50 (d, J = 8.4 Hz, 2H), 7.41 (d, J = 8.1 Hz, 2H), 7.00 (d, J = 56.1 Hz, 1H), 5.21 (d, J = 4.5 Hz, 1H), 4.33-4.30 (m, 1H), 1.87-1.76 (m, 1H), 0.83 (d, J = 6.6 Hz, 3H), 0.75 (d, J = 6.6 Hz, 3H). |
| 92 | 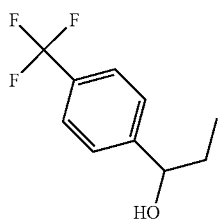 | 1-(4-(difluoromethyl)phenyl)propan-1-amine-4(5H)-one | $^1$H NMR (300 MHz, DMSO-d$_6$) δ: 7.51 (d, J = 8.1 Hz, 2H), 7.44 (d, J = 7.8 Hz, 2H), 7.00 (d, J = 56.1 Hz, 1H), 5.23 (d, J = 4.2 Hz, 1H), 4.53-4.48 (m, 1H), 1.66-1.56 (m, 2H), 0.82 (t, J = 7.2 Hz, 3H). |
| 93 | 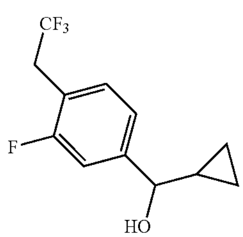 [SMILES: OC(c1ccc(CC(F)(F)F)c(F)c1)C1CC1] | cyclopropyl(3-fluoro-4-(2,2,2-trifluoroethyl)phenyl)methanol | GC-MS MS (+EI) = 247.9 |
| 94 | 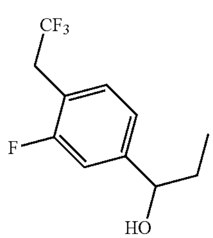 [SMILES: CCC(O)c1ccc(CC(F)(F)F)c(F)c1] | 1-(3-fluoro-4-(2,2,2-trifluoroethyl)phenyl)propan-1-ol | $^1$H NMR (300 MHz, DMSO-d$_6$) δ: 7.40-7.35 (m, 1H), 7.20-7.15 (m, 2H), 5.26 (d, J = 4.5 Hz, 1H), 4.50-4.40 (m, 1H), 3.66 (q, J = 11.4 Hz, 2H), 1.65-1.50 (m, 2H), 0.81 (t, J = 6.3 Hz, 3H). |
| 95 | 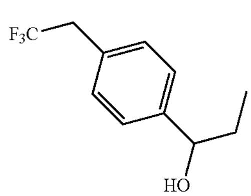 | 1-(4-(2,2,2-trifluoroethyl)phenyl)propan-1-ol | $^1$H NMR (400 MHz, CDCl$_3$) δ: 7.34 (d, J = 8.0 Hz, 2H), 7.27 (d, J = 8.0 Hz, 2H), 4.62 (t, J = 6.8 Hz, 1H), 3.36 (q, J = 10.8 Hz, 2H), 1.84-1.70 (m, 2H), 0.92 (t, J = 7.2 Hz, 3H). |

TABLE 9-continued

The following compounds were prepared using the procedures similar to those described in Preparatory Example 78 using the appropriate starting materials.

| Prep Ex No. | Structure | IUPAC Name | $^1$H NMR or Exact Mass [M + H]$^+$ |
|---|---|---|---|
| 96 | 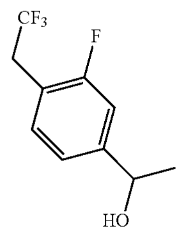 | 1-(3-fluoro-4-(2,2,2-trifluoroethyl)phenyl)ethan-1-ol | $^1$H NMR (300 MHz, DMSO-d$_6$) δ: 7.42-7.38 (m, 1H), 7.22-7.18 (m, 2H), 5.29 (d, J = 4.2 Hz, 1H), 4.77-4.69 (m, 1H), 3.64 (q, J = 11.4 Hz, 2H), 1.29 (d, J = 6.8 Hz, 3H). |
| 97 | 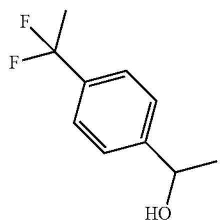 | 1-(4-(1,1-difluoroethyl)phenyl)ethan-1-ol | $^1$H NMR (300 MHz, CDCl$_3$) δ: 7.49 (d, J = 8.4 Hz, 2H), 7.42 (d, J = 8.1 Hz, 2H), 4.91 (q, J = 6.4 Hz, 1H), 1.89 (t, J = 18.0 Hz, 3H), 1.50 (d, J = 6.6 Hz, 3H). |
| 98 | 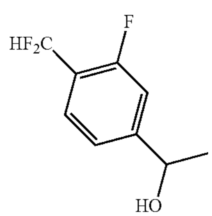 | 1-(4-(difluoromethyl)-3-fluorophenyl)ethan-1-ol | $^1$H NMR (300 MHz, CDCl$_3$) δ: 7.58-7.53 (m, 1H), 7.22 (d, J = 7.5 Hz, 1H), 7.18 (d, J = 11.4 Hz, 1H), 6.88 (t, J = 54.9 Hz, 1H), 4.93 (q, J = 6.3 Hz, 1H), 1.49 (d, J = 6.3 Hz, 3H). |
| 99 | 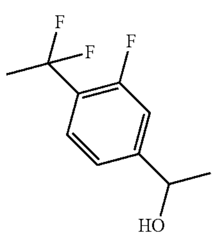 | 1-(4-(1,1-difluoroethyl)-3-fluorophenyl)ethan-1-ol | $^1$H NMR (300 MHz, DMSO-d$_6$) δ: 7.53-7.49 (m, 1H), 7.33-7.26 (m, 2H), 5.38 (d, J = 4.4 Hz, 1H), 4.79-7.74 (m, 1H), 1.99 (t, J = 18.3 Hz, 3H), 1.32 (d, J = 6.4 Hz, 3H) |
| 100 | 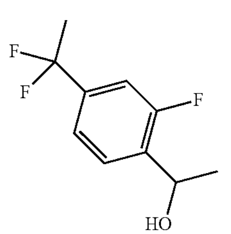 | 1-(4-(1,1-difluoroethyl)-2-fluorophenyl)ethan-1-ol | $^1$H NMR (400 MHz, CDCl$_3$) δ: 7.59-7.55 (m, 1H), 7.30 (d, J = 8.0 Hz, 1H), 7.18 (d, J = 10.8 Hz, 1H), 5.22 (q, J = 6.4 Hz, 1H), 1.91 (t, J = 18.4 Hz, 3H), 1.52 (d, J = 6.4 Hz, 3H). |
| 101 | 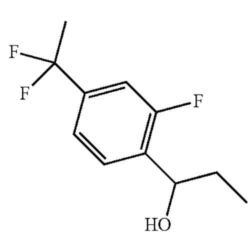 | 1-(4-(1,1-difluoroethyl)-2-fluorophenyl)propan-1-ol | $^1$H NMR (400 MHz, CDCl$_3$) δ: 7.55-7.51 (m, 1H), 7.29 (d, J = 8.0 Hz, 1H), 7.17 (d, J = 10.8 Hz, 1H), 4.97 (t, J = 6.4 Hz, 1H), 1.91 (t, J = 18.0 Hz, 3H), 1.83-1.77 (m, 2H), 0.98 (t, J = 6.4 Hz, 3H). |

TABLE 9-continued

The following compounds were prepared using the procedures similar to those described in Preparatory Example 78 using the appropriate starting materials.

| Prep Ex No. | Structure | IUPAC Name | $^1$H NMR or Exact Mass [M + H]$^+$ |
|---|---|---|---|
| 102 | 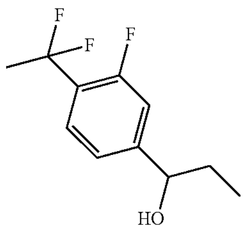 | 1-(4-(1,1-difluoroethyl)-3-fluorophenyl)propan-1-ol | $^1$H NMR (400 MHz, CDCl$_3$) δ: 7.55-7.51 (m, 1H), 7.18-7.15 (m, 2H), 4.67 (t, J = 6.4 Hz, 1H), 2.02 (t, J = 18.4 Hz, 3H), 1.86-1.7.5 (m, 2H), 0.96 (t, J = 7.6 Hz, 3H). |
| 103 | 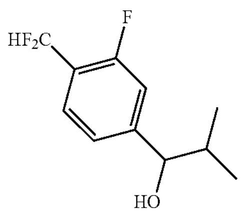 | 1-(4-(difluoromethyl)-3-fluorophenyl)-2-methylpropan-1-ol | $^1$H NMR (300 MHz, CDCl$_3$) δ: 7.57-7.52 (m, 1H), 7.17 (d, J = 8.1 Hz, 1H), 7.13 (d, J = 8.1 Hz, 1H), 6.88 (t, J = 54.9 Hz, 1H), 4.45 (d, J = 8.0 Hz, 1H), 1.95-1.85 (m, 1H), 0.95 (d, J = 6.9 Hz, 3H), 0.86 (d, J = 6.9 Hz, 3H). |
| 104 | 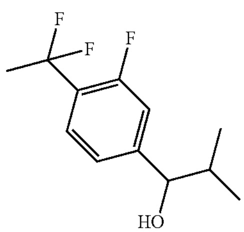 [SMILES: CC(C)C(O)c1ccc(C(C)(F)F)c(F)c1] | 1-(4-(1,1-difluoroethyl)-3-fluorophenyl)-2-methylpropan-1-ol | $^1$H NMR (300 MHz, DMSO-d$_6$) δ; 7.49-7.43 (m, 1H), 7.21-7.16 (m, 2H), 5.28 (d, J = 4.5 Hz, 1H), 4.30 (t, J = 8.1 Hz, 1H), 1.95 (t, J = 18.4 Hz, 3H), 1.83-1.72 (m, 1H), 0.76 (d, J = 6.9 Hz, 3H), 0.75 (d, J = 6.9 Hz, 3H). |
| 105 | 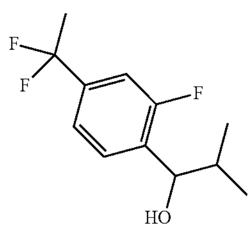 [SMILES: CC(C)C(O)c1ccc(C(C)(F)F)cc1F] | 1-(4-(1,1-difluoroethyl)-2-fluorophenyl)-2-methylpropan-1-ol | $^1$H NMR (400 MHz, DMSO-d$_6$) δ: 7.52-7.48 (m, 1H), 7.29 (d, J = 8.0 Hz, 1H), 7.17 (d, J = 10.8 Hz, 1H), 4.75 (d, J = 6.8 Hz, 1H), 2.10-1.95 (m, 1H), 1.91 (t, J = 18.0 Hz, 3H), 0.99 (d, J = 6.8 Hz, 3H), 0.85 (d, J = 6.4 Hz, 3H). |
| 106 | 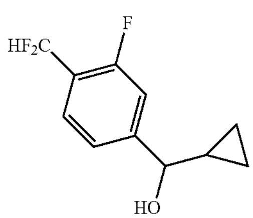 | cyclopropyl(4-(difluoromethyl)-3-fluorophenyl)methanol | $^1$H-NMR (400 MHz, CDCl$_3$) δ: 7.56 (d, J = 7.6 Hz, 1H), 7.29 (d, J = 8.0 Hz, 1H), 7.25 (d, J = 11.6 Hz, 1H), 6.89 (t, J = 55.2 Hz, 1H), 4.15-4.09 (m, 1H), 4.04 (d, J = 8.4 Hz, 1H), 1.18-1.13 (m, 1H), 0.68-0.61 (m, 2H), 0.51-0.42 (m, 2H) |
| 107 | 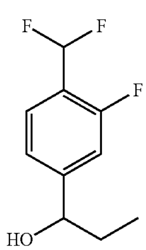 | 1-(4-(Difluoromethyl)-3-fluorophenyl)propan-1-ol | $^1$H NMR (300 MHz, CDCl$_3$) δ: 7.58-7.53 (m, 1H), 7.21-7.14 (m, 2H), 6.88 (t, J = 55.2 Hz, 1H), 4.66 (t, J = 6.6 Hz, 1H), 1.84 (br, 1H), 1.79-1.72 (m, 2H), 0.93 (t, J = 7.5 Hz, 3H). |

TABLE 9-continued

The following compounds were prepared using the procedures similar to those described in Preparatory Example 78 using the appropriate starting materials.

| Prep Ex No. | Structure | IUPAC Name | $^1$H NMR or Exact Mass [M + H]$^+$ |
|---|---|---|---|
| 108 | 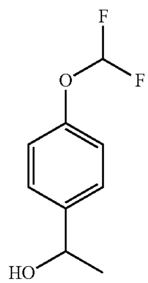 | 1-(4-(difluoromethoxy)phenyl)ethan-1-ol | $^1$H NMR (500 MHz, CDCl$_3$) δ: 7.39 (d, J = 8.7 Hz, 2H), 7.12 (d, J = 8.6 Hz, 2H), 6.52 (t, J = 74.1 Hz, 1H), 4.92 (m, 1H), 1.96 (br s, 1H), 1.50 (d, J = 6.5 Hz, 3H) |
| 109 | 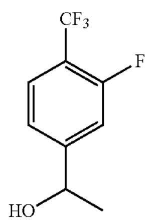 | 1-(3-fluoro-4-(trifluoromethyl)phenyl)ethan-1-ol | $^1$H NMR (500 MHz, CDCl$_3$) δ: 7.60 (t, J = 7.5 Hz, 1H), 7.26 (m, 2H), 4.98 (m, 1H), 1.96 (br s, 1H), 1.53 (d, J = 6.5 Hz, 3H) |

PREPARATIVE EXAMPLE 110

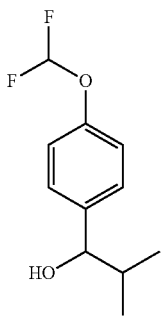

1-(4-(Difluoromethoxy)phenyl)-2-methylpropan-1-ol (Scheme 18)

To a solution of 4-(difluoromethoxy)benzaldehyde (2.00 g, 11.6 mmol) in THF (30 mL) was added isopropylmagnesium bromide solution (3 M in THF, 3.7 mL, 11.6 mmol) dropwise under nitrogen atmosphere at −78° C. The resulting mixture was warmed to RT and stirred for another 16 h. The reaction mixture was quenched with water (20 mL), diluted with a solution of sat. aq. NH$_4$Cl (30 mL) and extracted with ethyl acetate (3×50 mL). The combined organic layers were washed with brine (3×100 mL), dried over sodium sulfate, filtered, and concentrated under vacuum. The residue was purified by silica gel column chromatography (0-10% ethyl acetate in petroleum ether) to afford the title compound as a solid. $^1$H NMR (400 MHz, CDCl$_3$) δ: 7.31 (d, J=8.8 Hz, 2H), 7.10 (d, J=8.4 Hz, 2H), 6.52 (t, J=74.0 Hz, 1H), 4.39 (d, J=6.8 Hz, 1H), 2.00-1.90 (m, 1H), 0.98 (d, J=6.4 Hz, 6H).

TABLE 10

The following compounds were prepared using the procedures similar to those described in Preparatory Example 110 using the appropriate starting materials.

| Prep Ex No. | Structure | IUPAC Name | $^1$H NMR or Exact Mass [M + H]$^+$ |
|---|---|---|---|
| 111 | 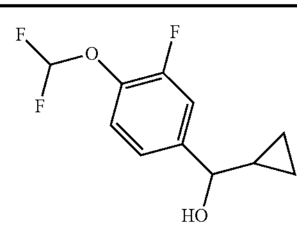 | cyclopropyl(4-(difluoromethoxy)-3-fluorophenyl)methanol | $^1$H NMR (300 MHz, CDCl$_3$) δ: 7.30-7.27 (m, 1H), 7.24-7.15 (m, 2H), 6.54 (t, J = 74.0 Hz, 1H), 3.97 (d, J = 8.4 Hz, 1H), 1.85 (br, 1H), 1.19-1.12 (m, 1H), 0.68-0.60 (m, 2H), 0.49-0.38 (m, 2H). |

TABLE 10-continued

The following compounds were prepared using the procedures similar to those described in Preparatory Example 110 using the appropriate starting materials.

| Prep Ex No. | Structure | IUPAC Name | $^1$H NMR or Exact Mass [M + H]$^+$ |
|---|---|---|---|
| 112 | 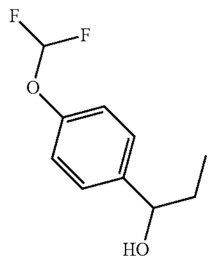 | 1-(4-(difluoromethoxy)phenyl)propan-1-ol | $^1$H NMR (300 MHz, CDCl$_3$) δ: 7.32 (d, J = 8.6 Hz, 2H), 7.07 (d, J = 8.6 Hz, 2H), 6.48 (t, J = 74.0 Hz, 1H), 4.58 (t, J = 6.6 Hz, 1H), 1.90-1.60 (m, 2H), 0.89 (t, J = 7.4 Hz, 3H). |
| 113 | 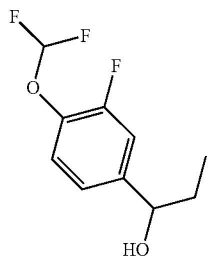 | 1-(4-(difluoromethoxy)-3-fluorophenyl)propan-1-ol | $^1$H NMR (300 MHz, CDCl$_3$) δ: 7.24-7.17 (m, 2H), 7.11 (d, J = 8.0 Hz, 1H), 6.56 (t, J = 73.6 Hz, 1H), 4.63 (t, J = 6.4 Hz, 2H), 1.89-1.68 (m, 2H), 0.95 (t, J = 7.2 Hz, 3H). |
| 114 | 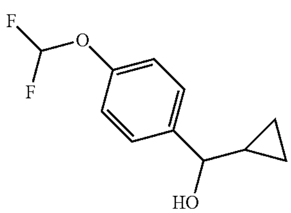 [SMILES: OC(c1ccc(OC(F)F)cc1)C1CC1] | cyclopropyl(4-(difluoromethoxy)phenyl)methanol | $^1$H NMR (300 MHz, CDCl$_3$) δ: 7.43 (d, J = 8.4 Hz, 2H), 7.11 (d, J = 8.4 Hz, 2H), 6.50 (t, J = 74.0 Hz, 1H), 4.01 (d, J = 8.4 Hz, 1H), 0.90-0.80 (m, 1H), 0.71-0.32 (m, 4H). |
| 115 | 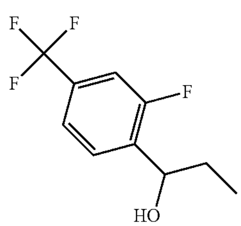 | 1-(2-fluoro-4-(trifluoromethyl)phenyl)propan-1-ol | $^1$H NMR (300 MHz, CDCl$_3$) δ: 7.66-7.61 (m, 1H), 7.43 (d, J = 8.1 Hz, 1H), 7.29 (d, J = 11.4 Hz, 1H), 5.01 (t, J = 6.3 Hz, 1H), 1.86-1.76 (m, 2H), 0.97 (t, J = 7.2 Hz, 3H). |
| 116 | 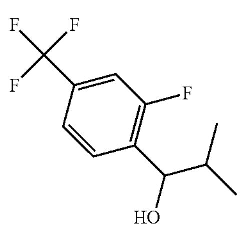 [SMILES: CC(C)C(O)c1ccc(C(F)(F)F)cc1F] | 1-(2-fluoro-4-(trifluoromethyl)phenyl)-2-methylpropan-1-ol | $^1$H NMR (400 MHz, DMSO-d$_6$) δ: 7.71-7.67 (m, 1H), 7.59 (d, J = 9.2 Hz, 2H), 5.45 (d, J = 4.8 Hz, 1H), 4.63 (t, J = 5.2 Hz, 1.89-1.81 (m, 1H), 0.85 (d, J = 6.4 Hz, 3H), 0.81 (d, J = 6.8 Hz, 3H) |
| 117 | 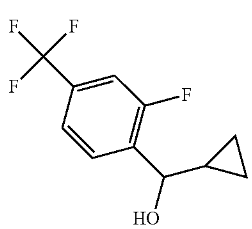 [SMILES: OC(c1ccc(C(F)(F)F)cc1F)C1CC1] | cyclopropyl(2-fluoro-4-(trifluoromethyl)phenyl)methanol | $^1$H NMR (400 MHz, DMSO-d$_6$) δ: 7.75-7.70 (m, 1H), 7.55 (d, J = 9.2 Hz, 2H), 5.48 (d, J = 4.5 Hz, 1H), 4.39-4.35 (m, 1H), 1.10-1.00 (m, 1H), 0.50-0.25 (m, 4H) |

TABLE 10-continued

The following compounds were prepared using the procedures similar to those described in Preparatory Example 110 using the appropriate starting materials.

| Prep Ex No. | Structure | IUPAC Name | $^1$H NMR or Exact Mass [M + H]$^+$ |
|---|---|---|---|
| 118 | 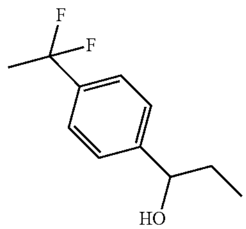 | 1-(4-(1,1-difluoroethyl)phenyl)propan-1-ol | $^1$H NMR (400 MHz, DMSO-d$_6$) δ: 7.49 (d, J = 8.1 Hz, 2H), 7.40 (d, J = 8.1 Hz, 2H), 5.20 (d, J = 4.5 Hz, 1H), 4.52-4.46 (m, 1H), 1.95 (t, J = 11.4 Hz, 3H), 1.65-1.55 (m, 2H), 0.82 (t, J = 7.5 Hz, 3H). |
| 119 | 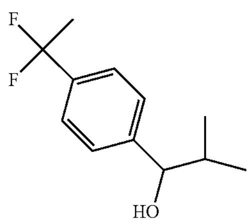 | 1-(4-(1,1-difluoroethyl)phenyl)-2-methylpropan-1-ol | $^1$H NMR (300 MHz, CDCl$_3$) δ: 7.49 (d, J = 8.1 Hz, 2H), 7.38 (d, J = 8.1 Hz, 2H), 4.44 (d, J = 6.6 Hz, 1H), 1.93 (t, J = 18.0 Hz, 3H), 1.00 (d, J = 6.8 Hz, 3H), 0.84 (d, J = 6.8 Hz, 3H). |
| 120 | 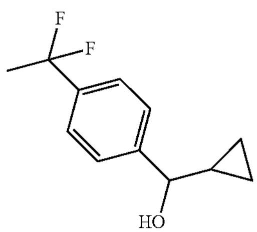 | cyclopropyl(4-(1,1-difluoroethyl)phenyl)methanol | $^1$H NMR (300 MHz, DMSO-d$_6$) δ: 7.51-7.46 (m, 4H), 5.26 (d, J = 4.4 Hz, 1H), 4.06-3.99 (m, 1H), 1.93 (t, J = 18.4 Hz, 3H), 1.04-0.98 (m, 1H), 0.46-0.30 (m, 4H). |
| 121 | 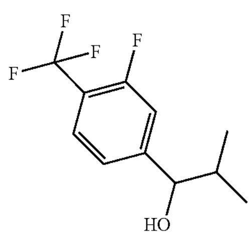 [SMILES: CC(C)C(O)c1ccc(C(F)(F)F)c(F)c1] | 1-(3-fluoro-4-(trifluoromethyl)phenyl)-2-methylpropan-1-ol | $^1$H NMR (400 MHz, CDCl$_3$) δ: 7.58-7.54 (m, 1H), 7.25-7.13 (m, 2H), 4.49 (d, J = 6.0 Hz, 1H), 2.02-1.85 (m, 1H), 0.95 (d, J = 6.8 Hz, 3H), 0.88 (d, J = 6.8 Hz, 3H). |
| 122 | 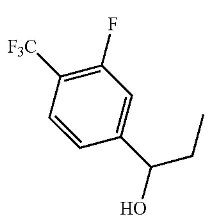 | 1-(3-fluoro-4-(trifluoromethyl)phenyl)propan-1-ol | $^1$H NMR (400 MHz, CDCl$_3$) δ: 7.59-7.55 (m, 1H), 7.27-7.19 (m, 2H), 4.68 (t, J = 6.4 Hz, 1H), 1.85-1.74 (m, 2H), 0.94 (t, J = 7.2 Hz, 3H) |
| 123 | 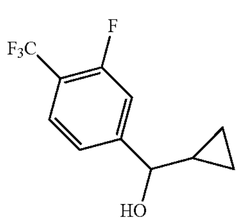 [SMILES: OC(c1ccc(C(F)(F)F)c(F)c1)C1CC1] | cyclopropyl(3-fluoro-4-(trifluoromethyl)phenyl)methanol | $^1$H NMR (400 MHz, CDCl$_3$) δ: 7.70-7.62 (m, 1H), 7.52-7.45 (m, 2H), 4.06 (d, J = 8.4 Hz, 1H), 1.20-1.10 (m, 1H), 0.70-0.62 (m, 2H), 0.55-0.45 (m, 2H). |

TABLE 10-continued

The following compounds were prepared using the procedures similar to those described in Preparatory Example 110 using the appropriate starting materials.

| Prep Ex No. | Structure | IUPAC Name | $^1$H NMR or Exact Mass [M + H]$^+$ |
|---|---|---|---|
| 124 | 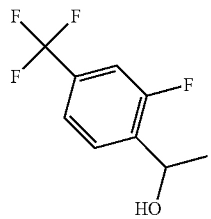 | 1-(2-fluoro-4-(trifluoromethyl)phenyl)ethan-1-ol | $^1$H NMR (400 MHz, CDCl$_3$) δ: 7.71-7.67 (m, 1H), 7.47 (d, J = 8.0 Hz, 1H), 7.31 (d, J = 10.0 Hz, 1H), 5.27 (q, J = 6.4 Hz, 1H), 1.87 (br, 1H), 1.55 (d, J = 6.4 Hz, 3H). |
| 125 | 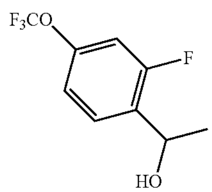 | 1-(2-fluoro-4-(trifluoromethoxy)phenyl)ethan-1-ol | $^1$H NMR (500 MHz, CDCl$_3$) δ: 7.57 (t, J = 8.4 Hz, 1H), 7.07 (d, J = 8.4 Hz, 1H), 6.96 (d, J = 10.6 Hz, 1H), 5.22 (m, 1H), 1.95 (br s, 1H), 1.54 (d, J = 6.5 Hz, 3H). |
| 126 | 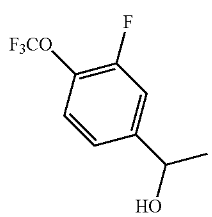 | 1-(3-fluoro-4-(trifluoromethoxy)phenyl)ethan-1-ol | $^1$H NMR (500 MHz, CDCl$_3$) δ: 7.31-7.26 (m, 2H), 7.17 (d, J = 8.4 Hz, 1H, 1H), 4.93 (m, 1H), 1.99 (br s, 1H), 1.51 (d, J = 6.5 Hz, 1H). |

PREPARATORY EXAMPLE 127

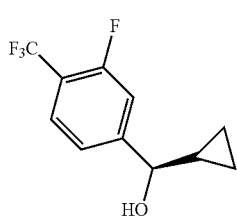 [SMILES: O[C@@H](c1ccc(C(F)(F)F)c(F)c1)C1CC1]

(R)-Cyclopropyl(3-fluoro-4-(trifluoromethyl)phenyl)methanol (Scheme 19)

To a solution of cyclopropyl(3-fluoro-4-(trifluoromethyl)phenyl)methanone (0.30 g, 1.3 mmol) in DCM (10 mL) was added (S)-2-methyl-CBS-oxazaborolidine (1 M in THF, 0.26 mL, 0.26 mmol) dropwise at 0° C. The reaction solution was degassed with nitrogen 3 times and stirred under nitrogen. Borane-dimethyl sulfide complex (10 M, 0.13 mL, 1.3 mmol) was added dropwise to the reaction solution. The resulting reaction mixture was stirred at room temperature for 4 h. The reaction mixture was then quenched with MeOH (10 mL) and concentrated under vacuum. The residue was purified by silica gel column chromatography (25% ethyl acetate in hexanes) to afford the title compound as an oil. $^1$H NMR (400 MHz, CDCl$_3$) δ: 7.70-7.62 (m, 1H), 7.52-7.45 (m, 2H), 4.06 (d, J=8.4 Hz, 1H), 1.15-1.05 (m, 1H), 0.70-0.40 (m, 4H).

TABLE 11

The following compounds were prepared using the procedures similar to those described in Preparatory Example 127 using the appropriate starting materials.

| Prep Ex No. | Structure | IUPAC Name | ¹H NMR or Exact Mass [M + H]⁺ |
|---|---|---|---|
| 128 | 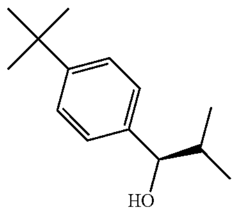 | (R)-1-(4-(tert-butyl)phenyl)-2-methylpropan-1-ol | ¹H NMR (400 MHz, CDCl₃) δ: 7.36 (d, J = 8.4 Hz, 2H), 7.25 (d, J = 8.0 Hz, 2H), 4.33 (d, J = 7.2 Hz, 1H), 2.03-1.90 (m, 1H), 1.33 (s, 9H), 1.02 (d, J = 6.8 Hz, 3H), 0.80 (d, J = 6.8 Hz, 3H). |
| 129 | 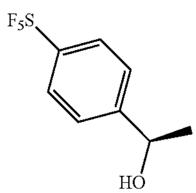 | (R)-1-(4-(pentafluorosulfanyl)phenyl)ethan-1-ol | ¹H NMR (400 MHz, CDCl₃) δ: 7.73 (d, J = 8.8 Hz, 2H), 7.47 (d, J = 8.8 Hz, 2H), 4.96 (q, J = 6.5 Hz, 1H), 1.50 (d, J = 6.5 Hz, 3H). |

TABLE 12

The following compounds were commercially available or prepared using the literature procedures provided in the table using the appropriate starting materials.

| Prep Ex No. | Structure | IUPAC Name | Literature/commercial source |
|---|---|---|---|
| 130 | 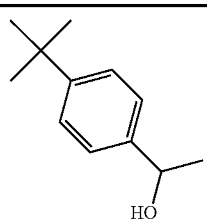 | 1-(4-(tert-butyl)phenyl)ethan-1-ol | *J. Am. Chem. Society*, 2005, 127, 12228. |
| 131 | 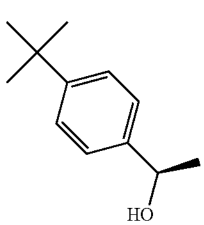 | (R)-1-(4-tert-butylphenyl)ethanol | *J. Org. Chem.* 2002, 67, 5301 |

EXAMPLES 1 AND 2

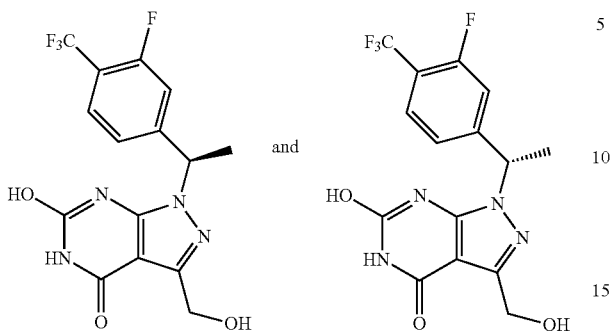

and (R)- and (S)-1-(1-(3-Fluoro-4-(trifluoromethyl)phenyl)ethyl)-6-hydroxy-3-(hydroxymethyl)-1H-pyrazolo[3,4-d]pyrimidin-4(5H)-one (Scheme 20)

Step 1. 3-((Benzyloxy)methyl)-1-(1-(3-fluoro-4-(trifluoromethyl)phenyl)ethyl)-1H-pyrazolo[3,4-d]pyrimidine-4,6-diol To a solution of 5-amino-3-((benzyloxy)methyl)-1-(1-(3-fluoro-4-(trifluoromethyl)phenyl)ethyl)-1H-pyrazole-4-carboxamide (0.22 g, 0.5 mmol) in 1,4-dioxane (4 mL) at 0° C. was added triphosgene (0.15 g, 0.5 mmol) followed by dropwise addition of TEA (0.14 mL, 1.0 mmol). The reaction solution was warmed slowly to RT and was stirred for additional 5 h at room temperature. The reaction solution was quenched with water (5 mL) and extracted with EtOAc (2×10 mL). The combined organic layers were dried over $Na_2SO_4$, filtered, and concentrated under vacuum. The residue was purified by silica gel column chromatography (0-70% ethyl acetate in petroleum ether) to afford the title compound as a solid. MS=463.1 (+ESI).

Step 2. (R)- and (S)-1-(1-(3-Fluoro-4-(trifluoromethyl)phenyl)ethyl)-6-hydroxy-3-(hydroxymethyl)-1H-pyrazolo[3,4-d]pyrimidin-4(5H)-one The racemic title compound was prepared using procedures similar to those described in step 2 of Preparatory Example 75 using 3-((benzyloxy)methyl)-1-(1-(3-fluoro-4-(trifluoromethyl)phenyl)ethyl)-6-hydroxy-1H-pyrazolo[3,4-d]pyrimidin-4(5H)-one and 10% palladium on carbon in the presence of hydrogen to afford a solid. The enantiopure title compounds were obtained by chiral preparative HPLC (Chiralpak AS-H, 80% isopropanol in hexanes (0.1% TFA)). The faster-eluting enantiomer of the title compound (Example 1) was obtained as a solid. MS=373.1 (+ESI). $^1$H NMR (300 MHz, DMSO-$d_6$) δ:10.54 (br s, 1H), 7.80-7.74 (m, 1H), 7.42 (d, J=12.0 Hz, 1H), 7.28 (d, J=8.1 Hz, 1H), 5.82 (q, J=6.9 Hz, 1H), 5.30 (t, J=6.0 Hz, 1H), 4.53 (d, J=6.0 Hz, 2H), 1.78 (d, J=6.9 Hz, 3H). The slower-eluting enantiomer of the title compound (Example 2) was obtained as a solid. MS=373.1 (+ESI). $^1$H NMR (300 MHz, DMSO-$d_6$) δ: 10.54 (br s, 1H), 7.80-7.74 (m, 1H), 7.42 (d, J=12.0 Hz, 1H), 7.28 (d, J=8.1 Hz, 1H), 5.82 (q, J=6.9 Hz, 1H), 5.30 (t, J=6.0 Hz, 1H), 4.53 (d, J=6.0 Hz, 2H), 1.78 (d, J=6.9 Hz, 3H).

EXAMPLES 3 AND 4

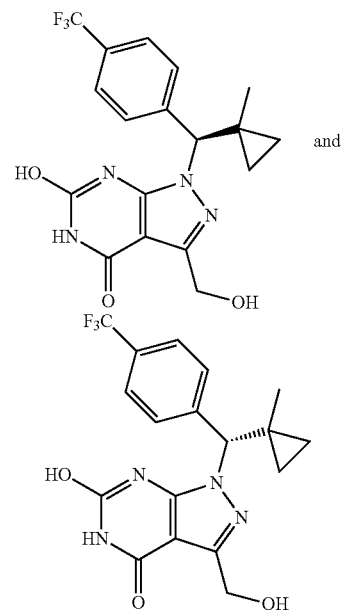

and (R)- and (S)-6-Hydroxy-3-(hydroxymethyl)-1-((1-methylcyclopropyl)(4-(trifluoromethyl)phenyl)methyl)-1H-pyrazolo[3,4-d]pyrimidin-4(5H)-one (Scheme 20)

Step 1. 3-((Benzyloxy)methyl)-6-hydroxy-1-((1-methylcyclopropyl)(4-(trifluoromethyl)phenyl)methyl)-1H-pyrazolo[3,4-d]pyrimidin-4(5H)-one To a mixture of 5-amino-3-((benzyloxy)methyl)-1-((1-methylcyclopropyl)(4-(trifluoromethyl)phenyl)methyl)-1H-pyrazole-4-carboxamide (0.15 g, 0.3 mmol) in dioxane (5 mL) at RT was added 4-nitrophenyl chloroformate (99 mg, 0.5 mmol). The reaction mixture was heated to 70° C., stirred for 2 h, and cooled to room temperature. The mixture was diluted with water (10 mL) and extracted with EtOAc (3×10 mL). The combined organic layers were washed with water (3×10 mL), brine (3×10 mL), dried over $Na_2SO_4$, filtered, and concentrated under vacuum. The residue was purified by silica gel column chromatography (0-70% ethyl acetate in petroleum ether) to afford the title compound as an oil. MS=485.1 (+ESI).

Step 2. (R)- and (S)-6-Hydroxy-3-(hydroxymethyl)-1-((1-methylcyclopropyl)(4-(trifluoro methyl)phenyl)methyl)-1H-pyrazolo[3,4-d]pyrimidin-4(5H)-one The racemic title compound was prepared using procedures similar to those described in step 2 of Preparatory Example 75 using 3-((benzyloxy)methyl)-6-hydroxy-1-((1-methylcyclopropyl)(4-(trifluoromethyl)phenyl)methyl)-1H-pyrazolo[3,4-d]

pyrimidin-4(5H)-one in the presence of 20% palladium hydroxide and hydrogen to afford a solid. The enantiopure title compounds were obtained by chiral preparative HPLC (Chiralpak IA, 8% EtOH in hexanes (0.1% TFA)). The faster-eluting enantiomer of the title compound (Example 3) was obtained as a solid. MS=395.2 (+ESI). $^1$H NMR (300 MHz, DMSO-d$_6$) δ: 12.01 (s, 1H), 11.00 (s, 1H), 7.75 (d, J=8.1 Hz, 2H), 7.56 (d, J=8.4 Hz, 2H), 5.41 (s, 1H), 5.14 (t, J=6.3 Hz, 1H), 4.57 (d, J=6.0 Hz, 2H), 1.12 (s, 3H), 0.68-0.56 (m, 3H), 0.54-0.44 (m, 1H). The slower-eluting enantiomer of the title compound (Example 4) was obtained as a solid. MS=395.2 (+ESI). $^1$H NMR (300 MHz, DMSO-d$_6$) δ: 12.01 (s, 1H), 11.00 (s, 1H), 7.75 (d, J=8.1 Hz, 2H), 7.56 (d, J=8.4 Hz, 2H), 5.41 (s, 1H), 5.14 (t, J=6.3 Hz, 1H), 4.57 (d, J=6.0 Hz, 2H), 1.12 (s, 3H), 0.68-0.56 (m, 3H), 0.54-0.44 (m, 1H).

TABLE 13

The following compounds were prepared using procedures similar to those described in Examples 1, 2, 3, and 4 using appropriate starting materials. The appropriate cyclization conditions and deprotection conditions are also listed below. Where an "*" appears in any structure in a table it is intended to indicate a single stereoisomer where the absolute stereochemistry has not been determined.
Cyclization conditions: A: triphosgene, TEA, dioxane; B: 4-nitrophenyl chloroformate;
Deprotection conditions: C: 20% Pd(OH)$_2$/H$_2$; D: 10% Pd—C/H$_2$.

| Ex # | Structure | IUPAC Name | Exact Mass [M+H]$^+$ | C and DC* |
|---|---|---|---|---|
| 5 | 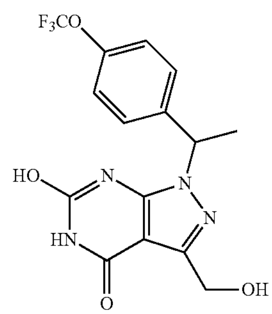 [SMILES: CC(c1ccc(OC(F)(F)F)cc1)n1nc(CO)c2c(=O)[nH]c(O)nc21] | 6-Hydroxy-3-(hydroxymethyl)-1-(trifluoromethoxy)phenyl)ethyl)-1H-pyrazolo[3,4-d]pyrimidin-4(5H)-one | Calc'd 371.1, found 371.1 | A,C |
| 6 | 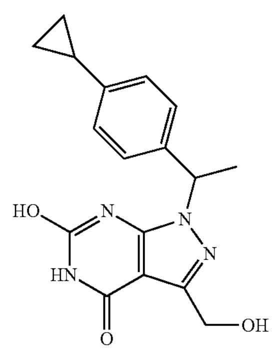 [SMILES: CC(c1ccc(C2CC2)cc1)n1nc(CO)c2c(=O)[nH]c(O)nc21] | 1-(1-(4-Cyclopropylphenyl)ethyl)-6-hydroxy-3-(hydroxymethyl)-1H-pyrazolo[3,4-d]pyrimidin-4(5H)-one | Calc'd 327.1, found 327.2 | A,C |
| 7 | 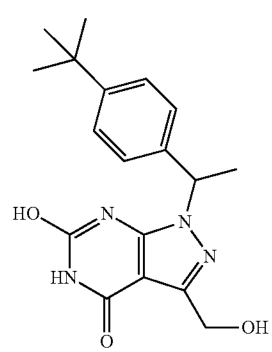 [SMILES: CC(c1ccc(C(C)(C)C)cc1)n1nc(CO)c2c(=O)[nH]c(O)nc21] | 1-(1-(4-tert-Butylphenyl)ethyl)-6-hydroxy-3-(hydroxymethyl)-1H-pyrazolo[3,4-d]pyrimidin-4(5H)-one | Calc'd 343.2, found 343.1 | A,C |

TABLE 13-continued

The following compounds were prepared using procedures similar to those described in Examples 1, 2, 3, and 4 using appropriate starting materials. The appropriate cyclization conditions and deprotection conditions are also listed below. Where an "*" appears in any structure in a table it is intended to indicate a single stereoisomer where the absolute stereochemistry has not been determined.
Cyclization conditions: A: triphosgene, TEA, dioxane; B: 4-nitrophenyl chloroformate;
Deprotection conditions: C: 20% Pd(OH)$_2$/H$_2$; D: 10% Pd—C/H$_2$.

| Ex # | Structure | IUPAC Name | Exact Mass [M+ H]$^+$ | C and DC* |
|---|---|---|---|---|
| 8 | 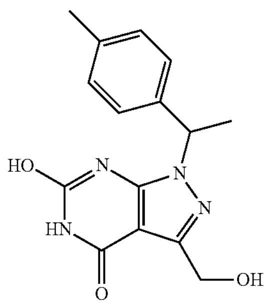 [SMILES: Cc1ccc(C(C)n2nc(CO)c3c(=O)[nH]c(O)nc32)cc1] | (6-Hydroxy-3-(hydroxymethyl)-1-(1-p-tolylethyl)-1H-pyrazolo[3,4-d]pyrimidin-4(5H)-one | Calc'd 301.1, found 301.2 | A,D |
| 9 | 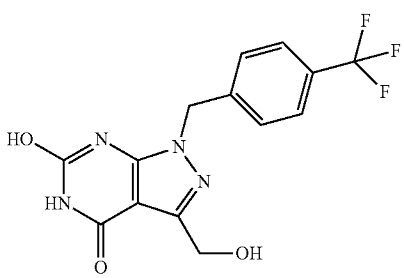 [SMILES: O=c1[nH]c(O)nc2c1c(CO)nn2Cc1ccc(C(F)(F)F)cc1] | 6-Hydroxy-3-(hydroxymethyl)-1-[4-(trifluoromethyl)benzyl]-1,5-dihydro-4H-pyrazolo[3,4-d]pyrimidin-4-one | Calc'd 341.1, found 340.9 | A,C |

*Cyclization and Deprotection Condition

TABLE 14

The following compounds were prepared using procedures similar to those described in Examples 1, 2, 3, and 4 using appropriate starting materials. Racemic products were separated using chiral columns specified in the table. For those pairs of enantiomers, the faster-eluting isomer is always listed first in this table.
Cyclization conditions: A: triphosgene, TEA, dioxane; B: 4-nitrophenyl chloroformate
Deprotection conditions: C. 20% Pd(OH)$_2$—C/H$_2$; D: 10% Pd—C/H$_2$.

| Ex # | Structure | IUPAC Name | Exact Mass [M + H]$^+$ | Chiral column | C and DC* |
|---|---|---|---|---|---|
| 10 | 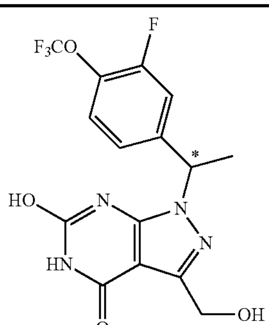 | (R)-or (S)-1-(1-(3-Fluoro-4-(trifluoromethoxy-)phenyl)ethyl)-6-hydroxy-3-(hydroxymethyl)-1H-pyrazolo[3,4-d]pyrimidin-4(5H)-one | Calc'd 389.1, found 389.3 | Chiralpak IC | A,D |

TABLE 14-continued

The following compounds were prepared using procedures similar to those described in Examples 1, 2, 3, and 4 using appropriate starting materials. Racemic products were separated using chiral columns specified in the table. For those pairs of enantiomers, the faster-eluting isomer is always listed first in this table.
Cyclization conditions: A: triphosgene, TEA, dioxane; B: 4-nitrophenyl chloroformate
Deprotection conditions: C. 20% Pd(OH)$_2$—C/H$_2$; D: 10% Pd—C/H$_2$.

| Ex # | Structure | IUPAC Name | Exact Mass [M + H]$^+$ | Chiral column | C and DC* |
|---|---|---|---|---|---|
| 11 | 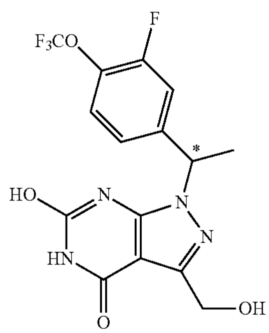 [SMILES: CC(c1ccc(OC(F)(F)F)c(F)c1)n1nc(CO)c2c(=O)[nH]c(O)nc21] | (S)-or (R)-1-(1-(3-Fluoro-4-(trifluoromethoxy)-phenyl)ethyl)-6-hydroxy-3-(hsdroxymethyl)-1H-pyrazolo[3,4-d]pyrimidin-4(5H)-one | Calc'd 389.1, found 389.3 | Chiralpak IC | A,D |
| 12 | 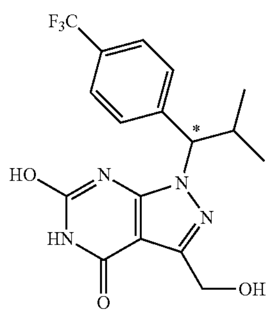 [SMILES: CC(C)C(c1ccc(C(F)(F)F)cc1)n1nc(CO)c2c(=O)[nH]c(O)nc21] | (R)-or (S)-6-Hydroxy-3-(hydroxymethyl)-1-(2-methyl-1-(4-(trifluoromethyl)phenyl)propyl)-1H-pyrazolo[3,4-d]pyrimidin-4(5H)-one | Calc'd 383.1, found 383.1 | Chiralpak AD-H | A,C |
| 13 | 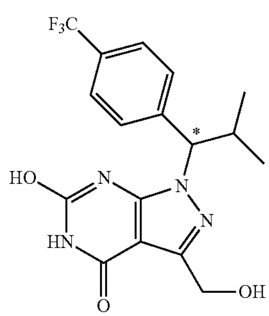 [SMILES: CC(C)C(c1ccc(C(F)(F)F)cc1)n1nc(CO)c2c(=O)[nH]c(O)nc21] | (S)- or (R)-6-Hydroxy-3-(hydroxymethyl)-1-(2-methyl-1-(4-(trifluoromethyl)phenyl)propyl)-1H-pyazolo[3,4-d]pyrimidin-4(5H)-one | Calc'd 383.1, found 383.1 | Chiralpak AD-H | A,C |
| 14 | 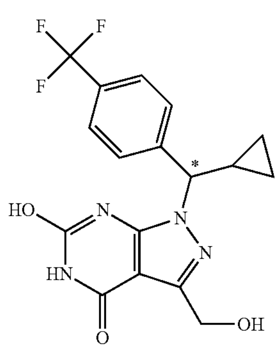 [SMILES: O=c1[nH]c(O)nc2c1c(CO)nn2C(c1ccc(C(F)(F)F)cc1)C1CC1] | (R)-or (S)-1-(Cyclopropyl(4-(trifluoromethyl)phenyl)methyl)-6-hydroxy-3-(hydroxymethyl)-1H-pyrazolo[3,4-d]pyrimidin-4(5H)-one | Calc'd 381.1, found 381.1 | Chiralcel OJ-H | A,C |

TABLE 14-continued

The following compounds were prepared using procedures similar to those described in Examples 1, 2, 3, and 4 using appropriate starting materials. Racemic products were separated using chiral columns specified in the table. For those pairs of enantiomers, the faster-eluting isomer is always listed first in this table.
Cyclization conditions: A: triphosgene, TEA, dioxane; B: 4-nitrophenyl chloroformate
Deprotection conditions: C. 20% Pd(OH)$_2$—C/H$_2$; D: 10% Pd—C/H$_2$.

| Ex # | Structure | IUPAC Name | Exact Mass [M + H]$^+$ | Chiral column | C and DC* |
|---|---|---|---|---|---|
| 15 | 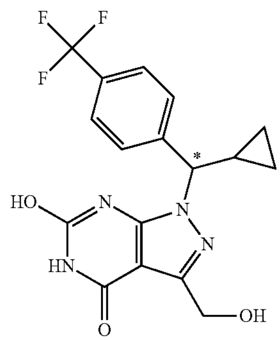 [SMILES: O=c1[nH]c(O)nc2c1c(CO)nn2C(c1ccc(C(F)(F)F)cc1)C1CC1] | (S) or (R)-1-(Cyclopropyl(4-(trifluoromethyl)phenyl)methyl)-6-hydroxy-3-(hydroxymethyl)-1H-pyrazolo[3,4-d]pyrimidin-4(5H)-one | Calc'd 381.1, found 381.1 | Chiralcel OJ-H | A,C |
| 16 | 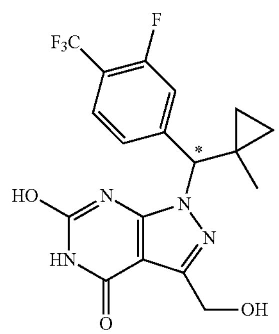 [SMILES: CC1(C(c2ccc(C(F)(F)F)c(F)c2)n2nc(CO)c3c(=O)[nH]c(O)nc32)CC1] | (R)-or (S)-1-((3-Fluoro-4-(Irifluoromethyl)phenyl)(1-melhylcyclopropyl)methyl)-6-hydroxy-3-(hydroxymethyl)-1H-pyrazolo[3,4-d]pyrimidin-4(5H)-one | Calc'd 413.1, found 413.2 | Venusil chiral OD-H | B,C |
| 17 | 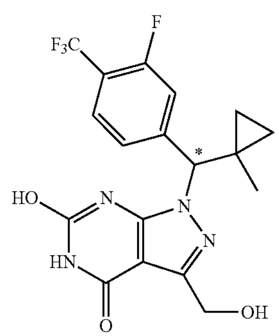 [SMILES: CC1(C(c2ccc(C(F)(F)F)c(F)c2)n2nc(CO)c3c(=O)[nH]c(O)nc32)CC1] | (S)-or (R)-1-((3-Fluoro-4-(trifluoromethyl)phenyl)(1-methylcyclopropyl(methyl)-6-hydroxy-3-(hydroxymethyl)-1H-pyrazolo[3,4-d]pyrimidin-4(5H)-one | Calc'd 413.1, found 413.2 | Venusil chiral OD-H | B,C |
| 18 | 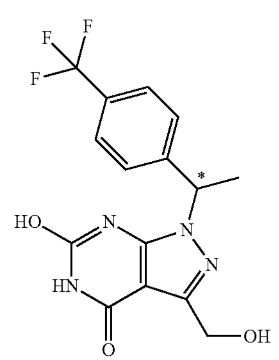 [SMILES: CC(c1ccc(C(F)(F)F)cc1)n1nc(CO)c2c(=O)[nH]c(O)nc21] | (R)- or (S)-6-Hydroxy-3-(hydroxymethyl)-1-{1-[4-(trinuoromethyl)phenyl]ethyl}-1,5-dihydro-4H-pyrazolo[3,4-d]pyrimidin-4-one | Calc'd 355.1, found 355.1 | Chiralcel OJ-H | A,C |

TABLE 14-continued

The following compounds were prepared using procedures similar to those described in Examples 1, 2, 3, and 4 using appropriate starting materials. Racemic products were separated using chiral columns specified in the table. For those pairs of enantiomers, the faster-eluting isomer is always listed first in this table.
Cyclization conditions: A: triphosgene, TEA, dioxane; B: 4-nitrophenyl chloroformate
Deprotection conditions: C. 20% Pd(OH)$_2$—C/H$_2$; D: 10% Pd—C/H$_2$.

| Ex # | Structure | IUPAC Name | Exact Mass [M + H]$^+$ | Chiral column | C and DC* |
|------|-----------|------------|------------------------|---------------|-----------|
| 19 | 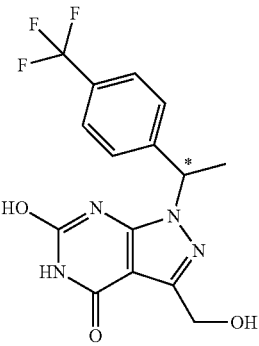 [SMILES: CC(c1ccc(C(F)(F)F)cc1)n1nc(CO)c2c(=O)[nH]c(O)nc21] | (S)- or (R)-6-Hydroxy-3-(hydroxymethyl)-1-{1-[4-(trifluoromethyl)phenyl]ethyl}-1,5-dihydro-4H-pyrazolo[3,4-d]pyrimidin-4-one | Calc'd 355.1, found 355.1 | Chiralcel OJ-H | A,C |
| 20 | 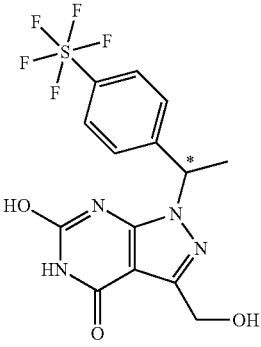 [SMILES: CC(c1ccc(S(F)(F)(F)(F)F)cc1)n1nc(CO)c2c(=O)[nH]c(O)nc21] | (R)- or (S)-6-Hydroxy-3-(hydroxymethyl)-1-{1-[4-(pentafluorosulfanyl)phenyl]ethyl}-1,5-dihydro-4H-pyrazolo[3,4-d]pyrimidin-4-one | Calc'd 413.1, found 413.1 | Chiralcel OJ-H | A,C |
| 21 | 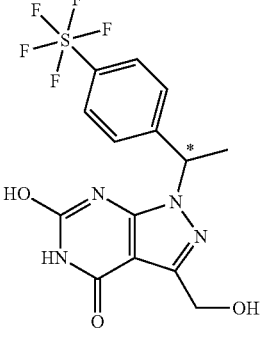 | (S)- or (R)-6-Hydroxy-3-(hydroxymethyl)-1-{1-[4-(pentafluorosulfanyl)phenyl]ethyl}-1,5-dihydro-4H-pyrazolo[3,4-d]pyrimidin-4-one | Calc'd 413.1, found 413.1 | Chiralcel OJ-H | A,C |

*Cyclization and Deprotection Condition

EXAMPLES 22 AND 23

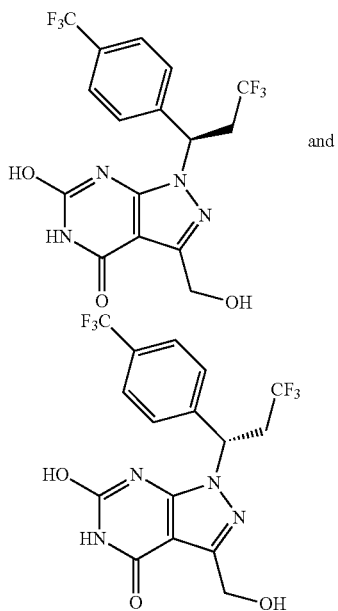

(R)- and (S)-6-Hydroxy-3-(hydroxymethyl)-1-(3,3,3-trifluoro-1-(4-(trifluoromethyl)phenyl)propyl)-1H-pyrazolo[3,4-d]pyrimidin-4(5H)-one (Scheme 21)

Step 1. 3-((Benzyloxy)methyl)-4,6-dimethoxy-1-(3,3,3-trifluoro-1-(4-(trifluoromethyl)phenyl)propyl)-1H-pyrazolo[3,4-d]pyrimidine The title compound was prepared using procedures similar to those described in step 1 of Preparatory Example 75 using 3,3,3-trifluoro-1-(4-(trifluoromethyl)phenyl)propan-1-ol and 3-((benzyloxy)methyl)-4,6-dimethoxy-1H-pyrazolo[3,4-d]pyrimidine from Preparatory Example 73 to afford an oil. MS=541.2 (+ESI).

Step 2. (4,6-Dimethoxy-1-(3,3,3-trifluoro-1-(4-(trifluoromethyl)phenyl)propyl)-1H-pyrazolo[3,4-d]pyrimidin-3-yl)methanol The title compound was prepared using procedures similar to those described in step 2 of Preparatory Example 75 using 3-((benzyloxy)methyl)-4,6-dimethoxy-1-(3,3,3-trifluoro-1-(4-(trifluoromethyl)phenyl)propyl)-1H-pyrazolo[3,4-d]pyrimidine to afford an oil. MS=451.0 (+ESI).

Step 3. (R)- and (S)-6-Hydroxy-3-(hydroxymethyl)-1-(3,3,3-trifluoro-1-(4-(trifluoromethyl)phenyl)propyl)-1H-pyrazolo[3,4-d]pyrimidin-4(5H)one To a solution of 4,6-dimethoxy-1-(3,3,3-trifluoro-1-(4-(trifluoromethyl)phenyl)propyl)-1H-pyrazolo[3,4-d]pyrimidin-3-yl)methanol (0.10 g, 0.2 mmol) in 1,4-dioxane (1.5 mL) at RT was added 4 M HCl in 1,4-dioxane (2 mL) dropwise. The reaction solution was heated to 80° C., stirred for 8 h, and cooled to room temperature. The mixture was diluted with sat. aq. NaHCO$_3$ (20 mL) and extracted with ethyl acetate (3×10 mL). The combined organic layers were washed with brine (3×20 mL), dried over sodium sulfate, filtered, and concentrated under reduced pressure. The residue was purified by preparative HPLC (X Bridge C18, 20-55% ACN in water (0.05% NH$_4$HCO$_3$)) to afford the racemic title compound as a solid. The enantiopure title compounds were obtained by chiral preparative HPLC (Phenomenex Lux 5 u Cellulose-4, AXIA Packed, 10% EtOH in hexanes). The faster-eluting enantiomer of the title compound (Example 22) was obtained as a solid. MS=423.1 (+ESI). $^1$H NMR (400 MHz, CD$_3$OD) δ: 7.78-7.71 (m, 4H), 6.04-5.99 (m, 1H), 4.76 (s, 2H), 3.70-3.62 (m, 1H), 3.18-3.10 (m, 1H). The slower-eluting enantiomer of the title compound (Example 23) was obtained as a solid. MS=423.0 (+ESI). $^1$H NMR (400 MHz, CD$_3$OD) δ: 7.74-7.69 (m, 4H), 6.04-6.01 (m, 1H), 4.77 (s, 2H), 3.71-3.62 (m, 1H), 3.22-3.10 (m, 1H).

EXAMPLE 24 AND 25

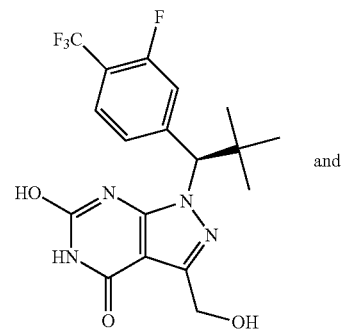

and

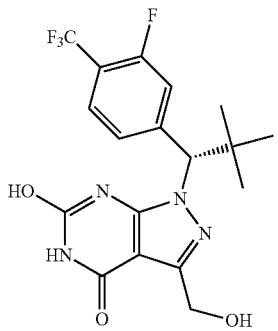

(R)- and (S)-1-(1-(3-Fluoro-4-(trifluoromethyl)phenyl)-2,2-dimethylpropyl)-6-hydroxy-3-(hydroxymethyl)-1H-pyrazolo[3,4-d]pyrimidin-4(5H)-one (Scheme 21)

Step 1. 3-(Benzyloxymethyl)-1-(1-(3-fluoro-4-(trifluoromethyl)phenyl)-22-dimethylpropyl)-4,6-dimethoxy-1H-pyrazolo[3,4-d]pyrimidine The title compound was prepared using procedures similar to those described in step 1 of Preparatory Example 75 using 1-(3-fluoro-4-(trifluoromethyl)phenyl)-2,2-dimethylpropan-1-ol and 3-((benzyloxy)methyl)-4,6-dimethoxy-H-pyrazolo[3,4-d]pyrimidine from Preparatory Example 73 to afford an oil. MS=533.3 (+ESI).

Step 2. (1-(1-(3-Fluoro-4-(trifluoromethyl)phenyl)-2,2-dimethylpropyl)-4,6-dimethoxy-1H-pyrazolo[3,4-d]pyrimidin-3-yl)methanol The title compound was prepared using procedures similar to those described in step 2 of Preparatory Example 75 using 3-(benzyloxymethyl)-1-(1-(3-fluoro-4-(trifluoromethyl)phenyl)-2,2-dimethylpropyl)-4,6-dimethoxy-1H-pyrazolo[3,4-d]pyrimidine to afford a solid. MS=443.1 (+ESI).

Step 3. (R)- and (S)-1-(1-(3-Fluoro-4-(trifluoromethyl)phenyl)-2,2-dimethylpropyl)-6-hydroxy-3-(hydroxymethyl)-1H-pyrazolo[3,4-d]pyrimidin-4(5H)-one To a solution of (1-(1-(3-fluoro-4-(trifluoromethyl)phenyl)-2,2-dimethylpropyl)-4,6-dimethoxy-1H-pyrazolo[3,4-d]pyrimidin-3-yl)methanol (60 mg, 0.14 mmol) in acetonitrile (0.5 mL) in a microwave tube at RT was added chlorotrimethylsilane (17 μL, 0.14 mmol) followed by sodium iodide (20.3 mg, 0.14 mmol). The reaction mixture was irradiated with microwave radiation at 90° C. for 30 min and was cooled to room temperature. The mixture was treated with sat. aq. sodium hydrogensulfite (2 mL) followed by dilution with water (10 mL) and extraction with ethyl acetate (3×15 mL). The combined organic layers were washed with brine (3×10 mL), dried over sodium sulfate, filtered, and concentrated under vacuum. The residue was purified by preparative HPLC (Xbridge RP18, 50-90% ACN in water (0.05% TFA)) to afford the title racemic compound as a solid. The enantiopure title compounds were obtained by chiral preparative HPLC (Chiracel OD-H, 5% ACN in hexanes (0.1% TFA)). The faster-eluting enantiomer of the title compound (Example 24) was obtained as a solid. MS=415.1 (+ESI); $^1$H NMR (300 MHz, CD$_3$OD-d$_4$) δ: 7.77-7.73 (m, 1H), 7.68-7.60 (m, 2H), 5.29 (s, 1H), 4.77 (s, 2H), 1.02 (s, 9H). The slower-eluting enantiomer of the title compound (Example 25) was obtained as a solid. MS=415.1 (+ESI); $^1$H NMR (300 MHz, CD$_3$OD-d$_4$) δ: 7.77-7.73 (m, 1H), 7.68-7.60 (m, 2H), 5.29 (s, 1H), 4.77 (s, 2H), 1.02 (s, 9H).

EXAMPLE 26

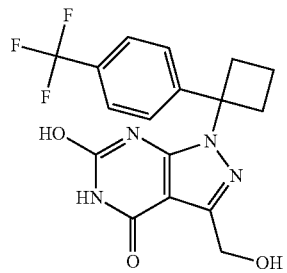 [SMILES: O=c1[nH]c(O)nc2c1c(CO)nn2C1(c2ccc(C(F)(F)F)cc2)CCC1]

6-Hydroxy-3-(hydroxymethyl)-1-(1-(4-(trifluoromethyl)phenyl)cyclobutyl)-1H-pyrazolo[3,4-d]pyrimidin-4(5H)-one (Scheme 21)

The title compound was prepared using procedures similar to those described in Examples 22 and 23 using appropriate starting materials to afford (Example 26) a solid. MS=381.2 (+ESI); $^1$H NMR (300 MHz, DMSO-d$_6$) δ: 11.42 (br, 1H), 10.28 (br, 1H), 7.72 (d, J=8.4 Hz, 2H), 7.43 (d, J=8.4 Hz, 2H), 5.35 (br, 1H), 4.57 (d, J=6.0 Hz, 2H), 3.20-3.01 (m, 2H), 2.96-2.75 (m, 2H), 2.15-1.89 (m, 2H).

TABLE 15

The following compounds were prepared using procedures similar to those described in Examples 22, 23, 24, and 25 using appropriate starting materials. Racemic products were separated using chiral columns specified in the table. For those pairs of enantiomers, the fast-eluting isomer is always listed first in this table.
Benzyl deprotection conditions: A: 20% Pd(OH)$_2$—C/H$_2$; B: 10% Pd—C/H$_2$.
Methyl deprotection conditions: C: HCl in EtOAc or 1,4-dioxane; D: TMSI, MeCN.

| Ex#. | Structure | IUPAC Name | Exact Mass [M + H]$^+$ | Column Chiral | DC* |
|---|---|---|---|---|---|
| 27 | 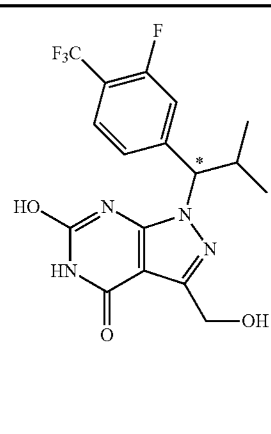 | (R)- or (S)-1-(1-(3-Fluoro-4-(trifluoromethyl)phenyl)-2-methylpropyl)-6-hydroxy-3-(hydroxymethyl)-1H-pyrazolo[3,4-d]pyrimidin-4(5H)-one | Calc'd 401.1, found 401.1 | Chiralpak IA | A,C |

TABLE 15-continued

The following compounds were prepared using procedures similar to those described in Examples 22, 23, 24, and 25 using appropriate starting materials. Racemic products were separated using chiral columns specified in the table. For those pairs of enantiomers, the fast-eluting isomer is always listed first in this table.
Benzyl deprotection conditions: A: 20% Pd(OH)$_2$—C/H$_2$; B: 10% Pd—C/H$_2$.
Methyl deprotection conditions: C: HCl in EtOAc or 1,4-dioxane; D: TMSI, MeCN.

| Ex#. | Structure | IUPAC Name | Exact Mass [M + H]$^+$ | Column Chiral | DC* |
|---|---|---|---|---|---|
| 28 | 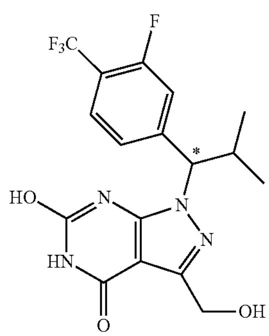 [SMILES: CC(C)C(c1ccc(C(F)(F)F)c(F)c1)n1nc(CO)c2c(=O)[nH]c(O)nc21] | (S)- or (R)-1-(1-(3-Fluoro-4-(trifluoromethyl)phenyl)-2-methylpropyl)-6-hydroxy-3-(hydroxymethyl)-1H-pyrazolo[3,4-d]pyrimidin-4(5H)-one | Calc'd 401.1, found 401.3 | Chiralpak IA | A,C |
| 29 | 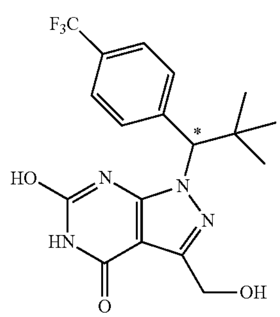 [SMILES: CC(C)(C)C(c1ccc(C(F)(F)F)cc1)n1nc(CO)c2c(=O)[nH]c(O)nc21] | (R)- or (S)-1-(2,2-Dimethyl-1-(4-(trifluoromethyl)phenyl)propyl)-6-hydroxy-3-(hydroxymethyl)-1H-pyrazolo[3,4-d]pyrimidin-4(5H)-one | Calc'd 397.1, found 397.1 | Chiralpak AD-H | A,D |
| 30 | 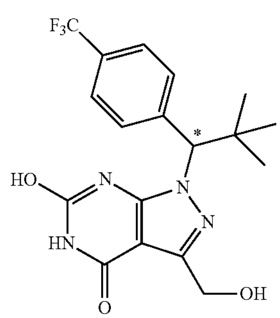 [SMILES: CC(C)(C)C(c1ccc(C(F)(F)F)cc1)n1nc(CO)c2c(=O)[nH]c(O)nc21] | (S)- or (R)-1-(2,2-Dimethyl-1-(4-(trifluoromethyl)phenyl)propyl)-6-hydroxy-3-(hydroxymethyl)-1H-pyrazolo[3,4-d]pyrimidin-4(5H)-one | Calc'd 397.1, found 397.1 | Chiralpak AD-H | A,D |
| 31 | 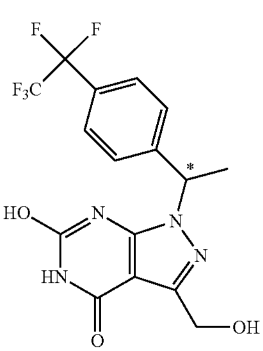 [SMILES: CC(c1ccc(C(F)(F)C(F)(F)F)cc1)n1nc(CO)c2c(=O)[nH]c(O)nc21] | (R)- or (S)-6-Hydroxy-3-(hydroxymethyl)-1-(1-(4-(perfluoroethyl)phenyl)ethyl)-1H-pyrazolo[3,4-d]pyrimidin-4(5H)-one | Calc'd 405.1, found 405.0 | Chiralpak AS-H | A,C |

TABLE 15-continued

The following compounds were prepared using procedures similar to those described in Examples 22, 23, 24, and 25 using appropriate starting materials. Racemic products were separated using chiral columns specified in the table. For those pairs of enantiomers, the fast-eluting isomer is always listed first in this table.
Benzyl deprotection conditions: A: 20% Pd(OH)$_2$—C/H$_2$; B: 10% Pd—C/H$_2$.
Methyl deprotection conditions: C: HCl in EtOAc or 1,4-dioxane; D: TMSI, MeCN.

| Ex#. | Structure | IUPAC Name | Exact Mass [M + H]$^+$ | Column Chiral | DC* |
|---|---|---|---|---|---|
| 32 | 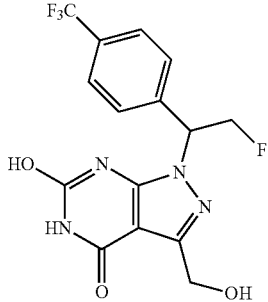 [SMILES: O=c1[nH]c(O)nc2c1c(CO)nn2C(CF)c1ccc(C(F)(F)F)cc1] | (S)- or (R)-6-Hydroxy-3-(hydroxymethyl)-1-(1-(4-(perfluoroethyl)phenyl)ethyl)-1H-pyrazolo[3,4-d]pyrimidin-4(5H)-one | Calc'd 405.1, found 405.0 | Chiralpak AS-H | A,C |

*Deprotection Condition

EXAMPLE 33

1-(2-Fluoro-1-(4-(trifluoromethyl)phenyl)ethyl)-6-hydroxy-3-(hydroxymethyl)-1H-pyrazolo[3,4-d]pyrimidin-4(5H)-one (Scheme 21)

Step 1. Methyl 2-(3-((benzyloxy)methyl)-4,6-dimethoxy-1H-pyrazolo[3,4-d]pyrimidin-1-yl)-2-(4-(trifluoromethyl)phenyl)acetate To a solution of 3-((benzyl-oxy)methyl)-4,6-dimethoxy-1H-pyrazolo[3,4-d]pyrimidine (0.56 g, 1.9 mmol) in DMF (11 mL) at room temperature was added sodium hydride (0.11 g, 2.8 mmol). The reaction mixture was stirred for 1 h at RT whereupon a solution of methyl 2-bromo-2-(4-(trifluoromethyl)phenyl)acetate (0.83 g, 2.8 mmol) (*Tetrahedron*, 2011, 67, 758 6) in DMF (3 mL) was added dropwise. The reaction mixture was stirred for 16 h at room temperature whereupon water (10 mL) was added and then extracted with EtOAc (3×30 mL). The combined organic fractions were washed with water (2×20 mL), brine (20 mL), dried over Na$_2$SO$_4$, filtered, an d concentrated under reduced pressure. The residue was purified by silica gel column chromatograph y (0-30% ethyl acetate in petroleum ether) to afford the title compound as an oil. MS=517.1 (+ESI).

Step 2. 2-(3-((Benzyloxy)methyl)-4,6-dimethoxy-1H-pyrazolo[3,4-d]pyrimidin-1-yl)-2-(4-(trifluoromethyl)phenyl)ethanol To a mixture of methyl 2-(3-((benzyloxy)methyl)-4,6-dimethoxy-1H-pyrazolo[3,4-d]pyrimidin-1-yl)-2-(4-(trifluoromethyl) phenyl)acetate (0.50 g, 1.0 mmol) in methanol (10 mL) at RT was added NaBH$_4$ (73 mg, 1.9 mmol). The reaction mixture was stirred at room temperature for 16 h and the mixture was concentrated under vacuum. The residue suspended in water (10 mL) and extracted with EtOAc (3×20 mL). The combined organic fractions were washed with brine (10 mL), dried over Na$_2$SO$_4$, filtered, and concentrated under vacuum to afford the title crude compound as an oil. MS=489.3 (+ESI).

Step 3. 3-((Benzyloxy)methyl)-1-(2-fluoro-1-(4-(trifluoromethyl)phenyl)ethyl)-4,6-dimethoxy-1H-pyrazolo[3,4-d]pyrimidine To a solution of 2-(3-((benzyloxy)methyl)-4,6-dimethoxy-1H-pyrazolo[3,4-d]pyrimidin-1-yl)-2-(4-(trifluoromethyl)phenyl)ethanol (0.10 g, 0.2 mmol) in DCM (3 mL) at 0° C. was added DAST (0.14 mL, 1.02 mmol) dropwise. The mixture was stirred at room temperature 1 h and was cooled to 0° C. The mixture was diluted with dichloromethane (15 mL) and the organic layer was washed with sat. aq. sodium hydrogen carbonate (2×10 mL). The organic layer was dried over Na$_2$SO$_4$, filtered and concentrated under reduced pressure. The residue was purified by silica gel column chromatography (0-35% ethyl acetate in petroleum ether) to afford the title compound as an oil. MS=491.3 (+ESI).

Step 4. 3-((Benzyloxy)methyl)-1-(2-fluoro-1-(4-(trifluoromethyl)phenyl)ethyl)-6-hydroxy-1H-pyrazolo[3,4-d]pyrimidin-4(5H)-one Iodotrimethylsilane (85 µL, 0.6 mmol) was added to the solution of 3-((benzyloxy)methyl)-1-(2-fluoro-1-(4-(trifluoromethyl)phenyl)ethyl)-4,6-dimethoxy- 1H-pyrazolo[3,4-d]pyrimidine (50 mg, 0.1 mmol) in DCM (3 mL) at room temperature. The resulting mixture was stirred for 2 h at 80° C., cooled to RT, and quenched with sat. aq. sodium bisulfate (2 mL). The resulting mixture was extracted with ethyl acetate (3×5 mL). The combined organic fractions were washed with brine (2×5 mL), dried over sodium sulfate, filtered, and concentrated under reduced pressure to afford the title compound as a solid. MS=463.2 (+ESI).

Step 5: 1-(2-Fluoro-1-(4-(trifluoromethyl)phenyl)ethyl)-6-hydroxy-3-(hydroxymethyl)-1H-pyrazolo[3,4-d]pyrimidin-4(5H)-one The title compound was prepared using procedures similar to those described in step of Preparatory Example 75 using 3-((benzyloxy)methyl)-1-(2-fluoro-1-(4-(trifluoromethyl)phenyl)ethyl)-6-hydroxy-1H-pyrazolo[3,4-d]pyrimidin-4(5H)-one to afford (Example 33) as a solid. MS=373.1 (+ESI). $^1$H NMR (400 MHz, DMSO-$d_6$) δ: 12.26 (br, 1H), 11.03 (br, 1H), 7.80 (d, J=8.4 Hz, 2H), 7.64 (d, J=8.4 Hz, 2H), 6.15-6.08 (m, 1H), 5.30-5.13 (m, 2H), 5.10-5.06 (m, 1H), 4.59-4.55 (m, 2H).

EXAMPLES 34 AND 35

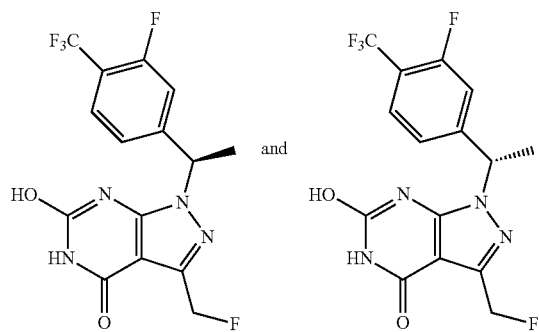 [SMILES: C[C@H](c1ccc(C(F)(F)F)c(F)c1)n1nc(CF)c2c(=O)[nH]c(O)nc21 ; C[C@@H](c1ccc(C(F)(F)F)c(F)c1)n1nc(CF)c2c(=O)[nH]c(O)nc21]

(R)- and (S)-1-(1-(3-Fluoro-4-(trifluoromethyl)phenyl)ethyl)-3-(fluoromethyl)-6-hydroxy-H-pyrazolo[3,4-d]pyrimidin-4(5H)-one (Scheme 23)

Step 1. 5-Amino-1-(1-(3-fluoro-4-(trifluoromethyl)phenyl)ethyl)-3-(hydroxymethyl)-1H-pyrazole-4-carboxamide The title compound was prepared using procedures similar to those described in step 2 of Preparatory Example 75 using 5-amino-3-((benzyloxy)methyl)-1-(1-(3-fluoro-4-(trifluoromethyl)phenyl)ethyl)-1H-pyrazole-4-carboxamide to afford an oil. $^1$H NMR (300 MHz, CD$_3$OD) δ: 7.56-7.50 (m, 1H), 7.10-7.02 (m, 2H), 5.43 (q, J=6.9 Hz, 1H), 4.49 (s, 2H), 1.72 (d, J=6.9 Hz, 3H).

Step 2. 5-Amino-1-(1-(3-fluoro-4-(trifluoromethyl)phenyl)ethyl)-3-(fluoromethyl)-1H-pyrazole-4-carboxamide The title compound was prepared using procedures similar to those described in step 3 of Example 33 using 5-amino-1-(1-(3-fluoro-4-(trifluoromethyl)phenyl)ethyl)-3-(hydroxymethyl)-1H-pyrazole-4-carboxamide to afford an oil. MS=349.1 (+ESI).

Step 3. (R)- and (S)-1-(1-(3-Fluoro-4-(trifluoromethyl)phenyl)ethyl)-3-(fluoromethyl)-6-hydroxy-1H-pyrazolo[3,4-d]pyrimidin-4(5H)-one To a pressure tube containing a solution 5-amino-1-(1-(3-fluoro-4-(trifluoromethyl)phenyl)ethyl)-3-(fluoromethyl)-1H-pyrazole-4-carboxamide (0.23 g, 0.7 mmol) in 1,4-dioxane (1 mL) at RT was added ethyl chloroformate (0.143 g, 1.3 mmol). The tube was capped, heated to 100° C., and stirred for 16 h. The reaction mixture was cooled to room temperature and water (5 mL) was added. The mixture was extracted with DCM (3×10 mL) and the combined organic layers were dried over Na$_2$SO$_4$, filtered, and concentrated under vacuum. The residue was purified by preparative HPLC (X Bridge C18, 30-70% ACN in water (0.05% TFA)) to afford the racemic title compound as a solid. The enantiopure title compounds were obtained by chiral preparative HPLC (Chiralpak AS-H, 80% isopropanol in hexanes (0.1% TFA)). The faster-eluting enantiomer of the title compound (Example 34) was obtained as a solid. MS=375.1 (+ESI). $^1$H NMR (300 MHz, DMSO-$d_6$) δ: 12.18 (br s, 1H), 11.00 (br s, 1H), 7.82-7.75 (m, 1H), 7.46 (d, J=12.0 Hz, 1H), 7.29 (d, J=8.7 Hz, 1H), 5.89 (q, J=7.2 Hz, 1H), 5.44 (d, J=47.4 Hz, 2H), 1.82 (d, J=7.2 Hz, 3H). The slower-eluting enantiomer of the title compound (Example 35) was obtained as a solid. MS 375.1 (+ESI). $^1$H NMR (300 MHz, DMSO-$d_6$) δ: 12.18 (br s, 1H), 11.00 (br s, 1H), 7.82-7.75 (m, 1H), 7.46 (d, J=12.0 Hz, 1H), 7.29 (d, J=8.7 Hz, 1H), 5.89 (q, J=7.2 Hz, 1H), 5.44 (d, J=47.4 Hz, 2H), 1.82 (d, J=7.2 Hz, 3H).

TABLE 16

The following compounds were prepared using procedures similar to those described in Examples 34 and 35 using appropriate starting materials. The benzyl group deprotection and cyclization conditions are listed below.
Deprotection(Bn) conditions: A: 20% Pd(OH)$_2$/H$_2$; B: 10% Pd—C/H$_2$.
Cyclization conditions: C: triphosgene, TEA, dioxane; D: ethyl chloroformate, 1,4-dioxane

| Ex # | Structure | IUPAC Name | Exact Mass [M + H]$^+$ | C and DC* |
|---|---|---|---|---|
| 36 | 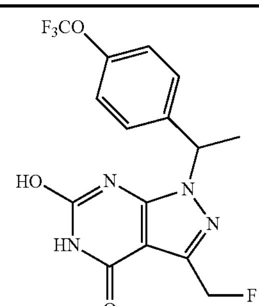 | 3-(Fluoromethyl)-6-hydroxy-1-(1-(4-(trifluoromethoxy)phenyl)ethyl)-1H-pyrazolo[3,4-d]pyrimidin-4(5H)-one | Calc'd 373.1, found 373.1 | B,D |

TABLE 16-continued

The following compounds were prepared using procedures similar to those described in Examples 34 and 35 using appropriate starting materials. The benzyl group deprotection and cyclization conditions are listed below.

Deprotection(Bn) conditions: A: 20% Pd(OH)$_2$/H$_2$; B: 10% Pd—C/H$_2$.
Cyclization conditions: C: triphosgene, TEA, dioxane; D: ethyl chloroformate, 1,4-dioxane

| Ex # | Structure | IUPAC Name | Exact Mass [M + H]$^+$ | C and DC* |
|---|---|---|---|---|
| 37 | 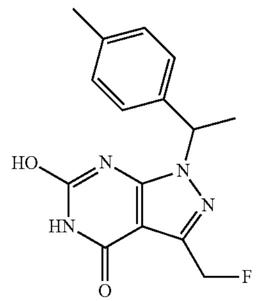 [SMILES: Cc1ccc(C(C)n2nc(CF)c3c(=O)[nH]c(O)nc32)cc1] | 3-(Fluoromethyl)-6-hydroxy-1-(1-p-tolylethyl)-1H-pyrazolo[3,4-d]pyrimidin-4(5H)-one | Calc'd 303.1, found 303.2 | B,D |
| 38 | 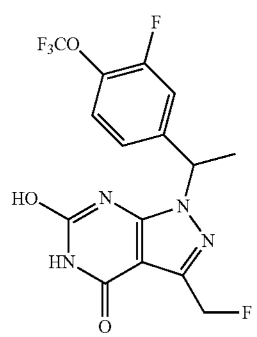 [SMILES: CC(c1ccc(OC(F)(F)F)c(F)c1)n1nc(CF)c2c(=O)[nH]c(O)nc21] | 1-(1-(3-Fluoro-4-(trifluoromethoxy)phenyl)ethyl)-3-(fluoromethyl)-6-hydroxy-1H-pyrazolo[3,4-d]pyrimidin-4(5H)-one | Calc'd 391.1, found 391.1 | B,C |
| 39 | 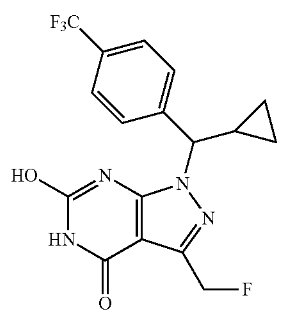 [SMILES: O=c1[nH]c(O)nc2c1c(CF)nn2C(c1ccc(C(F)(F)F)cc1)C1CC1] | 1-(Cyclopropyl(4-(trifluoromethyl)phenyl)methyl)-3-(fluoromethyl)-6-hydroxy-1H-pyrazolo[3,4-d]pyrimidin-4(5H)-one | Calc'd 383.1, found 383.1 | A,C |
| 40 | 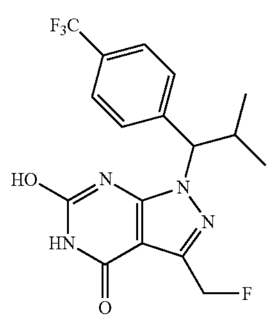 [SMILES: CC(C)C(c1ccc(C(F)(F)F)cc1)n1nc(CF)c2c(=O)[nH]c(O)nc21] | 3-(Fluoromethyl)-6-hydroxy-1-(2-methyl-1-(4-(trifluoromethyl)phenyl)propyl)-1H-pyrazolo[3,4-d]pyrimidin-4(5H)-one | Calc'd 385.1, found 385.1 | B,C |

TABLE 16-continued

The following compounds were prepared using procedures similar to those described in Examples 34 and 35 using appropriate starting materials. The benzyl group deprotection and cyclization conditions are listed below.

Deprotection(Bn) conditions: A: 20% Pd(OH)$_2$/H$_2$; B: 10% Pd—C/H$_2$.

Cyclization conditions: C: triphosgene, TEA, dioxane; D: ethyl chloroformate, 1,4-dioxane

| Ex # | Structure | IUPAC Name | Exact Mass [M + H]$^+$ | C and DC* |
|---|---|---|---|---|
| 41 | 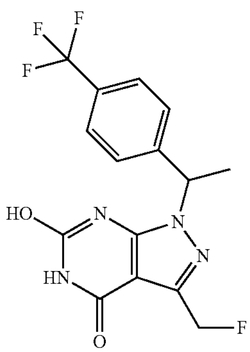 [SMILES: CC(c1ccc(C(F)(F)F)cc1)n1nc(CF)c2c(=O)[nH]c(O)nc21] | 3-(Fluoromethyl)-6-hydroxy-1-{1-[4-(trifluoromethyl)phenyl]ethyl}-1,5-dihydro-4H-pyrazolo[3,4-d]pyrimidin-4-one | Calc'd 357.1, found 357.2 | B,C |

*Cyclization and Deprotection Condition

TABLE 17

The following compounds were prepared using procedures similar to those described in Examples 34 and 35 using appropriate starting materials. Racemic products were separated using chiral columns specified in the table. For those pairs of enantiomers, the faster-eluting isomer is always listed first in this table.
Deprotection(Bn) conditions: A: 20% Pd(OH)$_2$/H$_2$
Cyclization conditions: B: 4-nitrophenyl chloroformate.

| Ex # | Structure | IUPAC Name | Exact Mass [M + H]$^+$ | Chiral column | C/DC* |
|---|---|---|---|---|---|
| 42 | 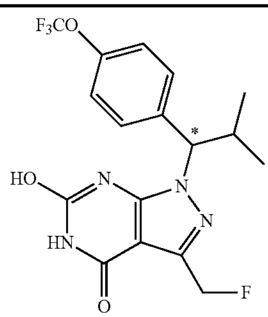 | (R)- or (S)-3-(Fluoromethyl)-6-hydroxy-1-(2-methyl-1-(4-(trifluoromethoxy)phenyl)propyl)-1H-pyrazolo[3,4-d]pyrimidin-4(5H)-one | Calc'd 401.1, found 401.2 | Chiralcel OD-H | A,B |
| 43 | 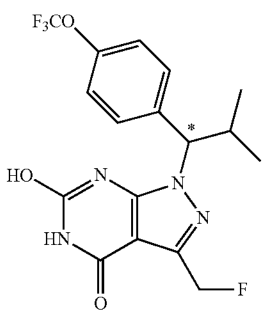 [SMILES: CC(C)C(c1ccc(OC(F)(F)F)cc1)n1nc(CF)c2c(=O)[nH]c(O)nc21] | (S)- or (R)-3-(Fluoromethyl)-6-hydroxy-1-(2-methyl-1-(4-(trifluoromethoxy)phenyl)propyl)-1H-pyrazolo[3,4-d]pyrimidin-4(5H)-one | Calc'd 401.1, found 401.3 | Chiralcel OD-H | A,B |

*Cyclization and Deprotection Condition

EXAMPLE 44 AND 45

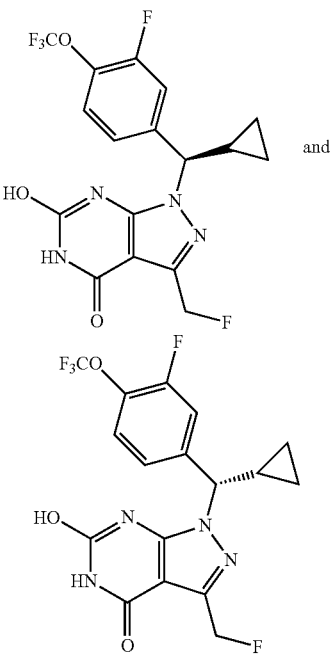

(R)- and (S)-1-(Cyclopropyl(3-fluoro-4-(trifluoromethoxy)phenyl)methyl)-3-(fluoromethyl)-6-hydroxy-1H-pyrazolo[3,4-d]pyrimidin-4(5H)-one (Scheme 24)

Step 1. 3-((Benzyloxy)methyl)-1-(cyclopropyl(3-fluoro-4-(trifluoromethoxy)phenyl)methyl)-4,6-dimethoxy-1H-pyrazolo[3,4-d]pyrimidine The title compound was prepared using procedures similar to those described in step 1 of Preparatory Example 75 using 3-((benzyloxy)methyl)-4,6-dimethoxy-1H-pyrazolo[3,4-d]pyrimidine from Preparatory Example 73 and cyclopropyl(3-fluoro-4-(trifluoromethoxy)phenyl)methanol as an oil. MS=533.5 (+ESI).

Step 2. (1-(Cyclopropyl(3-fluoro-4-(trifluoromethoxy)phenyl)methyl)-4,6-dimethoxy-1H-pyrazolo[3,4-d]pyrimidin-3-yl)methanol The title compound was prepared using procedures similar to those described in step 2 of Preparatory Example 75 using 3-((benzyloxy)methyl)-1-(cyclopropyl(3-fluoro-4-(trifluoromethoxy)phenyl)methyl)-4,6-dimethoxy-1H-pyrazolo[3,4-d]pyrimidine to afford an oil which was used in the next step directly without purification. MS=443.3 (+ESI).

Step 3. 1-(Cyclopropyl(3-fluoro-4-(trifluoromethoxy)phenyl)methyl)-3-(fluoromethyl)-4,6-dimethoxy-1H-pyrazolo[34-d]pyrimidine The title compound was prepared using procedures similar to those described in step 3 of Example 33 using (1-(cyclopropyl(3-fluoro-4-(trifluoromethoxy)phenyl)methyl)-4,6-dimethoxy-1H-pyrazolo[3,4-d]pyrimidin-3-yl)methanol to afford an oil. MS=445.2 (+ESI).

Step 4. (R)- and (S)-1-(Cyclopropyl(3-fluoro-4-(trifluoromethoxy)phenyl)methyl)-3-(fluoromethyl)-6-hydroxy-1H-pyrazolo[3,4-d]pyrimidin-4(5H)-one The racemic title compound was prepared using procedures similar to those described in step 4 of Examples 22 and 23 using 1-(cyclopropyl(3-fluoro-4-(trifluoromethoxy)phenyl)methyl)-3-(fluoromethyl)-4,6-dimethoxy-1H-pyrazolo[3,4-d]pyrimidine to afford a solid. The enantiopure title compounds were obtained by chiral preparative HPLC (Chiralpak IA, 15% EtOH in hexanes (0.1% TFA)). The faster-eluting enantiomer of the title compound (Example 44) was obtained as a solid. MS=417.2 (+ESI). $^1$H NMR (300 MHz, CD$_3$OD) δ: 7.45-7.37 (m, 2H), 7.26 (d, J=8.4 Hz, 1H), 5.45 (d, J=49.8 Hz, 2H), 4.72 (d, J=9.9 Hz, 1H), 1.91-1.83 (m, 1H), 0.89-0.82 (m, 1H), 0.73-0.64 (m, 1H), 0.58-0.42 (m, 2H). The slower-eluting enantiomer of the title compound (Example 45) was obtained as a solid. MS=417.2 (+ESI). $^1$H NMR (300 MHz, CD$_3$OD) δ: 7.45-7.37 (m, 2H), 7.26 (d, J=8.4 Hz, 1H), 5.45 (d, J=49.8 Hz, 2H), 4.72 (d, J=9.9 Hz, 1H), 1.91-1.83 (m, 1H), 0.89-0.82 (m, 1H), 0.73-0.64 (m, 1H), 0.58-0.42 (m, 2H).

TABLE 18

The following compounds were prepared using procedures similar to those described in Examples 44 and 45 using appropriate starting materials. For Examples 47, 48, 49, and 50, the required enantioenriched alcohol was used in the Mitsunobu step. The benzyl group and methoxy group deprotection conditions are also listed in the table.
Deprotection(Bn) conditions: A: 20% Pd(OH)$_2$/H$_2$; B: 10% Pd—C/H$_2$
Deprotection(Me) conditions: C: HCl in EtOAc or 1,4-dioxane; D: TMSI.

| Ex # | Structure | IUPAC Name | Exact Mass [M + H]$^+$ | DC* |
|---|---|---|---|---|
| 46 | ![structure] | 3-(Fluoromethyl)-6-hydroxy-1-(1-(4-(trifluoromethyl)phenyl)cyclobutyl)-1H-pyrazolo[3,4-d]pyrimidin-4(5H)-one | Calc'd 383.1, found 383.2 | A,C |

TABLE 18-continued

The following compounds were prepared using procedures similar to those described in Examples 44 and 45 using appropriate starting materials. For Examples 47, 48, 49, and 50, the required enantioenriched alcohol was used in the Mitsunobu step. The benzyl group and methoxy group deprotection conditions are also listed in the table.

Deprotection(Bn) conditions: A: 20% Pd(OH)$_2$/H$_2$; B: 10% Pd—C/H$_2$
Deprotection(Me) conditions: C: HCl in EtOAc or 1,4-dioxane; D: TMSI.

| Ex # | Structure | IUPAC Name | Exact Mass [M + H]$^+$ | DC* |
|---|---|---|---|---|
| 47 | 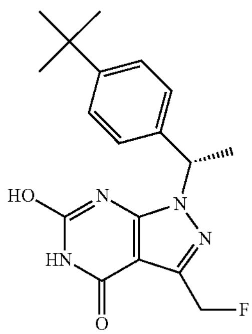 [SMILES: C[C@@H](c1ccc(C(C)(C)C)cc1)n1nc(CF)c2c(=O)[nH]c(O)nc21] | (S)-1-(1-(4-tert-Butylphenyl)ethyl)-3-(fluoromethyl)-6-hydroxy-1H-pyrazolo[3,4-d]pyrimidin-4(5H)-one | Calc'd 345.2, found 345.2 | A,C |
| 48 | 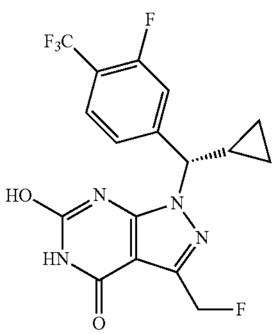 [SMILES: O=c1[nH]c(O)nc2c1c(CF)nn2[C@H](c1ccc(C(F)(F)F)c(F)c1)C1CC1] | (S)-1-(Cyclopropyl(3-fluoro-4-(trifluoromethyl)phenyl)methyl)-3-(fluoromethyl)-6-hydroxy-1H-pyrazolo[3,4-d]pyrimidin-4(5H)-one | Calc'd 401.1, found 401.2 | A,C |
| 49 | 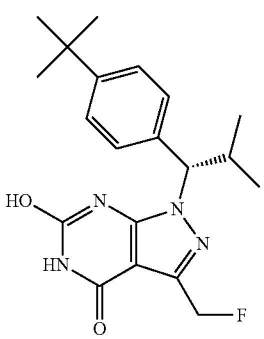 [SMILES: CC(C)[C@@H](c1ccc(C(C)(C)C)cc1)n1nc(CF)c2c(=O)[nH]c(O)nc21] | (S)-1-(1-(4-tert-Butylphenyl)-2-methylpropyl)-3-(fluoromethyl)-6-hydroxy-1H-pyrazolo[3,4-d]pyrimidin-4(5H)-one | Calc'd 373.2, found 373.2 | A,C |
| 50 | 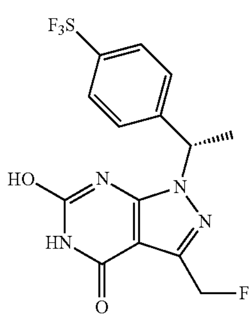 | (S)-3-(Fluoromethyl)-6-hydroxy-1-(1-(4-(pentafluorothio)phenyl)ethyl)-1H-pyrazolo[3,4-d]pyrimidin-4(5H)-one | Calc'd 415.1, found 415.1 | B,C |

TABLE 18-continued

The following compounds were prepared using procedures similar to those described in Examples 44 and 45 using appropriate starting materials. For Examples 47, 48, 49, and 50, the required enantioenriched alcohol was used in the Mitsunobu step. The benzyl group and methoxy group deprotection conditions are also listed in the table.
Deprotection(Bn) conditions: A: 20% Pd(OH)$_2$/H$_2$; B: 10% Pd—C/H$_2$
Deprotection(Me) conditions: C: HCl in EtOAc or 1,4-dioxane; D: TMSI.

| Ex # | Structure | IUPAC Name | Exact Mass [M + H]$^+$ | DC* |
|---|---|---|---|---|
| 51 | 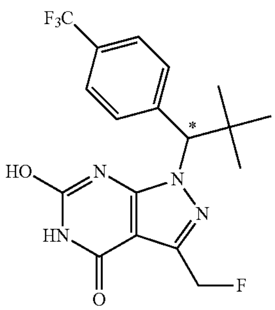 [SMILES: CC(C)(C)C(c1ccc(C(F)(F)F)cc1)n1nc(CF)c2c(=O)[nH]c(O)nc21] | (R)- or (S)-1-(2,2-Dimethyl-1-(4-(trifluoromethyl)phenyl)propyl)-3-(fluoromethsl)-6-hydroxy-1H-pyrazolo[3,4-d]pyrimidin-4(5H)-one | Calc'd 399.1, found 399.1 | A,D |
| 52 | 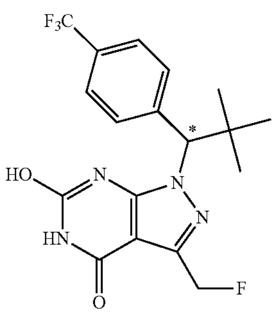 [SMILES: CC(C)(C)C(c1ccc(C(F)(F)F)cc1)n1nc(CF)c2c(=O)[nH]c(O)nc21] | (S)- or (R)-1-(2,2-Dimethyl-1-(4-(trifluoromethyl)phenyl)propyl)-3-(fluoromethyl)-6-hydroxy-1H-pyrazolo[3,4-d]pyrimidin-4(5H)-one | Calc'd 399.1, found 399.1 | A,D |

*Deprotection conditions:

TABLE 19

The following compounds were prepared using procedures similar to those described in Examples 44 and 45 using appropriate starting materials. Racemic products were separated using chiral columns specified in the table. For those pairs of enantiomers, the faster-eluting isomer is always listed first in this table. The deprotection conditions for each example are also listed in the table.
Deprotection(Bn) conditions: A: 20% Pd(OH)$_2$/H$_2$; B: 10% Pd—C/H$_2$
Deprotection(Me) conditions: C: HCl in EtOAc or 1,4-dioxane; D: TMSI.

| Ex# | Structure | IUPAC Name | Exact Mass [M + H]$^+$ | Chiral column | DC* |
|---|---|---|---|---|---|
| 53 | 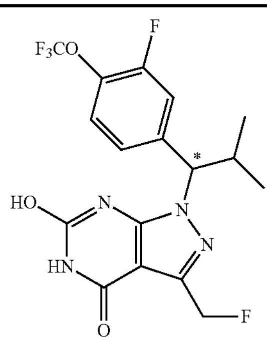 | (R)- or (S)-1-(1-(3-Fluoro-4-(trifluoromethoxy)phenyl)-2-methylpropyl)-3-(fluoromethyl)-6-hydroxy-1H-pyrazolo[3,4-d]pyrimidin-4(5H)-one | Calc'd 419.1, found 419.2 | Chiral pak IA | A,C |

TABLE 19-continued

The following compounds were prepared using procedures similar to those described in Examples 44 and 45 using appropriate starting materials. Racemic products were separated using chiral columns specified in the table. For those pairs of enantiomers, the faster-eluting isomer is always listed first in this table. The deprotection conditions for each example are also listed in the table.

Deprotection(Bn) conditions: A: 20% Pd(OH)$_2$/H$_2$; B: 10% Pd—C/H$_2$
Deprotection(Me) conditions: C: HCl in EtOAc or 1,4-dioxane; D: TMSI.

| Ex# | Structure | IUPAC Name | Exact Mass [M + H]$^+$ | Chiral column | DC* |
|---|---|---|---|---|---|
| 54 | 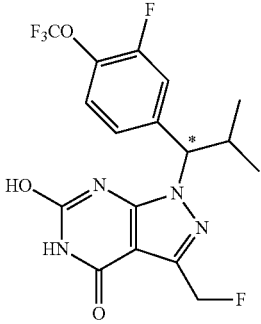 [SMILES: CC(C)C(c1ccc(OC(F)(F)F)c(F)c1)n1nc(CF)c2c(=O)[nH]c(O)nc21] | (S)- or (R)-1-(1-(3-Fluoro-4-(trifluoromethoxy)phenyl)-2-methylpropyl)-3-(fluoromethyl)-6-hydroxy-1H-pyrazolo[3,4-d]pyrimidin-4(5H)-one | Calc'd 419.1, found 419.2 | Chiral pak IA | A,C |
| 55 | 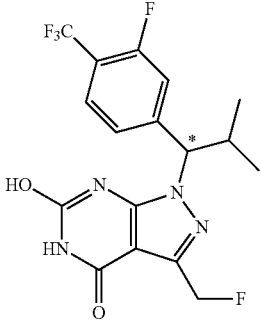 [SMILES: CC(C)C(c1ccc(C(F)(F)F)c(F)c1)n1nc(CF)c2c(=O)[nH]c(O)nc21] | (R)- or (S)-1-(1-(3-Fluoro-4-(trifluoromethyl)phenyl)-2-methylpropyl)-3-(fluoromethyl)-6-hydroxy-1H-pyrazolo[3,4-d]pyrimidin-4(5H)-one | Calc'd 403.1, found 403.2 | Chiral pak IA | A,C |
| 56 | 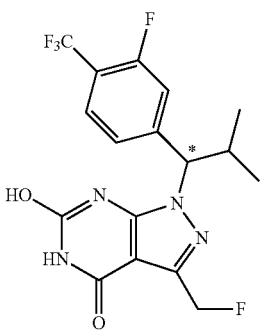 [SMILES: CC(C)C(c1ccc(C(F)(F)F)c(F)c1)n1nc(CF)c2c(=O)[nH]c(O)nc21] | (S)- or (R)-1-(1-(3-Fluoro-4-(trifluoromethyl)phenyl)-2-methylpropyl)-3-(fluoromethyl)-6-hydroxy-1H-pyrazolo[3,4-d]pyrimidin-4(5H)-one | Calc'd 403.1, found 403.1 | Chiral pak IA | A,C |

*Deprotection conditions:

EXAMPLE 57

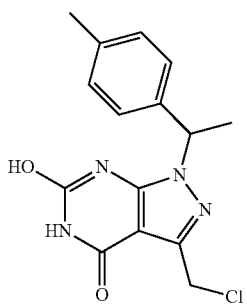 [SMILES: Cc1ccc(C(C)n2nc(CCl)c3c(=O)[nH]c(O)nc32)cc1]

3-(Chloromethyl)-6-hydroxy-1-(1-p-tolylethyl)-1H-pyrazolo[3,4-d]pyrimidin-4(5H)-one (Scheme 25)

Ethyl chloroformate (81 μL, 0.8 mmol) was added to a solution of 5-amino-1-(1-(3-fluoro-4-(trifluoromethyl)phenyl)ethyl)-3-(fluoromethyl)-1H-pyrazole-4-carboxamide (70 mg, 0.3 mmol) in 1,4-dioxane (1 mL) in a pressure tube. The tube was capped, heated to 100° C., and stirred for 2 days. The mixture was cooled to room temperature and diluted with water (5 mL) and extracted with EtOAc (3×5 mL). The combined organic layers were dried over $Na_2SO_4$, filtered, and concentrated under vacuum. The residue was purified by silica gel column chromatography (30% ethyl acetate in petroleum ether) to afford the title compound (Example 57) as a solid. MS=319.2, 321.2 (+ESI). $^1$H NMR (400 MHz, DMSO-$d_6$) δ: 12.17 (br, 1H), 10.96 (br, 1H), 7.19 (d, J=8.0 Hz, 2H), 7.15 (d, J=8.0 Hz, 2H), 5.75 (q, J=6.8 Hz, 1H), 4.75 (s, 2H), 2.26 (s, 3H), 1.76 (d, J=6.8 Hz, 3H).

TABLE 20

The following compounds were prepared using procedures similar to those described in Example 57 using appropriate starting materials.

| Ex # | Structure | IUPAC Name | Exact Mass [M + H]$^+$ |
|---|---|---|---|
| 58 | 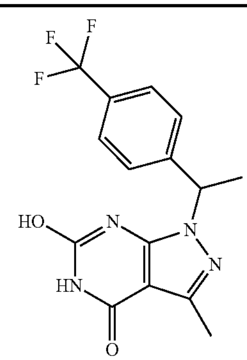 | 6-Hydroxy-3-methyl-1-{1-[4-(trifluoromethyl)phenyl]ethyl}-1,5-dihydro-4H-pyrazolo[3,4-d]pyrimidin-4-one | Calc'd 339.1, found 339.3 |
| 59 | 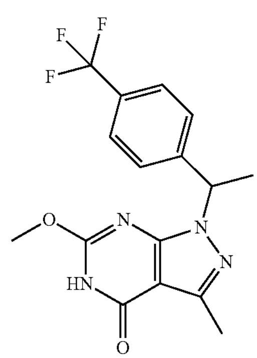 [SMILES: COc1nc2c(c(C)nn2C(C)c2ccc(C(F)(F)F)cc2)c(=O)[nH]1] | 6-Methoxy-3-methyl-1-{1-[4-(trifluoromethyl)phenyl]ethyl}-1,5-dihydro-4H-pyrazolo[3,4-d]pyrimidin-4-one | Calc'd 353.1, found 353.1 |
| 60 | 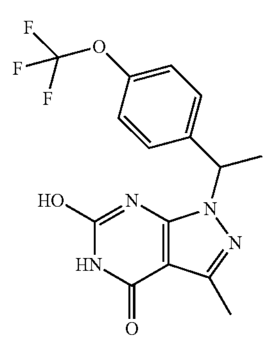 [SMILES: Cc1nn(C(C)c2ccc(OC(F)(F)F)cc2)c2nc(O)[nH]c(=O)c12] | 6-Hydroxy-3-methyl-1-{1-[4-(trifluoromethoxy)phenyl]ethyl}-1,5-dihydro-4H-pyrazolo[3,4-d]pyrimidin-4-one | Calc'd 355.1, found 355.1 |

TABLE 20-continued

The following compounds were prepared using procedures similar to those described in Example 57 using appropriate starting materials.

| Ex # | Structure | IUPAC Name | Exact Mass [M + H]+ |
|---|---|---|---|
| 61 | 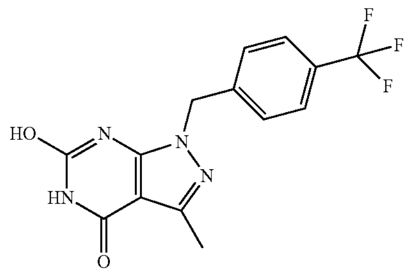 [SMILES: Cc1nn(Cc2ccc(C(F)(F)F)cc2)c2nc(O)[nH]c(=O)c12] | 6-Hydroxy-3-methyl-1-[4-(trifluoromethyl)benzyl]-1,5-dihydro-4H-pyrazolo[3,4-d]pyrimidin-4-one | Calc'd 325.1, found 325.2 |

EXAMPLES 62 AND 63

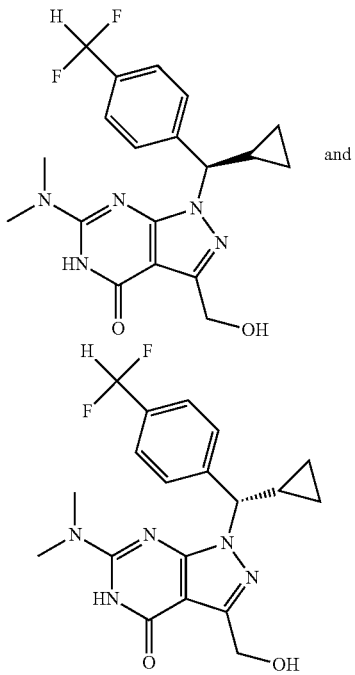

(R)- and (S)-1-(Cyclopropyl(4-(difluoromethyl)phenyl)methyl)-6-(dimethylamino)-3-(hydroxymethyl)-1H-pyrazolo[3,4-d]pyrimidin-4(5H)-one (Scheme 26)

Step 1. 3-(Benzyloxymethyl)-6-chloro-1-(cyclopropyl(4-(difluoromethyl)phenyl)methyl)-4-methoxy-1H-pyrazolo[3,4-d]pyrimidine The title compound was prepared using procedures similar to those described in step 1 of Preparatory Example 75 using cyclopropyl(4-(difluoromethyl)phenyl)methanol and 3-(benzyloxymethyl)-6-chloro-4-methoxy-1H-pyrazolo[3,4-d]pyrimidine to afford an oil. MS=485.2, 487.2 (+ESI).

Step 2. 3-((Benzyloxy)methyl)-1-(cyclopropyl(4-(difluoromethyl)phenyl)methyl)-6-(dimethylamino)-1H-pyrazolo[3,4-d]pyrimidin-4(5H)-one To a solution of 3-((benzyloxy)methyl)-6-chloro-1-(cyclopropyl(4-(difluoromethyl)phenyl)methyl)-4-methoxy-1H-pyrazolo[3,4-d]pyrimidine (100 mg, 0.07 mmol) in NMP (5 mL) at room temperature was added dimethylamine hydrochloride (0.11 g, 1.40 mmol) in one portion. The resulting mixture was heated to 100° C. and was stirred for 16 h. The mixture was cooled to room temperature, diluted with water (30 mL), and extracted with EtOAc (3×30 mL). The combined organic layers were washed with brine (1×60 mL), dried over $Na_2SO_4$, filtered, and concentrated under vacuum. The residue was purified by silica gel column chromatography (50% ethyl acetate in hexanes) to afford the title compound as a solid. MS=480.2 (+ESI).

Step 4. (R)- and (S)-1-(Cyclopropyl(4-(difluoromethyl)phenyl)methyl)-6-(dimethylamino)-3-(hydroxymethyl)-1H-pyrazolo[3,4-d]pyrimidin-4(5H)-one Boron trichloride (0.2 mL) was added to a mixture of 3-((benzyloxy)methyl)-1-(cyclopropyl (4-(difluoromethyl)phenyl)methyl)-6-(dimethylamino)-1H-pyrazolo[3,4-d]pyrimidin-4(5H)-one (90 mg, 0.2 mmol) in DCM (1 mL) at 0° C. The resulting reaction mixture was stirred for 10 min at 0° C., diluted with water (10 mL), and extracted with ethyl acetate (3×15 mL). The combined organic layers were washed with brine (3×10 mL), dried over anhydrous sodium sulfate, filtered, and concentrated under vacuum. The residue was purified by preparative HPLC (X Bridge C18, 30-80% ACN in water (0.05% $NH_4HCO_3$)) to afford the title compound as a solid. The enantiopure title compounds were obtained by chiral preparative HPLC (Chiralpak AS-H, 30% EtOH in hexanes). The faster-eluting enantiomer of the title compound (Example 62) was obtained as a solid. MS=390.2 (+ESI); $^1$H NMR (400 MHz, DMSO-$d_6$) δ: 10.73 (br, 1H), 7.52-7.49 (m, 4H), 7.01 (t, J=48.2 Hz, 1H), 5.18-5.10 (m, 1H), 4.87 (d, J=6.7 Hz, 1H), 4.57 (d, J=5.6 Hz, 2H), 3.07 (s, 6H), 1.97-1.82 (m, 1H), 0.79-0.70 (m, 1H), 0.62-0.50 (m, 2H), 0.42-0.31 (m, 1H). The slower-eluting enantiomer of the title compound (Example 63) was obtained as a solid. MS=390.2 (+ESI); $^1$H NMR (400 MHz, DMSO-$d_6$) δ: 10.73 (br s, 1H), 7.52-7.49 (m, 4H), 7.01 (t, J=48.2 Hz, 1H), 5.18-5.10 (m, 1H), 4.87 (d, J=6.7 Hz, 1H), 4.57 (d, J=5.6 Hz, 2H), 3.07 (s, 6H), 1.97-1.82 (m, 1H), 0.79-0.70 (m, 1H), 0.62-0.50 (m, 2H), 0.42-0.31 (m, 1H).

TABLE 21

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.

Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 64 | 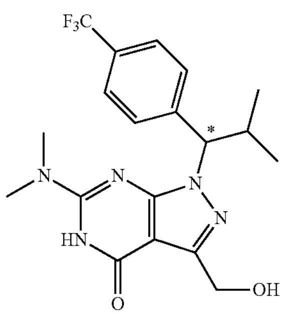 [SMILES: CC(C)C(c1ccc(C(F)(F)F)cc1)n1nc(CO)c2c(=O)[nH]c(N(C)C)nc21] | (R)- or (S)-6-Dimethylamino-3-(hydroxymethyl)-1-(2-methyl-1-(4-(trifluoromethyl)phenyl)propyl)-1H-pyrazolo[3,4-d]pyrimidin-4(5H)-one | Calc'd 410.2, found 409.9 | Chiralpak IA | A |
| 65 | 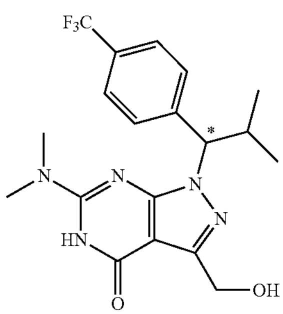 [SMILES: CC(C)C(c1ccc(C(F)(F)F)cc1)n1nc(CO)c2c(=O)[nH]c(N(C)C)nc21] | (S)- or (R)-6-Dimethylamino-3-(hydroxymethyl)-1-(2-methyl-1-(4-(trifluoromethyl)phenyl)propyl)-1H-pyrazolo[3,4-d]pyrimidin-4(5H)-one | Calc'd 410.2, found 409.9 | Chiralpak IA | A |
| 66 | 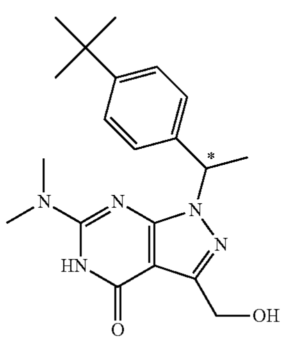 [SMILES: CC(c1ccc(C(C)(C)C)cc1)n1nc(CO)c2c(=O)[nH]c(N(C)C)nc21] | (R)- or (S)-1-(1-(4-tert-Butylphenyl)ethyl)-6-(dimethylamino)-3-(hydroxymethyl)-1H-pyrazolo[3,4-d]pyrimidin-4(5H)-one | Calc'd 370.2, found 370.3 | Chiralpak IA | A |
| 67 | 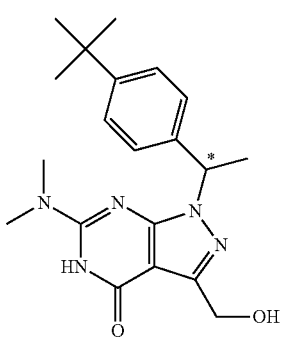 [SMILES: CC(c1ccc(C(C)(C)C)cc1)n1nc(CO)c2c(=O)[nH]c(N(C)C)nc21] | (S)- or (R)-1-(1-(4-tert-Butylphenyl)ethyl)-6-(dimethylamino)-3-(hydroxymethyl)-1H-pyrazolo[3,4-d]pyrimidin-4(5H)-one | Calc'd 370.2, found 370.3 | Chiralpak IA | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.

Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]+ | Chiral column | DC* |
|---|---|---|---|---|---|
| 68 | 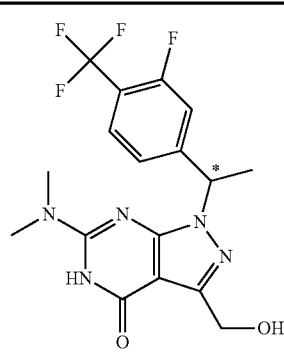 | (R)- or (S)-6-(Dimethylamino)-1-(1-(3-fluoro-4-(trifluoromethyl)phenyl)ethyl)-3-(hydroxymethyl)-1H-pyrazolo[3,4-d]pyrimidin-4(5H)-one | Calc'd 400.1, found 399.9 | Chiralpak IA | A |
| 69 | 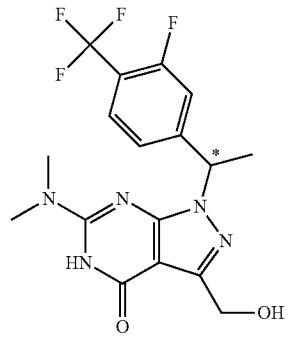 [SMILES: CC(c1ccc(C(F)(F)F)c(F)c1)n1nc(CO)c2c(=O)[nH]c(N(C)C)nc21] | (S)- or (R)-6-(Dimethylamino)-1-(1-(3-fluoro-4-(trifluoromethyl)phenyl)ethyl)-3-(hydroxymethyl)-1H-pyrazolo[3,4-d]pyrimidin-4(5H)-one | Calc'd 400.1, found 399.9 | Chiralpak IA | A |
| 70 | 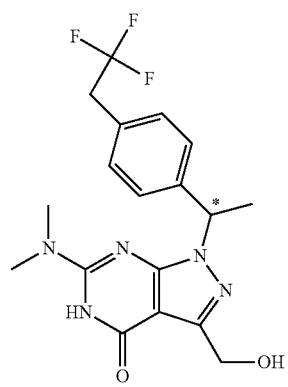 [SMILES: CC(c1ccc(CC(F)(F)F)cc1)n1nc(CO)c2c(=O)[nH]c(N(C)C)nc21] | (R)- or (S)-6-(Dimethylamino)-3-(hydroxymethyl)-1-(1-(4-(2,2,2-trifluoroethyl)phenyl)ethyl)-1H-pyrazolo[3,4-d]pyrimidin-4(5H)-one | Calc'd 396.2, found 396.1 | Chiralpak IA | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 71 | 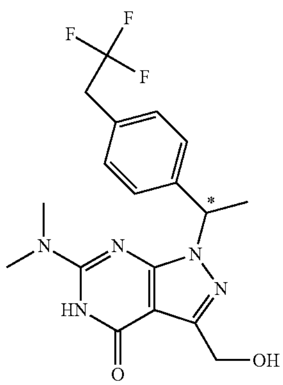 [SMILES: CC(c1ccc(CC(F)(F)F)cc1)n1nc(CO)c2c(=O)[nH]c(N(C)C)nc21] | (S)- or (R)-6-(Dimethylamino)-3-(hydroxymethyl)-1-(1-(4-(2,2,2-trifluoroethyl)phenyl)ethyl)-1H-pyrazolo[3,4-d]pyrimidin-4(5H)-one | Calc'd 396.2, found 396.1 | Chiralpak IA | A |
| 72 | 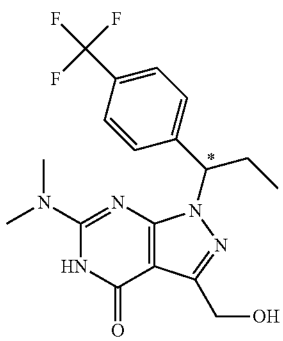 [SMILES: CCC(c1ccc(C(F)(F)F)cc1)n1nc(CO)c2c(=O)[nH]c(N(C)C)nc21] | (R)- or (S)-6-(Dimethylamino)-3-(hydroxymethyl)-1-(1-(4-(trifluoromethyl)phenyl)propyl)-1H-pyrazolo[3,4-d]pyrimidin-4(5H)-one | Calc'd 396.2, found 396.1 | Chiralpak AD-H | A |
| 73 | 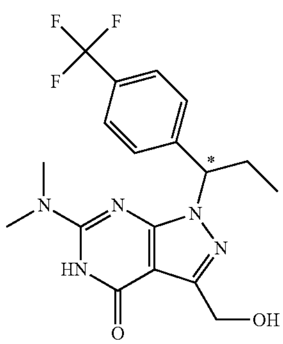 [SMILES: CCC(c1ccc(C(F)(F)F)cc1)n1nc(CO)c2c(=O)[nH]c(N(C)C)nc21] | (S)- or (R)-6-(Dimethylamino)-3-(hydroxymethyl)-1-(1-(4-(trifluoromethyl)phenyl)propyl)-1H-pyrazolo[3,4-d]pyrimidin-4(5H)-one | Calc'd 396.2, found 396.0 | Chiralpak AD-H | A |
| 74 | 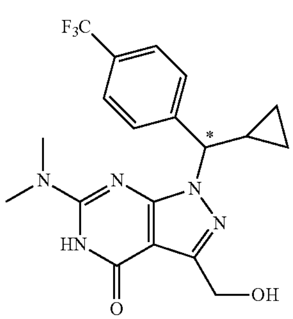 [SMILES: CN(C)c1nc2c(c(CO)nn2C(c2ccc(C(F)(F)F)cc2)C2CC2)c(=O)[nH]1] | (R)- or (S)-1-(Cyclopropyl(4-(trifluoromethyl)phenyl)methyl)-6-(dimethylamino)-3-(hydroxymethyl)-1H-pyrazolo[3,4-d]pyrimidin-4(5H)-one | Calc'd 408.2, found 408.1 | Chiral pak AS-H | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 75 | 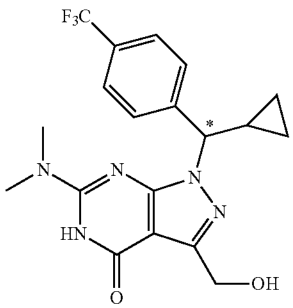 [SMILES: CN(C)c1nc2c(c(CO)nn2C(c2ccc(C(F)(F)F)cc2)C2CC2)c(=O)[nH]1] | (S)- or (R)-1-(Cyclopropyl(4-(trifluoromethyl)phenyl)methyl)-6-(dimethylamino)-3-(hydroxymethyl)-1H-pyrazolo[3,4-d]pyrimidin-4(5H)-one | Calc'd 408.2, found 408.0 | Chiral pak AS-H | B |
| 76 | 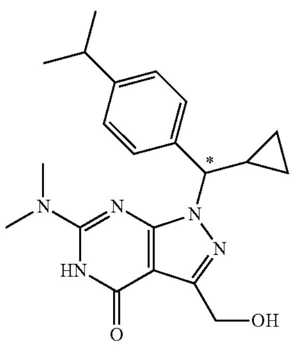 [SMILES: CC(C)c1ccc(C(C2CC2)n2nc(CO)c3c(=O)[nH]c(N(C)C)nc32)cc1] | (R)- or (S)-1-(Cyclopropyl(4-isopropylphenyl)methyl)-6-(dimethylamino)-3-(hydroxymethyl)-1H-pyrazolo[3,4-d]pyrimidin-4(5H)-one | Calc'd 382.2, found 382.1 | Chiralpak AD-H | B |
| 77 | 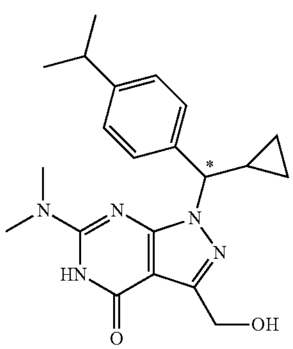 [SMILES: CC(C)c1ccc(C(C2CC2)n2nc(CO)c3c(=O)[nH]c(N(C)C)nc32)cc1] | (S)- or (R)-1-(Cyclopropyl(4-isopropxlphenyl)methyl)-6-(dimethylamino)-3-(hydroxymethyl)-1H-pyrazolo[3,4-d]pyrimidin-4(5H)-one | Calc'd 382.2, found 382.1 | Chiralpak AD-H | A |
| 78 | 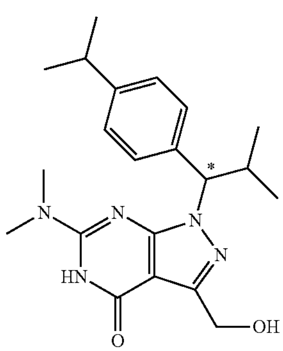 [SMILES: CC(C)c1ccc(C(C(C)C)n2nc(CO)c3c(=O)[nH]c(N(C)C)nc32)cc1] | (R)- or (S)-6-(Dimethylamino)-3-(hydroxymethyl)-1-(1-(4-isopropylphenyl)-2-methylpropyl)-1H-pyrazolo[3,4-d]pyrimidin-4(5H)-one | Calc'd 384.2, found 384.1 | Chiralpak IA | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.

Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 79 | 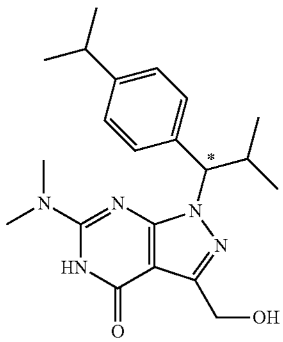 [SMILES: CC(C)c1ccc(C(C(C)C)n2nc(CO)c3c(=O)[nH]c(N(C)C)nc32)cc1] | (S)- or (R)-6-(Dimethylamino)-3-(hydroxymethyl)-1-(1-(4-isopropylphenyl)-2-methylpropyl)-1H-pyrazolo[3,4-d]pyrimidin-4(5H)-one | Calc'd 384.2, found 384.1 | Chiralpak IA | A |
| 80 | 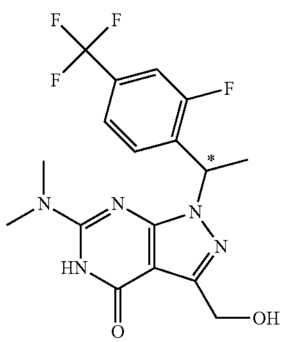 [SMILES: CC(c1ccc(C(F)(F)F)cc1F)n1nc(CO)c2c(=O)[nH]c(N(C)C)nc21] | (R)- or (S)-6-(Dimethylamino)-1-(1-(2-fluoro-4-(trifluoromethyl)phenyl)ethyl)-3-(hydroxymethyl)-1H-pyrazolo[3,4-d]pyrimidin-4(5H)-one | Calc'd 400.1, found | Chiralpak IC | A |
| 81 | 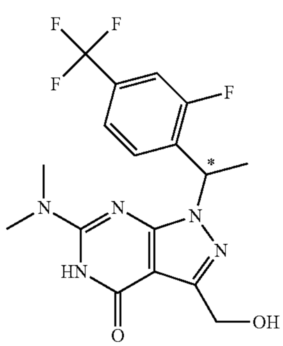 [SMILES: CC(c1ccc(C(F)(F)F)cc1F)n1nc(CO)c2c(=O)[nH]c(N(C)C)nc21] | (S)- or (R)-6-(Dimethylamino)-1-(1-(2-fluoro-4-(trifluorornethyl)phenyl)ethyl)-3-(hyrdroxymethyl)-1H-pyrazolo[3,4-d]pyrimidin-4(5H)-one | Calc'd 400.1, found | Chiralpak IC | A |
| 82 | 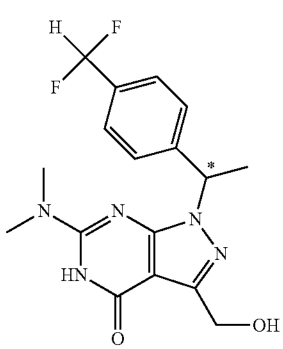 [SMILES: CC(c1ccc(C(F)F)cc1)n1nc(CO)c2c(=O)[nH]c(N(C)C)nc21] | (R)- or (S)-1-(1-(4-(Difluoromethyl)phenyl)ethyl)-6-(dimethylarnino)-3-(hydroxymethyl)-1H-pyrazolo[3,4-d]pyrimidin-4(5H)-one | Calc'd 364.2, found 364.2 | Venusil Chiral OD-H | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 83 | 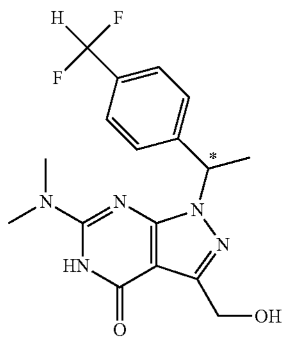 [SMILES: CC(c1ccc(C(F)F)cc1)n1nc(CO)c2c(=O)[nH]c(N(C)C)nc21] | (S)- or (R)-1-(1-(4-(Difluoromethyl)phenyl)ethyl)-6-(dimethylamino)-3-(hydroxymethyl)-1H-pyrazolo[3,4-d]pyrimidin-4(5H)-one | Calc'd 364.2, found 364.1 | Venusil Chiral OD-H | A |
| 84 | 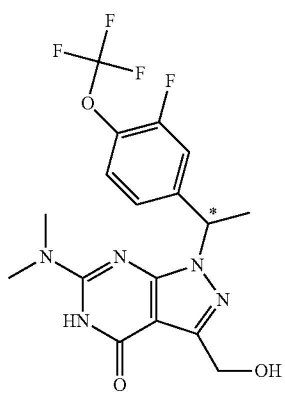 [SMILES: CC(c1ccc(OC(F)(F)F)c(F)c1)n1nc(CO)c2c(=O)[nH]c(N(C)C)nc21] | (R)- or (S)-6-(Dimethylamino)-1-(1-(3-fluoro-4-(trifluoromethoxy)phenyl)ethyl)-3-(hydroxymethyl)-1H-pyrazolo[3,4-d]pyrimidin-4(5H)-one | Calc'd 416.1, found 415.9 | Chiralpak IA | A |
| 85 | 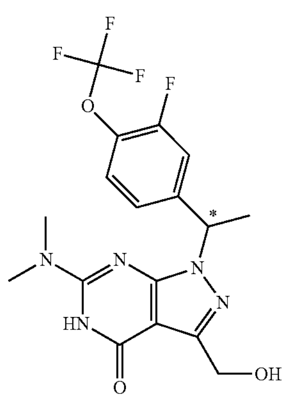 [SMILES: CC(c1ccc(OC(F)(F)F)c(F)c1)n1nc(CO)c2c(=O)[nH]c(N(C)C)nc21] | (S)- or (R)-6-(Dimethylamino)-1-(1-(3-fluoro-4-(trifluoromethoxy)phenyl)ethyl)-3-(hydroxymethyl)-1H-pyrazolo[3,4-d]pyrimidin-4(5H)-one | Calc'd 416.1, found 415.9 | Chiralpak IA | A |
| 86 | 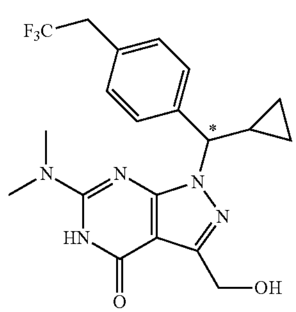 [SMILES: CN(C)c1nc2c(c(CO)nn2C(c2ccc(CC(F)(F)F)cc2)C2CC2)c(=O)[nH]1] | (R)- or (S)-1-(Cyclopropyl(4-(2,2,2-trifluoroethyl)phenyl)methyl)-6-(dimethylamino)-3-(hydroxymethyl)-1H-pyrazolo[3,4-d]pyrimidin-4(5H)-one | Calc'd 422.2, found 422.0 | Chiralpak AS-H | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 87 | 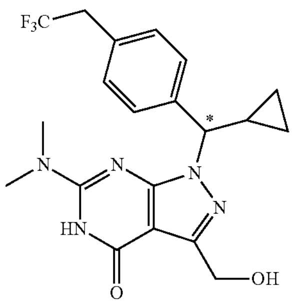 [SMILES: CN(C)c1nc2c(c(CO)nn2C(c2ccc(CC(F)(F)F)cc2)C2CC2)c(=O)[nH]1] | (S)- or (R)-1-(Cyclopropyl(4-(2,2,2-trifluoroethyl)phenyl)methyl)-6-(dimethylamino)-3-(hydroxymethyl)-1H-pyrazolo[3,4-d]pyrimidin-4(5H)-one | Calc'd 422.2, found 422.0 | Chiralpak AS-H | A |
| 88 | 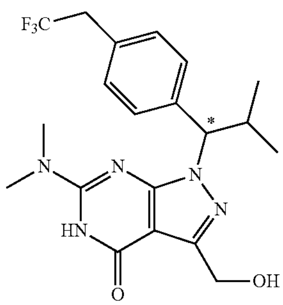 [SMILES: CC(C)C(c1ccc(CC(F)(F)F)cc1)n1nc(CO)c2c(=O)[nH]c(N(C)C)nc21] | (R)- or (S)-6-(Dimethylamino)-3-(hydroxymethyl)-1-(2-methyl-1-(4-(2,2,2-trifluoroethyl)phenyl)propyl)-1H-pyrazolo[3,4-d]pyrimidin-4(5H)-one | Calc'd 424.2, found 424.1 | (R,R) WHELK-01 5/100 Kromasil | A |
| 89 | 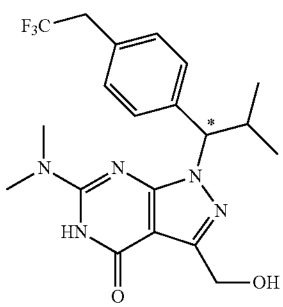 [SMILES: CC(C)C(c1ccc(CC(F)(F)F)cc1)n1nc(CO)c2c(=O)[nH]c(N(C)C)nc21] | (S)- or (R)-6-(Dimethylamino)-3-(hydroxymethyl)-1-(2-methyl-1-(4-(2,2,2-trifluoroethyl)phenyl)propyl)-1H-pyrazolo[3,4-d]pyrimidin-4(5H)-one | Calc'd 424.2, found 424.1 | (R,R)WH ELK-01 5/100 Kromasil | A |
| 90 | 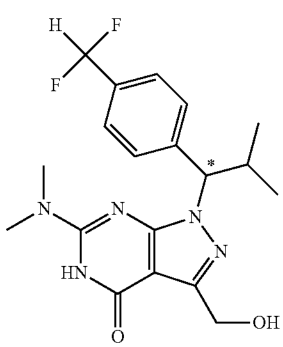 [SMILES: CC(C)C(c1ccc(C(F)F)cc1)n1nc(CO)c2c(=O)[nH]c(N(C)C)nc21] | (R)- or (S)-1-(1-(4-(Difluoromethyl)phenyl)-2-methylpropyl)-6-(dimethylamino)-3-(hydroxymethyl)-1H-pyrazolo[3,4-d]pyrimidin-4(5H)-one | Calc'd 392.2, found 392.2 | Chiralpak IA | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 91 | 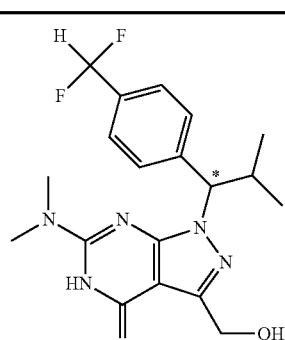 | (S)- or (R)-1-(1-(4-(Difluoromethyl)phenyl)-2-methylpropyl)-6-(dimethylamino)-3-(hydroxymethyl)-1H-pyrazolo[3,4-d]pyrimidin-4(5H)-one | Calc'd 392.2, found 392.2 | Chiralpak IA | A |
| 92 | 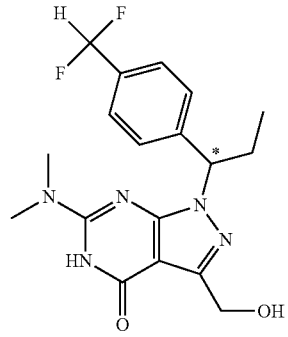 [SMILES: CCC(c1ccc(C(F)F)cc1)n1nc(CO)c2c(=O)[nH]c(N(C)C)nc21] | (R)- or (S)-1-(1-(4-(Difluoromethyl)phenyl)propyl)-6-(dimethylamino)-3-(hydroxymethyl)-1H-pyrazolo[3,4-d]pyrimidin-4(5H)-one | Calc'd 378.2, found 378.2 | Chiralpak IA | A |
| 93 | 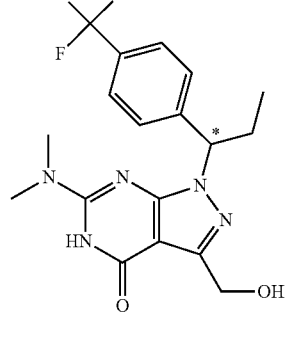 | (S)- or (R)-1-(1-(4-(Difluoromethyl)phenyl)propyl)-6-(dimethylamino)-3-(hydroxymethyl)-1H-pyrazolo[3,4-d]pyrimidin-4(5H)-one | Calc'd 378.2, found 378.0 | Chiralpak IA | A |
| 94 | 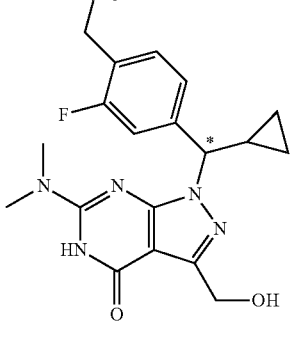 | (R)- or (S)-1-(Cyclopropyl(3-fluoro-4-(2,2,2-trifluoroethyl)phenyl)methyl)-6-(dimethylamino)-3-(hydroxymethyl)-1H-pyrazolo[3,4-d]pyrimidin-4(5H)-one | Calc'd 440.2, found 440.1 | Chiralpak IA | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 95 | 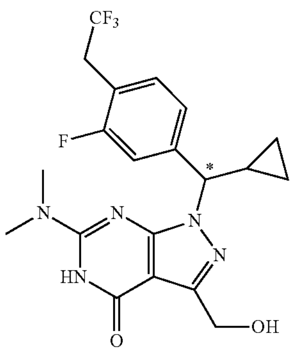 [SMILES: CN(C)c1nc2c(c(CO)nn2C(c2ccc(CC(F)(F)F)c(F)c2)C2CC2)c(=O)[nH]1] | (S)- or (R)-1-(Cyclopropyl(3-fluoro-4-(2,2,2-trifluoroethyl)phenyl)methyl)-6-(dimethylamino)-3-(hydroxymethyl)-1H-pyrazolo[3,4-d]pyrimidin-4(5H)-one | Calc'd 440.2, found 440.1 | Chiralpak IA | A |
| 96 | 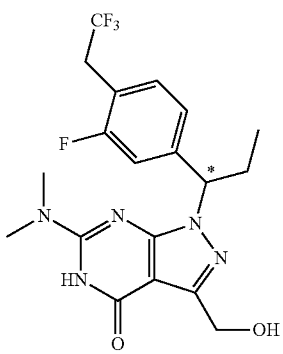 [SMILES: CCC(c1ccc(CC(F)(F)F)c(F)c1)n1nc(CO)c2c(=O)[nH]c(N(C)C)nc21] | (R)- or (S)-6-(Dimethylamino)-1-(1-(3-fluoro-4-(2,2,2-trifluoroethyl)phenyl)propyl)-3-(hydroxymethyl)-1H-pyrazolo[3,4-d]pyrimidin-4(5H)-one | Calc'd 428.2, found 428.1 | Chiralpak IA | A |
| 97 | 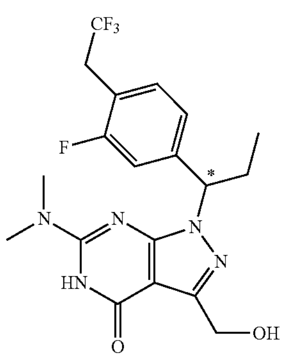 [SMILES: CCC(c1ccc(CC(F)(F)F)c(F)c1)n1nc(CO)c2c(=O)[nH]c(N(C)C)nc21] | (S)- or (R)-6-(Dimethylamino)-1-(1-(3-fluoro-4-(2,2,2-trifluoroethyl)phenyl)propyl)-3-(hydroxymethyl)-1H-pyrazolo[3,4-d]pyrimidin-4(5H)-one | Calc'd 428.2, found 428.1 | Chiralpak IA | A |
| 98 | 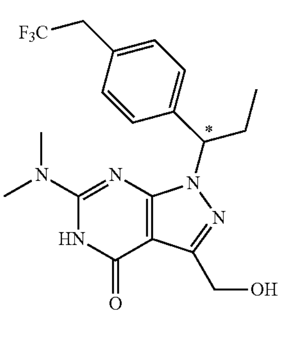 [SMILES: CCC(c1ccc(CC(F)(F)F)cc1)n1nc(CO)c2c(=O)[nH]c(N(C)C)nc21] | (R)- or (S)-6-(Dimethylamino)-3-(hydroxymethyl)-1-(1-(4-(2,2,2-trifluoroethyl)phenyl)propyl)-1H-pyrazolo[3,4-d]pyrimidin-4(5H)-one | Calc'd 410.2, found 410.1 | Chiralpak IA | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 99 | 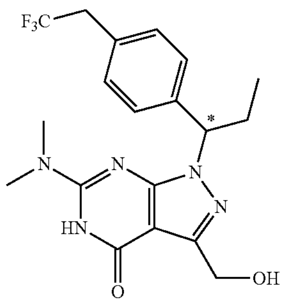 [SMILES: CCC(c1ccc(CC(F)(F)F)cc1)n1nc(CO)c2c(=O)[nH]c(N(C)C)nc21] | (S)- or (R)-6-(Dimethyiamino)-3-(hydroxymethyl)-1-(1-(4-(2,2,2-trifluoroethyl)phenyl)propyl)-1H-pyrazolo[3,4-d]pyrimidin-4(5H)-one | Calc'd 410.2, found 410.1 | Chiralpak IA | A |
| 100 | 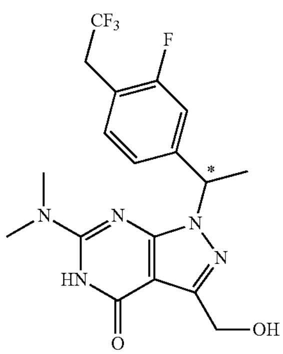 [SMILES: CC(c1ccc(CC(F)(F)F)c(F)c1)n1nc(CO)c2c(=O)[nH]c(N(C)C)nc21] | (R)- or (S)-6-(Dimethylamino)-1-(1-(3-fluoro-4-(2,2,2-trifluoroethyl)phenyl)ethyl)-3-(hydroxymethyl)-1H-pyrazolo[3,4-d]pyrimidin-4(5H)-one | Calc'd 414.2, found 414.0 | Chiralpak IA | A |
| 101 | 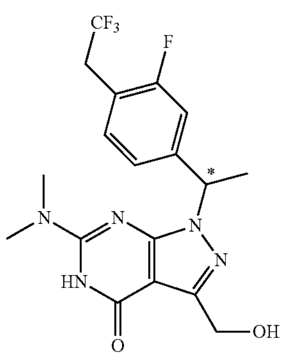 [SMILES: CC(c1ccc(CC(F)(F)F)c(F)c1)n1nc(CO)c2c(=O)[nH]c(N(C)C)nc21] | (S)- or (R)-6-(Dimethylamino)-1-(1-(3-fluoro-4-(2,2,2-trifluoroethyl)phenyl)ethyl)-3-(hydroxymethyl)-1H-pyrazolo[3,4-d]pyrimidin-4(5H)-one | Calc'd 414.2, found 414.0 | Chiralpak IA | A |
| 102 | 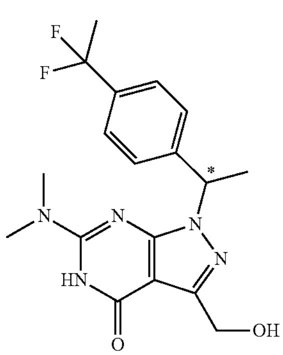 [SMILES: CC(c1ccc(C(C)(F)F)cc1)n1nc(CO)c2c(=O)[nH]c(N(C)C)nc21] | (R)- or (S)-1-(1-(4-(1,1-Difluoroethyl)phenyl)ethyl)-6-(dimethylamino)-3-(hydroxymethyl)-1H-pyrazolo[3,4-d]pyrimidin-4(5H)-one | Calc'd 378.2, found 378.1 | Chiralpak IA | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.

Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 103 | 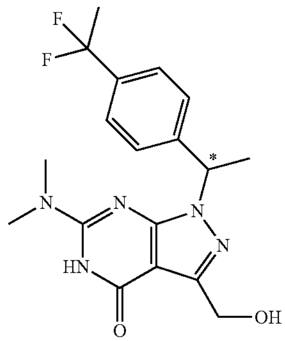 [SMILES: CC(c1ccc(C(C)(F)F)cc1)n1nc(CO)c2c(=O)[nH]c(N(C)C)nc21] | (S)- or (R)-1-(1-(4-(1,1-Difluoroethyl)phenyl)ethyl)-6-(dimethylamino)-3-(hydroxymethyl)-1H-pyrazolo[3,4-d]pyrimidin-4(5H)-one | Calc'd 378.2, found 378.1 | Chiralpak IA | A |
| 104 | 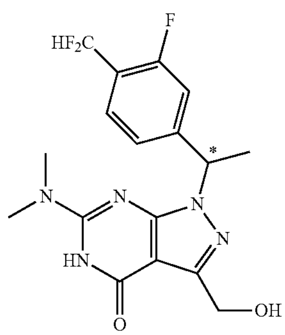 | (R)- or (S)-1-(1-(4-(Difluoromethyl)-3-fluorophenyl)ethyl)-6-(dimethylamino)-3-(hydroxymethyl)-1H-pyrazolo[3,4-d]pyrimidin-4(5H)-one | Calc'd 382.1, found 382.0 | Chiralpak IA | A |
| 105 | 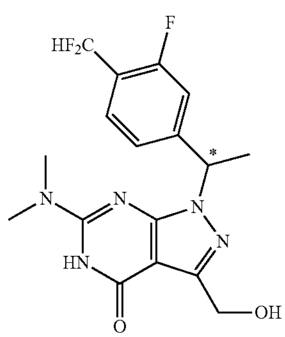 | (S)- or (R)-1-(1-(4-(Difluoromethyl)-3-fluorophenyl)ethyl)-6-(dimethylamino)-3-(hydroxymethyl)-1H-pyrazolo[3,4-d]pyrimidin-4(5H)-one | Calc'd 382.1, found 381.9 | Chiralpak IA | A |
| 106 | 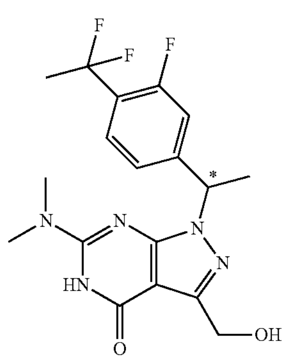 [SMILES: CC(c1ccc(C(C)(F)F)c(F)c1)n1nc(CO)c2c(=O)[nH]c(N(C)C)nc21] | (R)- or (S)-1-(1-(4-(1,1-Difluoroethyl)-3-fluorophenyl)ethyl)-6-(dimethylamino)-3-(hydroxymethyl)-1H-pyrazolo[3,4-d]pyrimidin-4(5H)-one | Calc'd 396.2, found 396.3 | Chiralpak IA | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 107 | 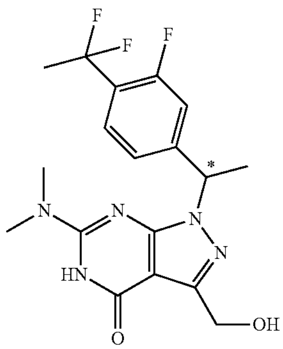 [SMILES: CC(c1ccc(C(C)(F)F)c(F)c1)n1nc(CO)c2c(=O)[nH]c(N(C)C)nc21] | (S)- or (R)-1-(1-(4-(1,1-Difluoroethyl)-3-fluorophenyl)ethyl)-6-(dimethylamino)-3-(hydroxymethyl)-1H-pyrazolo[3,4-d]pyrimidin-4(5H)-one | Calc'd 396.2, found 396.3 | Chiralpak IA | A |
| 108 | 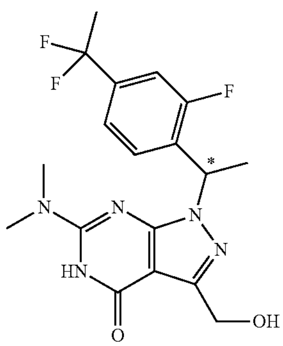 [SMILES: CC(c1ccc(C(C)(F)F)cc1F)n1nc(CO)c2c(=O)[nH]c(N(C)C)nc21] | (R)- or (S)-1-(1-(4-(1,1-Difluoroethyl)-2-fluorophenyl)ethyl)-6-(dimethylamino)-3-(hydroxymethyl)-1H-pyrazolo[3,4-d]pyrimidin-4(5H)-one | Calc'd 396.2, found 396.1 | CHIRALCEL OJ-H | A |
| 109 | 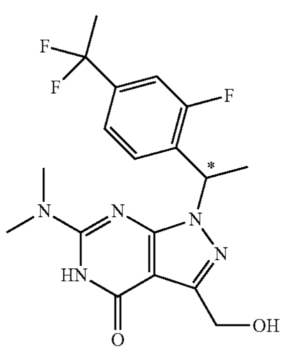 [SMILES: CC(c1ccc(C(C)(F)F)cc1F)n1nc(CO)c2c(=O)[nH]c(N(C)C)nc21] | (S)- or (R)-1-(1-(4-(1,1-Difluoroethyl)-2-fluorophenyl)ethyl)-6-(dimethylamino)-3-(hydroxymethyl)-1H-pyrazolo[3,4-d]pyrimidin-4(5H)-one | Calc'd 396.2, found 396.1 | CHIRALCEL OJ-H | A |
| 110 | 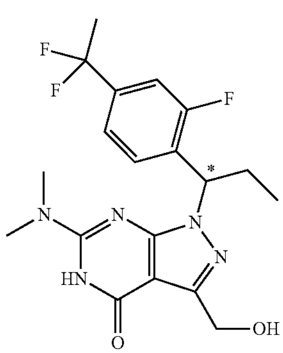 [SMILES: CCC(c1ccc(C(C)(F)F)cc1F)n1nc(CO)c2c(=O)[nH]c(N(C)C)nc21] | (R)- or (S)-1-(1-(4-(1,1-Difluoroethyl)-2-fluorophenyl)propyl)-6-(dimethylamino)-3-(hydroxymethyl)-1H-pyrazolo[3,4-d]pyrimidin-4(5H)-one | Calc'd 410.2, found 410.1 | AXIA Packed | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 111 | 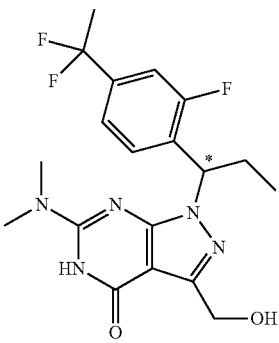 [SMILES: CCC(c1ccc(C(C)(F)F)cc1F)n1nc(CO)c2c(=O)[nH]c(N(C)C)nc21] | (S)- or (R)-1-(1-(4-(1,1-Difluoroethyl)-2-fluorophenyl)propyl)-6-(dimethylamino)-3-(hydroxymethyl)-1H-pyrazolo[3,4-d]pyrimidin-4(5H)-one | Calc'd 410.2, found 410.1 | AXIA Packed | A |
| 112 | 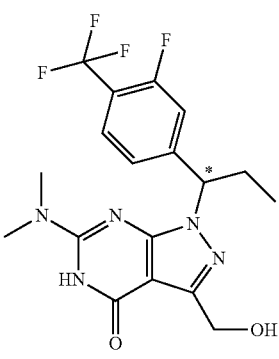 [SMILES: CCC(c1ccc(C(F)(F)F)c(F)c1)n1nc(CO)c2c(=O)[nH]c(N(C)C)nc21] | (R)- or (S)-1-(1-(4-(1,1-Difluoroethyl)-3-fluorophenyl)propyl)-6-(dimethylamino)-3-(hydroxymethyl)-1H-pyrazolo[3,4-d]pyrimidin-4(5H)-one | Calc'd 410.2, found 410.1 | Chiralpak IA | A |
| 113 | 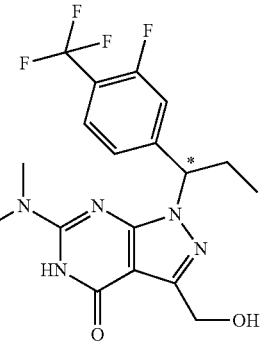 | (S)- or (R)-1-(1-(4-(1,1-Difluoroethyl)-3-fluorophenyl)propyl)-6-(dimethylamino)-3-(hydroxymethyl)-1H-pyrazolo[3,4-d]pyrimidin-4(5H)-one | Calc'd 410.2, found 410.1 | Chiralpak IA | A |
| 114 | 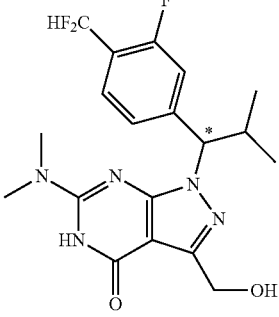 | (S)- or (R)-1-(1-(4-(Difluoromethyl)-3-fluorophenyl)-2-methylpropyl)-6-(dimethylamino)-3-(hydroxymethyl)-1H-pyrazolo[3,4-d]pyrimidin-4(5H)-one | Calc'd 410.2, found 410.0 | Chiralpak IA | B |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 115 | 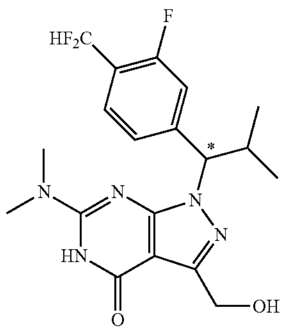 | (R)- or (S)-1-(1-(4-(Difluoromethyl)-3-fluorophenyl)-2-methylpropyl)-6-(dimethylamino)-3-(hydroxymethyl)-1H-pyrazolo[3,4-d]pyrimidin-4(5H)-one | Calc'd 410.2, found 410.1 | Chiralpak IA | B |
| 116 | 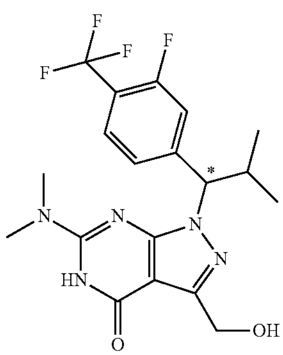 [SMILES: CC(C)C(c1ccc(C(F)(F)F)c(F)c1)n1nc(CO)c2c(=O)[nH]c(N(C)C)nc21] | (R)- or (S)-1-(1-(4-(1,1-Difluoroethyl)-3-fluorophenyl)-2-methylpropyl)-6-(dimethylamino)-3-(hydroxymethyl)-1H-pyrazolo[3,4-d]pyrimidin-4(5H)-one | Calc'd 424.2, found 424.1 | Chiralpak IA | A |
| 117 | 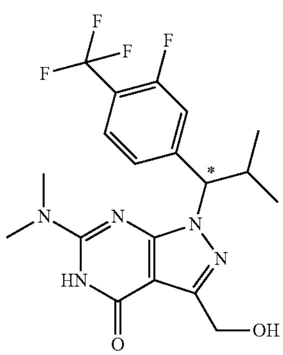 [SMILES: CC(C)C(c1ccc(C(F)(F)F)c(F)c1)n1nc(CO)c2c(=O)[nH]c(N(C)C)nc21] | (R)- or (S)-1-(1-(4-(1,1-Difluoroethyl)-3-fluorophenyl)-2-methylpropyl)-6-(dimethylamino)-3-(hydroxymethyl)-1H-pyrazolo[3,4-d]pyrimidin-4(5H)-one | Calc'd 424.2, found 424.1 | Chiralpak IA | A |
| 118 | 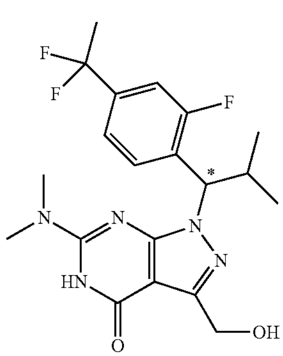 [SMILES: CC(C)C(c1ccc(C(C)(F)F)cc1F)n1nc(CO)c2c(=O)[nH]c(N(C)C)nc21] | (R)- or (S)-1-(1-(4-(1,1-Difluoroethyl)-2-fluorophenyl)-2-methylpropyl)-6-(dimethylamino)-3-(hydroxymethyl)-1H-pyrazolo[3,4-d]pyrimidin-4(5H)-one | Calc'd 424.2, found 424.1 | AXIA Packed | A |

TABLE 21-continued

The following compounds were prepared using procedures similar to those described in Examples 62 and 63 using appropriate starting materials and the benzyl group deprotection conditions listed in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 119 | 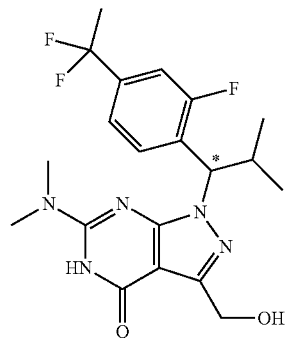 [SMILES: CC(C)C(c1ccc(C(C)(F)F)cc1F)n1nc(CO)c2c(=O)[nH]c(N(C)C)nc21] | (S)- or (R)-(1-(4-(1,1-Difluoroethyl)-2-fluorophenyl)-2-methylpropyl)-6-(dimethylamino)-3-(hydroxymethyl)-1H-pyrazolo[3,4-d]pyrimidin-4(5H)-one | Calc'd 424.2, found 424.0 | AXIA Packed | A |

*Deprotection conditions:

EXAMPLES 120 AND 121

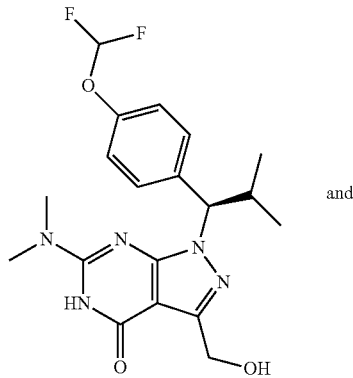

and

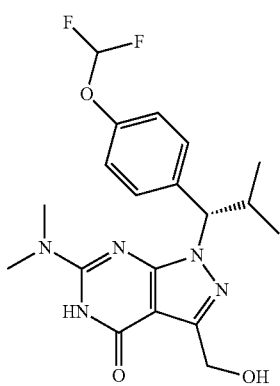

(R)- and (S)-1-(1-(4-(Difluoromethoxy)phenyl)-2-methylpropyl)-6-(dimethylamino)-3-(hydroxymethyl)-1H-pyrazolo[3,4-d]pyrimidin-4(5H)-one (Scheme 26)

Step 1. 3-(Benzyloxymethyl)-6-chloro-1-(1-(4-(difluoromethoxy)phenyl)-2-methylpropyl)-4-methoxy-1H-pyrazolo[3,4-d]pyrimidine The title compound was prepared using procedures similar to those described in step 1 of Preparatory Example 75 using 3-((benzyloxy)methyl)-6-chloro-4-methoxy-1H-pyrazolo[3,4-d]pyrimidine and 1-(4-(difluoromethoxy)phenyl)-2-methylpropan-1-ol to afford an oil. MS=503.1, 505.1 (+ESI).

Step 2. 3-(Benzyloxymethyl)-1-(1-(4-(difluoromethoxy)phenyl)-2-methylpropyl)-6-(dimethylamino)-1H-pyrazolo[3,4-d]pyrimidin-4(5H)-one The title compound was prepared using procedures similar to those described in step 3 of Examples 62 and 63 using 3-((benzyloxy)methyl)-6-chloro-1-(1-(4-(difluoromethoxy)phenyl)-2-methylpropyl)-4-methoxy-1H-pyrazolo[3,4-d]pyrimidine to afford a solid. MS=498.2 (+ESI).

Step 3. (R)- and (S)-1-(1-(4-(Difluoromethoxy)phenyl)-2-methylpropyl)-6-(dimethylamino)-3-(hydroxymethyl)-1H-pyrazolo[3,4-d]pyrimidin-4(5H)-one The title racemic compound was prepared using procedures similar to those described in step 2 of Preparatory Example 75 using 3-((benzyloxy)methyl)-1-(1-(4-(difluoromethoxy)phenyl)-2-methylpropyl)-6-(dimethylamino)-1H-pyrazolo[3,4-d]pyrimidin-4(5H)-one to afford a solid. The enantiopure title compounds were obtained by chiral preparative HPLC (Phenomenex Lux 5 u Cellulose-4, AXIA Packed, 30% EtOH in hexanes). The faster-eluting enantiomer of the title compound (Example 120) was obtained as a solid. MS=408.0 (+ESI). $^1$H NMR (400 MHz, DMSO-d$_6$) δ:10.76 (br s, 1H), 7.56 (d, J=8.4 Hz, 2H), 7.13 (d, J=8.0 Hz, 2H), 7.19 (t, J=74.0 Hz, 1H), 5.14 (d, J=10.8 Hz, 1H), 5.11 (br, 1H), 4.56 (s, 2H), 3.12 (s, 6H), 2.81-2.79 (m, 1H), 0.79 (d, J=7.2 Hz, 6H). The slower-eluting enantiomer of the title compound (Example 121) was obtained as a solid. MS=408.1 (+ESI). $^1$H NMR (400 MHz, DMSO-d$_6$) δ: 10.76 (br s, 1H), 7.56 (d, J=8.4 Hz, 2H), 7.13 (d, J=8.0 Hz, 2H), 7.19 (t, J=74.0 Hz, 1H), 5.14 (d, J=10.8 Hz, 1H), 5.11 (br, 1H), 4.56 (s, 2H), 3.12 (s, 6H), 2.81-2.79 (m, 1H), 0.79 (d, J=7.2 Hz, 6H).

TABLE 22

The following compounds were prepared using procedures similar to those described in Examples 120 and 121 using appropriate starting materials the benzyl group deprotection conditions in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 122 | 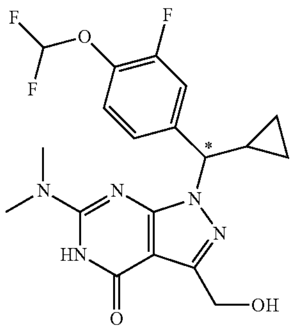 [SMILES: CN(C)c1nc2c(c(CO)nn2C(c2ccc(OC(F)F)c(F)c2)C2CC2)c(=O)[nH]1] | (R)- or (S)-1-(Cyclopropyl(4-(difluoromethoxy)-3-fluorophenyl)methyl)-6-(dimethylamino)-3-(hydroxymethyl)-1H-pyrazolo[3,4-d]pyrimidin-4(5H)-one | Calc'd 424.2, found 424.0 | Chiralpak IA | B |
| 123 | 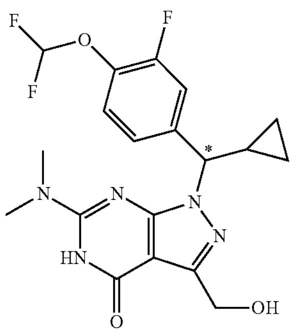 [SMILES: CN(C)c1nc2c(c(CO)nn2C(c2ccc(OC(F)F)c(F)c2)C2CC2)c(=O)[nH]1] | (S)- or (R)-1-(Cyclopropyl(4-(difluoromethoxy)-3-fluorophenyl)methyl)-6-(dimethylamino)-3-(hydroxymethyl)-1H-pyrazolo[3,4-d]pyrimidin-4(5H)-one | Calc'd 424.2, found 424.0 | Chiralpak IA | B |
| 124 | 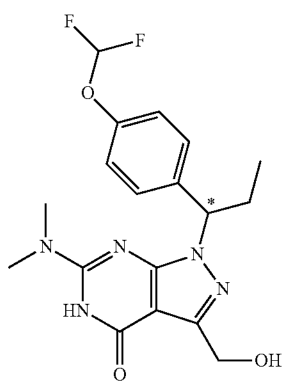 [SMILES: CCC(c1ccc(OC(F)F)cc1)n1nc(CO)c2c(=O)[nH]c(N(C)C)nc21] | (R)- or (S)-1-(1-(4-(Difluoromethoxy)phenyl)propyl)-6-(dimethylamino)-3-(hydroxymethyl)-1H-pyrazolo[3,4-d]pyrimidin-4(5H)-one | Calc'd 394.2, found 394.2 | CHIRALCEL OJ-H | B |
| 125 | 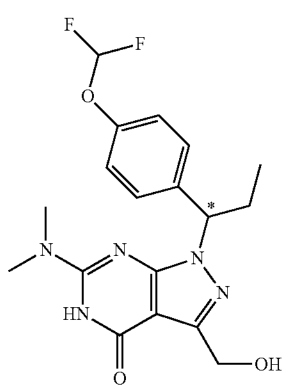 [SMILES: CCC(c1ccc(OC(F)F)cc1)n1nc(CO)c2c(=O)[nH]c(N(C)C)nc21] | (S)- or (R)-1-(1-(4-(Difluoromethoxy)phenyl)propyl)-6-(dimethylamino)-3-(hydroxymethyl)-1H-pyrazolo[3,4-d]pyrimidin-4(5H)-one | Calc'd 394.2, found 394.2 | CHIRALCEL OJ-H | B |

TABLE 22-continued

The following compounds were prepared using procedures similar to those described in Examples 120 and 121 using appropriate starting materials the benzyl group deprotection conditions in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 126 | 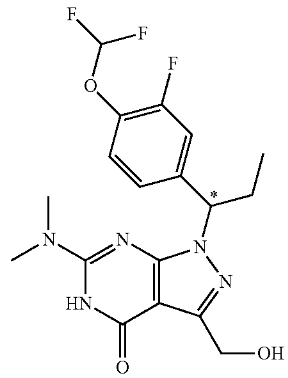 [SMILES: CCC(c1ccc(OC(F)F)c(F)c1)n1nc(CO)c2c(=O)[nH]c(N(C)C)nc21] | (R)- or (S)-1-(1-(4-(Difluoromethoxy)-3-fluorophenyl)propyl)-6-(dimethylamino)-3-(hydroxymethyl)-1H-pyrazolo[3,4-d]pyrimidin-4(5H)-one | Calc'd 412.2, found 412.0 | Chiralpak AS-H | A |
| 127 | 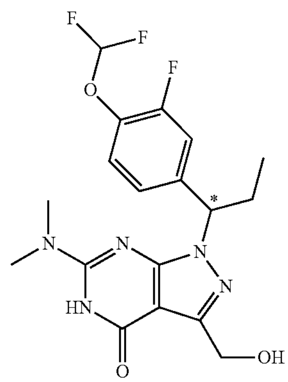 [SMILES: CCC(c1ccc(OC(F)F)c(F)c1)n1nc(CO)c2c(=O)[nH]c(N(C)C)nc21] | (S)- or (R)-1-(1-(4-(Difluoromethoxy)-3-fluorophenyl)propyl)-6-(dimethylamino)-3-(hydroxymethyl)-1H-pyrazolo[3,4-d]pyrimidin-4(5H)-one | Calc'd 412.2, found 412.0 | Chiralpak AS-H | A |
| 128 | 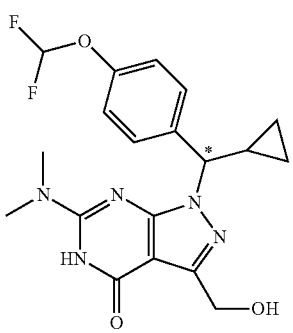 [SMILES: CN(C)c1nc2c(c(CO)nn2C(c2ccc(OC(F)F)cc2)C2CC2)c(=O)[nH]1] | (R)- or (S)-1-(Cyclopropyl(4-(difluoromethoxy)phenyl)methyl)-6-(dimethylamino)-3-(hydroxymethyl)-1H-pyrazolo[3,4-d]pyrimidin-4(5H)-one | Calc'd 406.2, found 406.0 | Chiralpak AS-H | B |
| 129 | 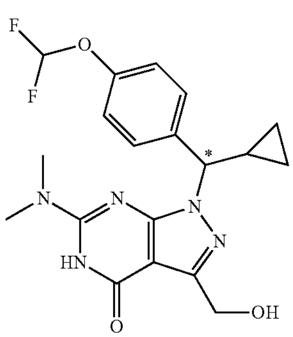 [SMILES: CN(C)c1nc2c(c(CO)nn2C(c2ccc(OC(F)F)cc2)C2CC2)c(=O)[nH]1] | (S)- or (R)-(Cyclopropyl(4-(difluoromethoxy)phenyl)methyl)-6-(dimethylamino)-3-(hydroxymethyl)-1H-pyrazolo[3,4-d]pyrimidin-4(5H)-one | Calc'd 406.2, found 406.0 | Chiralpak AS-H | B |

TABLE 22-continued

The following compounds were prepared using procedures similar to those described in Examples 120 and 121 using appropriate starting materials the benzyl group deprotection conditions in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 130 | 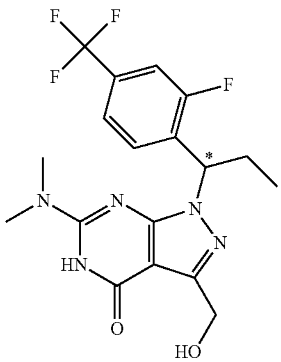 [SMILES: CCC(c1ccc(C(F)(F)F)cc1F)n1nc(CO)c2c(=O)[nH]c(N(C)C)nc21] | (R)- or (S)-6-(Dimethylamino)-1-(1-(2-fluoro-4-(trifluoromethyl)phenyl)propyl)-3-(hydroxymethyl)-1H-pyrazolo[3,4-d]pyrimidin-4(5H)-one | Calc'd 414.2, found 414.0 | Chiralpak AS-H | A |
| 131 | 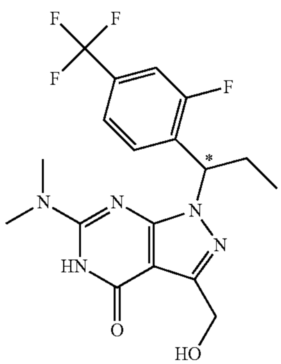 [SMILES: CCC(c1ccc(C(F)(F)F)cc1F)n1nc(CO)c2c(=O)[nH]c(N(C)C)nc21] | (S)- or (R)-6-(Dimethylamino)-1-(1-(2-fluoro-4-(trifluoromethyl)phenyl)propyl)-3-(hydroxymethyl)-1H-pyrazolo[3,4-d]pyrimidin-4(5H)-one | Calc'd 414.2, found 414.0 | Chiralpak AS-H | A |
| 132 | 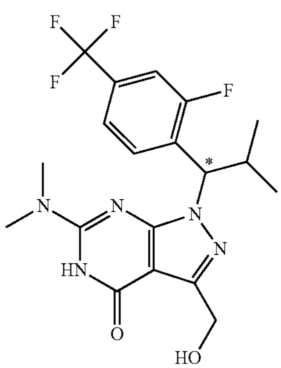 [SMILES: CC(C)C(c1ccc(C(F)(F)F)cc1F)n1nc(CO)c2c(=O)[nH]c(N(C)C)nc21] | (R)- or (S)-6-(Dimethylamino)-1-(1-(2-fluoro-4-(trifluoromethyl)phenyl)-2-methylpropyl)-3-(hydroxymethyl)-1H-pyrazolo[3,4-d]pyrimidin-4(5H)-one | Calc'd 428.2, found 428.0 | Chiralpak AS-H | A |
| 133 | 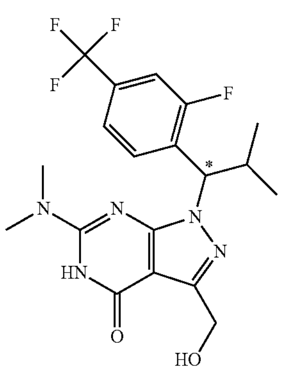 [SMILES: CC(C)C(c1ccc(C(F)(F)F)cc1F)n1nc(CO)c2c(=O)[nH]c(N(C)C)nc21] | (S)- or (R)-6-(Dimethylamino)-1-(1-(2-fluoro-4-(trifluoromethyl)phenyl)-2-methylpropyl)-3-(hydroxymethyl)-1H-pyrazolo[3,4-d]pyrimidin-4(5H)-one | Calc'd 428.2, found 428.0 | Chiralpak AS-H | A |

TABLE 22-continued

The following compounds were prepared using procedures similar to those described in Examples 120 and 121 using appropriate starting materials the benzyl group deprotection conditions in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 134 | 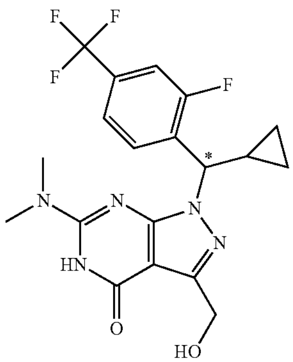 [SMILES: CN(C)c1nc2c(c(CO)nn2C(c2ccc(C(F)(F)F)cc2F)C2CC2)c(=O)[nH]1] | (R)- or (S)-1-(Cyclopropyl(2-fluoro-4-(trifluoromethyl)phenyl)methyl)-6-(dimethylamino)-3-(hydroxymethyl)-1H-pyrazolo[3,4-d]pyrimidin-4(5H)-one | Calc'd 426.2, found 426.1 | Chiralpak IA | A |
| 135 | 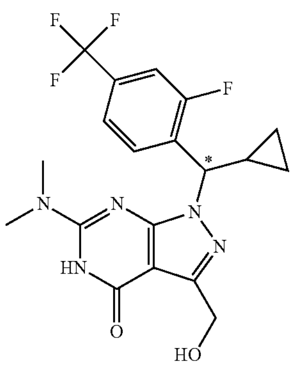 [SMILES: CN(C)c1nc2c(c(CO)nn2C(c2ccc(C(F)(F)F)cc2F)C2CC2)c(=O)[nH]1] | (S)- or (R)-1-(Cyclopropyl(2-fluoro-4-(trifluoromethyl)phenyl)methyl)-6-(dimethylamino)-3-(hydroxymethyl)-1H-pyrazolo[3,4-d]pyrimidin-4(5H)-one | Calc'd 426.2, found 426.1 | Chiralpak IA | A |
| 136 | 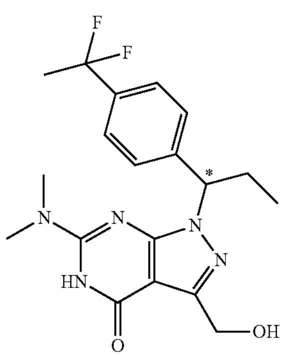 [SMILES: CCC(c1ccc(C(C)(F)F)cc1)n1nc(CO)c2c(=O)[nH]c(N(C)C)nc21] | (R)- or (S)-1-(1-(4-(1,1-Difluoroethyl)phenyl)propyl)-6-(dimethylamino)-3-(hydroxymethyl)-1H-pyrazolo[3,4-d]pyrimidin-4(5H)-one | Calc'd 392.2, found 392.1 | Chiralpak AD-H | A |
| 137 | 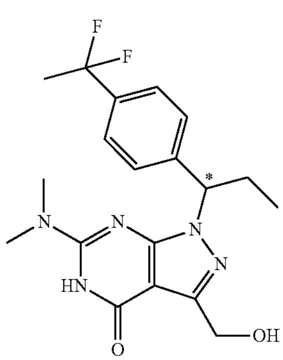 [SMILES: CCC(c1ccc(C(C)(F)F)cc1)n1nc(CO)c2c(=O)[nH]c(N(C)C)nc21] | (S)- or (R)-1-(1-(4-(1,1-Difluoroethyl)phenyl)propyl)-6-(dimethylamino)-3-(hydroxymethyl)-1H-pyrazolo[3,4-d]pyrimidin-4(5H)-one | Calc'd 392.2, found 392.1 | Chiralpak AD-H | A |

TABLE 22-continued

The following compounds were prepared using procedures similar to those described in Examples 120 and 121 using appropriate starting materials the benzyl group deprotection conditions in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]$^+$ | Chiral column | DC* |
|---|---|---|---|---|---|
| 138 | 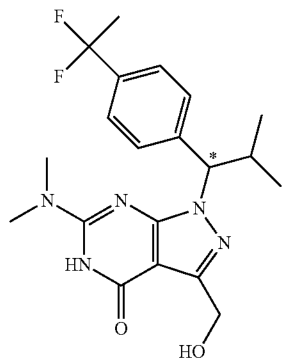 [SMILES: CC(C)C(c1ccc(C(C)(F)F)cc1)n1nc(CO)c2c(=O)[nH]c(N(C)C)nc21] | (R)- or (S)-1-(1-(4-(1,1-Difluoroethyl)phenyl)-2-methylpropyl)-6-(dimethylamino)-3-(hydroxymethyl)-1H-pyrazolo[3,4-d]pyrimidin-4(5H)-one | Calc'd 406.2, found 406.1 | Chiralpak IA | A |
| 139 | 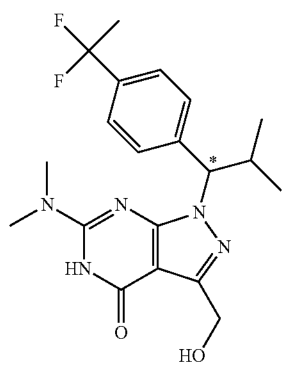 [SMILES: CC(C)C(c1ccc(C(C)(F)F)cc1)n1nc(CO)c2c(=O)[nH]c(N(C)C)nc21] | (S)- or (R)-1-(1-(4-(1,1-Difluoroethyl)phenyl)-2-methylpropyl)-6-(dimethylamino)-3-(hydroxymethyl)-1H-pyrazolo[3,4-d]pyrimidin-4(5H)-one | Calc'd 406.2, found 406.1 | Chiralpak IA | A |
| 140 | 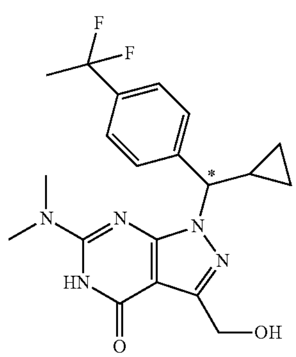 [SMILES: CN(C)c1nc2c(c(CO)nn2C(c2ccc(C(C)(F)F)cc2)C2CC2)c(=O)[nH]1] | (R)- or (S)-1-(Cyclopropyl(4-(1,1-difluoroethyl)phenyl)methyl)-6-(dimethylamino)-3-(hydroxymethyl)-1H-pyrazolo[3,4-d]pyrimidin-4(5H)-one | Calc'd 404.2, found 404.2 | Chiralpak AS-H | A |
| 141 | 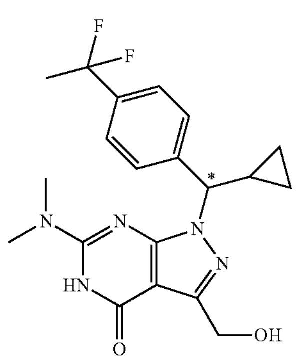 [SMILES: CN(C)c1nc2c(c(CO)nn2C(c2ccc(C(C)(F)F)cc2)C2CC2)c(=O)[nH]1] | (S)- or (R)-1-(Cyclopropyl(4-(1,1-difluoroethyl)phenyl)methyl)-6-(dimethylamino)-3-(hydroxymethyl)-1H-pyrazolo[3,4-d]pyrimidin-4(5H)-one | Calc'd 404.2, found 404.2 | Chiralpak AS-H | A |

TABLE 22-continued

The following compounds were prepared using procedures similar to those described in Examples 120 and 121 using appropriate starting materials the benzyl group deprotection conditions in the table. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$ or BBr$_3$.

| Ex # | Structure | IUPAC Name | Exact Mass [M + H]⁺ | Chiral column | DC* |
|---|---|---|---|---|---|
| 142 | 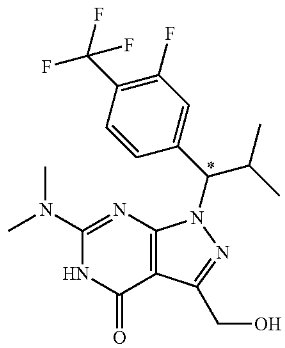 [SMILES: CC(C)C(c1ccc(C(F)(F)F)c(F)c1)n1nc(CO)c2c(=O)[nH]c(N(C)C)nc21] | (R)- or (S)-6-(Dimethylamino)-1-(1-(3-fluoro-4-(trifluoromethyl)phenyl)-2-methylpropyl)-3-(hydroxymethyl)-1H-pyrazolo[3,4-d]pyrimidin-4(5H)-one | Calc'd 428.2, found 428.3 | Chiralpak IA | A |
| 143 | 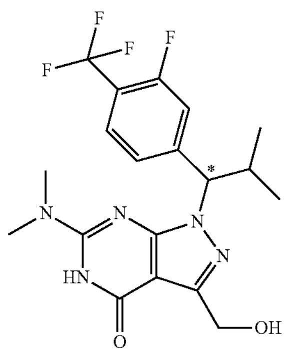 [SMILES: CC(C)C(c1ccc(C(F)(F)F)c(F)c1)n1nc(CO)c2c(=O)[nH]c(N(C)C)nc21] | (S)- or (R)-6-(Dimethylamino)-1-(1-(3-fluoro-4-(trifluoromethyl)phenyl)-2-methylpropyl)-3-(hydroxymethyl)-1H-pyrazolo[3,4-d]pyrimidin-4(5H)-one | Calc'd 428.2, found 428.3 | Chiralpak IA | A |
| 144 | 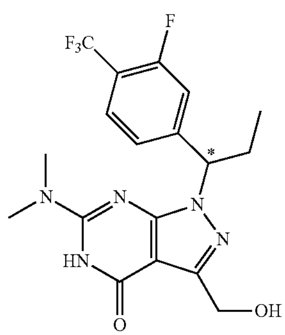 [SMILES: CCC(c1ccc(C(F)(F)F)c(F)c1)n1nc(CO)c2c(=O)[nH]c(N(C)C)nc21] | (R)- or (S)-6-(Dimethylamino)-1-(1-(3-fluoro-4-(trifluoromethyl)phenyl)propyl)-3-(hydroxymethyl)-1H-pyrazolo[3,4-d]pyrimidin-4(5H)-one | Calc'd 414.2, found 414.0 | Chiralpak IA | A |
| 145 | 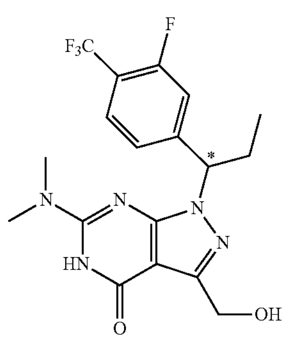 [SMILES: CCC(c1ccc(C(F)(F)F)c(F)c1)n1nc(CO)c2c(=O)[nH]c(N(C)C)nc21] | (S)- or (R)-6-(Dimethylamino)-1-(1-(3-fluoro-4-(trifluoromethyl)phenyl)propyl)-3-(hydroxymethyl)-1H-pyrazolo[3,4-d]pyrimidin-4(5H)-one | Calc'd 414.2, found 414.1 | Chiralpak IA | A |

*Deprotection conditions:

EXAMPLES 146 AND 147

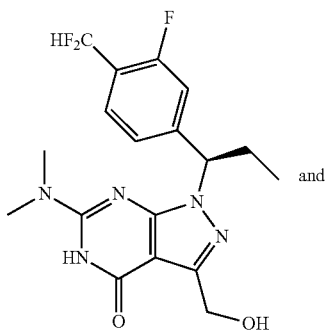

and

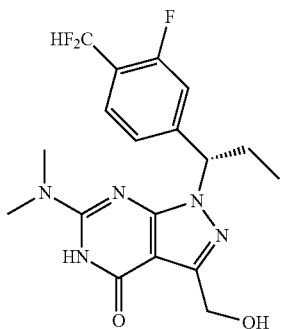

(R)- and (S)-1-(1-(4-(Difluoromethyl)-3-fluorophenyl)propyl)-6-(dimethylamino)-3-(hydroxymethyl)-1H-pyrazolo[3,4-d]pyrimidin-4(5H)-one (Scheme 27)

Step 1. 3-((Benzyloxy)methyl)-6-chloro-1-(1-(4-(difluoromethyl)-3-fluorophenyl)propyl)-4-methoxy-1H-pyrazolo[3,4-d]pyrimidine The title compound was prepared using procedures similar to those described in step 1 of Preparatory Example 75 using 1-(4-(difluoromethyl)-3-fluorophenyl)propan-1-ol and 3-((benzyloxy)methyl)-6-chloro-4-methoxy-1H-pyrazolo[3,4-d]pyrimidine to afford a solid. MS=491.0 (+ESI).

Step 2. 3-((Benzyloxy)methyl)-1-(1-(4-(difluoromethyl)-3-fluorophenyl)propyl)-4-methoxy-N,N-dimethyl-1H-pyrazolo[3,4-d]pyrimidin-6-amine The title compound was prepared using procedures similar to those described in step 3 of Examples 62 and 63 using 3-((benzyloxy)methyl)-6-chloro-1-(1-(4-(difluoromethyl)-3-fluorophenyl)propyl)-4-methoxy-1H-pyrazolo[3,4-d]pyrimidine and $K_2CO_3$ to afford a solid. MS=500.1 (+ESI).

Step 3. 3-((Benzyloxy)methyl)-1-(1-(4-(difluoromethyl)-3-fluorophenyl)propyl)-6-(dimethylamino)-1H-pyrazolo[3,4-d]pyrimidin-4(5H)-one 3-((Benzyloxy)methyl)-1-(1-(4-(difluoromethyl)-3-fluorophenyl)propyl)-4-methoxy-N,N-dimethyl-1H-pyrazolo[3,4-d]pyrimidin-6-amine (0.45 g, 0.9 mmol) and sodium cyanide (44 mg, 0.9 mmol) were dissolved in DMSO (2 mL) at RT. The reaction solution was heated to 130° C., stirred for 1 h, and was cooled to room temperature. The mixture was diluted with water (25 mL) and extracted with EtOAc (3×10 mL). The combined organic layers were washed with brine (3×50 mL), dried over anhydrous sodium sulfate, filtered, and concentrated under vacuum to afford the title compound as an oil. MS=486.1 (+ESI).

Step 4. (R)- and (S)-1-(1-(4-(Difluoromethyl)-3-fluorophenyl)propyl)-6-(dimethylamino)-3-(hydroxymethyl)-1H-pyrazolo[3,4-d]pyrimidin-4(5H)-one To a mixture of 3-((benzyloxy)methyl)-1-(1-(4-(difluoromethyl)-3-fluorophenyl)propyl)-6-(dimethylamino)-1H-pyrazolo[3,4-d]pyrimidin-4(5H)-one (0.30 g, 0.6 mmol) in dichloromethane (3 mL) was added a solution of boron trichloride (1 M in $CH_2Cl_2$, 0.6 mL, 0.6 mmol) at 0° C. The reaction was stirred for 3 h at 0° C. whereupon methanol (10 mL) was added. The reaction mixture was diluted with water (25 mL) and extracted with EtOAc (3×10 mL). The combined organic layers were washed with brine (3×20 mL), dried over anhydrous sodium sulfate, filtered, and concentrated under vacuum. The residue was purified by silica gel column chromatography (0-50% ethyl acetate in hexanes) to afford the racemic title compound as a solid. The enantiopure title compounds were obtained by chiral preparative HPLC (Chiralpak IA, 20% isopropanol in hexanes). The faster-eluting enantiomer of the title compound (Example 146) was obtained as a solid. MS=396.1 (+ESI). $^1$H NMR (400 MHz, $CDCl_3$) δ: 9.49 (br s, 1H), 7.56-7.52 (m, 1H), 7.31-7.22 (m, 2H), 6.85 (t, J=54.8 Hz, 1H), 5.55-5.51 (m, 1H), 4.84 (s, 1H), 3.23 (s, 6H), 2.55-2.48 (m, 1H), 2.26-2.12 (m, 1H), 0.92 (t, J=7.2 Hz, 3H). The slower-eluting enantiomer of the title compound (Example 147) was obtained as a solid. MS=396.1 (+ESI). $^1$H NMR (400 MHz, $CDCl_3$) δ: 9.49 (br s, 1H), 7.56-7.52 (m, 1H), 7.31-7.22 (m, 2H), 6.85 (t, J=54.8 Hz, 1H), 5.55-5.51 (m, 1H), 4.84 (s, 1H), 3.23 (s, 6H), 2.55-2.48 (m, 1H), 2.26-2.12 (m, 1H), 0.92 (t, J=7.2 Hz, 3H).

TABLE 23

The following compounds were prepared using procedures similar to those described in Examples 146 and 147 using appropriate starting materials. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$;
Deprotection(Me) conditions: D: HCl in EtOAc or 1,4-dioxane; E: TMSI; F: NaCN.

| Ex # | Structure | IUPAC Name | Exact Mass [M + H]$^+$ | Chiral column | DC* |
|---|---|---|---|---|---|
| 148 | 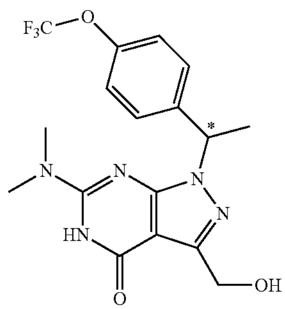 [SMILES: CC(c1ccc(OC(F)(F)F)cc1)n1nc(CO)c2c(=O)[nH]c(N(C)C)nc21] | (R)- or (S)-6-(Dimethylamino)-3-(hydroxymethyl)-1-(1-(4-(trifluoromethoxy)phenyl)ethyl)-1H-pyrazolo[3,4-d]pyrimidin-4(5H)-one | Calc'd 398.1, found 398.0 | Chiralpak IA | B,F |
| 149 | 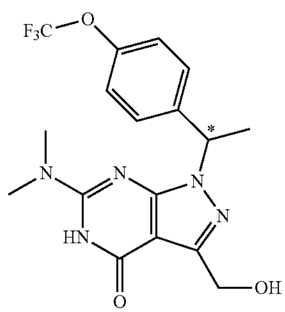 [SMILES: CC(c1ccc(OC(F)(F)F)cc1)n1nc(CO)c2c(=O)[nH]c(N(C)C)nc21] | (S)- or (R)-6-(Dimethylamino)-3-(hydroxymethyl)-1-(1-(4-(trifluoromethoxy)phenyl)ethyl)-1H-pyrazolo[3,4-d]pyrimidin-4(5H)-one | Calc'd 398.1, found 398.0. | Chiralpak IA | B,F |
| 150 | 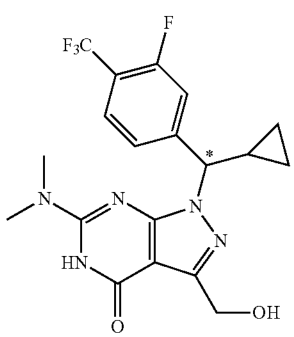 [SMILES: CN(C)c1nc2c(c(CO)nn2C(c2ccc(C(F)(F)F)c(F)c2)C2CC2)c(=O)[nH]1] | (R)- or (S)-1-(Cyclopropyl(3-fluoro-4-(trifluoromelhyl)phenyl)methyl)-6-(dimethylamino)-3-(hydroxymethyl)-1H-pyrazolo[3,4-d]pyrimidin-4(5H)-one | Calc'd 426.2, found 426.2 | Chiralpak AD-H | B,E |
| 151 | 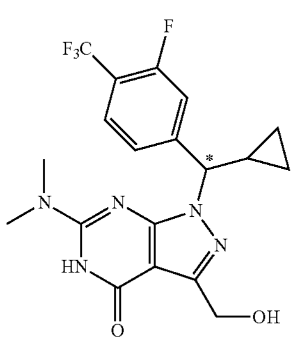 [SMILES: CN(C)c1nc2c(c(CO)nn2C(c2ccc(C(F)(F)F)c(F)c2)C2CC2)c(=O)[nH]1] | (S)- or (R)-1-(Cyclopropyl(3-fluoro-4-(trifluoromethyl)phenyl)methyl)-6-(dimethylamino)-3-(hydroxymethyl)-1H-pyrazolo[3,4-d]pyrimidin-4(5H)-one | Calc'd 426.2, found 426.2 | Chiralpak AD-H | B,E |

TABLE 23-continued

The following compounds were prepared using procedures similar to those described in Examples 146 and 147 using appropriate starting materials. Racemic products were separated using chiral columns specified in the table. For those pairs of enantiomers, the faster-eluting isomer is always listed first in this table.
Deprotection(Bn) conditions: A: 20% Pd(OH)$_2$/H$_2$; B: 10% Pd—C/H$_2$; C: BCl$_3$;
Deprotection(Me) conditions: D: HCl in EtOAc or 1,4-dioxane; E: TMSI; F: NaCN.

| Ex # | Structure | IUPAC Name | Exact Mass [M + H]$^+$ | Chiral column | DC* |
|---|---|---|---|---|---|
| 152 | 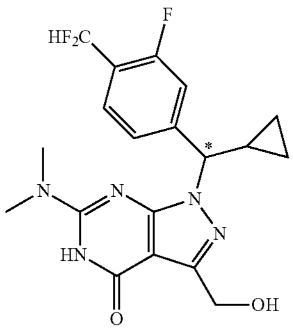 | (R)- or (S)-1-(Cyclopropyl(4-(difluoromethyl)-3-fluorophenyl)methyl)-6-(dimethylamino)-3-(hydroxymethyl)-1H-pyrazolo[3,4-d]pyrimidin-4(5H)-one | Calc'd 408.2, found 408.1. | Chiralpak AS-H | A,F |
| 153 | 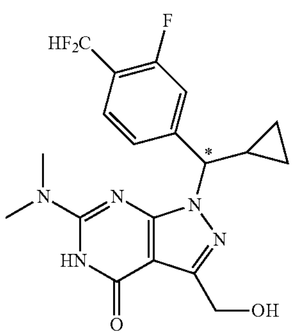 | (S)- or (R)-1-(Cyclopropyl(4-(difluoromethyl)-3-fluorophenyl)methyl)-6-(dimethylamino)-3-(hydroxymethyl)-1H-pyrazolo[3,4-d]pyrimidin-4(5H)-one | Calc'd 408.2, found 408.1. | Chiralpak AS-H | A,F |

*Deprotection Conditions

EXAMPLE 154

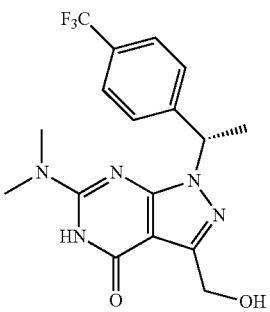

(S)-6-(Dimethylamino)-3-(hydroxymethyl)-1-(1-(4-(trifluoromethyl)phenyl)ethyl)-1H-pyrazolo[3,4-d]pyrimidin-4(5H)-one (Scheme 28)

Step 1. (S)-3-((Benzyloxy)methyl)-6-chloro-4-methoxy-1-(1-(4-(trifluoromethyl)phenyl)ethyl)-1H-pyrazolo[3,4-d]pyrimidine To a solution of 3-((benzyloxy)methyl)-6-chloro-4-methoxy-1H-pyrazolo[3,4-d]pyrimidine (1.0 g, 3.3 mmol) in toluene (20 mL) at RT under N$_2$ was added (R)-1-(4-(trifluoromethyl)phenyl)ethanol (0.87 g, 4.6 mmol), PPh$_3$ (2.6 g, 9.8 mmol) followed by dropwise addition of DIAD (1.91 ml, 9.84 mmol). The mixture was stirred at room temperature overnight whereupon the mixture was diluted with EtOAc (50 mL). The organic layer was washed with sat. aq. NaHCO$_3$ and brine, dried over Na$_2$SO$_4$, filtered, and concentrated under reduced pressure. The residue was purified by silica gel column chromatography (0-100% EtOAc in hexanes) to afford the title compound as a clear oil. ¹H NMR (CDCl₃, 500 MHz) δ: 7.59 (m, 5H), 7.40 (m, 4H), 6.20 (s, 1H), 4.81 (s, 2H), 4.62 (s, 2H), 4.18 (s, 3H), 1.01 (d, J=7.5 Hz, 3H). MS=476.9 (M+H)⁺.

Step 2. (S)-3-((Benzyloxy)methyl)-4-methoxy-N,N-dimethyl-1-(1-(4-(trifluoromethyl)phenyl)ethyl)-1H-pyrazolo[3,4-d]pyrimidin-6-amine To a solution of (S)-3-((benzyloxy)methyl)-6-chloro-4-methoxy-1-(1-(4-(trifluoromethyl)phenyl)ethyl)-1H-pyrazolo[3,4-d]pyrimidine (100 mg, 0.21 mmol) in 2-propanol (2 mL) in a microwave vial was added 2.0 M dimethylamine in THF (0.52 mL, 1.05 mmol) and TEA (0.029 mL, 0.21 mmol). The vial was capped, heated to reflux, and was stirred overnight. The mixture was cooled to rt and was concentrated under reduced pressure. The residue was purified by silica gel column chromatography (0-100% EtOAc in hexanes) to afford the title compound as a solid. MS=485.9 (M+H)⁺.

Step 3. (S)-(6-(Dimethylamino)-4-methoxy-1-(1-(4-(trifluoromethyl)phenyl)ethyl)-1H-pyrazolo[3,4-d]pyrimidin-3-yl)methanol To a solution of (S)-3-((benzyloxy)methyl)-4-methoxy-N,N-dimethyl-1-(1-(4-(trifluoromethyl)phenyl)ethyl)-1H-pyrazolo[3,4-d]pyrimidin-6-amine (100 mg, 0.21 mmol) in MeOH (10 mL) at RT was added 20% Pd(OH)₂ (58 mg, 0.082 mmol) under N₂. The mixture was evacuated and was stirred under a H₂ balloon for 1.5 h. The mixture was purged with N₂, filtered through a pad of Celite™, and the filtrate was concentrated under reduced pressure. The residue was purified by reverse-phase chromatography (Sure Fire C18 column, 30-90% ACN in water (0.05% TFA)) to afford the title compound as a solid. ¹H NMR (CDCl₃, 500 MHz) δ: 7.58 (d, J=8.0 Hz, 2H), 7.54 (d, J=8.0 Hz, 2H), 6.01 (m, 1H), 4.82 (s, 2H), 4.03 (s, 3H), 3.23 (s, 6H), 1.99 (d, J=7.0 Hz, 3H). MS=396.0 (M+H)⁺.

Step 4. (S)-6-(Dimethylamino)-3-(hydroxymethyl)-1-(1-(4-(trifluoromethyl)phenyl)ethyl)-1H-pyrazolo[3,4-d]pyrimidin-4(5H)-one To a solution of (S)-(6-(dimethylamino)-4-methoxy-1-(1-(4-(trifluoromethyl)phenyl)ethyl)-1H-pyrazolo[3,4-d]pyrimidin-3-yl)methanol (36 mg, 0.091 mmol) in EtOAc (0.5 mL) added 6 M HCl (1.0 ml, 6.4 mmol). The mixture was heated to 80° C. and was stirred for 12 h. The mixture was cooled to rt and concentrated under reduced pressure. The residue was purified by reverse-phase chromatography (Surefire C18 column, 30-90% ACN in water (0.05% TFA)) to afford the title compound (Example 154) as a solid. ¹H NMR (CDCl₃, 500 MHz) δ: 9.60 (br s, 1H), 7.61 (d, J=8.5 Hz, 2H), 7.48 (d, J=8.5 Hz, 2H), 5.85 (m, 1H), 4.82 (s, 2H), 3.21 (s, 6H), 1.98 (d, J=7.0 Hz, 3H). MS=381.9 (M+H)⁺.

TABLE 24

The following compounds were prepared using procedures similar to those described for Example 154 using the appropriate starting materials.

| Example # | Structure | IUPAC Name | Exact Mass [M + H]⁺ |
|---|---|---|---|
| 155 | 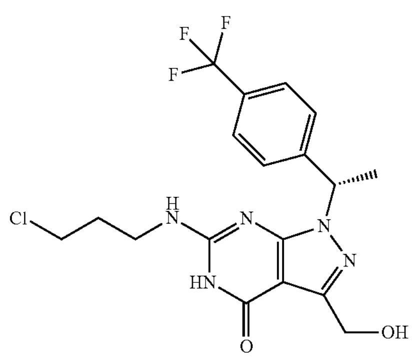 [SMILES: C[C@@H](c1ccc(C(F)(F)F)cc1)n1nc(CO)c2c(=O)[nH]c(NCCCCl)nc21] | 6-[(3-Chloropropyl)amino]-3-(hydroxymethyl)-1-{(1S)-1-[4-(trifluoromethyl)-phenyl]ethyl}-1,5-dihydro-4H-pyrazolo[3,4-d]pyrimidin-4-one | Calc'd 430.1, found 430.2 |
| 156 | 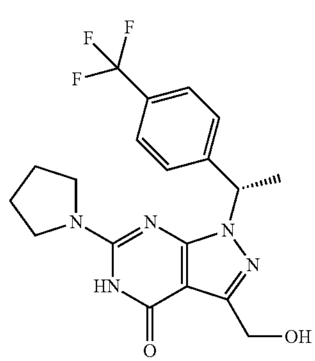 [SMILES: C[C@@H](c1ccc(C(F)(F)F)cc1)n1nc(CO)c2c(=O)[nH]c(N3CCCC3)nc21] | 3-(Hydroxymethyl)-6-pyrrolidin-1-yl-1-{(1S)-1-[4-(trifluoromethyl)phenyl]ethyl}-1,5-dihydro-4H-pyrazolo[3,4-d]pyrimidin-4-one | Calc'd 408.2, found 408.1 |

TABLE 24-continued

The following compounds were prepared using procedures similar to those described for Example 154 using the appropriate starting materials.

| Example # | Structure | IUPAC Name | Exact Mass [M + H]+ |
|---|---|---|---|
| 157 | 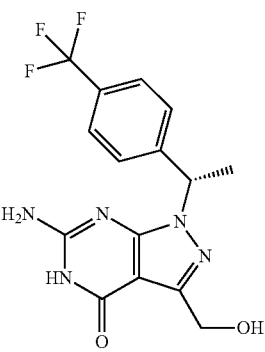 [SMILES: C[C@@H](c1ccc(C(F)(F)F)cc1)n1nc(CO)c2c(=O)[nH]c(N)nc21] | 6-Amino-3-(hydroxymethyl)-1-{(1S)-1-[4-(trifluoromethyl)phenyl]ethyl}-1,5-dihydro-4H-pyrazolo[3,4-d]pyrimidin-4-one | Calc'd 354.1, found 354.1 |

EXAMPLE 158

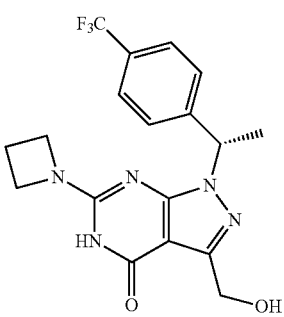 [SMILES: C[C@@H](c1ccc(C(F)(F)F)cc1)n1nc(CO)c2c(=O)[nH]c(N3CCC3)nc21]

(S)-6-(Azetidin-1-yl)-3-(hydroxymethyl)-1-(1-(4-(trifluoromethyl)phenyl)ethyl)-1,5-dihydro-4H-pyrazolo[3,4-d]pyrimidin-4-one (Scheme 29)

Step 1. (S)-6-(Azetidin-1-yl)-3-((benzyloxy)methyl)-4-methoxy-1-(1-(4-(trifluoromethyl)phenyl)ethyl)-1H-pyrazolo[3,4-d]pyrimidine The title compound was prepared using the procedure similar to those described in step 3 of Example 154 using (S)-3-((benzyloxy)methyl)-6-chloro-4-methoxy-1-(1-(4-(trifluoromethyl)phenyl)ethyl)-1H-pyrazolo[3,4-d]pyrimidine to afford an oil. MS=378.1 (M+H)+.

Step 2. (S)-6-(Azetidin-1-yl)-3-((benzyloxy)methyl)-1-(1-(4-(trifluoromethyl)phenyl)ethyl)-1H-pyrazolo[3,4-d]pyrimidin-4(5H)-one To a solution of (S)-6-(azetidin-1-yl)-3-((benzyloxy)methyl)-4-methoxy-1-(1-(4-(trifluoromethyl)phenyl)ethyl)-H-pyrazolo[3,4-d]pyrimidine (100 mg, 0.20 mmol) in DMSO (1 mL) under $N_2$ at rt was added NaCN (29.6 mg, 0.60 mmol). The mixture was heated to 130° C. and was stirred for 2 h at this temperature. The mixture was cooled to rt and was diluted with EtOAc and water. The layers were separated and the aqueous layer was extracted with EtOAc (3×). The organic layers were combined, dried over $Na_2SO_4$, filtered, and concentrated under reduced pressure. The residue was purified by silica gel column chromatography (0-100% EtOAc in hexanes) to afford the title compound as a solid. MS=484.1 (M+H)+.

Step 3. (S)-6-(Azetidin-1-yl)-3-(hydroxymethyl)-1-(1-(4-(trifluoromethyl)phenyl)ethyl)-1,5-dihydro-4H-pyrazolo[3,4-d]pyrimidin-4-one To a solution of (S)-6-(azetidin-1-yl)-3-((benzyloxy)methyl)-1-(1-(4-(trifluoromethyl)phenyl)ethyl)-1H-pyrazolo[3,4-d]pyrimidin-4(5H)-one (90 mg, 0.19 mmol) in MeOH (30 mL) added 20% Pd(OH)$_2$ (52 mg, 0.074 mmol) under $N_2$. The mixture was evacuated and was stirred under a $H_2$ balloon for 1.5 h. The mixture was purged with $N_2$, filtered through a pad of Celite™, and the filtrate was concentrated under reduced pressure. The residue was purified by reverse-phase HPLC chromatography (SureFire C18 column, 30-90% ACN in water (0.05% TFA)) to afford the title compound (Example 158 as a solid. $^1$H NMR (CDCl$_3$, 500 MHz) δ: 10.51 (br s, 1H), 7.59 (d, J=8.0 Hz, 2H), 7.43 (d, J=8.0 Hz, 2H), 5.82 (m, 1H), 4.80 (s, 2H), 4.23 (m, 4H), 2.45 (s, 2H), 1.96 (d, J=7.5 Hz, 3H). MS=394.1 (M+H).

TABLE 25

The following compounds were prepared using procedures similar to those described for Example 158 using the appropriate starting materials.

| Ex # | Structure | IUPAC Name | Exact Mass [M + H]+ |
|------|-----------|------------|---------------------|
| 159 | 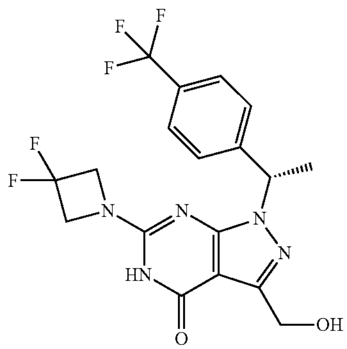 [SMILES: C[C@@H](c1ccc(C(F)(F)F)cc1)n1nc(CO)c2c(=O)[nH]c(N3CC(F)(F)C3)nc21] | 6-(3,3-Difluoroazetidin-1-yl)-3-(hydroxymethyl)-1-{(1S)-1-[4-(trifluoromethyl)phenyl]ethyl}-1,5-dihydro-4H-pyrazolo[3,4-d]pyrimidin-4-one | Calc'd 430.1, found 430.1 |
| 160 | 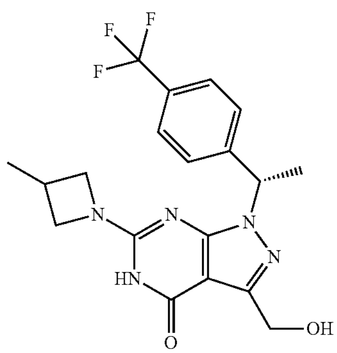 [SMILES: CC1CN(c2nc3c(c(CO)nn3[C@@H](C)c3ccc(C(F)(F)F)cc3)c(=O)[nH]2)C1] | 3-(Hydroxymethyl)-6-(3-methylazetidin-1-yl)-1-{(1S)-1-[4-(trifluoromethyl)phenyl]ethyl}-1,5-dihydro-4H-pyrazolo[3,4-d]pyrimidin-4-one | Calc'd 408.2, found 408.2 |
| 161 | 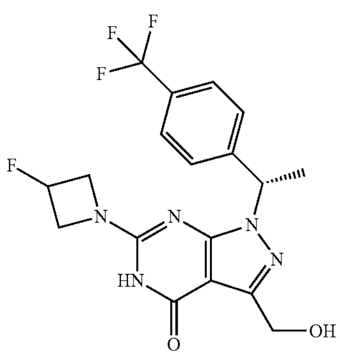 [SMILES: C[C@@H](c1ccc(C(F)(F)F)cc1)n1nc(CO)c2c(=O)[nH]c(N3CC(F)C3)nc21] | 6-(3-Fluoroazetidin-1-yl)-3-(hydroxymethyl)-1-{(1S)-1-[4-(trifluoromethyl)phenyl]ethyl}-1,5-dihydro-4H-pyrazolo[3,4-d]pyrimidin-4-one | Calc'd 412.1, found 411.8 |

EXAMPLES 162 AND 163

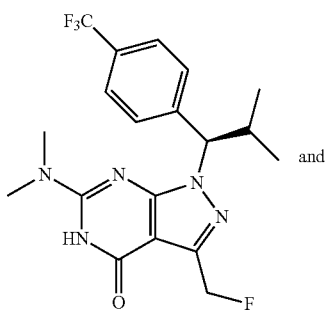

and

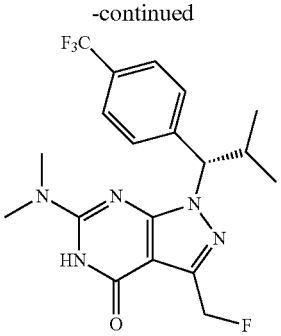

(R)- and (S)-6-(Dimethylamino)-3-(fluoromethyl)-1-(2-methyl-1-(4-(trifluoromethyl)phenyl)propyl)-1H-pyrazolo[3,4-d]pyrimidin-4(5H)-one (Scheme 30)

The racemic title compound was prepared using procedures similar to those described in step 3 of Example 33 using 6-(dimethylamino)-3-(hydroxymethyl)-1-(2-methyl-1-(4-(trifluoromethyl)phenyl)propyl)-1H-pyrazolo[3,4-d]pyrimidin-4(5H)-one prepared from Examples 62 and 63 to afford a solid. The enantiopure title compounds were obtained by chiral preparative HPLC (Chiralpak IA, 10% EtOH in hexanes). The faster-eluting enantiomer of the title compound (Example 162) was obtained as a solid. MS=412.0 (+ESI). $^1$H NMR (400 MHz, CD$_3$OD): 7.77 (d, J=8.4 Hz, 2H), 7.64 (d, J=8.4 Hz, 2H), 5.50 (d, J=48.0 Hz, 2H), 5.32 (d, J=10.8 Hz, 1H), 3.21 (s, 6H), 2.97 (m, 1H), 0.92 (d, J=6.8 Hz, 6H). The slower-eluting enantiomer of the title compound (Example 163) was obtained as a solid. MS=412.0 (+ESI). $^1$H NMR (400 MHz, CD$_3$OD): 7.77 (d, J=8.4 Hz, 2H), 7.64 (d, J=8.4 Hz, 2H), 5.50 (d, J=48.0 Hz, 2H), 5.32 (d, J=10.8 Hz, 1H), 3.21 (s, 6H), 2.97 (m, 1H), 0.92 (d, J=6.8 Hz, 6H).

TABLE 26

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]$^+$ | Chiral column |
|---|---|---|---|---|
| 164 | [structure] | (R)- or (S)-6-(Dimethylamino)-3-(fluoromethyl)-1-(1-(4-(trifluoromethoxy)phenyl)ethyl)-1H-pyrazolo[3,4-d]pyrimidin-4(5H)-one | Calc'd 400.1, found 399.9 | Chiralpak IA |
| 165 | [structure] | (S)- or (R)-6-(Dimethylamino)-3-(fluoromethyl)-1-(1-(4-(trifluoromethoxy)phenyl)ethyl)-1H-pyrazolo[3,4-d]pyrimidin-4(5H)-one | Calc'd 400.1, found 400.0 | Chiralpak IA |
| 166 | [structure] | (R)- or (S)-6-(Dimethylamino)-1-(1-(3-fluoro-4-(trifluoromethoxy)phenyl)ethyl)-3-(fluoromethyl)-1H-pyrazolo[3,4-d]pyrimidin-4(5H)-one | Calc'd 418.1, found 417.9 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 167 | 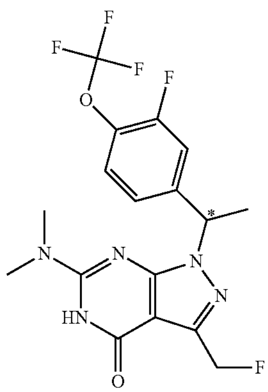 [SMILES: CC(c1ccc(OC(F)(F)F)c(F)c1)n1nc(CF)c2c(=O)[nH]c(N(C)C)nc21] | (S)- or (R)-6-(Dimethylamino)-1-(1-(3-fluoro-4-(trifluoromethoxy)phenyl)ethyl)-3-(fluoromethyl)-1H-pyrazolo[3,4-d]pyrimidin-4(5H)-one | Calc'd 418.1, found 417.9 | Chiralpak IA |
| 168 | 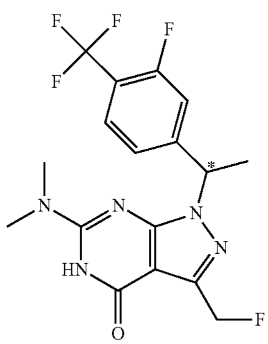 [SMILES: CC(c1ccc(C(F)(F)F)c(F)c1)n1nc(CF)c2c(=O)[nH]c(N(C)C)nc21] | (R)- or (S)-6-(Dimethylamino)-1-(1-(3-fluoro-4-(trifluoromethyl)phenyl)ethyl)-3-(fluoromethyl)-1H-pyrazolo[3,4-d]pyrimidin-4(5H)-one | Calc'd 402.1, found 401.9 | Chiralpak IA |
| 169 | 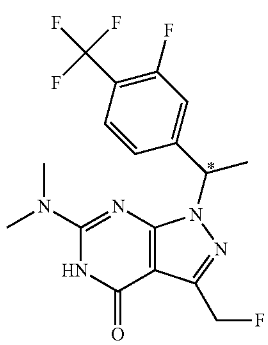 [SMILES: CC(c1ccc(C(F)(F)F)c(F)c1)n1nc(CF)c2c(=O)[nH]c(N(C)C)nc21] | (S)- or (R)-6-(Dimethylamino)-1-(1-(3-fluoro-4-(trifluoromethyl)phenyl)ethyl)-3-(fluoromethyl)-1H-pyrazolo[3,4-d]pyrimidin-4(5H)-one | Calc'd 402.1, found 401.9 | Chiralpak IA |
| 170 | 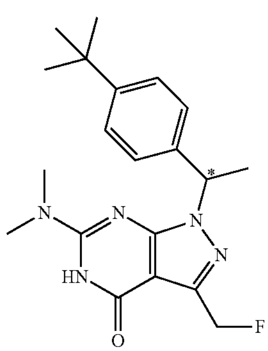 [SMILES: CC(c1ccc(C(C)(C)C)cc1)n1nc(CF)c2c(=O)[nH]c(N(C)C)nc21] | (R)- or (S)-1-(1-(4-tert-Butylphenyl(ethyl)-6-(dimethylamino)-3-(fluoromethyl)-1H-pyrazolo[3,4-d]pyrimidin-4(5H)-one | Calc'd 372.2, found 372.2 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]$^+$ | Chiral column |
|---|---|---|---|---|
| 171 | 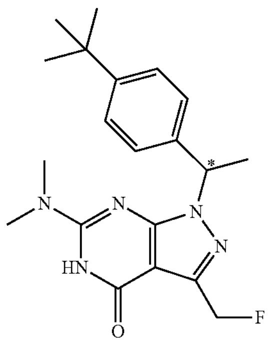 [SMILES: CC(c1ccc(C(C)(C)C)cc1)n1nc(CF)c2c(=O)[nH]c(N(C)C)nc21] | (S)- or (R)-1-(1-(4-tert-Butylphenyl)ethyl)-6-(dimethylamino)-3-(fluoromethyl)-1H-pyrazolo[3,4-d]pyrimidin-4(5H)-one | Calc'd 372.2, found 372.2 | Chiralpak IA |
| 172 | 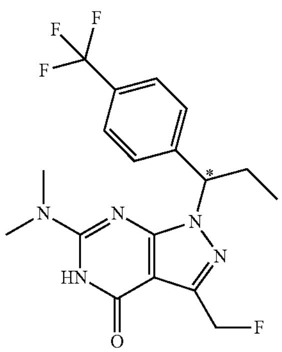 [SMILES: CCC(c1ccc(C(F)(F)F)cc1)n1nc(CF)c2c(=O)[nH]c(N(C)C)nc21] | (R)- or (S)-6-(Dimethylamino)-3-(fluoromethyl)-1-(1-(4-(trifluoromethyl)phenyl)propyl)-1H-pyrazolo[3,4-d]pyrimidin-4(5H)-one | Calc'd 398.2, found 398.1 | Chiralpak IA |
| 173 | 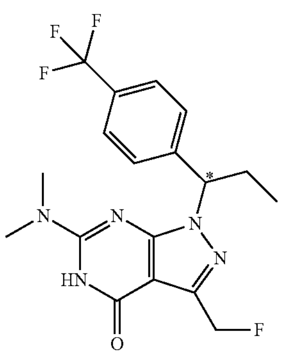 [SMILES: CCC(c1ccc(C(F)(F)F)cc1)n1nc(CF)c2c(=O)[nH]c(N(C)C)nc21] | (S)- or (R)-6-(Dimethylamino)-3-(fluoromethyl)-1-(1-(4-(trifluoromethyl)phenyl)propyl)-1H-pyrazolo[3,4-d]pyrimidin-4(5H)-one | Calc'd 398.2, found 398.1 | Chiralpak IA |
| 174 | 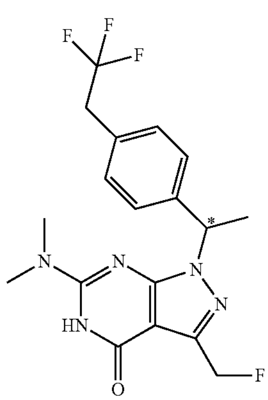 [SMILES: CC(c1ccc(CC(F)(F)F)cc1)n1nc(CF)c2c(=O)[nH]c(N(C)C)nc21] | (R)- or (S)-6-(Dimethylamino)-3-(fluoromethyl)-1-(1-(4-(2,2,2-trifluoroethyl)phenyl)ethyl)-1H-pyrazolo[3,4-d]pyrimidin-4(5H)-one | Calc'd 398.2, found 398.1 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 175 | 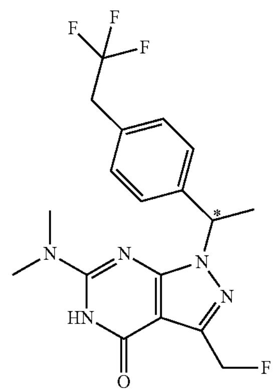 [SMILES: CC(c1ccc(CC(F)(F)F)cc1)n1nc(CF)c2c(=O)[nH]c(N(C)C)nc21] | (S)- or (R)-6-(Dimethylamino)-3-(fluoromethyl)-1-(1-(4-(2,2,2-trifluoroethyl)phenyl)ethyl)-1H-pyrazolo[3,4-d]pyrimidin-4(5H)-one | Calc'd 398.2, found 398.1 | Chiralpak IA |
| 176 | 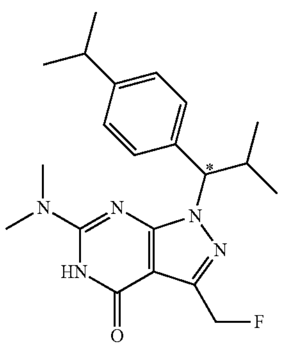 [SMILES: CC(C)c1ccc(C(C(C)C)n2nc(CF)c3c(=O)[nH]c(N(C)C)nc32)cc1] | (R)- or (S)-6-(Dimethylamino)-3-(fluoromethyl)-1-(1-(4-isopropylphenyl)-2-methylpropyl)-1H-pyrazolo[3,4-d]pyrimidin-4(5H)-one | Calc'd 386.2, found 386.1 | Chiralpak IA |
| 177 | 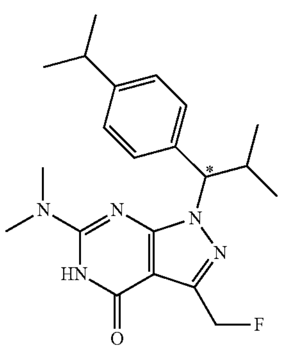 [SMILES: CC(C)c1ccc(C(C(C)C)n2nc(CF)c3c(=O)[nH]c(N(C)C)nc32)cc1] | (S)- or (R)-6-(Dimethylamino)-3-(fluoromethyl)-1-(1-(4-isopropylphenyl)-2-methylpropyl)-1H-pyrazolo[3,4-d]pyrimidin-4(5H)-one | Calc'd 386.2, found 386.1 | Chiralpak IA |
| 178 | 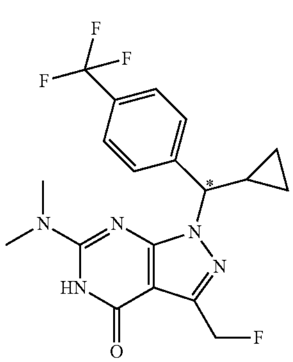 | (R)- or (S)-1-(Cyclopropyl(4-(trifluoromethyl)phenyl)methyl)-6-(dimethylamino)-3-(fluoromethyl)-1H-pyrazolo[3,4-d]pyrimidin-4(5H)-one | Calc'd 410.2, found 410.1 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 179 | 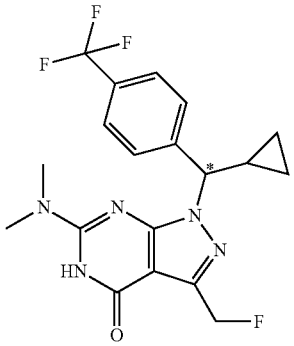 [SMILES: CN(C)c1nc2c(c(CF)nn2C(c2ccc(C(F)(F)F)cc2)C2CC2)c(=O)[nH]1] | (S)- or (R)-1-(Cyclopropyl(4-(trifluoromethyl)phenyl)methyl)-6-(dimethylamino)-3-(fluoromethyl)-1H-pyrazolo[3,4-d]pyrimidin-4(5H)-one | Calc'd 410.2, found 410.1 | Chiralpak IA |
| 180 | 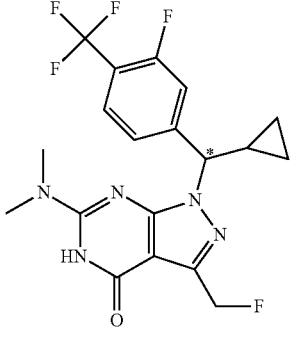 [SMILES: CN(C)c1nc2c(c(CF)nn2C(c2ccc(C(F)(F)F)c(F)c2)C2CC2)c(=O)[nH]1] | (R)- or (S)-1-(Cyclopropyl(3-fluoro-4-(trifluoromethyl)phenyl)methyl)-6-(dimethylamino)-3-(fluoromethyl)-1H-pyrazolo[3,4-d]pyrimidin-4(5H)-one | Calc'd 428.2, found 428.0 | Chiralpak IA |
| 181 | 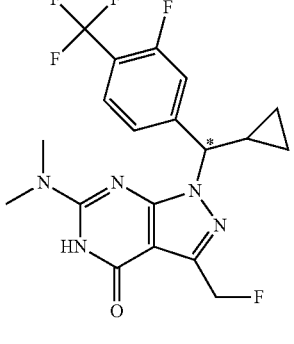 | (S)- or (R)-1-(Cyclopropyl(3-fluoro-4-(trifluoromethyl)phenyl)methyl)-6-(dimethylamino)-3-(fluoromethyl)-1H-pyrazolo[3,4-d]pyrimidin-4(5H)-one | Calc'd 428.2, found 428.0 | Chiralpak IA |
| 182 | 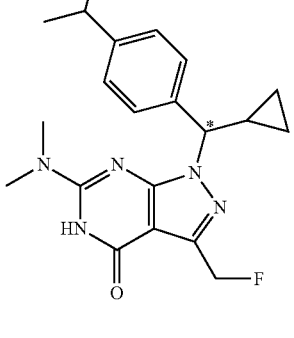 | (R)- or (S)-1-(Cyclopropyl(3-fluoro-4-(trifluoromethyl)phenyl)methyl)-6-(dimethylamino)-3-(fluoromethyl)-1H-pyrazolo[3,4-d]pyrimidin-4(5H)-one | Calc'd 384.2, found 384.2 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 183 | 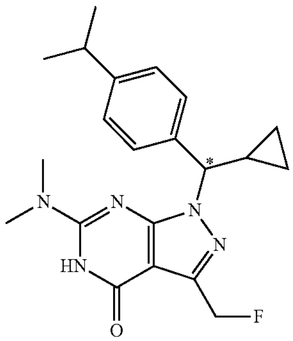 [SMILES: CC(C)c1ccc(C(C2CC2)n2nc(CF)c3c(=O)[nH]c(N(C)C)nc32)cc1] | (R)- or (S)-1-(Cyclopropyl(4-isopropylphenyl)methyl)-6-(dimethylamino)-3-(fluoromethyl)-1H-pyrazolo[3,4-d]pyrimidin-4(5H)-one | Calc'd 384.2, found 384.2 | Chiralpak IA |
| 184 | 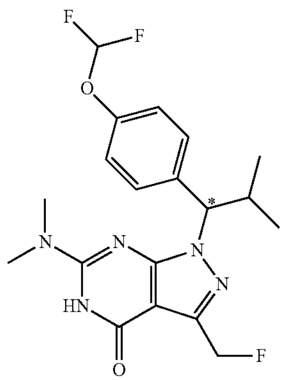 [SMILES: CC(C)C(c1ccc(OC(F)F)cc1)n1nc(CF)c2c(=O)[nH]c(N(C)C)nc21] | (R)- or (S)-1-(1-(4-(Difluoromethoxy)phenyl)-2-methylpropyl)-6-(dimethylamino)-3-(fluoromethyl)-1H-pyrazolo[3,4-d]pyrimidin-4(5H)-one | Calc'd 410.2, found 410.0 | Chiralpak IA |
| 185 | 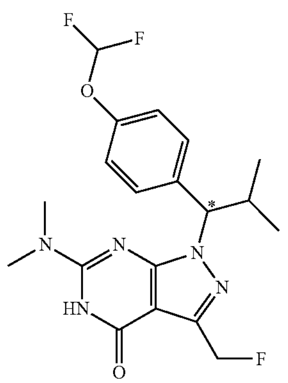 [SMILES: CC(C)C(c1ccc(OC(F)F)cc1)n1nc(CF)c2c(=O)[nH]c(N(C)C)nc21] | (S)- or (R)-1-(1-(4-(Difluoromethoxy)phenyl)-2-methylpropyl)-6-(dimethylamino)-3-(fluoromethyl)-1H-pyrazolo[3,4-d]pyrimidin-4(5H)-one | Calc'd 410.2, found 410.0 | Chiralpak IA |
| 186 | 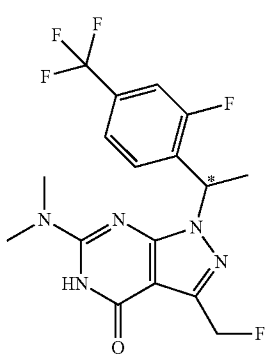 [SMILES: CC(c1ccc(C(F)(F)F)cc1F)n1nc(CF)c2c(=O)[nH]c(N(C)C)nc21] | (R)- or (S)-6-(Dimethylamino)-1-(1-(2-fluoro-4-(trifluoromethyl)phenyl)ethyl)-3-(fluoromethyl)-1H-pyrazolo[3,4-d]pyrimidin-4(5H)-one | Calc'd 402.1, found 402.1 | AXIA Packed |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 187 | 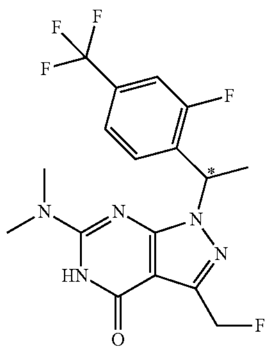 [SMILES: CC(c1ccc(C(F)(F)F)cc1F)n1nc(CF)c2c(=O)[nH]c(N(C)C)nc21] | (S)- or (R)-6-(Dimethylamino)-1-(1-(2-fluoro-4-(trifluoromethyl)phenyl)ethyl)-3-(fluoromethyl)-1H-pyrazolo[3,4-d]pyrimidin-4(5H)-one | Calc'd 402.1, found 402.1 | AXIA Packed |
| 188 | 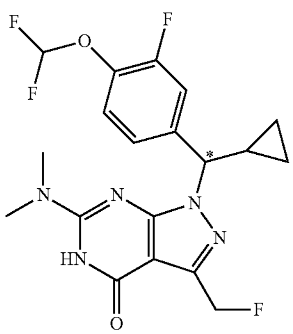 [SMILES: CN(C)c1nc2c(c(CF)nn2C(c2ccc(OC(F)F)c(F)c2)C2CC2)c(=O)[nH]1] | (R)- or (S)-1-(Cyclopropyl(4-(difluoromethoxy)-3-fluorophenyl)methyl)-6-(dimethylamino)-3-(fluoromethyl)-1H-pyrazolo[3,4-d]pyrimidin-4(5H)-one | Calc'd 426.2, found 426.0 | Chiralpak IA |
| 189 | 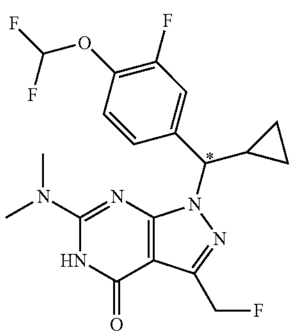 [SMILES: CN(C)c1nc2c(c(CF)nn2C(c2ccc(OC(F)F)c(F)c2)C2CC2)c(=O)[nH]1] | (S)- or (R)-1-(Cyclopropyl(4-(difluoromethoxy)-3-fluorophenyl)methyl)-6-(dimethylamino)-3-(fluoromethyl)-1H-pyrazolo[3,4-d]pyrimidin-4(5H)-one | Calc'd 426.2, found 426.0 | Chiralpak IA |
| 190 | 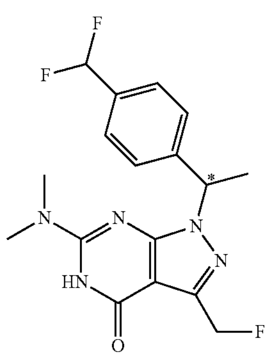 [SMILES: CC(c1ccc(C(F)F)cc1)n1nc(CF)c2c(=O)[nH]c(N(C)C)nc21] | (R)- or (S)-1-(1-(4-(Difluoromethyl)phenyl)ethyl)-6-(dimethylamino)-3-(fluoromethyl)-1H-pyrazolo[3,4-d]pyrimidin-4(5H)-one | Calc'd 366.2, found 366.1 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]$^+$ | Chiral column |
|---|---|---|---|---|
| 191 | 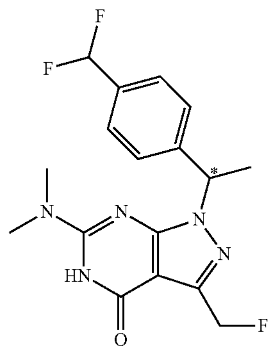 [SMILES: CC(c1ccc(C(F)F)cc1)n1nc(CF)c2c(=O)[nH]c(N(C)C)nc21] | (S)- or (R)-1-(1-(4-(Difluoromethyl)phenyl)ethyl)-6-(dimethylamino)-3-(fluoromethyl)-1H-pyrazolo[3,4-d]pyrimidin-4(5H)-one | Calc'd 366.2, found 366.1 | Chiralpak IA |
| 192 | 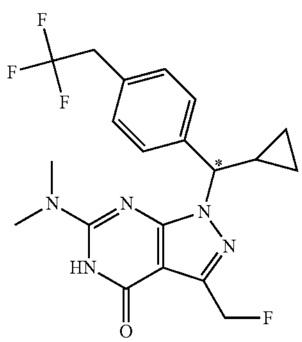 [SMILES: CN(C)c1nc2c(c(CF)nn2C(c2ccc(CC(F)(F)F)cc2)C2CC2)c(=O)[nH]1] | (R)- or (S)-1-(Cyclopropyl(4-(2,2,2-trifluoroethyl)phenyl)methyl)-6-(dimethylamino)-3-(fluoromethyl)-1H-pyrazolo[3,4-d]pyrimidin-4(5H)-one | Calc'd 424.2, found 424.1 | Chiralpak IC |
| 193 | 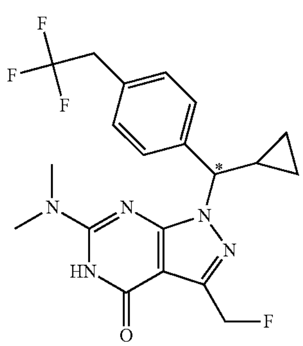 [SMILES: CN(C)c1nc2c(c(CF)nn2C(c2ccc(CC(F)(F)F)cc2)C2CC2)c(=O)[nH]1] | (S)- or (R)-1-(Cyclopropyl(4-(2,2,2-trifluoroethyl)phenyl)methyl)-6-(dimethylamino)-3-(fluoromethyl)-1H-pyrazolo[3,4-d]pyrimidin-4(5H)-one | Calc'd 424.2, found 424.1 | Chiralpak IC |
| 194 | 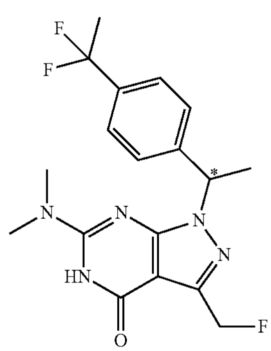 [SMILES: CC(c1ccc(C(C)(F)F)cc1)n1nc(CF)c2c(=O)[nH]c(N(C)C)nc21] | (R)- or (S)-1-(1-(4-(1,1-Difluoroethyl)phenyl)ethyl)-6-(dimethylamino)-3-(fluoromethyl)-1H-pyrazolo[3,4-d]pyrimidin-4(5H)-one | Calc'd 380.2, found 380.0 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 195 | 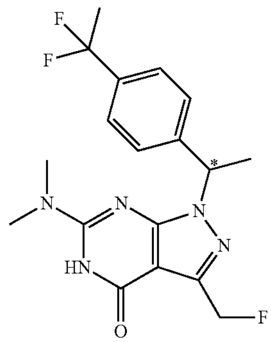 [SMILES: CC(c1ccc(C(C)(F)F)cc1)n1nc(CF)c2c(=O)[nH]c(N(C)C)nc21] | (S)- or (R)-1-(1-(4-(1,1-Difluoroethyl)phenyl)ethyl)-6-(dimethylamino)-3-(fluoromethyl)-1H-pyrazolo[3,4-d]pyrimidin-4(5H)-one | Calc'd 380.2, found 380.1 | Chiralpak IA |
| 196 | 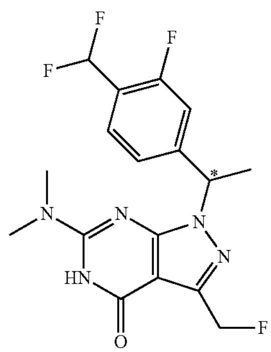 [SMILES: CC(c1ccc(C(F)F)c(F)c1)n1nc(CF)c2c(=O)[nH]c(N(C)C)nc21] | (R)- or (S)-1-(1-(4-(Difluoromethyl)-3-fluorophenyl)ethyl)-6-(dimethylamino)-3-(fluoromethyl)-1H-pyrazolo[3,4-d]pyrimidin-4(5H)-one | Calc'd 384.1, found 384.1 | Chiralpak AS-H |
| 197 | 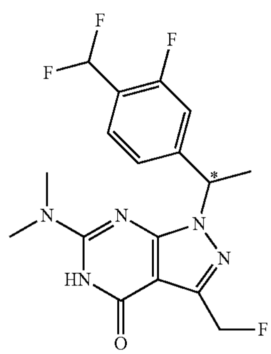 [SMILES: CC(c1ccc(C(F)F)c(F)c1)n1nc(CF)c2c(=O)[nH]c(N(C)C)nc21] | (S)- or (R)-1-(1-(4-(Difluoromethyl)-3-fluorophenyl)ethyl)-6-(dimethylamino)-3-(fluoromethyl)-1H-pyrazolo[3,4-d]pyrimidin-4(5H)-one | Calc'd 384.1, found 384.0 | Chiralpak AS-H |
| 198 | 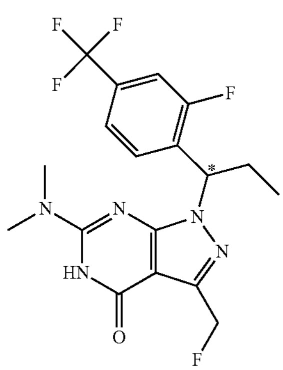 [SMILES: CCC(c1ccc(C(F)(F)F)cc1F)n1nc(CF)c2c(=O)[nH]c(N(C)C)nc21] | (R)- or (S)-6-(Dimethylamino)-1-(1-(2-fluoro-4-(trifluoromethyl)phenyl)propyl)-3-(fluoromethyl)-1H-pyrazolo[3,4-d]pyrimidin-4(5H)-one | Calc'd 416.2, found 416.1 | Chiralpak AD-H |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 199 | 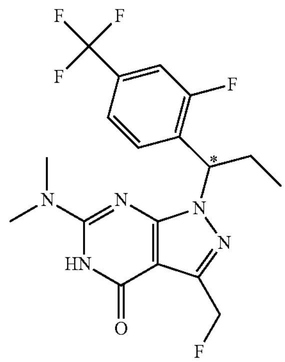 [SMILES: CCC(c1ccc(C(F)(F)F)cc1F)n1nc(CF)c2c(=O)[nH]c(N(C)C)nc21] | (S)- or (R)-6-(Dimethylamino)-1-(1-(2-fluoro-4-(trifluoromethyl)phenyl)propyl)-3-(fluoromethyl)-1H-pyrazolo[3,4-d]pyrimidin-4(5H)-one | Calc'd 416.2, found 416.1 | Chiralpak AD-H |
| 200 | 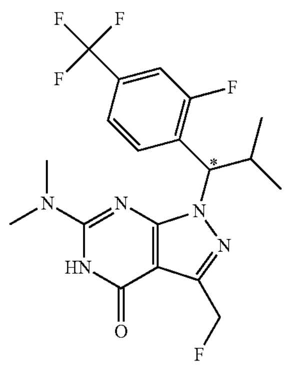 [SMILES: CC(C)C(c1ccc(C(F)(F)F)cc1F)n1nc(CF)c2c(=O)[nH]c(N(C)C)nc21] | (R)- or (S)-6-(Dimethylamino)-1-(1-(2-fluoro-4-(trifluoromethyl)phenyl)-2-methylpropyl)-3-(fluoromethyl)-1H-pyrazolo[3,4-d]pyrimidin-4(5H)-one | Calc'd 430.2, found 430.2 | Chiralpak AS-H |
| 201 | 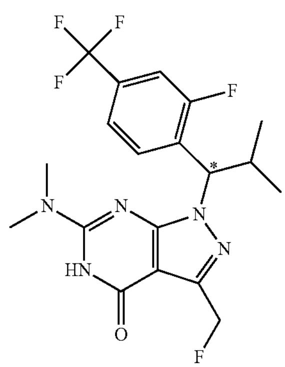 [SMILES: CC(C)C(c1ccc(C(F)(F)F)cc1F)n1nc(CF)c2c(=O)[nH]c(N(C)C)nc21] | (S)- or (R)-6-(Dimethylamino)-1-(1-(2-fluoro-4-(trifluoromethyl)phenyl)-2-methylpropyl)-3-(fluoromethyl)-1H-pyrazolo[3,4-d]pyrimidin-4(5H)-one | Calc'd 430.2, found 430.2 | Chiralpak AS-H |
| 202 | 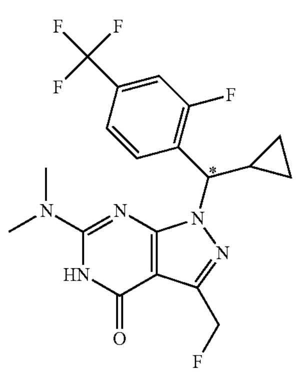 [SMILES: CN(C)c1nc2c(c(CF)nn2C(c2ccc(C(F)(F)F)cc2F)C2CC2)c(=O)[nH]1] | (R)- or (S)-1-(Cyclopropyl(2-fluoro-4-(trifluoromethyl)phenyl)methyl)-6-(dimethylamino)-3-(fluoromethyl)-1H-pyrazolo[3,4-d]pyrimidin-4(5H)-one | Calc'd 428.2, found 428.2 | Chiralpak AD-H |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]⁺ | Chiral column |
|---|---|---|---|---|
| 203 | 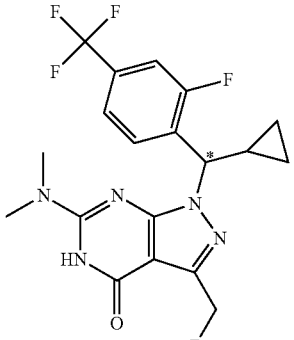 | (S)- or (R)-1-(Cyclopropyl(2-fluoro-4-(trifluoromethyl)phenyl)methyl)-6-(dimethylamino)-3-(fluoromethyl)-1H-pyrazolo[3,4-d]pyrimidin-4(5H)-one | Calc'd 428.2, found 428.2 | Chiralpak AD-H |
| 204 | 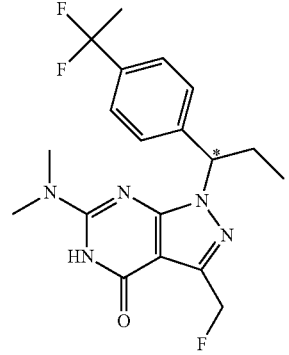 [SMILES: CCC(c1ccc(C(C)(F)F)cc1)n1nc(CF)c2c(=O)[nH]c(N(C)C)nc21] | (R)- or (S)-1-(1-(4-(1,1-Difluoroethyl)phenyl)propyl)-6-(dimethylamino)-3-(fluoromethyl)-1H-pyrazolo[3,4-d]pyrimidin-4(5H)-one | Calc'd 394.2, found 394.1 | Chiralpak IA |
| 205 | 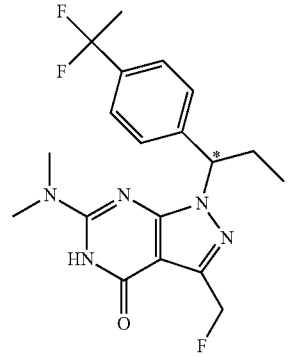 [SMILES: CCC(c1ccc(C(C)(F)F)cc1)n1nc(CF)c2c(=O)[nH]c(N(C)C)nc21] | (S)- or (R)-1-(1-(4-(1,1-Difluoroethyl)phenyl)propyl)-6-(dimethylamino)-3-(fluoromethyl)-1H-pyrazolo[3,4-d]pyrimidin-4(5H)-one | Calc'd 394.2, found 394.1 | Chiralpak IA |
| 206 | 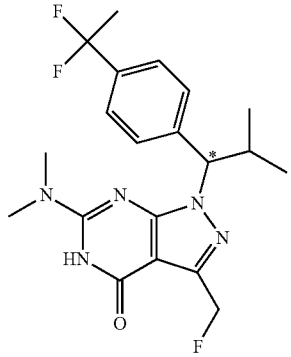 [SMILES: CC(C)C(c1ccc(C(C)(F)F)cc1)n1nc(CF)c2c(=O)[nH]c(N(C)C)nc21] | (R)- or (S)-1-(1-(4-(1,1-Difluoroethyl)phenyl)-2-methylpropyl)-6-(dimethylamino)-3-(fluoromethyl)-1H-pyrazolo[3,4-d]pyrimidin-4(5H)-one | Calc'd 408.2, found 408.1 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 207 | 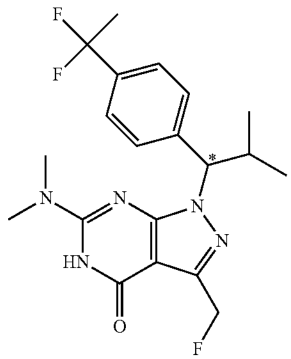 [SMILES: CC(C)C(c1ccc(C(C)(F)F)cc1)n1nc(CF)c2c(=O)[nH]c(N(C)C)nc21] | (S)- or (R)-1-(1-(4-(1,1-Difluoroethyl)phenyl)-2-methylpropyl)-6-(dimethylamino)-3-(fluoromethyl)-1H-pyrazolo[3,4-d]pyrimidin-4(5H)-one | Calc'd 408.2, found 408.1 | Chiralpak IA |
| 208 | 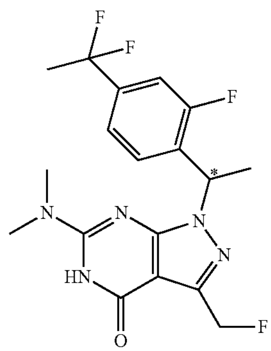 [SMILES: CC(c1ccc(C(C)(F)F)cc1F)n1nc(CF)c2c(=O)[nH]c(N(C)C)nc21] | (R)- or (S)-1-(1-(4-(1,1-Difluoroethyl)-2-fluorophenyl)ethyl)-6-(dimethylamino)-3-(fluoromethyl)-1H-pyrazolo[3,4-d]pyrimidin-4(5H)-one | Calc'd 398.2, found 398.1 | (R,R) WHELK-01 5/100 Kromasil |
| 209 | 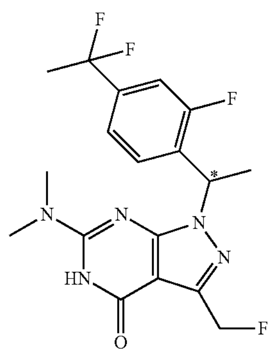 [SMILES: CC(c1ccc(C(C)(F)F)cc1F)n1nc(CF)c2c(=O)[nH]c(N(C)C)nc21] | (S)- or (R)-1-(1-(4-(1,1-Difluoroethyl)-2-fluorophenyl)ethyl)-6-(dimethylamino)-3-(fluoromethyl)-1H-pyrazolo[3,4-d]pyrimidin-4(5H)-one | Calc'd 398.2, found 398.1 | (R,R) WHELK-01 5/100 Kromasil |
| 210 | 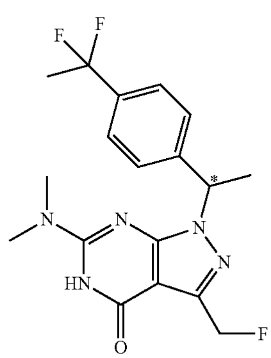 [SMILES: CC(c1ccc(C(C)(F)F)cc1)n1nc(CF)c2c(=O)[nH]c(N(C)C)nc21] | (R)- or (S)-1-(1-(4-(1,1-Difluoroethyl)-3-fluorophenyl)ethyl)-6-(dimethylamino)-3-(fluoromethyl)-1H-pyrazolo[3,4-d]pyrimidin-4(5H)-one | Calc'd 398.2, found 398.3 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 211 | 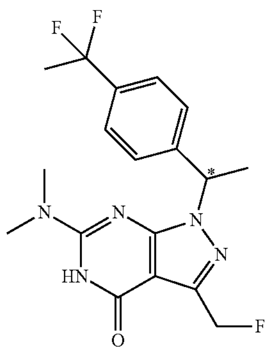 [SMILES: CC(c1ccc(C(C)(F)F)cc1)n1nc(CF)c2c(=O)[nH]c(N(C)C)nc21] | (S)- or (R)-1-(1-(4-(1,1-Difluoroethyl)-3-fluorophenyl)ethyl)-6-(dimethylamino)-3-(fluoromethyl)-1H-pyrazolo[3,4-d]pyrimidin-4(5H)-one | Calc'd 398.2, found 398.2 | Chiralpak IA |
| 212 | 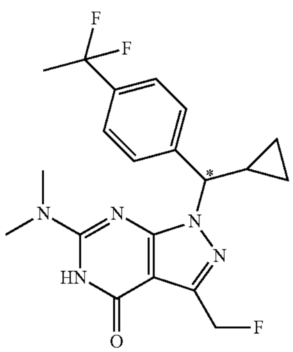 [SMILES: CN(C)c1nc2c(c(CF)nn2C(c2ccc(C(C)(F)F)cc2)C2CC2)c(=O)[nH]1] | (R)- or (S)-1-(Cyclopropyl(4-(1,1-difluoroethyl)phenyl)methyl)-6-(dimethylamino)-3-(fluoromethyl)-1H-pyrazolo[3,4-d]pyrimidin-4(5H)-one | Calc'd 406.2, found 406.2 | Chiralpak IA |
| 213 | 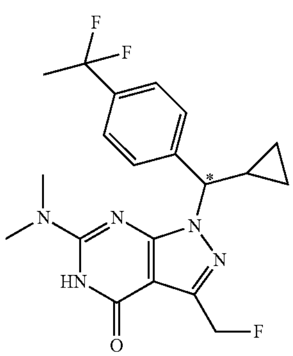 [SMILES: CN(C)c1nc2c(c(CF)nn2C(c2ccc(C(C)(F)F)cc2)C2CC2)c(=O)[nH]1] | (S)- or (R)-1-(Cyclopropyl(4-(1,1-difluoroethyl)phenyl)methyl)-6-(dimethylamino)-3-(fluoromethyl)-1H-pyrazolo[3,4-d]pyrimidin-4(5H)-one | Calc'd 406.2, found 406.3 | Chiralpak IA |
| 214 | 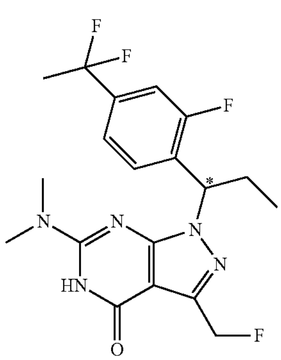 [SMILES: CCC(c1ccc(C(C)(F)F)cc1F)n1nc(CF)c2c(=O)[nH]c(N(C)C)nc21] | (R)- or (S)-1-(1-(4-(1,1-Difluoroethyl)-2-fluorophenyl)propyl)-6-(dimethylamino)-3-(fluoromethyl)-1H-pyrazolo[3,4-d]pyrimidin-4(5H)-one | Calc'd 412.2, found 412.1 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]$^+$ | Chiral column |
|---|---|---|---|---|
| 215 | 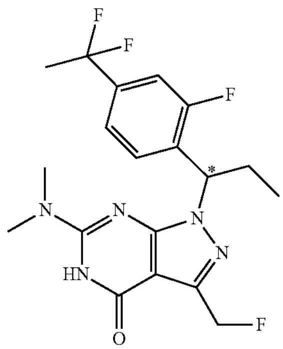 [SMILES: CCC(c1ccc(C(C)(F)F)cc1F)n1nc(CF)c2c(=O)[nH]c(N(C)C)nc21] | (S)- or (R)-1-(1-(4-(1,1-Difluoroethyl)-2-fluorophenyl)propyl)-6-(dimethylamino)-3-(fluoromethyl)-1H-pyrazolo[3,4-d]pyrimidin-4(5H)-one | Calc'd 412.2, found 412.0 | Chiralpak IA |
| 216 | 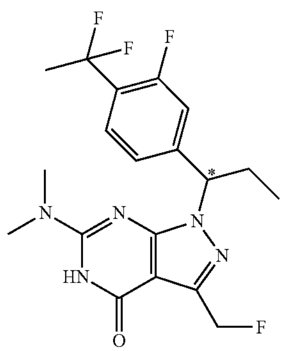 [SMILES: CCC(c1ccc(C(C)(F)F)c(F)c1)n1nc(CF)c2c(=O)[nH]c(N(C)C)nc21] | (R)- or (S)-1-(1-(4-(1,1-Difluoroethyl)-3-fluorophenyl)propyl)-6-(dimethylamino)-3-(fluoromethyl)-1H-pyrazolo[3,4-d]pyrimidin-4(5H)-one | Calc'd 412.2, found 412.0 | Chiralpak IA |
| 217 | 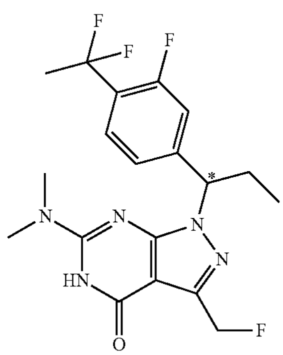 [SMILES: CCC(c1ccc(C(C)(F)F)c(F)c1)n1nc(CF)c2c(=O)[nH]c(N(C)C)nc21] | (S)- or (R)-1-(1-(4-(1,1-Difluoroethyl)-3-fluorophenyl)propyl)-6-(dimethylamino)-3-(fluoromethyl)-1H-pyrazolo[3,4-d]pyrimidin-4(5H)-one | Calc'd 412.2, found 412.1 | Chiralpak IA |
| 218 | 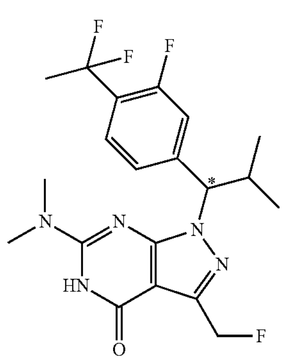 [SMILES: CC(C)C(c1ccc(C(C)(F)F)c(F)c1)n1nc(CF)c2c(=O)[nH]c(N(C)C)nc21] | (R)- or (S)-1-(1-(4-(1,1-Difluoroethyl)-3-fluorophenyl)-2-methylpropyl)-6-(dimethylamino)-3-(fluoromethyl)-1H-pyrazolo[3,4-d]pyrimidin-4(5H)-one | Calc'd 426.2, found 426.1 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 219 | 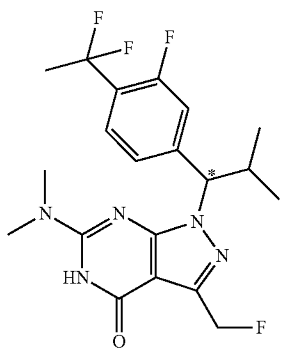 [SMILES: CC(C)C(c1ccc(C(C)(F)F)c(F)c1)n1nc(CF)c2c(=O)[nH]c(N(C)C)nc21] | (S)- or (R)-1-(1-(4-(1,1-Difluoroethyl)-3-fluorophenyl)-2-methylpropyl)-6-(dimethylamino)-3-(fluoromethyl)-1H-pyrazolo[3,4-d]pyrimidin-4(5H)-one | Calc'd 426.2, found 426.0 | Chiralpak IA |
| 220 | 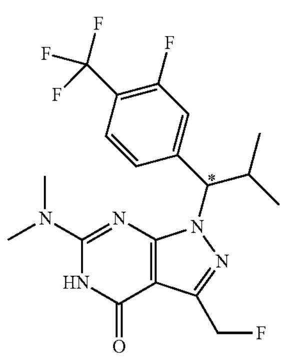 [SMILES: CC(C)C(c1ccc(C(F)(F)F)c(F)c1)n1nc(CF)c2c(=O)[nH]c(N(C)C)nc21] | (R)- or (S)-6-(Dimethylamino)-1-(1-(3-fluoro-4-(trifluoromethyl)phenyl)-2-methylpropyl)-3-(fluoromethyl)-1H-pyrazolo[3,4-d]pyrimidin-4(5H)-one | Calc'd 430.2, found 430.0 | Chiralpak IA |
| 221 | 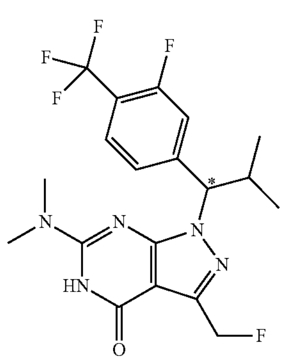 [SMILES: CC(C)C(c1ccc(C(F)(F)F)c(F)c1)n1nc(CF)c2c(=O)[nH]c(N(C)C)nc21] | (S)- or (R)-6-Dimethylamino-1-(1-(3-fluoro-4-trifluoromethyl)phenyl)-2-methylpropyl)-3-(fluoromethyl)-1H-pyrazolo[3,4-d]pyrimidin-4(5H)-one | Calc'd 430.2, found 430.0 | Chiralpak IA |

TABLE 26-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]$^+$ | Chiral column |
|---|---|---|---|---|
| 222 | 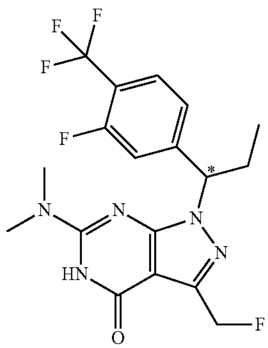 [SMILES: CCC(c1ccc(C(F)(F)F)c(F)c1)n1nc(CF)c2c(=O)[nH]c(N(C)C)nc21] | (R)- or (S)-6-(Dimethylamino)-1-(1-(3-fluoro-4-(trifluoromethyl)phenyl)propyl)-3-(fluoromethyl)-1H-pyrazolo[3,4-d]pyrimidin-4(5H)-one | Calc'd 416.2, found 416.0 | Chiralpak AS-H |
| 223 | 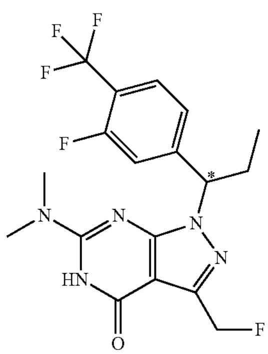 [SMILES: CCC(c1ccc(C(F)(F)F)c(F)c1)n1nc(CF)c2c(=O)[nH]c(N(C)C)nc21] | (S)- or (R)-6-(Dimethylamino)-1-(1-(3-fluoro-4-(trifluoromethyl)phenyl)propyl)-3-(fluoromethyl)-1H-pyrazolo[3,4-d]pyrimidin-4(5H)-one | Calc'd 416.2, found 416.0 | Chiralpak AS-H |

EXAMPLE 224

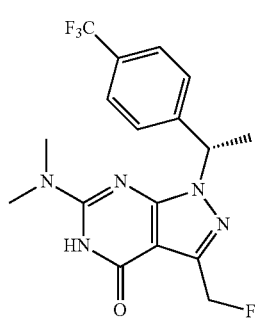 [SMILES: C[C@@H](c1ccc(C(F)(F)F)cc1)n1nc(CF)c2c(=O)[nH]c(N(C)C)nc21]

(S)-6-(Dimethylamino)-3-(fluoromethyl)-1-(1-(4-(trifluoromethyl)phenyl)ethyl)-1H-pyrazolo[3,4-d]pyrimidin-4(5H)-one (Scheme 31)

To a solution of (S)-6-(dimethylamino)-3-(hydroxymethyl)-1-(1-(4-(trifluoromethyl)phenyl)ethyl)-1H-pyrazolo[3,4-d]pyrimidin-4(5H)-one (30 mg, 0.079 mmol) from Example 154 in DCM (1 mL) in plastic vial at RT under $N_2$ was added DAST (10.4 µL, 0.079 mmol) dropwise. The mixture was stirred at room temperature for 1 h whereupon water was added and the mixture was concentrated under reduced pressure. The residue was purified by reverse-phase HPLC chromatography (SureFire C18 column, 30-90% ACN in water (0.05% TFA)) to afford the title compound (Example 224) as a solid. $^1$H NMR (CDCl$_3$, 500 MHz) δ: 10.01 (br s, 1H), 7.59 (d, J=8.0 Hz, 2H), 7.39 (d, J=8.0 Hz, 2H), 5.82 (m, 1H), 5.61 (m, 1H), 5.43 (m, 1H), 3.23 (s, 6H), 1.98 (d, J=7.0 Hz, 3H). MS=383.2 (M+H)+.

TABLE 27

The following compounds were prepared using procedures similar to those described for Example 224 using the appropriate starting materials.

| Ex# | Structure | IUPAC Name | Exact Mass [M + H]+ |
|---|---|---|---|
| 225 | 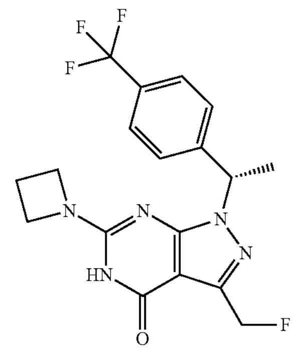 [SMILES: C[C@@H](c1ccc(C(F)(F)F)cc1)n1nc(CF)c2c(=O)[nH]c(N3CCC3)nc21] | 6-Azetidin-1-yl-3-(fluoromethyl)-1-{(1S)-1-[4-(trifluoromethyl)phenyl]ethyl}-1,5-dihydro-4H-pyrazolo[3,4-d]pyrimidin-4-one | Calc'd 396.1, found 395.9 |
| 226 | 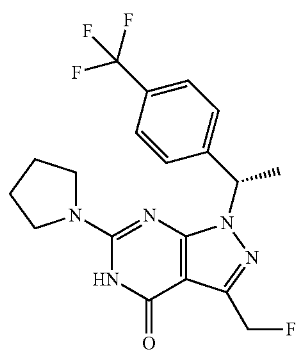 [SMILES: C[C@@H](c1ccc(C(F)(F)F)cc1)n1nc(CF)c2c(=O)[nH]c(N3CCCC3)nc21] | 3-(Fluoromethyl)-6-pyrrolidin-1-yl-1-{(1S)-1-[4-(trifluoromethyl)phenyl]ethyl}-1,5-dihydro-4H-pyrazolo[3,4-d]pyrimidin-4-one | Calc'd 410.2, found 410.1 |

EXAMPLES 227 AND 228

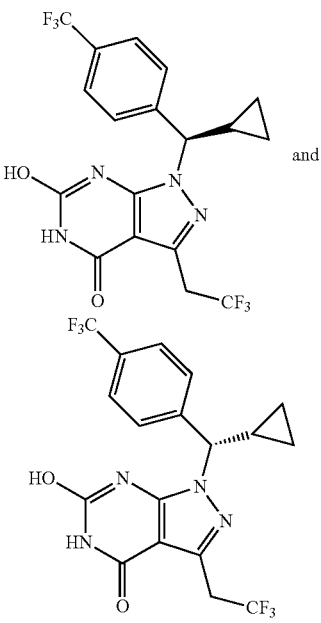

(R)- and (S)-1-(Cyclopropyl(4-(trifluoromethyl)phenyl)methyl)-6-hydroxy-3-(2,2,2-trifluoroethyl)-1H-pyrazolo[3,4-d]pyrimidin-4(5H)-one (Scheme 32)

The racemic title compound was prepared using procedures similar to those described in step 1 of Examples 1 and 2 using 5-amino-1-(cyclopropyl(4-(trifluoromethyl)phenyl)methyl)-3-(2,2,2-trifluoroethyl)-1H-pyrazole-4-carboxamide prepared from Preparatory Example 55 to afford a solid. The enantiopure title compounds were obtained by chiral preparative HPLC (Chiralpak AD-H, 30% EtOH in hexanes (0.1% TFA)). The faster-eluting enantiomer of the title compound (Example 227) was obtained as a solid. MS=433.1 (+ESI). $^1$H NMR (400 MHz, CD$_3$OD): 7.66 (d, J=8.4 Hz, 2H), 7.61 (d, J=8.4 Hz, 2H), 4.88 (d, J=12.4 Hz, 1H), 3.78-3.66 (m, 2H), 0.95-0.82 (m, 2H), 0.73-0.67 (m, 1H), 0.67-0.58 (m, 1H), 0.57-0.43 (m, 1H). The slower-eluting enantiomer of the title compound (Example 228) was obtained as a solid. MS=433.1 (+ESI). $^1$H NMR (400 MHz, CD$_3$OD): 7.66 (d, J=8.4 Hz, 2H), 7.61 (d, J=8.4 Hz, 2H), 4.88 (d, J=12.4 Hz, 1H), 3.78-3.66 (m, 2H), 0.95-0.82 (m, 2H), 0.73-0.67 (m, 1H), 0.67-0.58 (m, 1H), 0.57-0.43 (m, 1H).

TABLE 28

The following racemic compounds were prepared using procedures similar to those described in Examples 227 and 228 using appropriate starting materials using the cyclization conditions listed.
Cyclization conditions: A: triphosgene, TEA, dioxane; B: ethyl chloroformate.

| Ex # | Structure | IUPAC Name | Exact Mass [M + H]+ | C** |
|---|---|---|---|---|
| 229 | 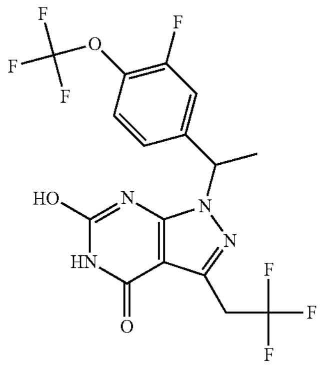 [SMILES: CC(c1ccc(OC(F)(F)F)c(F)c1)n1nc(CC(F)(F)F)c2c(=O)[nH]c(O)nc21] | 1-(1-(3-Fluoro-4-(trifluoromethoxy)phenyl)ethyl)-6-hydroxy-3-(2,2,2-trifluoroethyl)-1H-pyrazolo[3,4-d]pyrimidin-4(5H)-one | Calc'd 441.1, found 441.1 | B |
| 230 | 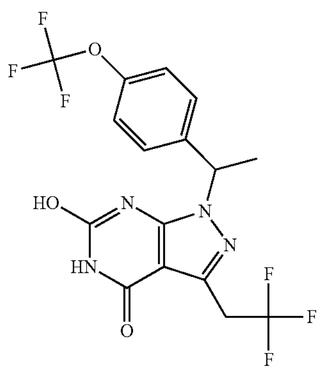 [SMILES: CC(c1ccc(OC(F)(F)F)cc1)n1nc(CC(F)(F)F)c2c(=O)[nH]c(O)nc21] | 6-Hydroxy-3-(2,2,2-trifluoroethyl)-1-(1-(4-(trifluoromethoxy)phenyl)ethyl)-1H-pyrazolo[3,4-d]pyrimidin-4(5H)-one | Calc'd 423.1, found 423.2 | A |
| 231 | 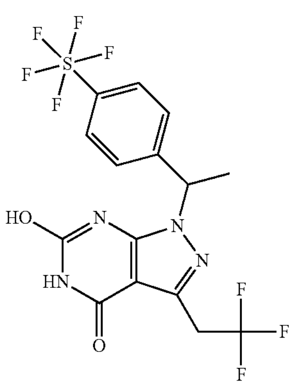 [SMILES: CC(c1ccc(S(F)(F)(F)(F)F)cc1)n1nc(CC(F)(F)F)c2c(=O)[nH]c(O)nc21] | 6-Hydroxy-3-(2,2,2-trifluoroethyl)-1-(1-(4-(pentafluorosulfanyl)phenyl)ethyl)-1H-pyrazolo[3,4-d]pyrimidin-4(5H)-one | Calc'd 465.1, found 465.1 | B |

**= Cyclization method

TABLE 29

The following compounds were prepared using procedures similar to those described in Examples 227 and 228 using appropriate starting materials and the cyclization conditions listed in the table. Racemic products were separated using chiral columns specified in the table. For those pairs of enantiomers, the faster-eluting isomer is always listed first in this table.
Cyclization conditions: A: triphosgene, TEA, dioxane; B: 4-nitrophenyl chloroformate; C: ethyl chloroformate.

| Ex# | Structure | IUPAC Name | Exact Mass [M + H]+ | Chiral column | C** |
|---|---|---|---|---|---|
| 232 | 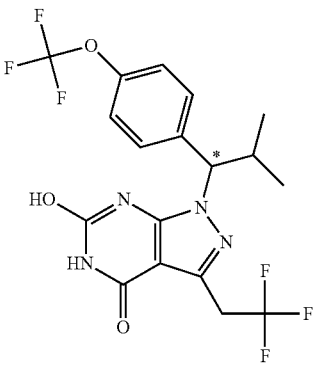 [SMILES: CC(C)C(c1ccc(OC(F)(F)F)cc1)n1nc(CC(F)(F)F)c2c(=O)[nH]c(O)nc21] | (R)- or (S)-6-Hydroxy-1-(2-methyl-1-(4-(trifluoromethoxy)phenyl)propyl)-3-(2,2,2-trifluoroethyl)-1H-pyrazolo[3,4-d]pyrimidin-4(5H)-one | Calc'd 451.1, found 451.2 | Chiralpak IA | B |
| 233 | 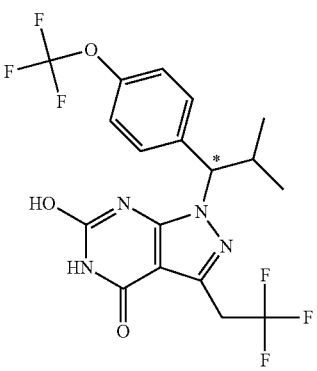 [SMILES: CC(C)C(c1ccc(OC(F)(F)F)cc1)n1nc(CC(F)(F)F)c2c(=O)[nH]c(O)nc21] | (S)- or (R)-6-Hydroxy-1-(2-methyl-1-(4-(trifluoromethoxy)phenyl)propyl)-3-(2,2,2-trifluoroethyl)-1H-pyrazolo[3,4-d]pyrimidin-4(5H)-one | Calc'd 451.1, found 451.2 | Chiralpak IA | B |
| 234 | 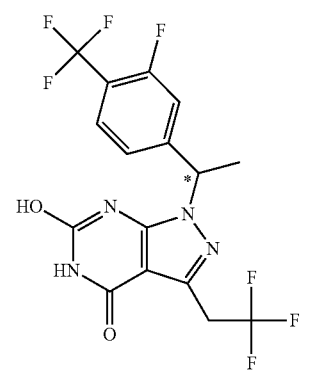 | (R)- or (S)-1-(1-(3-Fluoro-4-(trifluoromethyl)phenyl)ethyl)-6-hydroxy-3-(2,2,2-trifluoroethyl)-1H-pyrazolo[3,4-d]pyrimidin-4(5H)-one | Calc'd 425.1, found 425.0 | Chiralpak IA | B |

TABLE 29-continued

The following compounds were prepared using procedures similar to those described in Examples 227 and 228 using appropriate starting materials and the cyclization conditions listed in the table. Racemic products were separated using chiral columns specified in the table. For those pairs of enantiomers, the faster-eluting isomer is always listed first in this table.

Cyclization conditions: A: triphosgene, TEA, dioxane; B: 4-nitrophenyl chloroformate; C: ethyl chloroformate.

| Ex# | Structure | IUPAC Name | Exact Mass [M + H]+ | Chiral column | C** |
|---|---|---|---|---|---|
| 235 | 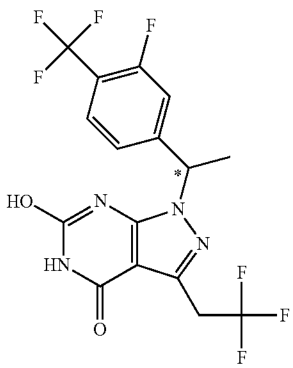 [SMILES: CC(c1ccc(C(F)(F)F)c(F)c1)n1nc(CC(F)(F)F)c2c(=O)[nH]c(O)nc21] | (S)- or (R)-1-(1-(3-Fluoro-4-(triduoromethyl)phenyl)ethyl)-6-hydroxy-3-(2,2,2-trifluoroethyl)-1H-pyrazolo[3,4-d]pyrimidin-4(5H)-one | Calc'd 425.1, found 425.1 | Chiralpak IA | B |
| 236 | 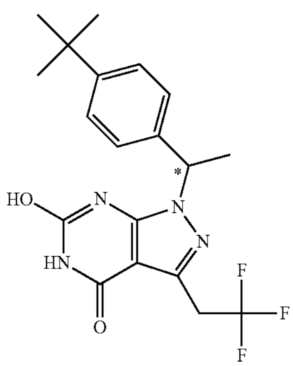 [SMILES: CC(c1ccc(C(C)(C)C)cc1)n1nc(CC(F)(F)F)c2c(=O)[nH]c(O)nc21] | (R)- or (S)-1-(1-(4-tert-Butylphenyl)ethyl)-6-hydroxy-3-(2,2,2-trifluoroethyl)-1H-pyrazolo[3,4-d]pyrimidin-4(5H)-one | Calc'd 395.2, found 395.1 | Chiralpak IA | B |
| 237 | 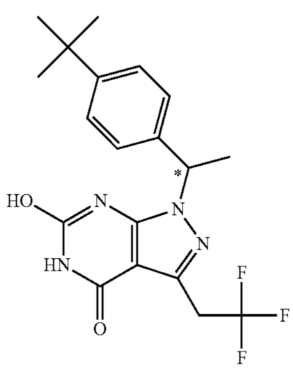 [SMILES: CC(c1ccc(C(C)(C)C)cc1)n1nc(CC(F)(F)F)c2c(=O)[nH]c(O)nc21] | (S)- or (R)-1-(1-(4-tert-Butylphenyl)ethyl)-6-hydroxy-3-(2,2,2-trifluoroethyl)-1H-pyrazolo[3,4-d]pyrimidin-4(5H)-one | Calc'd 395.2, found 395.2 | Chiralpak IA | B |

TABLE 29-continued

The following compounds were prepared using procedures similar to those described in Examples 227 and 228 using appropriate starting materials and the cyclization conditions listed in the table. Racemic products were separated using chiral columns specified in the table. For those pairs of enantiomers, the faster-eluting isomer is always listed first in this table.

Cyclization conditions: A: triphosgene, TEA, dioxane; B: 4-nitrophenyl chloroformate; C: ethyl chloroformate.

| Ex# | Structure | IUPAC Name | Exact Mass [M + H]+ | Chiral column | C** |
|---|---|---|---|---|---|
| 238 | 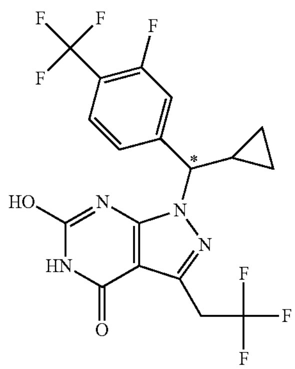 [SMILES: O=c1[nH]c(O)nc2c1c(CC(F)(F)F)nn2C(c1ccc(C(F)(F)F)c(F)c1)C1CC1] | (R)- or (S)-1-(Cyclopropyl(3-fluoro-4-(trifluoromethyl)phenyl)methyl)-6-hydroxy-3-(2,2,2-trifluoroethyl)-1H-pyrazolo[3,4-d]pyrimidin-4(5H)-one | Calc'd 451.1, found 451.3 | Chiralpak IA | B |
| 239 | 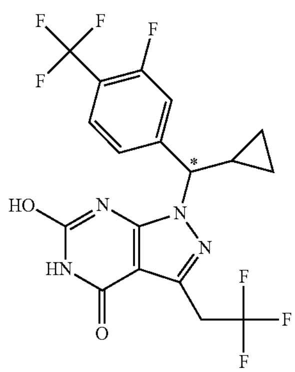 [SMILES: O=c1[nH]c(O)nc2c1c(CC(F)(F)F)nn2C(c1ccc(C(F)(F)F)c(F)c1)C1CC1] | (S)- or (R)-1-(Cyclopropyl(3-fluoro-4-(trifluoromethyl)phenyl)methyl)-6-hydroxy-3-(2,2,2-trifluoroethyl)-1H-pyrazolo[3,4-d]pyrimidin-4(5H)-one | Calc'd 451.1, found 451.3 | Chiralpak IA | B |
| 240 | 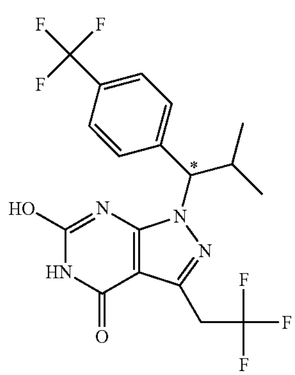 [SMILES: CC(C)C(c1ccc(C(F)(F)F)cc1)n1nc(CC(F)(F)F)c2c(=O)[nH]c(O)nc21] | (R)- or (S)-6-Hxdroxy-1-(2-methyl-1-(4-(trifluoromethyl)phenyl)propyl)-3-(2,2,2-trifluoroethyl)-1H-pyrazolo[3,4-d]pyrimidin-4(5H)-one | Calc'd 435.1, found 435.3 | Chiralpak IA | B |

TABLE 29-continued

The following compounds were prepared using procedures similar to those described in Examples 227 and 228 using appropriate starting materials and the cyclization conditions listed in the table. Racemic products were separated using chiral columns specified in the table. For those pairs of enantiomers, the faster-eluting isomer is always listed first in this table.
Cyclization conditions: A: triphosgene, TEA, dioxane; B: 4-nitrophenyl chloroformate; C: ethyl chloroformate.

| Ex# | Structure | IUPAC Name | Exact Mass [M + H]+ | Chiral column | C** |
|---|---|---|---|---|---|
| 241 | 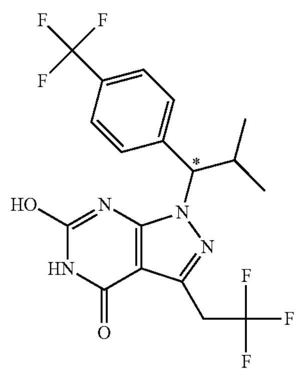 [SMILES: CC(C)C(c1ccc(C(F)(F)F)cc1)n1nc(CC(F)(F)F)c2c(=O)[nH]c(O)nc21] | (S)- or (R)-6-Hydroxy-1-(2-methyl-1-(4-(trifluoromethyl)phenyl)propyl)-3-(2,2,2-trifluoroethyl)-1H-pyrazolo[3,4-d]pyrimidin-4(5H)-one | Calc'd 435.1, found 435.3 | Chiralpak IA | B |
| 242 | 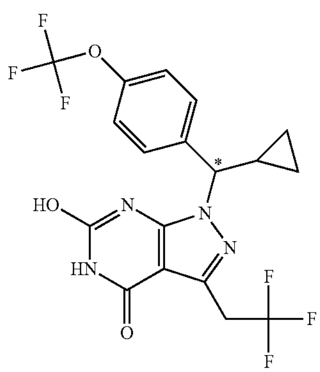 [SMILES: O=c1[nH]c(O)nc2c1c(CC(F)(F)F)nn2C(c1ccc(OC(F)(F)F)cc1)C1CC1] | (R)- or (S)-1-(Cyclopropyl(4-(trifluoromethoxy)phenyl)methyl)-6-hydroxy-3-(2,2,2-trifluoroethyl)-1H-pyrazolo[3,4-d]pyrimidin-4(5H)-one | Calc'd 449.1, found 449.3 | Chiralpak IA | B |
| 243 | 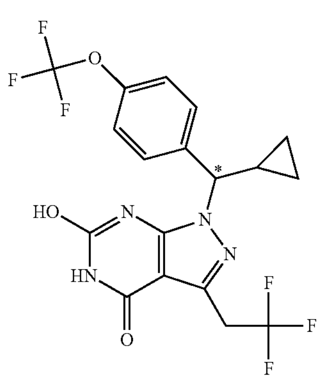 [SMILES: O=c1[nH]c(O)nc2c1c(CC(F)(F)F)nn2C(c1ccc(OC(F)(F)F)cc1)C1CC1] | (S)- or (R)-1-(Cyclopropyl(4-(trifluoromethoxy)phenyl)methyl)-6-hydroxy-3-(2,2,2-trifluoroethyl)-1H-pyrazolo[3,4-d]pyrimidin-4(5H)-one | Calc'd 449.1, found 449.4 | Chiralpak IA | B |

TABLE 29-continued

The following compounds were prepared using procedures similar to those described in Examples 227 and 228 using appropriate starting materials and the cyclization conditions listed in the table. Racemic products were separated using chiral columns specified in the table. For those pairs of enantiomers, the faster-eluting isomer is always listed first in this table.

Cyclization conditions: A: triphosgene, TEA, dioxane; B: 4-nitrophenyl chloroformate; C: ethyl chloroformate.

| Ex# | Structure | IUPAC Name | Exact Mass [M + H]+ | Chiral column | C** |
|---|---|---|---|---|---|
| 244 | 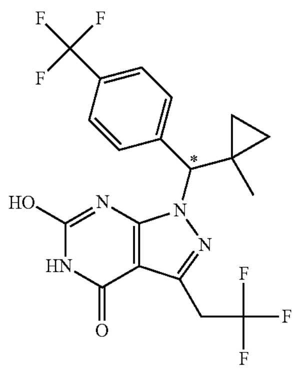 [SMILES: CC1(C(c2ccc(C(F)(F)F)cc2)n2nc(CC(F)(F)F)c3c(=O)[nH]c(O)nc32)CC1] | (R)- or (S)-6-Hydroxy-1-((1-methylcyclopropyl)(4-(trifluoromethyl)phenyl)methyl)-3-(2,2,2-trifluoroethyl)-1H-pyrazolo[3,4-d]pyrimidin-4(5H)-one | Calc'd 447.1, found 447.1 | Chiralpak IA | B |
| 245 | 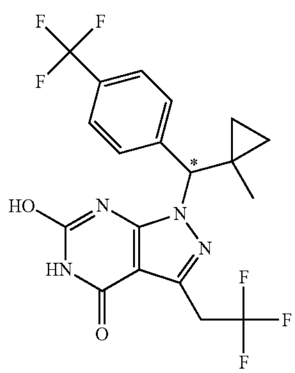 [SMILES: CC1(C(c2ccc(C(F)(F)F)cc2)n2nc(CC(F)(F)F)c3c(=O)[nH]c(O)nc32)CC1] | (S)- or (R)-6-Hydroxy-1-((1-methylcyclopropyl)(4-(trifluoromethyl)phenyl)methyl)-3-(2,2,2-trifluoroethyl)-1H-pyrazolo[3,4-d]pyrimidin-4(5H)-one | Calc'd 447.1, found 447.1 | Chiralpak IA | B |
| 246 | 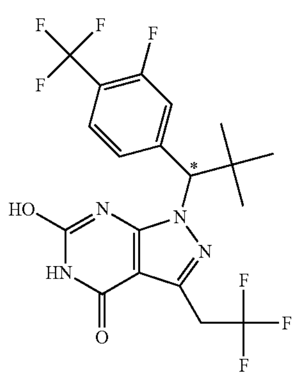 [SMILES: CC(C)(C)C(c1ccc(C(F)(F)F)c(F)c1)n1nc(CC(F)(F)F)c2c(=O)[nH]c(O)nc21] | (R)- or (S)-1-(1-(3-Fluoro-4-(trifluoromethyl)phenyl)-2,2-dimethylpropyl)-6-hydroxy-3-(2,2,2-trifluoroethyl)-1H-pyrazolo[3,4-d]pyrimidin-4(5H)-one | Calc'd 467.1, found 467.3 | AXIA Packed | B |

TABLE 29-continued

The following compounds were prepared using procedures similar to those described in Examples 227 and 228 using appropriate starting materials and the cyclization conditions listed in the table. Racemic products were separated using chiral columns specified in the table. For those pairs of enantiomers, the faster-eluting isomer is always listed first in this table.
Cyclization conditions: A: triphosgene, TEA, dioxane; B: 4-nitrophenyl chloroformate; C: ethyl chloroformate.

| Ex# | Structure | IUPAC Name | Exact Mass [M + H]+ | Chiral column | C** |
|---|---|---|---|---|---|
| 247 | 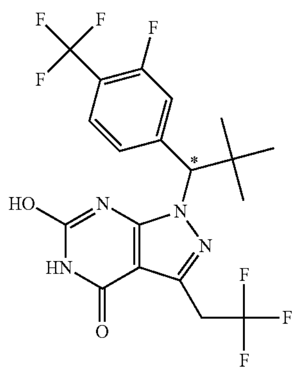 [SMILES: CC(C)(C)C(c1ccc(C(F)(F)F)c(F)c1)n1nc(CC(F)(F)F)c2c(=O)[nH]c(O)nc21] | (S)- or (R)-1-(1-(3-Fluoro-4-(trifluoromethyl)phenyl)-2,2-dimethylpropyl)-6-hydroxy-3-(2,2,2-trifluoroethyl)-1H-pyrazolo[3,4-d]pyrimidin-4(5H)-one | Calc'd 467.1, found 467.3 | AXIA Packed | B |
| 248 | 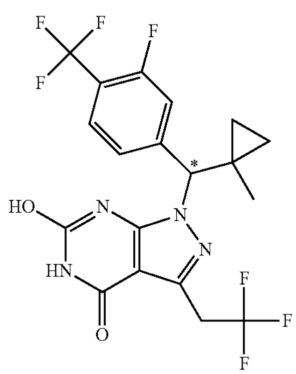 [SMILES: CC1(C(c2ccc(C(F)(F)F)c(F)c2)n2nc(CC(F)(F)F)c3c(=O)[nH]c(O)nc32)CC1] | (R)- or (S)-1-((3-Fluoro-4-(trifluoromethyl)phenyl)(1-methylcyclopropyl)methyl)-6-hydroxy-3-(2,2,2-trifluoroethyl)-1H-pyrazolo[3,4-d]pyrimidin-4(5H)-one | Calc'd 465.1, found 465.3 | AXIA Packed | B |
| 249 | 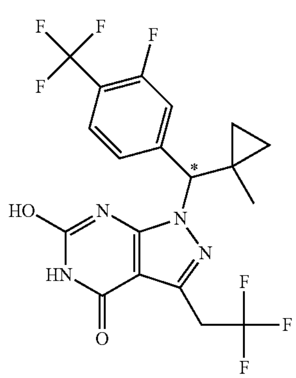 [SMILES: CC1(C(c2ccc(C(F)(F)F)c(F)c2)n2nc(CC(F)(F)F)c3c(=O)[nH]c(O)nc32)CC1] | (S)- or (R)-1-((3-Fluoro-4-(trifluoromethyl)phenyl)(1-methylcyclopropyl)methyl)-6-hydroxy-3-(2,2,2-trifluoroethyl)-1H-pyrazolo[3,4-d]pyrimidin-4(5H)-one | Calc'd 465.1, found 465.3 | AXIA Packed | B |

TABLE 29-continued

The following compounds were prepared using procedures similar to those described in Examples 227 and 228 using appropriate starting materials and the cyclization conditions listed in the table. Racemic products were separated using chiral columns specified in the table. For those pairs of enantiomers, the faster-eluting isomer is always listed first in this table.
Cyclization conditions: A: triphosgene, TEA, dioxane; B: 4-nitrophenyl chloroformate; C: ethyl chloroformate.

| Ex# | Structure | IUPAC Name | Exact Mass [M + H]$^+$ | Chiral column | C** |
|---|---|---|---|---|---|
| 250 | 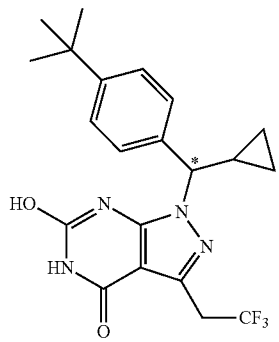 [SMILES: CC(C)(C)c1ccc(C(C2CC2)n2nc(CC(F)(F)F)c3c(=O)[nH]c(O)nc32)cc1] | (R)- or (S)-1-((4-tert-Butylphenyl)(cyclopropyl)methyl)-6-hydroxy-3-(2,2,2-trifluoroethyl)-1H-pyrazolo[3,4-d]pyrimidin-4(5H)-one | Calc'd 421.2, found 419.2 (-ESI) | Chiralpak IA | B |
| 251 | 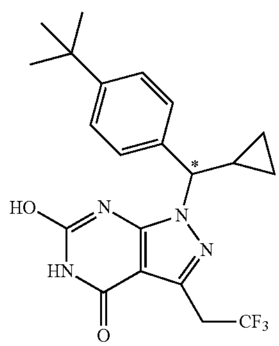 [SMILES: CC(C)(C)c1ccc(C(C2CC2)n2nc(CC(F)(F)F)c3c(=O)[nH]c(O)nc32)cc1] | (S)- or (R)-1-((4-tert-Butylphenyl)(cyclopropyl)methyl)-6-hydroxy-3-(2,2,2-trifluoroethyl)-1H-pyrazolo[3,4-d]pyrimidin-4(5H)-one | Calc'd 421.2, found 419.2 (-ESI) | Chiralpak IA | B |
| 252 | 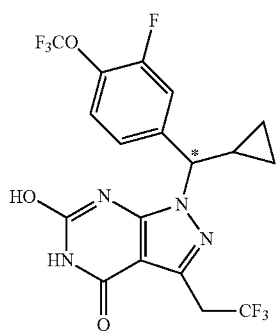 [SMILES: O=c1[nH]c(O)nc2c1c(CC(F)(F)F)nn2C(c1ccc(OC(F)(F)F)c(F)c1)C1CC1] | (R)- or (S)-1-(Cyclopropyl(3-fluoro-4-(trifluoromethoxy)phenyl)methyl)-6-hydroxy-3-(2,2,2-trifluoroethyl)-1H-pyrazolo[3,4-d]pyrimidin-4(5H)-one | Calc'd 467.1, found 467.2 | Chiralpak IA | B |
| 253 | 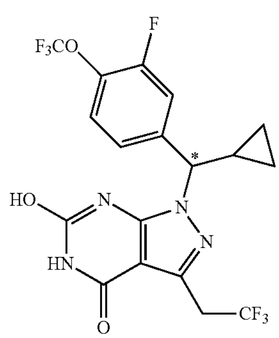 [SMILES: O=c1[nH]c(O)nc2c1c(CC(F)(F)F)nn2C(c1ccc(OC(F)(F)F)c(F)c1)C1CC1] | (S)- or (R)-1-(Cyclopropyl(3-fluoro-4-(trifluoromethoxy)phenyl)methyl)-6-hydroxy-3-(2,2,2-trifluoroethyl)-1H-pyrazolo[3,4-d]pyrimidin-4(5H)-one | Calc'd 467.1, found 467.2 | Chiralpak IA | B |

TABLE 29-continued

The following compounds were prepared using procedures similar to those described in Examples 227 and 228 using appropriate starting materials and the cyclization conditions listed in the table. Racemic products were separated using chiral columns specified in the table. For those pairs of enantiomers, the faster-eluting isomer is always listed first in this table.
Cyclization conditions: A: triphosgene, TEA, dioxane; B: 4-nitrophenyl chloroformate; C: ethyl chloroformate.

| Ex# | Structure | IUPAC Name | Exact Mass [M + H]+ | Chiral column | C** |
|---|---|---|---|---|---|
| 254 | 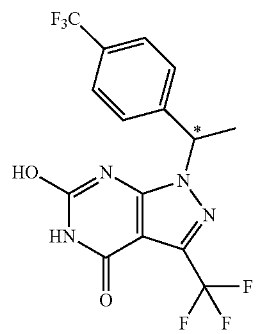 [SMILES: CC(c1ccc(C(F)(F)F)cc1)n1nc(C(F)(F)F)c2c(=O)[nH]c(O)nc21] | (R)- or (S)-6-Hydroxy-3-(trifluoromethyl)-1-(1-(4-(trifluoromethyl)phenyl)ethyl)-1H-pyrazolo[3,4-d]pyrimidin-4(5H)-one | Calc'd 393.1, found 393.0 | Chiralpak IB | B |
| 255 | 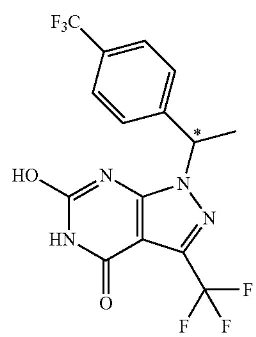 [SMILES: CC(c1ccc(C(F)(F)F)cc1)n1nc(C(F)(F)F)c2c(=O)[nH]c(O)nc21] | (S)- or (R)-6-Hydroxy-3-(trifluoromethyl)-1-(1-(4-(trifluoromethyl)phenyl)ethyl)-1H-pyrazolo[3,4-d]pyrimidin-4(5H)-one | Calc'd 393.1, found 391.1 | Chiralpak IB | B |
| 256 | 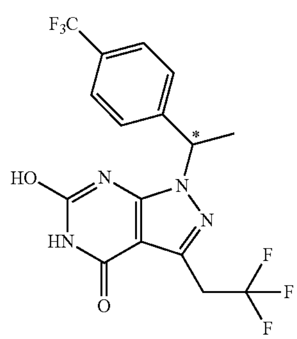 [SMILES: CC(c1ccc(C(F)(F)F)cc1)n1nc(CC(F)(F)F)c2c(=O)[nH]c(O)nc21] | (R)- or (S)-6-Hydroxy-3-(2,2,2-trifluoroethyl)-1-{1-[4-(trifluoromethyl)phenyl]ethyl}-1,5-dihydro-4H-pyrazolo[3,4-d]pyrimidin-4-one | Calc'd 407.1, found 407.1 | Chiracel OJ | B |
| 257 | 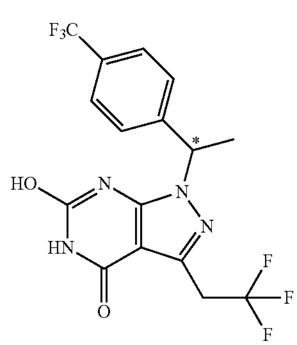 [SMILES: CC(c1ccc(C(F)(F)F)cc1)n1nc(CC(F)(F)F)c2c(=O)[nH]c(O)nc21] | (S)- or (R)-6-Hydroxy-3-(2,2,2-trifluoroethyl)-1-{1-(4-(trifluoromethyl)phenyl]ethyl}-1,5-dihydro-4H-pyrazolo[3,4-d]pyrimidin-4-one | Calc'd 407.1, found 407.1 | Chiracel OJ | B |

**Cyclization method

EXAMPLE 258 AND 259

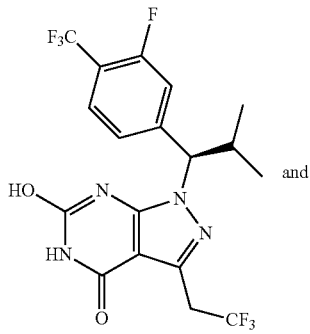

and

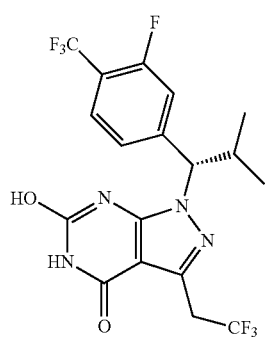

(R)- and (S)-1-(1-(3-Fluoro-4-(trifluoromethyl)phenyl)-2-methylpropyl)-6-hydroxy-3-(2,2,2-trifluoroethyl)-1H-pyrazolo[3,4-d]pyrimidin-4(5H)-one (Scheme 33)

Step 1. 1-(1-(3-Fluoro-4-(trifluoromethyl)phenyl)-2-methylpropyl)-4,6-dimethoxy-3-(2,2,2-trifluoroethyl)-1H-pyrazolo[3,4-d]pyrimidine The title compound was prepared using procedures similar to those described in step 1 of Preparatory Example 75 using 1-(3-fluoro-4-(trifluoromethyl)-phenyl)-2-methylpropan-1-ol and 4,6-dimethoxy-3-(2,2,2-trifluoroethyl)-1H-pyrazolo[3,4-d]pyrimidine from Preparatory Example 74 to afford an oil. MS=481.2 (+ESI).

Step 2. (R)- and (S)-1-(1-(3-Fluoro-4-(trifluoromethyl)phenyl)-2-methylpropyl)-6-hydroxy-3-(2,2,2-trifluoroethyl)-1H-pyrazolo[3,4-d]pyrimidin-4(5H)-one To a solution of 1-(1-(3-fluoro-4-(trifluoromethyl)phenyl)-2-methylpropyl)-4,6-dimethoxy-3-(2,2,2-trifluoroethyl)-1H-pyrazolo[3,4-d]pyrimidine (60 mg, 0.1 mmol) in ethyl acetate (1.5 mL) was added a saturated solution of hydrogen chloride in EtOAc (2 mL) at room temperature. The resulting mixture was stirred at 50° C. for 6 h, cooled to RT, and was concentrated under reduced pressure. The residue was purified by preparative HPLC (Gemini C18, 35-46% ACN in water (0.05% TFA)) to afford the title racemic compound as a solid. The enantiopure title compounds were obtained by chiral preparative HPLC (Chiralpak IA, 10% EtOH in hexanes (0.1% TFA)). The faster-eluting enantiomer of the title compound (Example 258) was obtained as a solid. MS=453.2 (+ESI). $^1$H NMR (400 MHz, CD$_3$OD) δ: 7.74-7.70 (m, 1H), 7.64-7.56 (m, 2H), 5.03 (d, J=10.4 Hz, 1H), 3.86-3.75 (m, 2H), 2.87-2.77 (m, 1H), 0.91 (d, J=6.4 Hz, 6H). The slower-eluting enantiomer of the title compound (Example 259) was obtained as a solid. MS=453.2 (+ESI). $^1$H NMR (400 MHz, CD$_3$OD) δ: 7.74-7.70 (m, 1H), 7.64-7.56 (m, 2H), 5.03 (d, J=10.4 Hz, 1H), 3.86-3.73 (m, 2H), 2.87-2.77 (m, 1H), 0.91 (d, J=6.4 Hz, 6H).

TABLE 30

The following compounds were prepared using procedures similar to those described in Examples 258 and 259 using appropriate starting materials. Racemic products were separated using chiral columns specified in the table. For those pairs of enantiomers, the faster-eluting isomer is always listed first in this table.
Deprotection(Me) conditions: A: HCl in EtOAc or 1,4-dioxane; B: TMSI, CH$_3$CN.

| Ex# | Structure | IUPAC Name | Exact Mass [M + H]$^+$ | Chiral column | DC* |
|---|---|---|---|---|---|
| 260 | 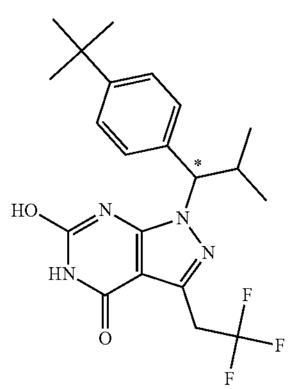 [SMILES: CC(C)C(c1ccc(C(C)(C)C)cc1)n1nc(CC(F)(F)F)c2c(=O)[nH]c(O)nc21] | (R)- or (S)-1-(1-(4-tert-Butylphenyl)-2-methylpropyl)-6-hydroxy-3-(2,2,2-trifluoroethyl)-1H-pyrazolo[3,4-d]pyrimidin-4(5H)-one | Calc'd 423.2, found 423.2 | Chiralpak IA | A |

TABLE 30-continued

The following compounds were prepared using procedures similar to those described in Examples 258 and 259 using appropriate starting materials. Racemic products were separated using chiral columns specified in the table. For those pairs of enantiomers, the faster-eluting isomer is always listed first in this table.
Deprotection(Me) conditions: A: HCl in EtOAc or 1,4-dioxane; B: TMSI, CH$_3$CN.

| Ex# | Structure | IUPAC Name | Exact Mass [M + H]$^+$ | Chiral column | DC* |
|---|---|---|---|---|---|
| 261 | 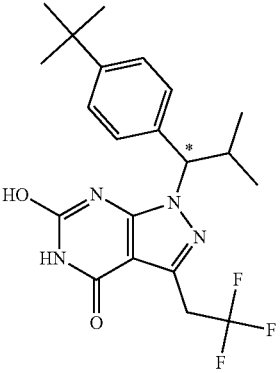 | (S)- or (R)-1-(1-(4-tert-Butylphenyl)-2-methylpropyl)-6-hydroxy-3-(2,2,2-trifluoroethyl)-1H-pyrazolo[3,4-d]pyrimidin-4(5H)-one | Calc'd 423.2, found 423.2 | Chiralpak IA | A |
| 262 | 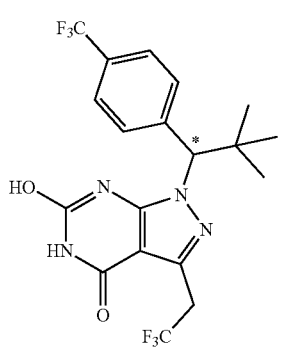 [SMILES: CC(C)(C)C(c1ccc(C(F)(F)F)cc1)n1nc(CC(F)(F)F)c2c(=O)[nH]c(O)nc21] | (R)- or (S)-1-(2,2-Dimethyl-1-(4-(trifluoromethyl)phenyl)propyl)-6-hydroxy-3-(2,2,2-trifluoroethyl)-1H-pyrazolo[3,4-d]pyrimidin-4(5H)-one | Calc'd 449.1, found 449.1 | Chiralpak IA | B |
| 263 | 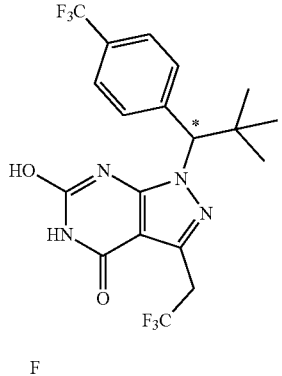 | (S)- or (R)-1-(2,2-Dimethyl-1-(4-(trifluoromethyl)phenyl)propyl)-6-hydroxy-3-(2,2,2-trifluoroethyl)-1H-pyrazolo[3,4-d]pyrimidin-4(5H)-one | Calc'd 449.1, found 449.1 | Chiralpak IA | B |
| 264 | 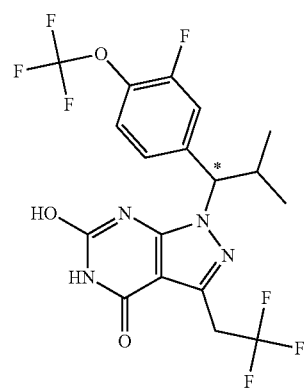 [SMILES: CC(C)C(c1ccc(OC(F)(F)F)c(F)c1)n1nc(CC(F)(F)F)c2c(=O)[nH]c(O)nc21] | (R)- or (S)-1-(1-(3-Fluoro-4-(trifluoromethoxy)phenyl)-2-methylpropyl)-6-hydroxy-3-(2,2,2-trifluoroethyl)-1H-pyrazolo[3,4-d]pyrimidin-4(5H)-one | Calc'd 469.1, found 469.3 | Chiralpak IA | A |

TABLE 30-continued

The following compounds were prepared using procedures similar to those described in Examples 258 and 259 using appropriate starting materials. Racemic products were separated using chiral columns specified in the table. For those pairs of enantiomers, the faster-eluting isomer is always listed first in this table.
Deprotection(Me) conditions: A: HCl in EtOAc or 1,4-dioxane; B: TMSI, CH₃CN.

| Ex# | Structure | IUPAC Name | Exact Mass [M + H]⁺ | Chiral column | DC* |
|---|---|---|---|---|---|
| 265 | 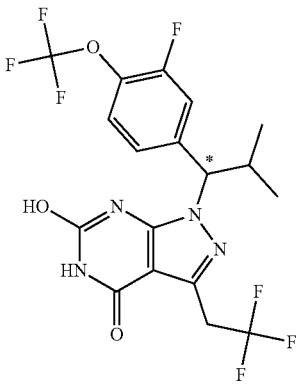 [SMILES: CC(C)C(c1ccc(OC(F)(F)F)c(F)c1)n1nc(CC(F)(F)F)c2c(=O)[nH]c(O)nc21] | (S)- or (R)-1-(1-(3-Fluoro-4-(trifluoromethoxy)phenyl)-2-methylpropyl)-6-hydroxy-3-(2,2,2-trifluoroethyl)-1H-pyrazolo[3,4-d]pyrimidin-4(5H)-one | Calc'd 469.1, found 469.3 | Chiralpak IA | A |
| 266 | 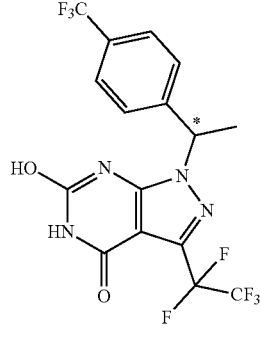 [SMILES: CC(c1ccc(C(F)(F)F)cc1)n1nc(C(F)(F)C(F)(F)F)c2c(=O)[nH]c(O)nc21] | (R)- or (S)-6-Hydroxy-3-(perfluoroethyl)-1-(1-(4-(trifluoromethyl)phenyl)ethyl)-1H-pyrazolo[3,4-d]pyrimidin-4(5H)-one | Calc'd 443.1, found 440.9 (M − 1) | Chiralpak IA | B |
| 267 | 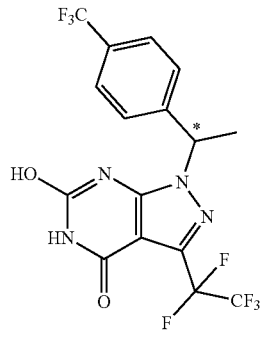 [SMILES: CC(c1ccc(C(F)(F)F)cc1)n1nc(C(F)(F)C(F)(F)F)c2c(=O)[nH]c(O)nc21] | (S)- or (R)-6-Hydroxy-3-(perfluoroethyl)-1-(1-(4-(trifluoromethyl)phenyl)ethyl)-1H-pyrazolo[3,4-d]pyrimidin-4(5H)-one | Calc'd 443.1, found 440.9 (M − 1) | Chiralpak IA | B |

*Deprotection conditions

EXAMPLE 268

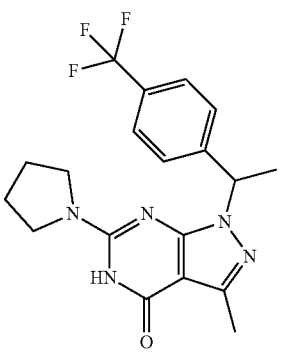 [SMILES: Cc1nn(C(C)c2ccc(C(F)(F)F)cc2)c2nc(N3CCCC3)[nH]c(=O)c12]

3-Methyl-6-pyrrolidin-1-yl-1-{1-[4-(trifluoromethyl)phenyl]ethyl}-1,5-dihydro-4H-pyrazolo[3,4-d]pyrimidin-4-one (Scheme 34)

Step 1. 6-Hydroxy-3-methyl-1-(1-(4-(trifluoromethyl)phenyl)ethyl)-1H-pyrazolo[3,4-d]pyrimidin-4(5H)-one To a microwave tube charged with 5-amino-3-methyl-1-(1-(4-(trifluoromethyl)phenyl)ethyl)-1H-pyrazole-4-carboxamide (200 mg, 0.64 mmol) from Preparative Example 68 was added urea (1.9 g, 32.0 mmol) at RT. The tube was heated to 170° C., stirred for 48 h, and was cooled to rt. The mixture was diluted with 1 M aqueous HCl and chloroform and the layers were separated. The aqueous layer was extracted with chloroform and the organic layers were combined. The organic layer was dried over MgSO$_4$, filtered, and concentrated under reduced pressure to afford the title compound which was used in the next step without purification. MS=339.1 (M+H).

Step 2. 6-Chloro-3-methyl-1-(1-(4-(trifluoromethyl)phenyl)ethyl)-1H-pyrazolo[3,4-d]pyrimidin-4(5H)-one To a microwave tube charged with a stir bar was added 6-hydroxy-3-methyl-1-(1-(4-(trifluoromethyl)phenyl)ethyl)-1H-pyrazolo[3,4-d]pyrimidin-4(5H)-one (200 mg, 0.59 mmol) followed by POCl$_3$ (2.76 mL, 29.6 mmol) and PCl$_5$ (246 mg, 1.182 mmol). The vial was sealed, heated to 100° C., and stirred overnight. The mixture was cooled to RT and was poured into ice followed by addition of solid NaHCO$_3$. The mixture was diluted with DCM, layers were separated, and the aqueous layer was extracted with DCM (3×). The organic layers were combined, dried over MgSO$_4$, filtered, and concentrated under reduced pressure. The residue was purified by silica gel column chromatography (0-5% MeOH in DCM) to afford the title compound. MS=357.8 (M+H).

Step 3. 3-Methyl-6-(methylamino)-1-(1-(4-(trifluoromethyl)phenyl)ethyl)-1,5-dihydro-4H-pyrazolo[3,4-d]pyrimidin-4-one 6-Chloro-3-methyl-1-(1-(4-(trifluoromethyl)phenyl)ethyl)-1H-pyrazolo[3,4-d]pyrimidin-4(5H)-one (9 mg, 0.025 mmol), pyrrolidine (2.5 μL, 0.030 mmol), TEA (3.5 μL, 0.025 mmol) were dissolved in 2-propanol (1.2 mL) and heated to reflux for 14 h. The mixture was cooled to rt and concentrated under reduced pressure. The residue was purified by silica gel column chromatography (0-5% MeOH in DCM) to afford the title compound (Example 268) as a solid. MS=392.1 (M+H). $^1$H NMR (500 MHz, CDCl$_3$): δ 9.25 (s, 1H); 7.55 (d, J=7.8 Hz, 2H); 7.47 (d, J=7.8 Hz, 2H); 5.85 (q, J=6.9 Hz, 1H); 3.57-3.55 (m, 4H); 2.50 (s, 3H); 2.05-2.03 (m, 4H); 1.92 (d, J=7.1 Hz, 3H)

TABLE 31

The following compounds were prepared using procedures similar to those described for Example 268 using the appropriate starting materials.

| Ex# | Structure | IUPAC Name | Exact Mass [M + H]+ |
|---|---|---|---|
| 269 | 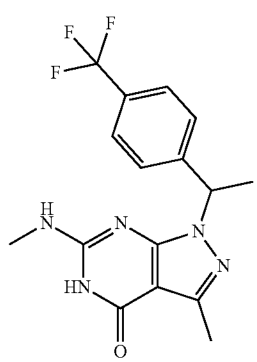 [SMILES: CNc1nc2c(c(C)nn2C(C)c2ccc(C(F)(F)F)cc2)c(=O)[nH]1] | 3-Methyl-6-(methylamino)-1-(1-(4-(trifluoromethyl)phenyl)ethyl)-1,5-dihydro-4H-pyrazolo[3,4-d]pyrimidin-4-one | Calc'd 352.2, found 352.1 |

TABLE 31-continued

The following compounds were prepared using procedures similar to those described for Example 268 using the appropriate starting materials.

| Ex# | Structure | IUPAC Name | Exact Mass [M + H]+ |
|---|---|---|---|
| 270 | 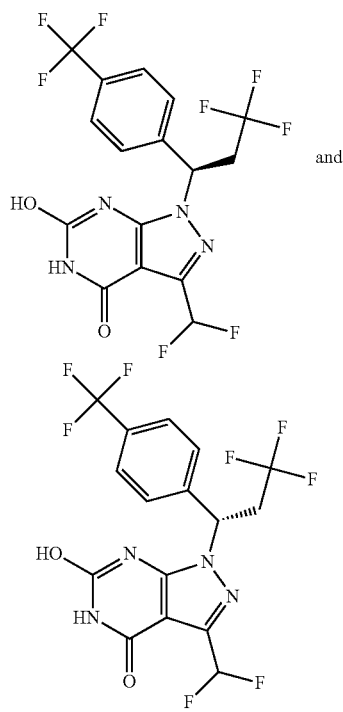 | 6-(Dimethylamino)-3-methyl-1-{1-[4-(trifluoromethyl)phenyl]ethyl}-1,5-dihydro-4H-pyrazolo[3,4-d]pyrimidin-4-one | Calc'd 366.2, found 366.1 |

EXAMPLES 271 AND 272

(R)- and (S) 3-(Difluoromethyl)-6-hydroxy-1-(3,3,3-trifluoro-1-(4-(trifluoromethyl)phenyl)propyl)-1H-pyrazolo[3,4-d]pyrimidin-4(5H)-one (Scheme 35)

Step 1. 3-((Benzyloxy)methyl)-4,6-dimethoxy-1-(3,3,3-trifluoro-1-(4-(trifluoromethyl)phenyl)propyl)-1H-pyrazolo[3,4-d]pyrimidine The title compound was prepared using procedures similar to those described in step 1 of Preparatory Example 75 using 3,3,3-trifluoro-1-(4-(trifluoromethyl)phenyl)propan-1-ol and 3-((benzyloxy)methyl)-4,6-dimethoxy-1H-pyrazolo[3,4-d]pyrimidine to afford a solid. MS=541.2 (+ESI).

Step 2. (4,6-Dimethoxy-1-(3,3,3-trifluoro-1-(4-(trifluoromethyl)phenyl)propyl)-1H-pyrazolo[3,4-d]pyrimidin-3-yl)methanol The title compound was prepared using procedures similar to those described in step 2 of Preparatory Example 75 using 3-((benzyloxy)methyl)-4,6-dimethoxy-1-(3,3,3-trifluoro-1-(4-(trifluoromethyl)phenyl)propyl)-1H-pyrazolo[3,4-d]pyrimidine to afford a solid. MS=451.1 (+ESI).

Step 3. 4,6-Dimethoxy-1-(3,3,3-trifluoro-1-(4-(trifluoromethyl)phenyl)propyl)-1H-pyrazolo[3,4-d]pyrimidine-3-carbaldehyde To a solution of oxalyl chloride (38 µL, 0.4 mmol) in DCM (10 mL) was added DMSO (63 µL, 0.9 mmol) in DCM (2 mL) dropwise at −78° C. The reaction solution was stirred at −78° C. for 20 min whereupon (4,6-dimethoxy-1-(3,3,3-trifluoro-1-(4-(trifluoromethyl)phenyl)propyl)-1H-pyrazolo[3,4-d]pyrimidin-3-yl)methanol (100 mg, 0.2 mmol) was added to the reaction solute on at −78° C. The mixture was stirred at −78° C. for 45 min whereupon TEA (1 mL) was added to the reaction solution mixture, which was then stirred for 20 min. The mixture was allowed to warm to RT where it was diluted with water (15 mL) and extracted with ethyl acetate (3×20 mL). The combined organic layers were washed with brine (2×20 mL), dried over sodium sulfate, filtered, and concentrated under vacuum. The residue was purified by silica gel column chromatography (0-25% ethyl acetate in petroleum ether) to afford the title compound as a solid. MS=449.3 (+ESI).

Step 4. 3-(Difluoromethyl)-4,6-dimethoxy-1-(3,3,3-trifluoro-1-(4-(trifluoromethyl)phenyl)propyl)-1H-pyrazolo[3,4-d]pyrimidine The title compound was prepared using procedures similar to those described in step 3 of Example 28 using 4,6-dimethoxy-1-(3,3,3-trifluoro-1-(4-(trifluoromethyl)phenyl)propyl)-1H-pyrazolo[3,4-d]pyrimidine-3-carbaldehyde to afford a solid. MS=471.0 (+ESI).

Step 5. (R)- and (S)-3-(Difluoromethyl)-6-hydroxy-1-(3,3,3-trifluoro-1-(4-(trifluoromethyl)phenyl)propyl)-1H-pyrazolo[3,4-d]pyrimidin-4(5H)-one The racemic title compound was prepared using procedures similar to those described in step 4 of Examples 22 and 23 using 4,6-dimethoxy-1-(3,3,3-trifluoro-1-(4-(trifluoromethyl)phenyl)propyl)-1H-pyrazolo[3,4-d]pyrimidine-3-carbaldehyde to afford a solid. The enantiopure title compounds were obtained by chiral preparative HPLC (Venusil Chiral OD-H, 20% EtOH in hexanes (0.1% TFA)). The faster-eluting enantiomer of the title compound (Example 271) was obtained as a solid. MS=441.0 (−ESI); $^1$H NMR (400 MHz, CD$_3$OD) δ: 7.74 (d, J=8.4 Hz, 2H), 7.70 (d, J=8.4 Hz, 2H), 6.93 (t, J=53.6 Hz, 1H), 6.12-6.08 (m, J=4.0, 5.6 Hz, 1H), 3.74-3.58 (m, 1H), 3.27-3.13 (m, 1H); The slower-eluting enantiomer of the title compound (Example 272) was obtained as a solid. MS=441.0 (−ESI); $^1$H NMR (400 MHz, CD$_3$OD) δ: 7.74 (d, J=8.4 Hz, 2H), 7.70 (d, J=8.4 Hz, 2H), 6.93 (t, J=53.6 Hz, 1H), 6.11-6.08 (m, 1H), 3.74-3.58 (m, 1H), 3.27-3.13 (m, 1H).

TABLE 32

The following compounds were prepared using procedures similar to those described in Examples 271 and 272 using appropriate starting materials. Racemic products were separated using chiral columns specified in the table. For those pairs of enantiomers, the faster-eluting isomer is always listed first in this table.

| Ex# | Structure | IUPAC Name | Exact Mass [M + H]$^+$ | Chiral column |
|---|---|---|---|---|
| 273 | 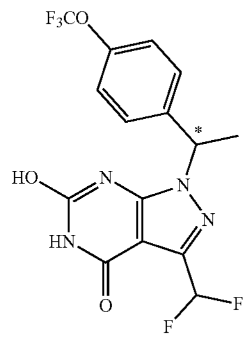 [SMILES: CC(c1ccc(OC(F)(F)F)cc1)n1nc(C(F)F)c2c(=O)[nH]c(O)nc21] | (R)- or (S)-3-(Difluoromethyl)-6-hydroxy-1-(1-(4-(trifluoromethoxy)phenyl)ethyl)-1H-pyrazolo[3,4-d]pyrimidin-4(5H)-one and | Calc'd 391.1, found 391.1 | Chiralpak IB |
| 274 | 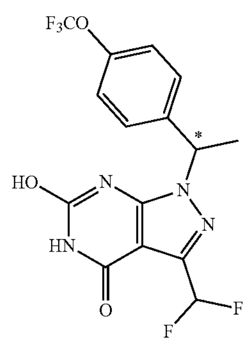 [SMILES: CC(c1ccc(OC(F)(F)F)cc1)n1nc(C(F)F)c2c(=O)[nH]c(O)nc21] | (S)- or (R)-3-(Difluoromethyl)-6-hydroxy-1-(1-(4-(trifluoromethoxy)phenyl)ethyl)-1H-pyrazolo[3,4-d]pyrimidin-4(5H)-one | Calc'd 391.1, found 391.1 | Chiralpak IB |
| 275 | 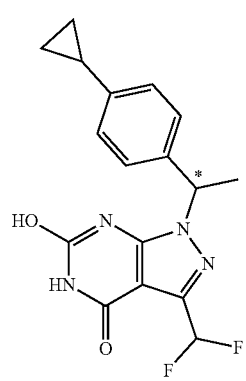 [SMILES: CC(c1ccc(C2CC2)cc1)n1nc(C(F)F)c2c(=O)[nH]c(O)nc21] | (R)- or (S)-1-(1-(4-Cyclopropylphenyl)ethyl)-3-(difluoromethyl)-6-hydroxy-1H-pyrazolo[3,4-d]pyrimidin-4(5H)-one | Calc'd 347.1, found 347.2 | Chiralpak IA |

TABLE 32-continued

The following compounds were prepared using procedures similar to those described in Examples 271 and 272 using appropriate starting materials. Racemic products were separated using chiral columns specified in the table. For those pairs of enantiomers, the faster-eluting isomer is always listed first in this table.

| Ex# | Structure | IUPAC Name | Exact Mass [M + H]+ | Chiral column |
|---|---|---|---|---|
| 276 | 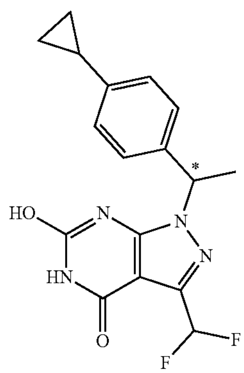 [SMILES: CC(c1ccc(C2CC2)cc1)n1nc(C(F)F)c2c(=O)[nH]c(O)nc21] | (S)- or (R)-1-(1-(4-Cyclopropylphenyl)ethyl)-3-(difluoromethyl)-6-hydroxy-1H-pyrazolo[3,4-d]pyrimidin-4(5H)-one | Calc'd 347.1, found 347.2 | Chiralpak IA |
| 277 | 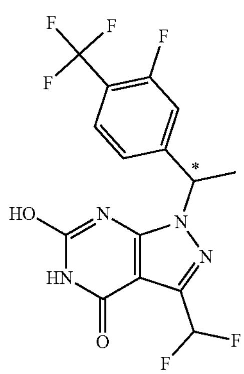 [SMILES: CC(c1ccc(C(F)(F)F)c(F)c1)n1nc(C(F)F)c2c(=O)[nH]c(O)nc21] | (R)- or (S)-3-(Difluoromethyl)-1-(1-(3-fluoro-4-(trifluoromethyl)phenyl)ethyl)-6-hydroxy-1H-pyrazolo[3,4-d]pyrimidin-4(5H)-one | Calc'd 393.1, found 391.0 (M − 1) | Chiralpak IB |
| 278 | 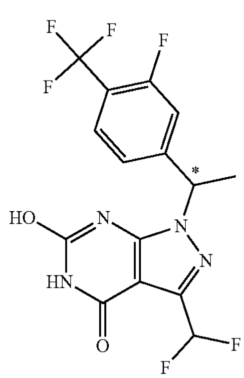 [SMILES: CC(c1ccc(C(F)(F)F)c(F)c1)n1nc(C(F)F)c2c(=O)[nH]c(O)nc21] | (S)- or (R)-3-(Difluoromethyl)-1-(1-(3-fluoro-4-(trifluoromethyl)phenyl)ethyl)-6-hydroxy-1H-pyrazolo[3,4-d]pyrimidin-4(5H)-one | Calc'd 393.1, found 393.2 | Chiralpak IB |

TABLE 32-continued

The following compounds were prepared using procedures similar to those described in Examples 271 and 272 using appropriate starting materials. Racemic products were separated using chiral columns specified in the table. For those pairs of enantiomers, the faster-eluting isomer is always listed first in this table.

| Ex# | Structure | IUPAC Name | Exact Mass [M + H]+ | Chiral column |
|---|---|---|---|---|
| 279 | 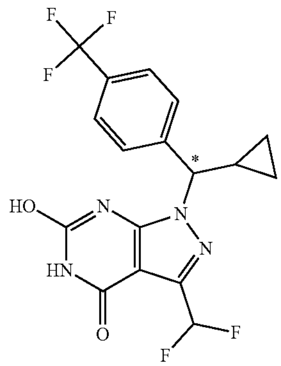 [SMILES: O=c1[nH]c(O)nc2c1c(C(F)F)nn2C(c1ccc(C(F)(F)F)cc1)C1CC1] | (R)- or (S)-1-(Cyclopropyl(4-(trifluoromethyl)phenyl)methyl)-3-(difluoromethyl)-6-hydroxy-1H-pyrazolo[3,4-d]pyrimidin-4(5H)-one | Calc'd 401.1, found 401.0 | Chiralpak IA |
| 280 | 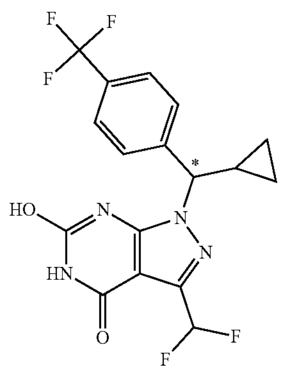 [SMILES: O=c1[nH]c(O)nc2c1c(C(F)F)nn2C(c1ccc(C(F)(F)F)cc1)C1CC1] | (S)- or (R)-1-(Cyclopropyl(4-(trifluoromethyl)phenyl)methyl)-3-(difluoromethyl)-6-hydroxy-1H-pyrazolo[3,4-d]pyrimidin-4(5H)-one | Calc'd 401.1, found 401.1 | Chiralpak IA |
| 281 | 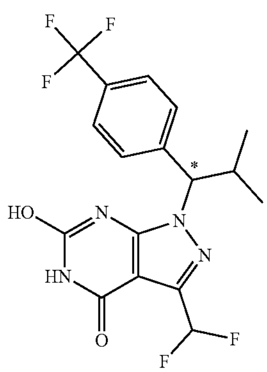 [SMILES: CC(C)C(c1ccc(C(F)(F)F)cc1)n1nc(C(F)F)c2c(=O)[nH]c(O)nc21] | (R)- or (S)-3-(Difluoromethyl)-6-hydroxy-1-(2-methyl-1-(4-(trifluoromethyl)phenyl)propyl)-1H-pyrazolo[3,4-d]pyrimidin-4(5H)-one | Calc'd 403.1, found 403.0 | Chiralpak IA |
| 282 | 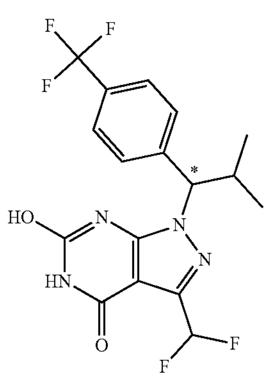 [SMILES: CC(C)C(c1ccc(C(F)(F)F)cc1)n1nc(C(F)F)c2c(=O)[nH]c(O)nc21] | (S)- or (R)-3-(Difluoromethyl)-6-hydroxy-1-(2-methyl-1-(4-(trifluoromethyl)phenyl)propyl)-1H-pyrazolo[3,4-d]pyrimidin-4(5H)-one | Calc'd 403.1, found 403.0 | Chiralpak IA |

TABLE 32-continued

The following compounds were prepared using procedures similar to those described in Examples 271 and 272 using appropriate starting materials. Racemic products were separated using chiral columns specified in the table. For those pairs of enantiomers, the faster-eluting isomer is always listed first in this table.

| Ex# | Structure | IUPAC Name | Exact Mass [M + H]+ | Chiral column |
|---|---|---|---|---|
| 283 | 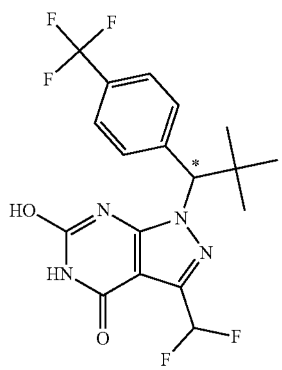 [SMILES: CC(C)(C)C(c1ccc(C(F)(F)F)cc1)n1nc(C(F)F)c2c(=O)[nH]c(O)nc21] | (R)- or (S)-3-(Difluoromethyl)-1-(2,2-dimethyl-1-(4-(trifluoromethyl)phenyl)propyl)-6-hydroxy-1H-pyrazolo[3,4-d]pyrimidin-4(5H)-one | Calc'd 417.1, found 415.0 (M − 1) | Chiralcel OD-H |
| 284 | 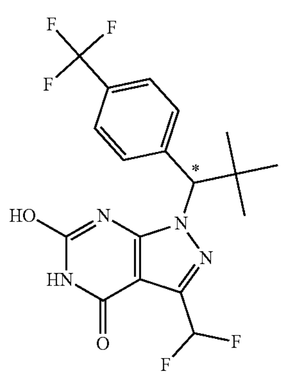 [SMILES: CC(C)(C)C(c1ccc(C(F)(F)F)cc1)n1nc(C(F)F)c2c(=O)[nH]c(O)nc21] | (S)- or (R)-3-(Difluoromethyl)-1-(2,2-dimethyl-1-(4-(trifluoromethyl)phenyl)propyl)-6-hydroxy-1H-pyrazolo[3,4-d]pyrimidin-4(5H)-one | Calc'd 417.1, found 415.0 (M − 1) | Chiralcel OD-H |
| 285 | 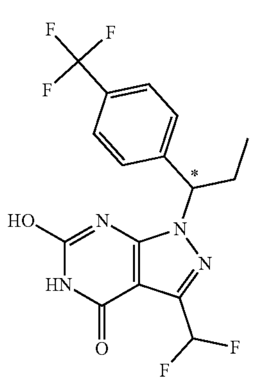 [SMILES: CCC(c1ccc(C(F)(F)F)cc1)n1nc(C(F)F)c2c(=O)[nH]c(O)nc21] | (R)- or (S)-3-(Difluoromethyl)-6-hydroxy-1-(1-(4-(trifluoromethyl)phenyl)propyl)-1H-pyrazolo[3,4-d]pyrimidin-4(5H)-one | Calc'd 389.1, found 387.0 (M − 1) | Chiralpak IB |

TABLE 32-continued

The following compounds were prepared using procedures similar to those described in Examples 271 and 272 using appropriate starting materials. Racemic products were separated using chiral columns specified in the table. For those pairs of enantiomers, the faster-eluting isomer is always listed first in this table.

| Ex# | Structure | IUPAC Name | Exact Mass [M + H]$^+$ | Chiral column |
|---|---|---|---|---|
| 286 | 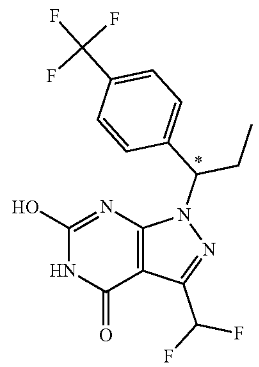 [SMILES: CCC(c1ccc(C(F)(F)F)cc1)n1nc(C(F)F)c2c(=O)[nH]c(O)nc21] | (S)- or (R)-3-(Difluoromethyl)-6-hydroxy-1-(1-(4-(trifluoromethyl)phenyl)propyl)-1H-pyrazolo[3,4-d]pyrimidin-4(5H)-one | Calc'd 389.1, found 387.0 (M − 1) | Chiralpak IB |
| 287 | 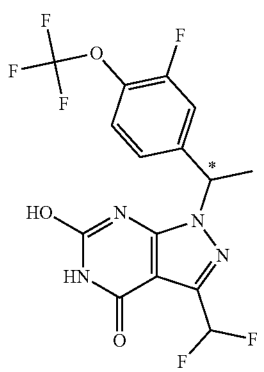 [SMILES: CC(c1ccc(OC(F)(F)F)c(F)c1)n1nc(C(F)F)c2c(=O)[nH]c(O)nc21] | (R)- or (S)-3-(Difluoromethyl)-1-(1-(3-fluoro-4-(trifluoromethoxy)phenyl)ethyl)-6-hydroxy-1H-pyrazolo[3,4-d]pyrimidin-4(5H)-one | Calc'd 409.1, found 409.1 | Chiralpak IB |
| 288 | 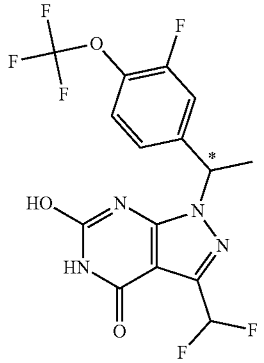 [SMILES: CC(c1ccc(OC(F)(F)F)c(F)c1)n1nc(C(F)F)c2c(=O)[nH]c(O)nc21] | (S)- or (R)-3-(Difluoromethyl)-1-(1-(3-fluoro-4-(trifluoromethoxy)phenyl)ethyl)-6-hydroxy-1H-pyrazolo[3,4-d]pyrimidin-4(5H)-one | Calc'd 409.1, found 409.1 | Chiralpak IB |

EXAMPLE 289

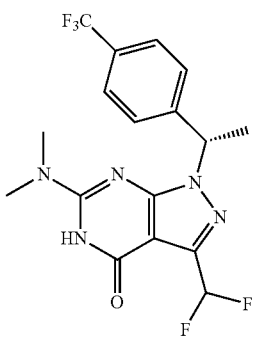 [SMILES: C[C@@H](c1ccc(C(F)(F)F)cc1)n1nc(C(F)F)c2c(=O)[nH]c(N(C)C)nc21]

(S)-3-(Difluoromethyl)-6-(dimethylamino)-1-(1-(4-(trifluoromethyl)phenyl)ethyl)-1H-pyrazolo[3,4-d]pyrimidin-4(5H)-one (Scheme 36)

Step 1. (S)-6-(Dimethylamino)-4-oxo-1-(1-(4-(trifluoromethyl)phenyl)ethyl)-4,5-dihydro-1H-pyrazolo[3,4-d]pyrimidine-3-carbaldehyde To a solution of (S)-6-(dimethylamino)-3-(hydroxymethyl)-1-(1-(4-(trifluoromethyl)phenyl)ethyl)-1H-pyrazolo[3,4-d]pyrimidin-4(5H)-one (100 mg, 0.26 mmol) in $CH_2Cl_2$ (3 mL) at RT under $N_2$ was added Dess-Martin periodinane (167 mg, 0.39 mmol). The mixture was stirred at room temperature for 3 h whereupon the mixture was concentrated to dryness under reduced pressure. The residue was purified by silica gel column chromatography (0-100% EtOAc in hexanes) to afford the title compound as a solid. MS=379.8 $(M+H)^+$.

Step 2. (S)-3-(Difluoromethyl)-6-(dimethylamino)-1-(1-(4-(trifluoromethyl)phenyl)ethyl)-1H-pyrazolo[3,4-d]pyrimidin-4(5H)-one To a solution of (S)-6-(dimethylamino)-4-oxo-1-(1-(4-(trifluoromethyl)phenyl)ethyl)-4,5-dihydro-1H-pyrazolo[3,4-d]pyrimidine-3-carbaldehyde (80 mg, 0.21 mmol) in $CH_2Cl_2$ (2 mL) at RT was added DAST (0.028 ml, 0.21 mmol) in plastic vial under $N_2$. The mixture was stirred at room temperature for 1 h whereupon water was added and the mixture was concentrated under reduced pressure. The residue was purified by reverse-phase HPLC chromatography (Surefire C18 column, 30-90% ACN in water (0.05% TFA)) to afford the title compound (Example 289) as a white solid. $^1H$ NMR (CDCl3, 500 MHz) δ: 10.82 (br s, 1H), 7.58 (d, J=8.0 Hz, 2H), 7.42 (d, J=8.0 Hz, 2H), 7.80 (t, J=7.5 Hz, 1H), 5.92 (m, 1H), 3.23 (s, 6H), 1.98 (d, J=7.5 Hz, 3H). MS=401.8 $(M+H)^+$.

EXAMPLES 291 AND 292

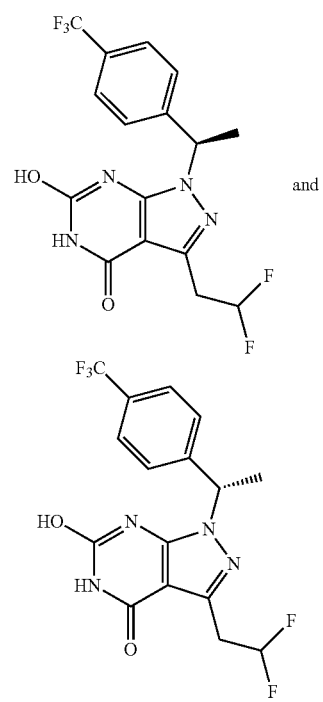

(R)- and (S)-3-(2,2-Difluoroethyl)-6-hydroxy-1-(1-(4-(trifluoromethyl)phenyl)ethyl)-1H-pyrazolo[3,4-d]pyrimidin-4(5H)-one (Scheme 37)

Step 1. 3-((Benzyloxy)methyl)-4,6-dimethoxy-1-(1-(4-(trifluoromethyl)phenyl)ethyl)-1H-pyrazolo[3,4-d]pyrimidine The title compound was prepared using procedures similar to those described in step 1 of Preparatory Example 75 using 3-((benzyloxy)methyl)-4,6-dimethoxy-1H-pyrazolo[3,4-d]pyrimidine from Preparatory Example 73 and 1-(4-(trifluoromethyl)phenyl)ethanol to afford an oil. MS=473.3 (+ESI).

TABLE 33

The following compounds were prepared using procedures similar to those described for Example 289 using the appropriate starting materials.

| Ex# | Structure | IUPAC Name | Exact Mass [M + H]+ |
|---|---|---|---|
| 290 | (structure) | 6-Azetidin-1-yl-3-(difluoromethyl)-1-{(1S)-1-[4-(trifluoromethyl)phenyl]ethyl}-1,5-dihydro-4H-pyrazolo[3,4-d]pyrimidin-4-one | Calc'd 414.1, found 414.1 |

Step 2. (4,6-Dimethoxy-1-(1-(4-(trifluoromethyl)phenyl)ethyl)-1H-pyrazolo[3,4-d]pyrimidin-3-yl) methanol The title compound was prepared using procedures similar to those described in step 2 of Preparatory Example 75 using 3-((benzyloxy)methyl)-4,6-dimethoxy-1-(1-(4-(trifluoromethyl)phenyl)ethyl)-1H-pyrazolo[3,4-d]pyrimidine to afford an oil. MS=383.3 (+ESI).

Step 3. 4,6-Dimethoxy-1-(1-(4-(trifluoromethyl)phenyl)ethyl)-1H-pyrazolo[3,4-d]pyrimidine-3-carbaldehyde The title compound was prepared using procedures similar to those described in step 3 of Preparatory Example 75 using (4,6-dimethoxy-1-(1-(4-(trifluoromethyl)phenyl)ethyl)-1H-pyrazolo[3,4-d]pyrimidin-3-yl)methanol to afford an oil. MS=381.1 (+ESI).

Step 4. 4,6-Dimethoxy-3-(2-methoxyvinyl)-1-(1-(4-(trifluoromethyl)phenyl)ethyl)-1H-pyrazolo[3,4-d]pyrimidine A solution of potassium 2-methylbutan-2-olate in toluene (0.5 M in toluene, 2.63 mL, 5.26 mmol) was added to a solution of (methoxymethyl)triphenyl-phosphoniumchloride (1.80 g, 5.26 mmol) in THF (7 mL) at −78° C. The reaction was warmed to −30° C., stirred for 1 h, and recooled to −78° C. 4,6-Dimethoxy-1-(1-(4-(trifluoromethyl)phenyl)ethyl)-1H-pyrazolo[3,4-d]pyrimidine-3-carbaldehyde (1.7 g, 4.4 mmol) in THF (3 mL) was added to the reaction mixture. The reaction mixture was warmed to room temperature and stirred for additional 16 h. Sat. aq. ammonium chloride (30 mL) was added and the mixture was concentrated under vacuum. The mixture was extracted with EtOAc (3×20 mL) and the organic fractions were combined. The organic layer was washed with water (2×50 mL), dried over $Na_2SO_4$, filtered, and concentrated under reduced pressure. The residue was purified by silica gel column chromatography (0-40% methanol in dichloromethane) to afford the title compound as a solid. MS=409.2 (+ESI).

Step 5. 2-(4,6-Dimethoxy-1-(1-(4-(trifluoromethyl)phenyl)ethyl)-1H-pyrazolo[3,4-d]pyrimidin-3-yl)acetaldehyde To a solution of 4,6-dimethoxy-3-(2-methoxyvinyl)-1-(1-(4-(trifluoromethyl)phenyl)ethyl)-1H-pyrazolo[3,4-d]pyrimidine (0.25 g, 0.6 mmol) in THF (1 mL) at room temperature was added 6 M aqueous HCl (2 mL). The reaction mixture was stirred at RT for 24 h whereupon water (10 mL) was added followed by extraction with ethyl acetate (3×10 mL). The combined organic layers were washed with brine (3×10 mL), dried over sodium sulfate, filtered, and concentrated under vacuum. The title compound was obtained as an oil which was used in the next step directly without purification. MS=395.2 (+ESI).

Step 6. 3-(2,2-Difluoroethyl)-4,6-dimethoxy-1-(1-(4-(trifluoromethyl)phenyl)ethyl)-1H-pyrazolo[3,4-d]pyrimidine The title compound was prepared using procedures similar to those described in step 4 of Example 33 using 2-(4,6-dimethoxy-1-(1-(4-(trifluoromethyl)phenyl)ethyl)-1H-pyrazolo[3,4-d]pyrimidin-3-yl)acetaldehyde to afford an oil. MS=417.3 (+ESI).

Step 7. (R)- and (S)-3-(2,2-Difluoroethyl)-6-hydroxy-1-(1-(4-(trifluoromethyl)phenyl)ethyl)-1H-pyrazolo[3,4-d]pyrimidin-4(5H)-one The title racemic compound was prepared using procedures similar to those described in step 4 of Examples 22 and 23 using 3-(2,2-difluoroethyl)-4,6-dimethoxy-1-(1-(4-(trifluoromethyl)phenyl)ethyl)-1H-pyrazolo[3,4-d]pyrimidine to afford a solid. The enantiopure title compounds were obtained by chiral preparative HPLC (Chiralpak AS-H, 10% EtOH in hexanes). The faster-eluting enantiomer of the title compound (Example 291) was obtained as a solid. MS=389.2 (+ESI). $^1$H NMR (300 MHz, DMSO-$d_6$) δ: 12.18 (br s, 1H), 10.99 (br s, 1H), 7.74 (d, J=8.4 Hz, 2H), 7.51 (d, J=8.1 Hz, 2H), 6.42 (t, J=60.0 Hz, 1H), 5.86 (q, J=6.9 Hz, 1H), 3.42-3.29 (m, 2H), 1.81 (d, J=6.9 Hz, 3H). The slower-eluting enantiomer of the title compound (Example 292) was obtained as a solid. MS=389.2 (+ESI). $^1$H NMR (300 MHz, DMSO-$d_6$) δ: 12.18 (br s, 1H), 10.99 (br s, 1H), 7.74 (d, J=8.4 Hz, 2H), 7.51 (d, J=8.1 Hz, 2H), 6.42 (t, J=60.0 Hz, 1H), 5.86 (q, J=6.9 Hz, 1H), 3.42-3.29 (m, 2H), 1.81 (d, J=6.9 Hz, 3H).

EXAMPLE 293

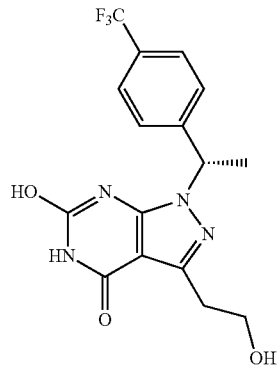 [SMILES: C[C@@H](c1ccc(C(F)(F)F)cc1)n1nc(CCO)c2c(=O)[nH]c(O)nc21]

(S)-6-Hydroxy-3-(2-hydroxyethyl)-1-(1-(4-(trifluoromethyl)phenyl)ethyl)-1H-pyrazolo[3,4-d]pyrimidin-4(5H)-one (Scheme 38)

Step 1. (S)-3-(2-(Benzyloxy)vinyl)-4,6-dimethoxy-1-(1-(4-(trifluoromethyl)phenyl)ethyl)-1H-pyrazolo[3,4-d]pyrimidine To a mixture of ((benzyloxy)methyl)triphenylphosphonium chloride (0.33 g, 0.8 mmol) in tetrahydrofuran (10 mL) at 0° C. under $N_2$ was added potassium 2-methylbutan-2-olate (0.10 g, 0.8 mmol) at 0° C. The reaction mixture was stirred for 30 min at 0° C. whereupon (S)-4,6-dimethoxy-1-(1-(4-(trifluoromethyl)phenyl)ethyl)-1H-pyrazolo[3,4-d]pyrimidine-3-carbaldehyde (0.20 g, 0.5 mmol) from step 5 of Examples 291 and 292 was added in one portion. The reaction mixture was stirred for 1 h at 0° C. and for an additional 3 h at RT. The resulting mixture was quenched with glacial acetic acid (0.1 mL), diluted with water (20 mL), and extracted with ethyl acetate (3×20 mL). The combined organic layers were washed with brine (3×20 mL), dried over sodium sulfate, filtered, and concentrated under vacuum. The residue was purified by silica gel column chromatography (30% ethyl acetate in petroleum ether) to afford the title compound as an oil. MS=485.2 (+ESI).

Step 2. (S)-3-(2-(Benzyloxy)vinyl)-6-hydroxy-1-(1-(4-(trifluoromethyl)phenyl)ethyl)-1H-pyrazolo[3,4-d]pyrimidin-4(5H)-one The title compound was prepared using procedures similar to those described in step 4 of Examples 120 and 121 using (S)-3-(2-(benzyloxy)vinyl)-4,6-dimethoxy-1-(1-(4-(trifluoromethyl)phenyl)ethyl)-1H-pyrazolo[3,4-d]pyrimidine to afford an oil. MS=457.2 (+ESI).

Step 3. (S)-6-Hydroxy-3-(2-hydroxyethyl)-1-(1-(4-(trifluoromethyl)phenyl)ethyl)-1H-pyrazole[3,4-d]pyrimidin-4(5H)-one The title compound was prepared using procedures similar to those described in step 2 of Preparatory Example 75 using (S)-3-(2-(benzyloxy)vinyl)-6-hydroxy-1-(1-(4-(trifluoromethyl)phenyl)ethyl)-1H-pyrazolo[3,4-d]pyrimidin-4(5H)-one to afford (Example 293) a solid. MS=369.1 (+ESI), $^1$H NMR (400 MHz, CD$_3$OD) δ: 7.63 (d, J=8.0 Hz, 2H), 7.52-7.37 (m, 2H), 5.86-5.74 (m, 1H), 3.92 (t, J=7.2 Hz, 2H), 3.06 (t, J=6.3 Hz, 2H), 1.91 (d, J=6.8 Hz, 3H).

EXAMPLES 294 AND 295

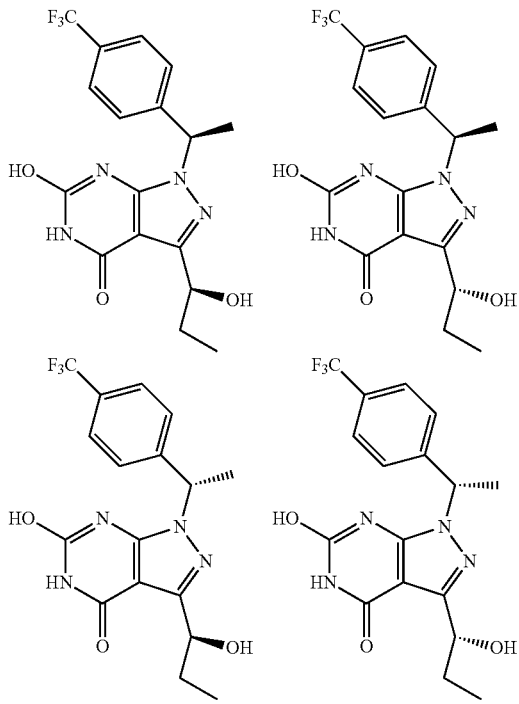

(R,S)- and (R,R)- and (S,S)- and (S,R)-6-Hydroxy-3-(1-hydroxypropyl)-1-(1-(4-(trifluoromethyl)phenyl)ethyl)-1H-pyrazolo[3,4-d]pyrimidin-4(5H)-one (Scheme 37)

Step 1. 4,6-Dimethoxy-1-(1-(4-(trifluoromethyl)phenyl)ethyl)-1H-pyrazolo[3,4-d]pyrimidine-3-carboxylic acid To the solution of 4,6-dimethoxy-1-(1-(4-(trifluoromethyl)phenyl)ethyl)-1H-pyrazolo[3,4-d]pyrimidine-3-carbaldehyde (0.25 g, 0.7 mmol) from step 5 of Examples 291 and 292 in ethanol (6 mL) and CH$_2$Cl$_2$ (3 mL) at RT was added a solution of silver nitrate (0.41 g, 2.6 mmol) in H$_2$O (2 mL). A solution of sodium hydroxide (0.21 g, 5.3 mmol) in H$_2$O (4 mL) was added dropwise and the resulting suspension was stirred for 3 h at room temperature. The mixture was diluted with water (10 mL), treated with 1 M aqueous HCl until pH ~3-4, and extracted with DCM (3×50 mL). The combined organic layers were washed with brine (3×50 mL), dried over Na$_2$SO$_4$, filtered, and concentrated under vacuum to afford the title compound as an oil. MS=397.0 (+ESI).

Step 2. Methyl 4,6-dimethoxy-1-(1-(4-(trifluoromethyl)phenyl)ethyl)-1H-pyrazolo [3,4-d]pyrimidine-3-carboxylate To the solution of 4,6-dimethoxy-1-(1-(4-(trifluoromethyl)phenyl)ethyl)-1H-pyrazolo[3,4-d]pyrimidine-3-carboxylic acid (0.21 g, 0.5 mmol) in MeOH (10 mL) was added thionyl chloride (0.12 mL, 1.6 mmol) dropwise. The reaction mixture was stirred for 18 h at room temperature and was concentrated under vacuum. The residue was purified by silica gel column chromatography (25% ethyl acetate in petroleum ether) to afford the title compound as a solid. MS=411.2 (+ESI).

Step 3. 1-(4,6-Dimethoxy-1-(1-(4-(trifluoromethyl)phenyl)ethyl)-1H-pyrazolo[3,4-d]pyrimidin-3-yl)propan-1-ol
To a solution of methyl 4,6-dimethoxy-1-(1-(4-(trifluoromethyl)phenyl)ethyl)-1H-pyrazolo[3,4-d]pyrimidine-3-carboxylate (80 mg, 0.2 mmol) and titanium isopropoxide (11.5 µL, 0.04 mmol) in THF (5 mL) at 0° C. under N$_2$ was added a solution of ethylmagnesium bromide (3 M in THF, 0.26 mL, 0.8 mmol). The reaction mixture was warmed to RT and stirred for 2 h. Brine (50 mL) was added to the mixture which was extracted with ethyl acetate (3×80 mL). The combined organic layers were washed with brine (100 mL), dried over sodium sulfate, filtered, and concentrated under reduced pressure. The residue was purified by silica gel column chromatography (50% ethyl acetate in petroleum ether) to afford the title compound as an oil. MS=411.2 (+ESI).

Step 4. (R,S)- and (R,R)- and (S,S)- and (S,R)-6-Hydroxy-3-(1-hydroxypropyl)-1-(1-(4-(trifluoromethyl)phenyl)ethyl)-1H-pyrazolo[3,4-d]pyrimidin-4(5H)-one A mixture of the four stereoisomeric title compounds was prepared using procedures similar to those described in step 4 of Examples 28 using 1-(4,6-dimethoxy-1-(1-(4-(trifluoromethyl)phenyl)ethyl)-1H-pyrazolo[3,4-d]pyrimidin-3-yl)propan-1-ol to afford a solid. The mixture of four stereoisomeric title compounds were separated by preparative HPLC (X Bridge RP C18, 25% ACN in water (0.1% NH$_4$HCO$_3$) to afford two products which each contained two stereoisomers. The faster-eluting stereoisomers of the title compound (Example 294) were obtained as a solid. MS (+ESI) m/z=383.0. $^1$H NMR (400 MHz, DMSO-d$_6$) δ: 9.50 (br s, 1H), 7.66 (d, J=8.0 Hz, 2H), 7.44 (d, J=8.4 Hz, 2H), 6.07 (d, J=7.2 Hz, 1H), 5.80-5.70 (m, 1H), 4.40-4.35 (m, 1H), 1.76 (d, J=7.2 Hz, 3H), 1.75-1.60 (m, 2H), 0.86 (t, J=7.2 Hz, 3H). The slower-eluting stereoisomers of the title compound (Example 295) were obtained as a solid. MS (+ESI) m/z=383.0. $^1$H NMR (400 MHz, DMSO-d$_6$) δ: 9.50 (br s, 1H), 7.66 (d, J=8.0 Hz, 2H), 7.44 (d, J=8.4 Hz, 2H), 5.87 (d, J=7.2 Hz, 1H), 5.80-5.70 (m, 1H), 4.40-4.35 (m, 1H), 1.76 (d, J=7.2 Hz, 3H), 1.75-1.60 (m, 2H), 0.86 (t, J=7.2 Hz, 3H).

EXAMPLES 296 AND 297

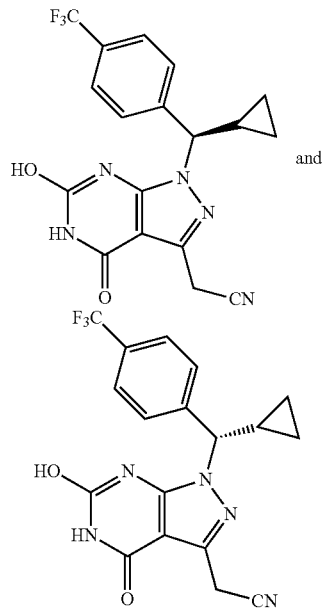

(R)- and (S)-2-(1-(Cyclopropyl(4-(trifluoromethyl)phenyl)methyl)-6-hydroxy-4-oxo-4,5-dihydro-1H-pyrazolo[3,4-d]pyrimidin-3-yl)acetonitrile (Scheme 38)

Step 1: 3-(Benzyloxymethyl)-1-(cyclopropyl(4-(trifluoromethyl)phenyl)methyl)-4,6-dimethoxy-1H-pyrazolo[3,4-d]pyrimidine The title compound was prepared using procedures similar to those described in step 1 of Preparatory Example 75 using cyclopropyl(4-(trifluoromethyl)phenyl)methanol and 3-(benzyloxymethyl)-4,6-dimethoxy-1H-pyrazolo[3,4-d]pyrimidine from Preparatory Example 73 to afford a solid. MS=499.4 (+ESI).

Step 2. (1-(Cyclopropyl(4-(trifluoromethyl)phenyl)methyl)-4,6-dimethoxy-1H-pyrazolo[3,4-d]pyrimidin-3-yl)methanol The title compound was prepared using procedures similar to those described in step 2 of Preparatory Example 75 using 3-(benzyloxymethyl)-1-(cyclopropyl(4-(trifluoromethyl)phenyl)methyl)-4,6-dimethoxy-1H-pyrazolo[3,4-d]pyrimidine to afford an oil. MS=409.3 (+ESI).

Step 3. (1-(Cyclopropyl(4-(trifluoromethyl)phenyl)methyl)-4,6-dimethoxy-1H-pyrazolo[3,4-d]pyrimidin-3-yl)methyl methanesulfonate To a solution of (1-(cyclopropyl(4-(trifluoromethyl)phenyl)methyl)-4,6-dimethoxy-1H-pyrazolo[3,4-d]pyrimidin-3-yl)methanol (0.24 g, 0.59 mmol) in DCM (2 mL) at RT was added triethylamine (0.16 mL, 1.18 mmol) followed by methanesulfonyl chloride (68 μL, 0.88 mmol). The reaction was stirred for 2 h at 25° C. whereupon water (15 mL) was added followed by and extraction with DCM (3×10 mL). The combined organic layers were washed with water (1×15 mL), dried over sodium sulfate, filtered, and concentrated under vacuum. The residue was purified by silica gel column chromatography (35% ethyl acetate in petroleum ether) to afford the title compound as an oil. MS=487.3 (+ESI).

Step 4. 2-(1-(Cyclopropyl(4-(trifluoromethyl)phenyl)methyl)-4,6-dimethoxy-1H-pyrazolo[3,4-d] pyrimidin-3-yl)acetonitrile To a mixture of (1-(cyclopropyl(4-(trifluoromethyl)phenyl)methyl)-4,6-dimethoxy-1H-pyrazolo[3,4-d]pyrimidin-3-yl)methyl methanesulfonate (0.18 g, 0.37 mmol) in acetonitrile (0.5 mL) at RT was added 18-crown-6 (49 mg, 0.19 mmol) followed by sodium cyanide (36 mg, 0.74 mmol). The reaction mixture was heated to 65° C., stirred for 2 h, and cooled to room temperature. Water (15 mL) was added followed by extraction with ethyl acetate (3×10 mL). The combined organic layers were washed with water (1×15 mL), dried over anhydrous sodium sulfate, filtered, and concentrated under vacuum. The residue was purified by silica gel column chromatography (30% ethyl acetate in petroleum ether) to afford the title compound as an oil. MS=418.2 (+ESI).

Step 5. (R)- and (S)-2-(1-(Cyclopropyl(4-(trifluoromethyl)phenyl)methyl)-6-hydroxy-4-oxo-4,5-dihydro-1H-pyrazolo[3,4-d]pyrimidin-3-yl)acetonitrile To a solution of 2-(1-(cyclopropyl(4-(trifluoromethyl)phenyl)methyl)-4,6-dimethoxy-1H-pyrazolo[3,4-d]pyrimidin-3-yl)acetonitrile (60 mg, 0.1 mmol) in DCM (1 mL) at room temperature was added iodotrimethylsilane (61 μL, 0.4 mmol). The mixture was stirred for 3 h at RT whereupon sat. aq. sodium bisulfite (15 mL) was added. The mixture was extracted with ethyl acetate (3×10 mL) and the organic layers were combined. The organic layer was washed with water (10 mL), dried over anhydrous sodium sulfate, filtered, and concentrated under reduced pressure. The residue was purified by preparative HPLC (X Bridge RP C18, 40-60% ACN in water (0.1% TFA)) to afford the racemic title compound as a solid. The enantiopure title compounds were obtained by chiral preparative HPLC (Chiralpak IA, 15% EtOH in hexanes (0.1% TFA)). The faster-eluting enantiomer of the title compound (Example 296) was obtained as a solid. MS=390.2 (+ESI). $^1$H NMR (300 MHz, CD$_3$OD) δ: 7.71-7.57 (m, 4H), 4.80 (d, J=9.6 Hz, 1H), 4.06 (s, 2H), 1.96-1.76 (m, 1H), 0.91-0.64 (m, 2H), 0.63-0.42 (m, 2H). The slower-eluting enantiomer of the title compound (Example 297) was obtained as a solid. MS=390.2 (+ESI). $^1$H NMR (300 MHz, CD$_3$OD) δ: 7.71-7.57 (m, 4H), 4.80 (d, J=9.6 Hz, 1H), 4.06 (s, 2H), 1.96-1.76 (m, 1H), 0.91-0.64 (m, 2H), 0.63-0.42 (m, 2H).

TABLE 34

The following compounds were prepared using procedures similar to those described in Examples 296 and 297 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]$^+$ | Chiral column |
|---|---|---|---|---|
| 298 | 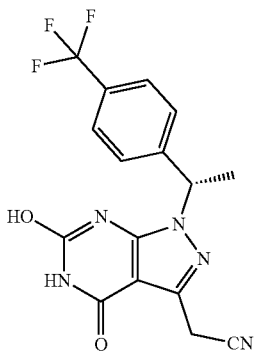 [SMILES: C[C@@H](c1ccc(C(F)(F)F)cc1)n1nc(CC#N)c2c(=O)[nH]c(O)nc21] | (S)-2-(6-Hydroxy-4-oxo-1-(1-(4-(trifluoromethyl)phenyl)ethyl)-4,5-dihydro-1H-pyrazolo[3,4-d]pyrimidin-3-yl)acetonitrile | Calc'd 364.1, found 364.1 | Chiralpak IA |

TABLE 34-continued

The following compounds were prepared using procedures similar to those described in Examples 296 and 297 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 299 | 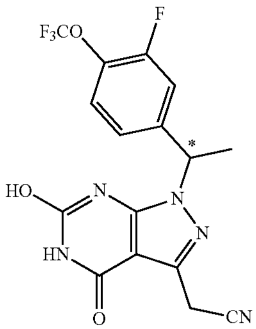 [SMILES: CC(c1ccc(OC(F)(F)F)c(F)c1)n1nc(CC#N)c2c(=O)[nH]c(O)nc21] | (R)- or (S)-2-(1-(1-(3-Fluoro-4-(trifluoromethoxy)phenyl)ethyl)-6-hydroxy-4-oxo-4,5-dihydro-1H-pyrazolo[3,4-d]pyrimidin-3-yl)acetonitrile | Calc'd 398.1, found 396(−ESI) | AXIA Packed |
| 300 | 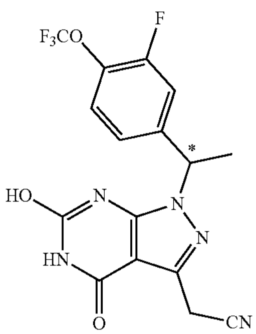 [SMILES: CC(c1ccc(OC(F)(F)F)c(F)c1)n1nc(CC#N)c2c(=O)[nH]c(O)nc21] | (S)- or (R)-2-(1-(1-(3-Fluoro-4-(trifluoromethoxy)phenyl)ethyl)-6-hydroxy-4-oxo-4,5-dihydro-1H-pyrazolo[3,4-d]pyrimidin-3-yl)acetonitrile | Calc'd 398.1, found 398.2 | AXIA Packed |

EXAMPLE 301

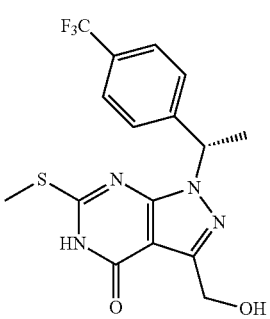 [SMILES: CSc1nc2c(c(CO)nn2[C@@H](C)c2ccc(C(F)(F)F)cc2)c(=O)[nH]1]

(S)-3-(Hydroxymethyl)-6-(methylthio)-1-(1-(4-(trifluoromethyl)phenyl)ethyl)-1H-pyrazolo[3,4-d]pyrimidin-4(5H)-one (Scheme 41)

Step 1. (S)-3-((Benzyloxy)methyl)-4-methoxy-6-(methylthio)-1-(1-(4-(trifluoromethyl)phenyl)ethyl)-1H-pyrazolo[3,4-d]pyrimidine To a solution of (S)-3-((benzyloxy)methyl)-6-chloro-4-methoxy-1-(1-(4-(trifluoromethyl)phenyl)ethyl)-1H-pyrazolo[3,4-d]pyrimidine (200 mg, 0.42 mmol) in anhydrous THF (1 mL) added sodium methanethiolate (44 mg, 0.63 mmol) at room temperature under $N_2$. The mixture was stirred at RT whereupon water (1 mL) was added followed by extraction with EtOAc (2×15 mL). The organic layers were combined, dried over sodium sulfate, filtered, and concentrated under reduced pressure. The residue was purified by silica gel column chromatography (0-100% EtOAc in hexanes) to afford the title compound as white solid. MS=489.2 (M+H).

Step 2: (S)-3-(Hydroxymethyl)-6-(methylthio)-1-(1-(4-(trifluoromethyl)phenyl)ethyl)-1H-pyrazolo[3,4-d]pyrimidin-4(5H)-one To a solution of (S)-3-((benzyloxy)methyl)-4-methoxy-6-(methylthio)-1-(1-(4-(trifluoromethyl)phenyl)ethyl)-1H-pyrazolo[3,4-d]pyrimidine (80 mg, 0.164 mmol) in $CH_3CN$ (1 mL) at room temperature under $N_2$ was added TMSI (0.111 ml, 0.819 mmol) dropwise. The mixture was stirred at RT for 1 h whereupon water (2 mL) was added. The mixture was extracted with EtOAc (3×10 mL), dried over $Na_2SO_4$, filtered, and concentrated under reduced pressure. The residue was purified by reverse-phase HPLC (Sunfire C18, 30-90% ACN in water (0.05% TFA)) to afford the title compound (Example 301) as a solid. $^1$H NMR ($CDCl_3$, 500 MHz) δ: 11.40 (br s, 1H), 7.60 (d, J=7.5 Hz, 2H), 7.49 (d, J=7.5 Hz, 2H), 6.01 (m, 1H), 4.89 (s, 3H), 2.62 (s, 3H), 1.99 (d, J=8.0 Hz, 3H). MS=385.0 (M+H).

TABLE 35

The following compound was prepared using procedures similar to those described for Example 301 except using sodium ethoxide and the appropriate starting materials.

| Ex # | Structure | IUPAC Name | Exact Mass [M + H]+ |
|---|---|---|---|
| 302 | 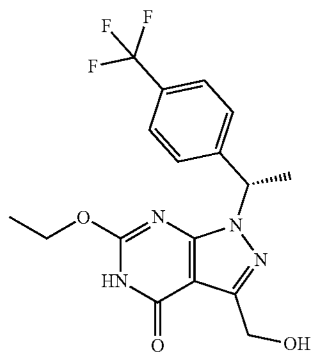 [SMILES: CCOc1nc2c(c(CO)nn2[C@@H](C)c2ccc(C(F)(F)F)cc2)c(=O)[nH]1] | 6-Ethoxy-3-(hydroxymethyl)-1-{(1S)-1-[4-(trifluoromethyl)phenyl]ethyl}-1,5-dihydro-4H-pyrazolo[3,4-d]pyrimidin-4-one | Calc'd 383.1, found 383.1 |

EXAMPLE 303

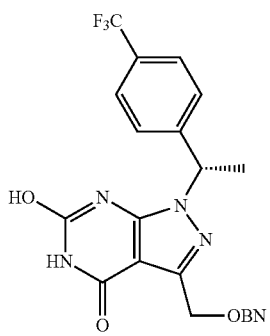

(S)-3-((Benzyloxy)methyl)-6-hydroxy-1-(1-(4-(trifluoromethyl)phenyl)ethyl)-1,5-dihydro-4H-pyrazolo[3,4-d]pyrimidin-4-one (Scheme 42)

Step 1. (S)-3-((Benzyloxy)methyl)-4,6-dimethoxy-1-(1-(4-(trifluoromethyl)phenyl)ethyl)-1H-pyrazolo[3,4-d]pyrimidine To a mixture of 3-((benzyloxy)methyl)-4,6-dimethoxy-1H-pyrazolo[3,4-d]pyrimidine (5.0 g, 16.7 mmol) from Preparatory Example 73 in toluene (25 ml) under N₂ at RT was added (R)-1-(4-(trifluoromethyl)phenyl)ethanol (2.6 mL, 16.7 mmol) dropwise. PPh₃ (13.1 g, 4.99 mmol) was added to the mixture portionwise followed by dropwise addition of DIAD (9.71 ml, 49.9 mmol) over ~10 min. The resulting mixture was stirred for 4 h at RT, then was diluted with water (25 mL) and extracted with ethyl acetate (3×120 mL). The combined organic layers were washed with water (2×50 mL) and brine (3×50 mL). The organic layer was dried over Na₂SO₄, filtered, and concentrated under reduced pressure. The residue was purified by silica gel column chromatography (0-55% EtOAc in hexanes) to afford the title compound as an oil. MS=473.3 (M+H).

Step 2. (S)-3-((Benzyloxy)methyl)-6-hydroxy-1-(1-(4-(trifluoromethyl)phenyl)ethyl)-1,5-dihydro-4H-pyrazolo[3,4-d]pyrimidin-4-one To a mixture of (S)-3-((benzyloxy)methyl)-4,6-dimethoxy-1-(1-(4-(trifluoromethyl)phenyl)ethyl)-1H-pyrazolo[3,4-d]pyrimidine (0.19 g, 0.40 mmol) in EtOAc (1 mL) at RT was added 6 M aqueous HCl (1 mL) dropwise. The reaction flask was affixed with a reflux condenser and was heated to 80° C. under a N₂ balloon and stirred for 18 h. The mixture was cooled to rt and was concentrated under reduced pressure. The residue was purified by reverse-phase HPLC (SunFire C18 column, 10-90% ACN in water (0.05% TFA)) to afford the title compound (Example 303) as a solid. ¹H NMR (CD₃OD, 500 MHz) δ: 7.64 (d, J=8.3 Hz, 2H), 7.48 (d, J=8.3 Hz, 2H), 7.35-7.22 (m, 5H), 5.72 (m, 1H), 4.73 (s, 2H), 4.63 (s, 2H), 1.93 (d, J=7.0 Hz, 3H). MS=445.3 (M+H).

EXAMPLE 304

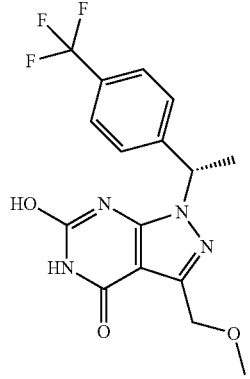 [SMILES: COCc1nn([C@@H](C)c2ccc(C(F)(F)F)cc2)c2nc(O)[nH]c(=O)c12]

(S)-6-Hydroxy-3-(methoxymethyl)-1-(1-(4-(trifluoromethyl)phenyl)ethyl)-1,5-dihydro-4H-pyrazolo[3,4-d]pyrimidin-4-one (Scheme 43)

Step 1. (S)-(4,6-Dimethoxy-1-(1-(4-(trifluoromethyl)phenyl)ethyl)-1H-pyrazolo[3,4-d]pyrimidin-3-yl)methanol To a round bottom flask charged with (S)-3-((benzyloxy)methyl)-4,6-dimethoxy-1-(1-(4-(trifluoromethyl)phenyl)ethyl)-1H-pyrazolo[3,4-d]pyrimidine (480 mg, 1.0 mmol) in MeOH (~5 mL) at RT was added 20% Pd(OH)₂ (0.22 g, 0.31 mmol) in a single portion. The flask was degassed under house vacuum and was filled with N₂ and this procedure was executed three additional times. The flask was degassed under house vacuum and was filled with H₂ (from a balloon)

and this protocol was executed three additional times. The reaction mixture was stirred vigorously under H₂ for 12 h at RT whereupon the mixture was purged with N₂ and was filtered through a pad of Celite™. The Celite™ pad was washed with MeOH (4×10 mL) and the resulting filtrate was concentrated under reduced pressure. The residue was purified by silica gel column chromatography (0-80% EtOAc in hexanes) to afford the title compound as a solid. MS=383.2 (M+H).

Step 2. (S)-(4,6-Dimethoxy-1-(1-(4-(trifluoromethyl)phenyl)ethyl)-1H-pyrazolo[3,4-d]pyrimidin-3-yl)methanol To a mixture of (S)-(4,6-dimethoxy-1-(1-(4-(trifluoromethyl)phenyl)ethyl)-1H-pyrazolo[3,4-d]pyrimidin-3-yl)methanol (100 mg, 0.26 mmol) in THF (2.6 mL) at 0° C. under N₂ was added 60% NaH in mineral oil (21 mg, 0.52 mmol) to afford a gray mixture. The resulting mixture was stirred for 20 min at 0° C. whereupon MeI (82 µL, 1.3 mmol) was added and the resulting mixture was stirred for 2 h at 0° C. The mixture was warmed to RT, stirred for 1 h, and treated with sat. aq. NH₄Cl (2 mL). The mixture was extracted with EtOAc (3×6 mL) and the organic layers were combined. The organic layer was washed with brine (1×4 mL), dried over Na₂SO₄, filtered, and concentrated under reduced pressure. The residue was purified by silica gel column chromatography (0-70% EtOAc in hexanes) to afford the title compound as a solid. MS=397.3 (M+H).

Step 3. (S)-6-Hydroxy-3-(methoxymethyl)-1-(1-(4-(trifluoromethyl)phenyl)ethyl)-1,5-dihydro-4H-pyrazolo[3,4-d]pyrimidin-4-one To a mixture of (S)-(4,6-dimethoxy-1-(1-(4-(trifluoromethyl)phenyl)ethyl)-1H-pyrazolo[3,4-d]pyrimidin-3-yl)methanol (95 mg, 0.24 mmol) in EtOAc (2 mL) at RT was added 6 M aqueous HCl (2 mL) to afford a homogenous mixture. The mixture was affixed with a reflux condenser, then the mixture was heated to 80° C. under N₂. The mixture was stirred for 12 h at 80° C. whereupon the mixture was cooled to RT and was concentrated under reduced pressure. The residue was purified by reverse-phase HPLC (SunFire C18 column, 10-90% ACN in water (0.05% TFA)) to afford the title compound (Example 304) as a solid. ¹H NMR (500 MHz, DMSO-d₆) δ: 12.10 (br s, 1H), 10.9 (br s, 1H), 7.72 (d, J=8.3 Hz, 2H), 7.50 (d, J=8.3 Hz, 2H), 5.85 (m, 1H), 4.46 (s, 3H), 3.26 (s, 2H), 1.80 (d, J=6.9 Hz, 3H). MS=369.1 (M+H).

EXAMPLES 305 AND 306

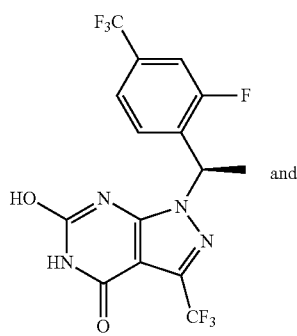

and

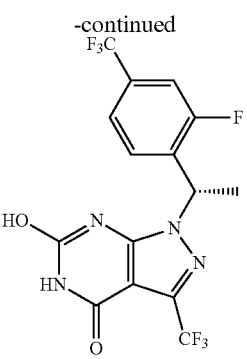

(R)- and (S)-1-(1-(2-Fluoro-4-(trifluoromethyl)phenyl)ethyl)-6-hydroxy-3-(trifluoromethyl)-1H-pyrazolo[3,4-d]pyrimidin-4(5H)-one (Scheme 44)

Step 1. 1-(1-(2-fluoro-4-(trifluoromethyl)phenyl)ethyl)-4,6-dimethoxy-3-(trifluoromethyl)-1H-pyrazolo[3,4-d]pyrimidine To a mixture of 4,6-dimethoxy-3-(trifluoromethyl)-1H-pyrazolo[3,4-d]pyrimidine (0.50 g, 2.0 mmol) from Preparatory Example 76 in toluene (7 ml) under N₂ at RT was added 1-(2-fluoro-4-(trifluoromethyl)phenyl)ethanol (0.46 g, 2.4 mmol) in one portion PPh₃ (1.59 g, 6.0 mmol) was added to the mixture portionwise followed by dropwise addition of DIAD (1.18 ml, 6.0 mmol) over ~10 min. The resulting mixture was stirred for 12 h at RT whereupon the mixture was diluted with water (3 mL) and extracted with ethyl acetate (3×25 mL). The combined organic layers were washed with water (2×10 mL) and brine (2×10 mL). The organic layer was dried (over Na₂SO₄), filtered, and concentrated under reduced pressure. The residue was purified by silica gel column chromatography (0-20% EtOAc in hexanes) to afford the title compound as an oil. MS=438.8 (M+H)

Step 2. (R)- and (S)-1-(1-(2-Fluoro-4-(trifluoromethyl)phenyl)ethyl)-6-hydroxy-3-(trifluoromethyl)-1H-pyrazolo[3,4-d]pyrimidin-4(5H)-one To a round bottom flask charged with a stir bar and 1-(1-(2-fluoro-4-(trifluoromethyl)phenyl)ethyl)-4,6-dimethoxy-3-(trifluoromethyl)-1H-pyrazolo[3,4-d]pyrimidine (0.66 g, 1.51 mmol) was added 4 M HCl in dioxane (6.0 ml, 24 mmol) and concentrated HCl (0.2 mL) at RT. The mixture was affixed with a reflux condenser and the mixture was heated to 80° C. while under N₂. The mixture was stirred for 12 h at 80° C. whereupon the mixture was cooled to rt and concentrated under reduced pressure. The residue was purified by reverse-phase HPLC (SunFire C18 column, 10-90% ACN in water (0.05% TFA)) to afford the title compound. The enantiopure title compounds were obtained by chiral SFC separation (Chiralcel OJ-H column, 13% methanol (0.1% NH₄OH)/CO₂). The faster-eluting enantiomer of the title compound (Example 305) was obtained as a solid. MS=411.2 (M+H). ¹H NMR (CD₃OD, 500 MHz) δ: 7.51 (m, 3H), 6.13 (m, 1H), 1.93 (d, J=6.5 Hz, 3H). The slower-eluting enantiomer of the title compound (Example 306) was obtained as a solid. MS=411.2 (M+H). ¹H NMR (CD₃OD, 500 MHz) δ: 7.51 (m, 3H), 6.13 (m, 1H), 1.93 (d, J=6.5 Hz, 3H).

TABLE 36

The following compounds were prepared using procedures similar to those described in Examples 305 and 306 using appropriate starting materials. Racemic products were separated using chiral columns using SFC chromatography specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 307 | 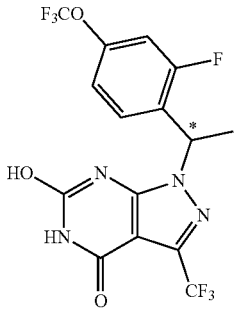 [SMILES: CC(c1ccc(OC(F)(F)F)cc1F)n1nc(C(F)(F)F)c2c(=O)[nH]c(O)nc21] | (R)- or (S)-1-{1-[2-Fluoro-4-(trifluoromethoxy)phenyl]ethyl}-6-hydroxy-3-(trifluoromethyl)-1,5-dihydro-4H-pyrazolo-[3,4-d]pyrimidin-4-one | Calc'd 427.1, found 427.2 | Chiralcel OZ-H |
| 308 | 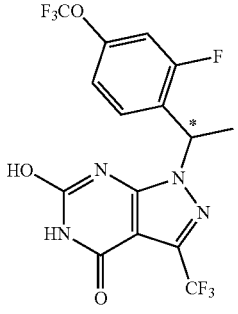 [SMILES: CC(c1ccc(OC(F)(F)F)cc1F)n1nc(C(F)(F)F)c2c(=O)[nH]c(O)nc21] | (S)- or (R)-1-{1-[2-Fluoro-4-(trifluoromethoxy)phenyl]ethyl}-6-hydroxy-3-(trifluoromethyl)-1,5-dihydro-4H-pyrazolo[3,4-d]pyrimidin-4-one | Calc'd 427.1, found 427.2 | Chiralcel OZ-H |
| 309 | 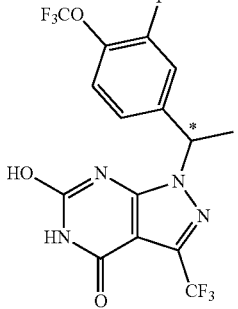 | (R)- or (S)-1-{1-[3-Fluoro-4-(trifluoromethoxy)phenyl]ethyl}-6-hydroxy-3-(trifluoromethyl)-1,5-dihydro-4H-pyrazolo[3,4-d]pyrimidin-4-one | Calc'd 427.1, found 427.1 | Chiralcel OZ-H |
| 310 | 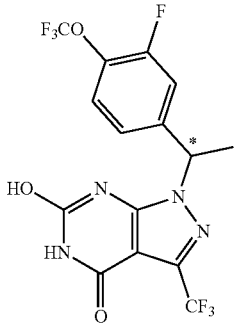 [SMILES: CC(c1ccc(OC(F)(F)F)c(F)c1)n1nc(C(F)(F)F)c2c(=O)[nH]c(O)nc21] | (S)- or (R)-1-{1-[3-Fluoro-4-(trifluoromethoxy)phenyl]ethyl}-6-hydroxy-3-(trifluoromethyl)-1,5-dihydro-4H-pyrazolo[3,4-d]pyrimidin-4-one | Calc'd 427.1, found 427.2 | Chiralcel OZ-H |

TABLE 36-continued

The following compounds were prepared using procedures similar to those described in Examples 305 and 306 using appropriate starting materials. Racemic products were separated using chiral columns using SFC chromatography specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 311 | 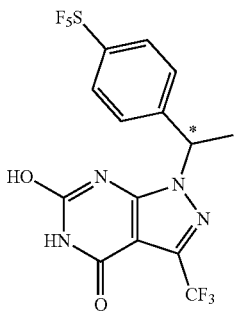 | (R)- or (S)-6-Hydroxy-1-{1-[4-(pentafluoro-lambda~6-sulfanyl)phenyl]ethyl}-3-(trifluoromethyl)-1,5-dihydro-4H-pyrazolo[3,4-d]pyrimidin-4-one | Calc'd 451.0, found 451.1 | Chiralpak AS-H |
| 312 | 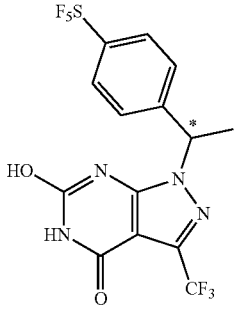 | (S)- or (R)-6-Hydroxy-1-{1-[4-(pentafluoro-lambda~6-sulfanyl)phenyl]ethyl}-3-(trifluoromethyl)-1,5-dihydro-4H-pyrazolo[3,4-d]pyrimidin-4-one | Calc'd 451.0, found 451.1 | Chiralpak AS-H |
| 313 | 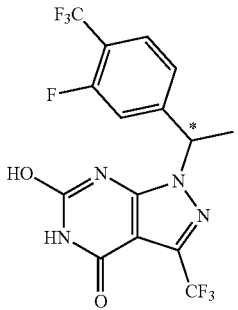 [SMILES: CC(c1ccc(C(F)(F)F)c(F)c1)n1nc(C(F)(F)F)c2c(=O)[nH]c(O)nc21] | (R)- or (S)-1-{1-[3-Fluoro-4-(trifluoromethyl)phenyl]ethyl}-6-hydroxy-3-(trifluoromethyl)-1,5-dihydro-4H-pyrazolo[3,4-d]pyrimidin-4-one | Calc'd 411.1, found 411.3 | Chiralpak IC |
| 314 | 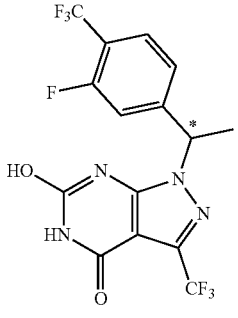 [SMILES: CC(c1ccc(C(F)(F)F)c(F)c1)n1nc(C(F)(F)F)c2c(=O)[nH]c(O)nc21] | (S)- or (R)-1-{1-[3-Fluoro-4-(trifluoromethyl)phenyl]ethyl}-6-hydroxy-3-(trifluoromethyl)-1,5-dihydro-4H-pyrazolo[3,4-d]pyrimidin-4-one | Calc'd 411.1, found 411.1 | Chiralpak IC |

TABLE 36-continued

The following compounds were prepared using procedures similar to those described in Examples 305 and 306 using appropriate starting materials. Racemic products were separated using chiral columns using SFC chromatography specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 315 | 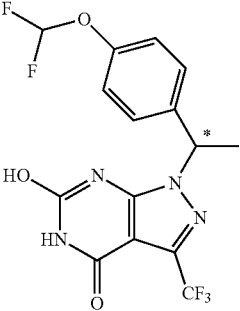 [SMILES: CC(c1ccc(OC(F)F)cc1)n1nc(C(F)(F)F)c2c(=O)[nH]c(O)nc21] | (R)- or (S)-1-{1-[4-(Difluoromethoxy)phenyl]ethyl}-6-hydroxy-3-(trifluoromethyl)-1,5-dihydro-4H-pyrazolo[3,4-d]pyrimidin-4-one | Calc'd 391.1, found 391.2 | Chrialpak AD-H |
| 316 | 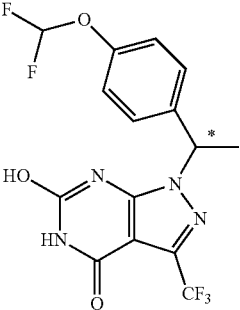 [SMILES: CC(c1ccc(OC(F)F)cc1)n1nc(C(F)(F)F)c2c(=O)[nH]c(O)nc21] | (S)- or (R)-1-{1-[4-(Difluoromethoxy)phenyl]ethyl}-6-hydroxy-3-(trifluoromethyl)-1,5-dihydro-4H-pyrazolo[3,4-d]pyrimidin-4-one | Calc'd 391.1, found 391.2 | Chrialpak AD-H |
| 317 | 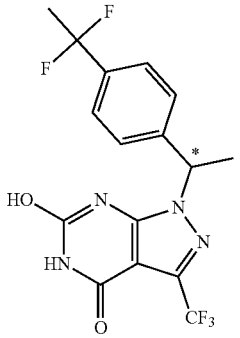 [SMILES: CC(c1ccc(C(C)(F)F)cc1)n1nc(C(F)(F)F)c2c(=O)[nH]c(O)nc21] | (R)- or (S)-1-(1-(4-(1,1-Difluoroethyl)phenyl)ethyl)-6-hydroxy-3-(trifluoromethyl)-1H-pyrazolo[3,4-d]pyrimidin-4(5H)-one | Calc'd 389.1, found 389.0. | Chiralpak IB |
| 318 | 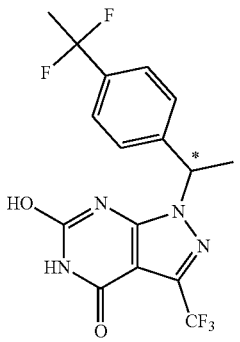 [SMILES: CC(c1ccc(C(C)(F)F)cc1)n1nc(C(F)(F)F)c2c(=O)[nH]c(O)nc21] | (S)- or (R)-1-(1-(4-(1,1-Difluoroethyl)phenyl)ethyl)-6-hydroxy-3-(trifluoromethyl)-1H-pyrazolo[3,4-d]pyrimidin-4(5H)-one | Calc'd 389.1, found 389.0. | Chiralpak IB |

TABLE 36-continued

The following compounds were prepared using procedures similar to those described in Examples 305 and 306 using appropriate starting materials. Racemic products were separated using chiral columns using SFC chromatography specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 319 | 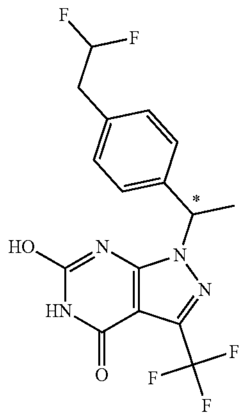 [SMILES: CC(c1ccc(CC(F)F)cc1)n1nc(C(F)(F)F)c2c(=O)[nH]c(O)nc21] | (R)- or (S)-1-(1-(4-(2,2-Difluoroethyl)phenyl)ethyl)-6-hydroxy-3-(trifluoromethyl)-1H-pyrazolo[3,4-d]pyrimidin-4(5H)-one | Calc'd 389.1, found 389.2. | Chiralpak IB |
| 320 | 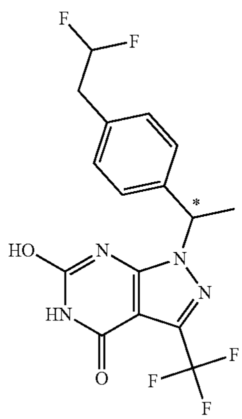 [SMILES: CC(c1ccc(CC(F)F)cc1)n1nc(C(F)(F)F)c2c(=O)[nH]c(O)nc21] | (S)- or (R)-1-(1-(4-(2,2-Difluoroethyl)phenyl)ethyl)-6-hydroxy-3-(trifluoromethyl)-1H-pyrazolo[3,4-d]pyrimidin-4(5H)-one | Calc'd 389.1, found 389.2. | Chiralpak IB |
| 321 | 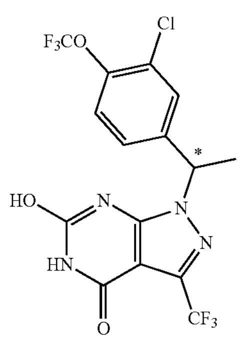 [SMILES: CC(c1ccc(OC(F)(F)F)c(Cl)c1)n1nc(C(F)(F)F)c2c(=O)[nH]c(O)nc21] | (R)- or (S)-1-(1-(3-Chloro-4-(trifluoromethoxy)phenyl)ethyl)-6-hydroxy-3-(trifluoromethyl)-1H-pyrazolo[3,4-d]pyrimidin-4(5H)-one | Calc'd 443.0; 445.0, found 442.9; 444.9. | Chiralpak IB |
| 322 | 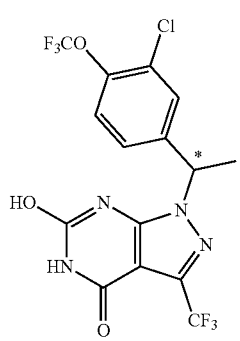 [SMILES: CC(c1ccc(OC(F)(F)F)c(Cl)c1)n1nc(C(F)(F)F)c2c(=O)[nH]c(O)nc21] | (S)- or (R)-1-(1-(3-Chloro-4-(trifluoromethoxy)phenyl)ethyl)-6-hydroxy-3-(trifluoromethyl)-1H-pyrazolo[3,4-d]pyrimidin-4(5H)-one | Calc'd 443.0; 445.0, found 443.0; 445.0. | Chiralpak IB |

TABLE 36-continued

The following compounds were prepared using procedures similar to those described in Examples 305 and 306 using appropriate starting materials. Racemic products were separated using chiral columns using SFC chromatography specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 323 | 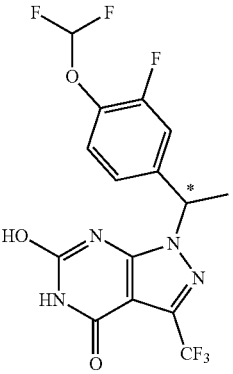 [SMILES: CC(c1ccc(OC(F)F)c(F)c1)n1nc(C(F)(F)F)c2c(=O)[nH]c(O)nc21] | (R)- or (S)-1-(1-(4-(Difluoromethoxy)-3-fluorophenyl)ethyl)-6-hydroxy-3-(trifluoromethyl)-1H-pyrazolo[3,4-d]pyrimidin-4(5H)-one | Calc'd 409.1, found 409.0. | Chiralpak IA |
| 324 | 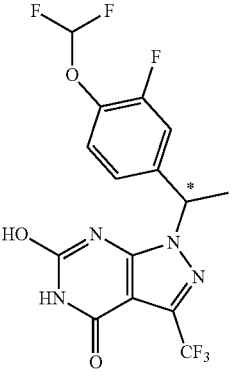 [SMILES: CC(c1ccc(OC(F)F)c(F)c1)n1nc(C(F)(F)F)c2c(=O)[nH]c(O)nc21] | (S)- or (R)-1-(1-(4-(Difluoromethoxy)-3-fluorophenyl)ethyl)-6-hydroxy-3-(trifluoromethyl)-1H-pyrazolo[3,4-d]pyrimidin-4(5H)-one | Calc'd 409.1, found 409.0. | Chiralpak IA |
| 325 | 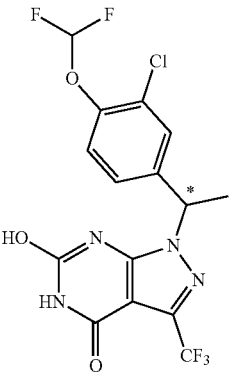 [SMILES: CC(c1ccc(OC(F)F)c(Cl)c1)n1nc(C(F)(F)F)c2c(=O)[nH]c(O)nc21] | (R)- or (S)-1-(1-(3-Chloro-4-(difluoromethoxy)phenyl)ethyl)-6-hydroxy-3-(trifluoromethyl)-1H-pyrazolo[3,4-d]pyrimidin-4(5H)-one | Calc'd 425.0; 427.0, found 424.9; 426.9. | Chiralpak AD-H |

TABLE 36-continued

The following compounds were prepared using procedures similar to those described in Examples 305 and 306 using appropriate starting materials. Racemic products were separated using chiral columns using SFC chromatography specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 326 | 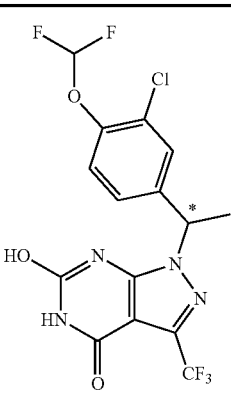 | (S)- or (R)-1-(1-(3-Chloro-4-(difluoromethoxy)phenyl)ethyl)-6-hydroxy-3-(trifluoromethyl)-1H-pyrazolo[3,4-d]pyrimidin-4(5H)-one | Calc'd 425.0; 427.0, found 425.0; 427.0. | Chiralpak AD-H |
| 327 | 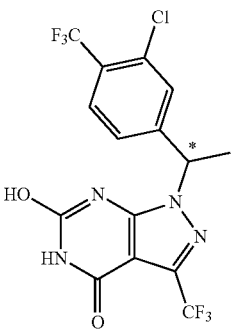 | (R)- or (S)-1-(1-(3-Chloro-4-(trifluoromethyl)phenyl)ethyl)-6-hydroxy-3-(trifluoromethyl)-1H-pyrazolo[3,4-d]pyrimidin-4(5H)-one | Calc'd 427.0; 429.0, found 427.0; 429.0. | Chiralpak IB |
| 328 | 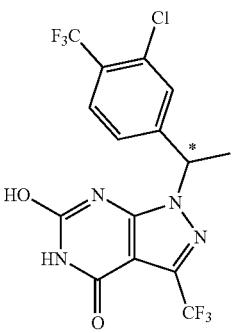 [SMILES: CC(c1ccc(C(F)(F)F)c(Cl)c1)n1nc(C(F)(F)F)c2c(=O)[nH]c(O)nc21] | (S)- or (R)-1-(1-(3-Chloro-4-(trifluoromethyl)phenyl)ethyl)-6-hydroxy-3-(trifluoromethyl)-1H-pyrazolo[3,4-d]pyrimidin-4(5H)-one | Calc'd 427.0; 429.0, found 427.0; 429.0. | Chiralpak IB |
| 329 | 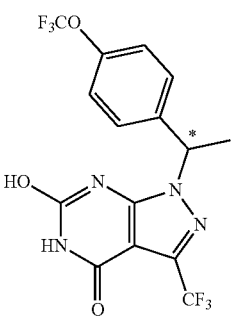 [SMILES: CC(c1ccc(OC(F)(F)F)cc1)n1nc(C(F)(F)F)c2c(=O)[nH]c(O)nc21] | (R)- or (S)-6-Hydroxy-1-(1-(4-(trifluoromethoxy)phenyl)ethyl)-3-(trifluoromethyl)-1H-pyrazolo[3,4-d]pyrimidin-4(5H)-one | Calc'd 407.1, found 407.0. | Chiralpak IB |

TABLE 36-continued

The following compounds were prepared using procedures similar to those described in Examples 305 and 306 using appropriate starting materials. Racemic products were separated using chiral columns using SFC chromatography specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 330 | 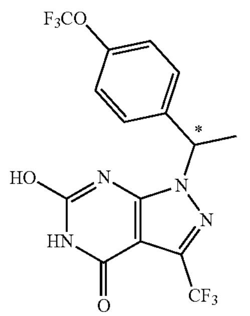 [SMILES: CC(c1ccc(OC(F)(F)F)cc1)n1nc(C(F)(F)F)c2c(=O)[nH]c(O)nc21] | (S)- or (R)-6-Hydroxy-1-(1-(4-(trifluoromethoxy)phenyl)ethyl)-3-(trifluoromethyl)-1H-pyrazolo[3,4-d]pyrimidin-4(5H)-one | Calc'd 407.1, found 407.0. | Chiralpak IB |
| 331 | 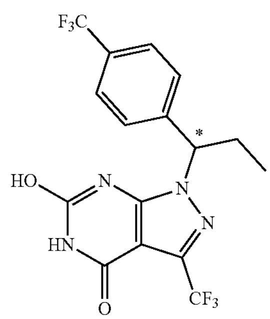 [SMILES: CCC(c1ccc(C(F)(F)F)cc1)n1nc(C(F)(F)F)c2c(=O)[nH]c(O)nc21] | (R)- or (S)-6-Hydroxy-3-(trifluoromethyl)-1-(1-(4-(trifluoromethyl)phenyl)propyl)-1H-pyrazolo[3,4-d]pyrimidin-4(5H)-one | Calc'd 407.1, found 407.0. | Chiralpak IB |
| 332 | 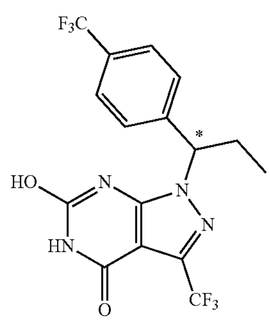 [SMILES: CCC(c1ccc(C(F)(F)F)cc1)n1nc(C(F)(F)F)c2c(=O)[nH]c(O)nc21] | (S)- or (R)-6-hydroxy-3-(trifluoromethyl)-1-(1-(4-(trifluoromethyl)phenyl)propyl)-1H-pyrazolo[3,4-d]pyrimidin-4(5H)-one | Calc'd 407.1, found 406.9. | Chiralpak IB |
| 333 | 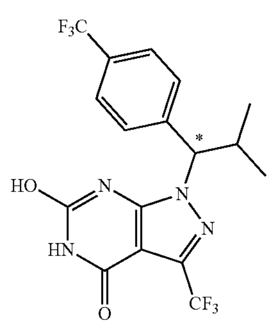 [SMILES: CC(C)C(c1ccc(C(F)(F)F)cc1)n1nc(C(F)(F)F)c2c(=O)[nH]c(O)nc21] | (R)- or (S)-6-Hydroxy-1-(2-methyl-1-(4-(trifluoromethyl)phenyl)propyl)-3-(trifluoromethyl)-1H-pyrazolo[3,4-d]pyrimidin-4(5H)-one | Calc'd 421.1, found 421.0. | Chiralpak IB |

TABLE 36-continued

The following compounds were prepared using procedures similar to those described in Examples 305 and 306 using appropriate starting materials. Racemic products were separated using chiral columns using SFC chromatography specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 334 | 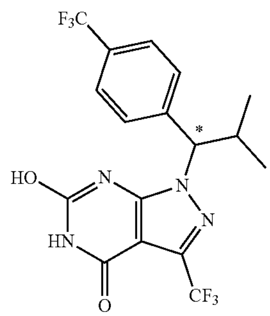 [SMILES: CC(C)C(c1ccc(C(F)(F)F)cc1)n1nc(C(F)(F)F)c2c(=O)[nH]c(O)nc21] | (S)- or (R)-6-Hydroxy-1-(2-methyl-1-(4-(trifluoromethyl)phenyl)propyl)-3-(trifluoromethyl)-1H-pyrazolo[3,4-d]pyrimidin-4(5H)-one | Calc'd 421.1, found 421.0. | Chiralpak IB |
| 335 | 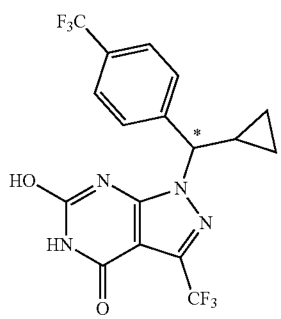 [SMILES: O=c1[nH]c(O)nc2c1c(C(F)(F)F)nn2C(c1ccc(C(F)(F)F)cc1)C1CC1] | (R)- or (S)-1-(Cyclopropyl(4-(trifluoromethyl)phenyl)methyl)-6-hydroxy-3-(trifluoromethyl)-1H-pyrazolo[3,4-d]pyrimidin-4(5H)-one | Calc'd 419.1, found 419.0. | Chiralcel OD-H |
| 336 | 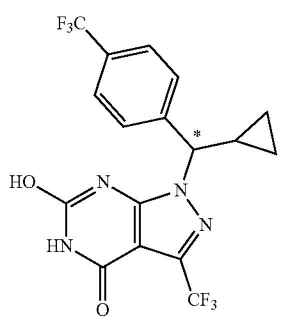 [SMILES: O=c1[nH]c(O)nc2c1c(C(F)(F)F)nn2C(c1ccc(C(F)(F)F)cc1)C1CC1] | (S)- or (R)-1-(Cyclopropyl(4-(trifluoromethyl)phenyl)methyl)-6-hydroxy-3-(trifluoromethyl)-1H-pyrazolo[3,4-d]pyrimidin-4(5H)-one | Calc'd 419.1, found 419.0. | Chiralcel OD-H |
| 337 | 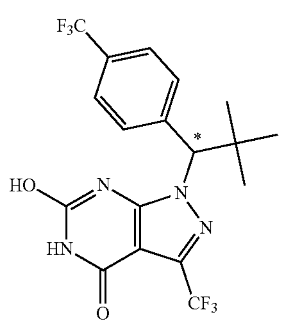 [SMILES: CC(C)(C)C(c1ccc(C(F)(F)F)cc1)n1nc(C(F)(F)F)c2c(=O)[nH]c(O)nc21] | (R)- or (S)-1-(2,2-Dimethyl-1-(4-(trifluoromethyl)phenyl)propyl)-6-hydroxy-3-(trifluoromethyl)-1H-pyrazolo[3,4-d]pyrimidin-4(5H)-one | Calc'd 435.1, found 435.0. | Chiralpak IB |

TABLE 36-continued

The following compounds were prepared using procedures similar to those described in Examples 305 and 306 using appropriate starting materials. Racemic products were separated using chiral columns using SFC chromatography specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 338 | 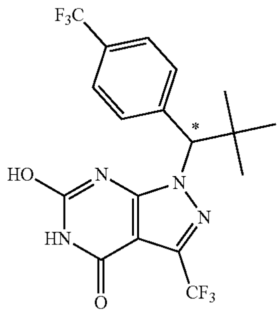 [SMILES: CC(C)(C)C(c1ccc(C(F)(F)F)cc1)n1nc(C(F)(F)F)c2c(=O)[nH]c(O)nc21] | (S)- or (R)-1-(2,2-Dimethyl-1-(4-(trifluoromethyl)phenyl)propyl)-6-hydroxy-3-(trifluoromethyl)-1H-pyrazolo[3,4-d]pyrimidin-4(5H)-one | Calc'd 435.1, found 435.0. | Chiralpak IB |

EXAMPLE 339

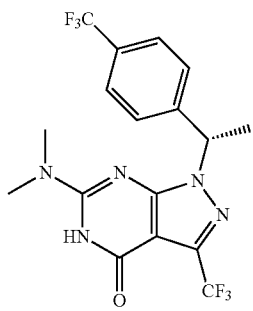 [SMILES: C[C@@H](c1ccc(C(F)(F)F)cc1)n1nc(C(F)(F)F)c2c(=O)[nH]c(N(C)C)nc21]

(S)-6-(Dimethylamino)-3-(trifluoromethyl)-1-(1-(4-(trifluoromethyl)phenyl)ethyl)-1H-pyrazolo[3,4-d]pyrimidin-4(5H)-one (Scheme 45)

Step 1. (S)-6-Chloro-3-(trifluoromethyl)-1-(1-(4-(trifluoromethyl)phenyl)ethyl)-1H-pyrazolo[3,4-d]pyrimidin-4(5H)-one To a flask charged with (S)-6-hydroxy-3-(trifluoromethyl)-1-(1-(4-(trifluoromethyl)phenyl)ethyl)-1H-pyrazolo[3,4-d]pyrimidin-4(5H)-one (135 mg, 0.344 mmol) from Example 255 at room temperature under $N_2$ was added $PCl_5$ (0.14 g, 0.69 mmol) followed by dropwise addition of $POCl_3$ (3.2 ml, 34 mmol). The mixture was stirred at 120° C. for 10 h, cooled to room temperature, and poured onto cold sat. aq. $NaHCO_3$. The mixture was extracted with EtOAc (3×30 mL) and the organic layers were combined. The organic layer was dried over $Na_2SO_4$, filtered, and concentrated under reduced pressure to afford the title compound as a solid. MS: 411.1 $(M+H)^+$.

Step 2. (S)-6-(Dimethylamino)-3-(trifluoromethyl)-1-(1-(4-(trifluoromethyl)phenyl)ethyl)-1H-pyrazolo[3,4-d]pyrimidin-4(5H)-one To a solution of (S)-6-chloro-3-(trifluoromethyl)-1-(1-(4-(trifluoromethyl)phenyl)ethyl)-1H-pyrazolo[3,4-d]pyrimidin-4(5H)-one in 2-propanol (1 mL) in a microwave vial at room temperature was added 2 M dimethylamine in THF (0.14 ml, 0.29 mmol) and TEA (0.041 ml, 0.29 mmol). The vial was purged with $N_2$, capped, and heated to 90° C. The mixture was stirred for 12 h, cooled to rt, and was diluted with EtOAc (10 mL). The organic layer was washed with sat. aq. $NH_4Cl$ and brine and was dried over $Na_2SO_4$. The organic layer was filtered and concentrated under reduced pressure. The residue was purified by reverse-phase HPLC chromatography (Surefire C18 column, 30-90% ACN in water (0.05% TFA)) to afford the title compound (Example 339) as a solid. $^1$H NMR ($CD_3OD$, 500 MHz) δ: 7.62 (d, J=7.5 Hz, 2H), 7.53 (d, J=7.5 Hz, 2H), 6.02 (m, 1H), 4.64 (s, 6H), 1.99 (d, J=7.0 Hz, 3H). MS=420.2 $(M+H)^+$.

TABLE 37

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex# | Structure | IUPAC Name | Exact Mass [M + H]+ | Chiral column |
|---|---|---|---|---|
| 340 | 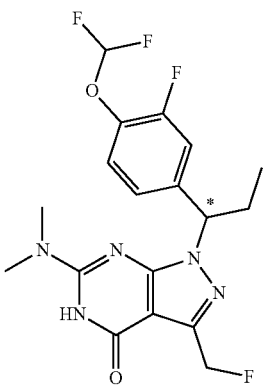 [SMILES: CCC(c1ccc(OC(F)F)c(F)c1)n1nc(CF)c2c(=O)[nH]c(N(C)C)nc21] | (R)- or (S)-1-(1-(4-(Difluoromethoxy)-3-fluorophenyl)propyl)-6-(dimethylamino)-3-(fluoromethyl)-1H-pyrazolo[3,4-d]pyrimidin-4(5H)-one | Calc'd 414.1, found 414.0. | Chiralpak IA |
| 341 | 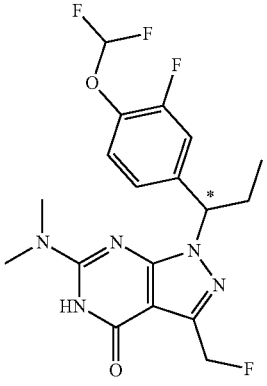 [SMILES: CCC(c1ccc(OC(F)F)c(F)c1)n1nc(CF)c2c(=O)[nH]c(N(C)C)nc21] | (S)- or (R)-1-(1-(4-(Difluoromethoxy)-3-fluorophenyl)propyl)-6-(dimethylamino)-3-(fluoromethyl)-1H-pyrazolo[3,4-d]pyrimidin-4(5H)-one | Calc'd 414.1, found 414.0. | Chiralpak IA |
| 342 | 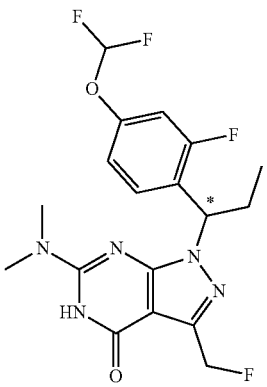 [SMILES: CCC(c1ccc(OC(F)F)cc1F)n1nc(CF)c2c(=O)[nH]c(N(C)C)nc21] | (R)- or (S)-1-(1-(4-(Difluoromethoxy)-2-fluorophenyl)propyl)-6-(dimethylamino)-3-(fluoromethyl)-1H-pyrazolo[3,4-d]pyrimidin-4(5H)-one | Calc'd 414.1, found 414.0. | Chiralpak AD-H-SL001 |

TABLE 37-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex# | Structure | IUPAC Name | Exact Mass [M + H]+ | Chiral column |
|---|---|---|---|---|
| 343 | 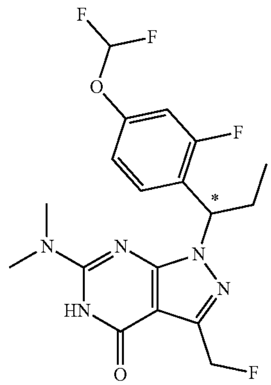 [SMILES: CCC(c1ccc(OC(F)F)cc1F)n1nc(CF)c2c(=O)[nH]c(N(C)C)nc21] | (S)- or (R)-1-(1-(4-(Difluoromethoxy)-2-fluorophenyl)propyl)-6-(dimethylamino)-3-(fluoromethyl)-1H-pyrazolo[3,4-d]pyrimidin-4(5H)-one | Calc'd 414.1, found 414.0. | Chiralpak AD-H-SL001 |
| 344 | 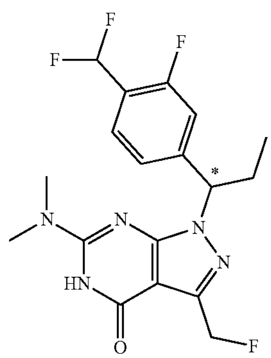 [SMILES: CCC(c1ccc(C(F)F)c(F)c1)n1nc(CF)c2c(=O)[nH]c(N(C)C)nc21] | (R)- or (S)-1-(1-(4-(Difluoromethyl)-3-fluorophenyl)propyl)-6-(dimethylamino)-3-(fluoromethyl)-1H-pyrazolo[3,4-d]pyrimidin-4(5H)-one | Calc'd 398.2, found 398.1. | Chiralpak IA |
| 345 | 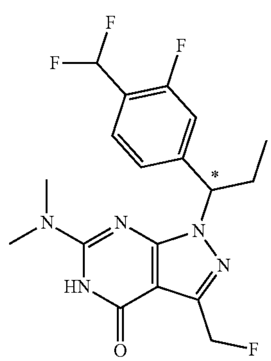 [SMILES: CCC(c1ccc(C(F)F)c(F)c1)n1nc(CF)c2c(=O)[nH]c(N(C)C)nc21] | (S)- or (R)-1-(1-(4-(Difluoromethyl)-3-fluorophenyl)propyl)-6-(dimethylamino)-3-(fluoromethyl)-1H-pyrazolo[3,4-d]pyrimidin-4(5H)-one | Calc'd 398.2, found 398.1. | Chiralpak IA |
| 346 | 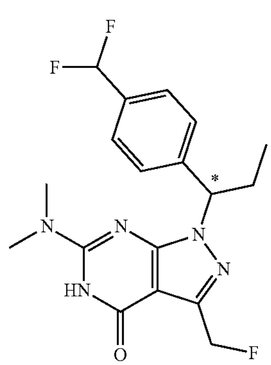 [SMILES: CCC(c1ccc(C(F)F)cc1)n1nc(CF)c2c(=O)[nH]c(N(C)C)nc21] | (R)- or (S)-1-(1-(4-(Difluoromethyl)phenyl)propyl)-6-(dimethylamino)-3-(fluoromethyl)-1H-pyrazolo[3,4-d]pyrimidin-4(5H)-one | Calc'd 380.2, found 380.2. | Chiralpak IA |

TABLE 37-continued

The following compounds were prepared using procedures similar to those described in Examples 162 and 163 using appropriate starting materials. Racemic products were separated using chiral columns specified in the table. For those pairs of enantiomers, the faster-eluting isomer is always listed first in this table.

| Ex# | Structure | IUPAC Name | Exact Mass [M + H]+ | Chiral column |
|---|---|---|---|---|
| 347 | 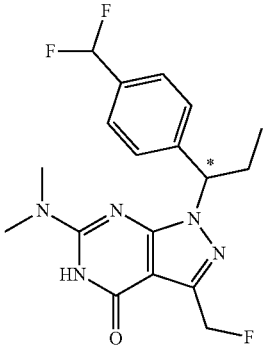 [SMILES: CCC(c1ccc(C(F)F)cc1)n1nc(CF)c2c(=O)[nH]c(N(C)C)nc21] | (S)- or (R)-1-(1-(4-(Difluoromethyl)phenyl)propyl)-6-(dimethylamino)-3-(fluoromethyl)-1H-pyrazolo[3,4-d]pyrimidin-4(5H)-one | Calc'd 380.2, found 380.2. | Chiralpak IA |
| 348 | 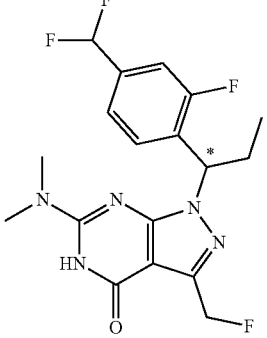 | (R)- or (S)-1-(1-(4-(difluoromethyl)-2-fluorophenyl)propyl)-6-(dimethylamino)-3-(fluoromethyl)-1H-pyrazolo[3,4-d]pyrimidin-4(5H)-one | Calc'd 398.2, found 398.2. | Chiralpak AD-H-SL001 |
| 349 | 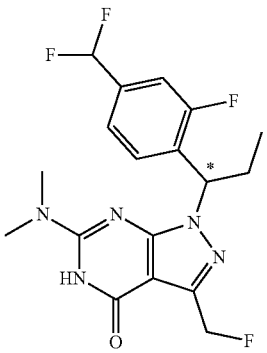 [SMILES: CCC(c1ccc(C(F)F)cc1F)n1nc(CF)c2c(=O)[nH]c(N(C)C)nc21] | (S)- or (R)-1-(1-(4-(difluoromethyl)-2-fluorophenyl)propyl)-6-(dimethylamino)-3-(fluoromethyl)-1H-pyrazolo[3,4-d]pyrimidin-4(5H)-one | Calc'd 398.2, found 398.2. | Chiralpak AD-H-SL001 |

TABLE 38

The following compounds were prepared using procedures similar to those described in Examples 63 and 64 using appropriate starting materials. Racemic products were separated using chiral columns specified in the table. For those pairs of enantiomers, the faster-eluting isomer is always listed first in this table.

| Ex# | Structure | IUPAC Name | Exact Mass [M + H]+ | Chiral column |
|---|---|---|---|---|
| 350 | 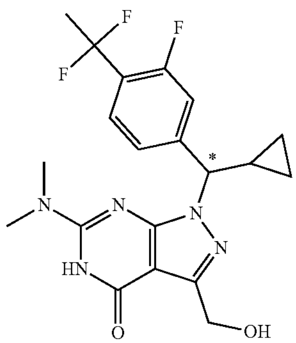 [SMILES: CN(C)c1nc2c(c(CO)nn2C(c2ccc(C(C)(F)F)c(F)c2)C2CC2)c(=O)[nH]1] | (R)- or (S)-1-(Cyclopropyl(4-(1,1-difluoroethyl)-3-fluorophenyl)methyl)-6-(dimethylamino)-3-(hydroxymethyl)-1H-pyrazolo[3,4-d]pyrimidin-4(5H)-one | Calc'd 422.2, found 422.2. | Chiralpak AD-H-SL001 |
| 351 | 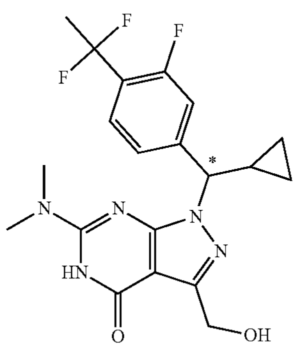 [SMILES: CN(C)c1nc2c(c(CO)nn2C(c2ccc(C(C)(F)F)c(F)c2)C2CC2)c(=O)[nH]1] | (S)- or (R)-1-(Cyclopropyl(4-(1,1-difluoroethyl)-3-fluorophenyl)methyl)-6-(dimethylamino)-3-(hydroxymethyl)-1H-pyrazolo[3,4-d]pyrimidin-4(5H)-one | Calc'd 422.2, found 422.2. | Chiralpak AD-H-SL001 |
| 352 | 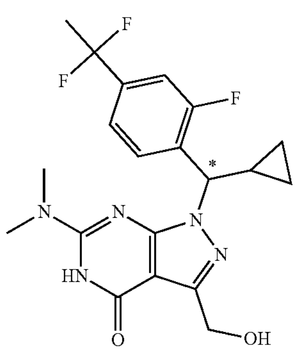 [SMILES: CN(C)c1nc2c(c(CO)nn2C(c2ccc(C(C)(F)F)cc2F)C2CC2)c(=O)[nH]1] | (R)- or (S)-1-(Cyclopropyl(4-(1,1-difluoroethyl)-2-fluorophenyl)methyl)-6-(dimethylamino)-3-(hydroxymethyl)-1H-pyrazolo[3,4-d]pyrimidin-4(5H)-one | Calc'd 422.2, found 422.1. | Chiralpak AD-H-SL001 |
| 353 | 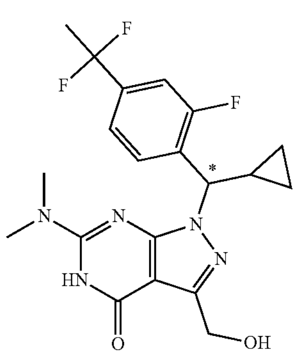 [SMILES: CN(C)c1nc2c(c(CO)nn2C(c2ccc(C(C)(F)F)cc2F)C2CC2)c(=O)[nH]1] | (S)- or (R)-1-(Cyclopropyl(4-(1,1-difluoroethyl)-2-fluorophenyl)methyl)-6-(dimethylamino)-3-(hydroxymethyl)-1H-pyrazolo[3,4-d]pyrimidin-4(5H)-one | Calc'd 422.2, found 422.1. | Chiralpak AD-H-SL001 |

EXAMPLES 354 AND 355

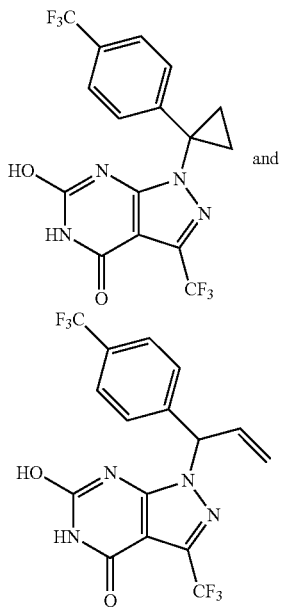

6-Hydroxy-3-(trifluoromethyl)-1-(1-(4-(trifluoromethyl)phenyl)cyclopropyl)-1H-pyrazolo[3,4-d]pyrimidin-4(5H)-one (Example 354) and 6-Hydroxy-3-(trifluoromethyl)-1-(1-(4-(trifluoromethyl)phenyl)allyl)-1H-pyrazolo[3,4-d]pyrimidin-4(5H)-one (Example 355) (Scheme 46)

Step 1. 4,6-Dimethoxy-3-(trifluoromethyl)-1-(1-(4-(trifluoromethyl)phenyl)cyclopropyl)-1H-pyrazolo[3,4-d]pyrimidine and 4,6-Dimethoxy-3-(trifluoromethyl)-1-(1-(4-(trifluoromethyl)phenyl)allyl)-1H-pyrazolo[3,4-d]pyrimidine To a stirred mixture of 4,6-dimethoxy-3-(trifluoromethyl)-1H-pyrazolo[3,4-d]pyrimidine (0.35 g, 1.4 mmol) from Preparatory Example 76, 1-(4-(trifluoromethyl)phenyl)cyclopropanol (0.34 g, 1.7 mmol) and triphenylphosphine (1.1 g, 4.2 mmol) in toluene (3 mL) under $N_2$ at room temperature was added DIAD (0.8 mL, 4.23 mmol) at room temperature. The reaction mixture was stirred at 50° C. for 2 h. The reaction solution was cooled, diluted with brine (10 mL) and extracted with EtOAc (3×10 mL). The combined organic layer was washed with brine (1×10 mL) and dried over anhydrous $Na_2SO_4$, filtered, and concentrated under reduced pressure. The residue was purified by silica gel column chromatography (0-10% EtOAc in hexanes) to afford a mixture of the title compounds as a solid. MS (+ESI) m/z=433.2.

Step 2. 6-Hydroxy-3-(trifluoromethyl)-1-(1-(4-(trifluoromethyl)phenyl)cyclopropyl)-1H-pyrazolo[3,4-d]pyrimidin-4(5H)-one and 6-Hydroxy-3-(trifluoromethyl)-1-(1-(4-(trifluoromethyl)phenyl)allyl)-1H-pyrazolo[3,4-d]pyrimidin-4(5H)-one To a stirred solution of 4,6-dimethoxy-3-(trifluoromethyl)-1-(1-(4-(trifluoromethyl)phenyl)cyclopropyl)-1H-pyrazolo[3,4-d]pyrimidine and 4,6-dimethoxy-3-(trifluoromethyl)-1-(1-(4-(trifluoromethyl)phenyl)allyl)-1H-pyrazolo[3,4-d]pyrimidine (60 mg, 0.14 mmol) in MeCN (1 mL) were added TMSCl (71 µL, 0.56 mmol) and sodium iodide (83 mg, 0.56 mmol) at room temperature. The reaction solution was stirred at 50° C. for 1 h. The reaction solution was cooled, extracted with EtOAc (3×10 mL). The combined organic layer was washed with brine (1×5 mL), dried over anhydrous $Na_2SO_4$, filtered, and concentrated under reduced pressure. The residue was purified twice by preparative HPLC (X Bridge C18, 30-60% ACN in water (0.05% $NH_4HCO_3$)). The faster-eluting isomer of the title compound 6-hydroxy-3-(trifluoromethyl)-1-(1-(4-(trifluoromethyl)phenyl)cyclopropyl)-1H-pyrazolo[3,4-d]pyrimidin-4(5H)-one (Example 354) was obtained as a solid. MS (+ESI) m/z=404.9. $^1$H NMR (400 MHz, $CD_3OD$) δ: 7.64 (d, J=8.4 Hz, 2H), 7.05 (d, J=8.4 Hz, 2H), 1.99-1.92 (m, 2H), 1.85-1.79 (m, 2H). The slower-eluting isomer of the title compound 6-hydroxy-3-(trifluoromethyl)-1-(1-(4-(trifluoromethyl)phenyl)allyl)-1H-pyrazolo[3,4-d]pyrimidin-4(5H)-one (Example 355) was obtained as a solid. MS (+ESI) m/z=405.0. $^1$H NMR (400 MHz, $CD_3OD$) δ: 7.76-7.66 (m, 4H), 5.67-5.64 (m, 1H), 5.31-5.28 (m, 2H), 4.89-4.86 (m, 1H).

EXAMPLES 356 AND 357

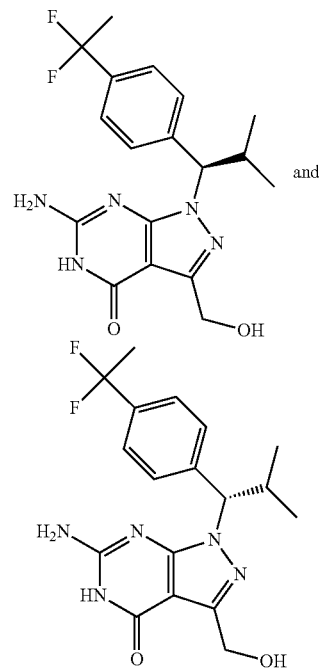

(R)- and (S)-6-Amino-1-(1-(4-(1,1-difluoroethyl)phenyl)-2-methylpropyl)-3-(hydroxymethyl)-1H-pyrazolo[3,4-d]pyrimidin-4(5H)-one (Scheme 47)

Step 1. 3-((Benzyloxy)methyl)-6-chloro-1-(1-(4-(1,1-difluoroethyl)phenyl)-2-methylpropyl)-4-methoxy-1H-pyrazolo[3,4-d]pyrimidine To a stirred mixture of 1-(4-(1,1-difluoroethyl)phenyl)-2-methylpropan-1-ol (1.9 g, 9.1 mmol) from Preparatory Example 119, 3-((benzyloxy)methyl)-6-chloro-4-methoxy-1H-pyrazolo[3,4-d]pyrimidine (2.30 g, 7.55 mmol) from Preparatory Example 77, and triphenylphosphine (5.9 g, 22.6 mmol) in toluene (5 mL) under $N_2$ at room temperature was added DIAD (4.4 mL, 23 mmol) dropwise. The reaction mixture was stirred at 25° C. for 2 h whereupon the mixture was diluted with brine (25 mL) and extracted with EtOAc (3×25 mL). The combined organic layer was washed with brine (1×25 mL) and dried over anhydrous Na$_2$SO$_4$, filtered, and concentrated under reduced pressure. The residue was purified by silica gel column chromatography (0-10% EtOAc in petroleum ether) to afford the title compound as a liquid. MS (+ESI) m/z=501.3; 503.3.

Step 2. 3-((Benzyloxy)methyl)-6-chloro-1-(1-(4-(1,1-difluoroethyl)phenyl)-2-methylpropyl)-1H-pyrazolo[3,4-d]pyrimidin-4(5H)-one To a stirred solution of 3-((benzyloxy)methyl)-6-chloro-1-(1-(4-(1,1-difluoroethyl)phenyl)-2-methylpropyl)-4-methoxy-H-pyrazolo[3,4-d]pyrimidine (0.55 g, 1.1 mmol) in THF (1 mL) was added 4 M HCl in dioxane (4 mL) at room temperature. The reaction mixture was heated to 80° C., stirred for 16 h, and was cooled to room temperature. The mixture was diluted with water (10 mL) and extracted with EtOAc (3×10 mL). The combined organic layer was washed with brine (1×10 mL) and dried over anhydrous Na$_2$SO$_4$, filtered, and concentrated under reduced pressure. The residue was purified by silica gel column chromatography (0-50% EtOAc in petroleum ether) to afford the title compound as a liquid. MS (+ESI) m/z=487.0; 489.0.

Step 3. 6-Amino-3-((benzyloxy)methyl)-1-(1-(4-(1,1-difluoroethyl)phenyl)-2-methylpropyl)-1H-pyrazolo[3,4-d]pyrimidin-4(5H)-one To a stirred solution of 3-((benzyloxy)methyl)-6-chloro-1-(1-(4-(1,1-difluoroethyl)phenyl)-2-methylpropyl)-1H-pyrazolo[3,4-d]pyrimidin-4(5H)-one (0.30 g, 0.62 mmol) in THF (1 mL) was added 2M NH$_3$ in MeOH (1.5 mL, 3.08 mmol) at room temperature. The reaction mixture was heated to 80° C., stirred for 16 h, and was cooled to room temperature. The mixture was diluted with water (10 mL) and extracted with EtOAc (3×10 mL). The combined organic layer was washed with brine (1×10 mL) and dried over anhydrous Na$_2$SO$_4$, filtered, and concentrated under reduced pressure. The residue was purified by silica gel column chromatography (0-50% EtOAc in petroleum ether) to afford the title compound as a liquid. MS (+ESI) m/z=468.3.

Step 4. (R)- and (S)-6-Amino-1-(1-(4-(1,1-difluoroethyl)phenyl)-2-methylpropyl)-3-(hydroxymethyl)-1H-pyrazolo[3,4-d]pyrimidin-4(5H)-one To a stirred mixture of 6-amino-3-((benzyloxy)methyl)-1-(1-(4-(1,1-difluoroethyl)phenyl)-2-methylpropyl)-1H-pyrazolo[3,4-d]pyrimidin-4(5H)-one (0.40 g, 0.86 mmol) in methanol (5 mL) at room temperature was added 20% Pd(OH)$_2$ on carbon (0.36 g, 2.6 mmol) in one portion. The reaction mixture was degassed under vacuum filling with H$_2$ three times. The mixture was stirred under a H$_2$ balloon for 4 h at room temperature. The reaction mixture was filtered through a pad of Celite and the filtrate was concentrated under reduced pressure. The residue was purified by silica gel column chromatography (0-70% EtOAc in petroleum ether) to afford the racemic title compound as a solid. The enantiopure title compounds were obtained by chiral preparative SFC (Chiralcel OJ-H, methanol (0.2% DEA)/CO$_2$). The faster-eluting enantiomer of the title compound (Example 356) was obtained as a solid. MS (+ESI) m/z=378.2. $^1$H NMR (300 MHz, CD$_3$OD) δ: 7.61 (d, J=8.1 Hz, 2H), 7.44 (d, J=8.4 Hz, 2H), 5.15 (d, J=11.1 Hz, 1H), 4.71 (s, 2H), 2.96-2.77 (m, 1H), 1.84 (t, J=18.3 Hz, 3H), 0.83 (d, J=6.9 Hz, 3H), 0.82 (d, J=6.6 Hz, 3H). The slower-eluting enantiomer of the title compound (Example 357) was obtained as a solid. MS (+ESI) m/z=378.2. $^1$H NMR (300 MHz, CD$_3$OD) δ: 7.61 (d, J=8.1 Hz, 2H), 7.44 (d, J=8.1 Hz, 2H), 5.15 (d, J=11.1 Hz, 1H), 4.71 (s, 2H), 2.96-2.77 (m, 1H), 1.84 (t, J=18.3 Hz, 3H), 0.83 (d, J=6.9 Hz, 3H), 0.82 (d, J=6.6 Hz, 3H).

EXAMPLES 358 AND 359

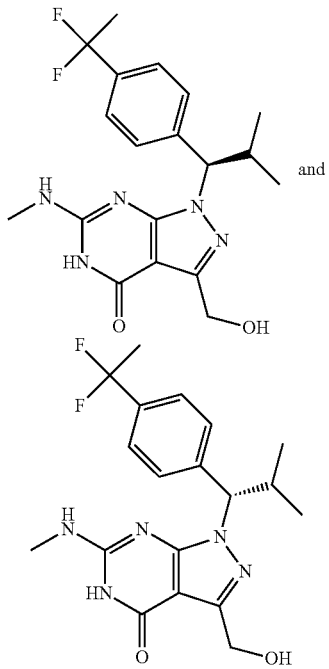

(R)- and (S)-1-(1-(4-(11-Difluoroethyl)phenyl)-2-methylpropyl)-3-(hydroxymethyl)-6-(methylamino)-1H-pyrazolo[3,4-d]pyrimidin-4(5H)-one (Scheme 48)

Step 1. 3-((Benzyloxy)methyl)-6-chloro-1-(1-(4-(1,1-difluoroethyl)phenyl)-2-methylpropyl)-4-methoxy-1H-pyrazolo[3,4-d]pyrimidine The title compound was prepared using procedures similar to those described in step 1 of Examples 356 and 357 using 1-(4-(1,1-difluoroethyl)phenyl)-2-methylpropan-1-ol from Preparatory Example 119 and 3-((benzyloxy)methyl)-6-chloro-4-methoxy-1H-pyrazolo[3,4-d]pyrimidine from Preparatory Example 77 to afford the title compound as a liquid. MS (+ESI) m/z=501.3; 503.3.

Step 2. 3-((Benzyloxy)methyl)-1-(1-(4-(1,1-difluoroethyl)phenyl)-2-methylpropyl)-6-(methylamino)-1H-pyrazolo[3,4-d]pyrimidin-4(5H)-one To a stirred solution of 3-((benzyloxy)methyl)-6-chloro-1-(1-(4-(1,1-difluoroethyl)phenyl)-2-methylpropyl)-4-methoxy-H-pyrazolo[3,4-d]pyrimidine (0.17 g, 0.34 mmol) in NMP (4 mL) at rt was added methylamine hydrochloride (0.12 g, 1.7 mmol) in one portion. The reaction mixture was heated to 100° C., stirred for 16 h, and cooled to room temperature. Solid K$_2$CO$_3$ (0.14 g, 1.0 mmol) was added to the reaction mixture and which was heated to 100° C. and stirred for additional 2 h. The reaction solution was cooled, diluted with water (10 mL) and extracted with EtOAc (3×10 mL). The combined organic layers was washed with brine (10 mL), dried over anhydrous Na$_2$SO$_4$, filtered, and concentrated under reduced pressure. The residue was purified by silica gel column chromatography (0-50% EtOAc in petroleum ether) to afford the title compound as a liquid. MS (+ESI) m/z=482.3.

Step 4. (R)- and (S)-1-(1-(4-(1,1-Difluoroethyl)phenyl)-2-methylpropyl)-3-(hydroxymethyl)-6-(methylamino)-1H- pyrazolo[3,4-d]pyrimidin-4(5H)-one The racemic title compound was prepared using procedures similar to those described in step 4 of Examples 356 and 357 using 3-((benzyloxy)methyl)-1-(1-(4-(1,1-difluoroethyl)phenyl)-2-methylpropyl)-6-(methylamino)-1H-pyrazolo[3,4-d]pyrimidin-4(5H)-one to afford a solid. The enantiopure title compounds were obtained by chiral preparative HPLC (Chiralpak-AD-H-SL001, 50% IPA in hexanes). The faster-eluting enantiomer of the title compound (Example 358) was obtained as a solid. MS (+ESI) m/z=392.2. $^1$H NMR (300 MHz, CD$_3$OD) δ: 7.62 (d, J=7.8 Hz, 2H), 7.45 (d, J=7.8 Hz, 2H), 5.21 (d, J=11.1 Hz, 1H), 4.70 (s, 2H), 2.98 (s, 3H), 2.96-2.85 (m, 1H), 1.84 (t, J=18.3 Hz, 3H), 0.85 (d, J=6.6 Hz, 3H), 0.84 (d, J=6.6 Hz, 3H). The slower-eluting enantiomer of the title compound (Example 359) was obtained as a solid. MS (+ESI) m/z=392.2. $^1$H NMR (300 MHz, CD$_3$OD) δ: 7.62 (d, J=7.8 Hz, 2H), 7.45 (d, J=7.8 Hz, 2H), 5.21 (d, J=11.1 Hz, 1H), 4.70 (s, 2H), 2.98 (s, 3H), 2.96-2.85 (m, 1H), 1.84 (t, J=18.3 Hz, 3H), 0.85 (d, J=6.6 Hz, 3H), 0.84 (d, J=6.6 Hz, 3H).

Assay

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) of about 50 µM or below would be considered a PDE2 inhibitor as defined herein.

In a typical experiment the PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccaccatggggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product # R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 µL. Solutions of test compounds were prepared in DMSO and serially diluted with DMSO to yield 8 µL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki~0.2 nM) at 1 µM concentration for 100% inhibition. Bay 60-7550 was obtained from Axxora via Fisher Scientific (cat# ALX-270-421-M025/cat#NC9314773). Put another way, any compound with Ki of ~0.2 to about 2 nM could be used at 1 to 10 µM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R7506 from Molecular Devices) and the activator cGMP (1 uM final concentration), prepared in the assay buffer (10 mM Tris HCl, pH 7.2, 10 mM MgCl$_2$, 0.05% NaN$_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 µL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

$$\text{Polarization } (mP) = 1000 * (S/So - P/Po)/(S/So + P/Po).$$

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\% \, mP - 100\% \, mP)(I\max - I\min)}{1 + \left[\left(10^{-pK_I}\left(1 + \frac{[\text{Substrate}]}{K_M}\right)\right)\right]^{nH}} +$$

$$100\% \, mP + (0\% \, mP - 100\% \, mP)(1 - I\max)$$

The median signal of the "0% inhibition controls" (0% mP) and the median signal of the "100% inhibition controls" (100% mP) are constants determined from the controls located in columns 1-2 and 23-24 of each assay plate. An apparent ($K_M$) for FAM-labeled cAMP of ~10 uM was used.

Selectivity for PDE2, as compared to other PDE families, was assessed using the IMAP® technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), human PDE2A1 (Cat#60020), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM $MgCl_2$, 0.05% $NaN_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE1A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 µM. Many of compounds within the present invention had activity in inhibiting the human PDE2 enzyme in the aforementioned assays, with a Ki of less than about 1 µM, preferably less than or about 0.1 µM. Additional data is provided in the following Examples. Such a result is indicative of the intrinsic activity of the compounds in use as inhibitors of the PDE2 enzyme. In general, one of ordinary skill in the art would appreciate that a substance is considered to effectively inhibit PDE2 activity if it has a Ki of less than or about 1 µM, preferably less than or about 0.1 µM. The present invention also includes compounds within the generic scope of the invention which possess activity as inhibitors of other phosphodiesterase enzymes.

In the following tables representative data for the compounds of formula I as PDE2 inhibitors as determined by the foregoing assays and as conducted in laboratory (Lab) A or B are shown. The PDE2 Ki is a measure of the ability of the test compound to inhibit the action of the PDE2 enzyme.

TABLE 39

PDE2 Ki's

| Ex # | Rhesus PDE2 Ki (nM) Lab A | Rhesus PDE2 Ki (nM) Lab B | Human PDE2 Ki (nM) Lab A | Human PDE2 Ki (nM) Lab B |
|---|---|---|---|---|
| 1 | NA | 13 | NA | 11 |
| 2 | NA | 364 | NA | NA |
| 3 | NA | NA | NA | NA |
| 4 | NA | NA | NA | 342 |
| 5 | 77 | 126 | 59 | NA |
| 6 | 78 | NA | 50 | NA |
| 7 | 51 | 64 | 27 | 59 |
| 8 | 411 | NA | NA | NA |
| 9 | ~548 | NA | NA | NA |
| 10 | 145 | 249 | NA | 185 |
| 11 | 14 | 34 | NA | 27 |
| 12 | NA | 192 | NA | NA |
| 13 | NA | 9.2 | NA | 8.3 |
| 14 | NA | 410 | NA | NA |
| 15 | NA | 17 | NA | 12 |
| 16 | NA | NA | NA | 702 |
| 17 | NA | NA | NA | 55 |
| 18 | >1000 | NA | NA | NA |
| 19 | 14 | 20 | 9.0 | 24 |
| 20 | ~684 | NA | NA | NA |
| 21 | 20 | 27 | 13 | 28 |
| 22 | NA | 253 | NA | NA |
| 23 | NA | ~2697 | NA | NA |
| 24 | NA | ~2274 | NA | NA |
| 25 | NA | 238 | NA | NA |
| 26 | NA | 50 | NA | 39 |
| 27 | NA | 5.2 | NA | 7.0 |
| 28 | NA | 117 | NA | NA |
| 29 | NA | 220 | NA | NA |
| 30 | NA | 2041 | NA | NA |
| 31 | NA | NA | NA | 50 |
| 32 | NA | NA | NA | ~1905 |
| 33 | NA | 50 | NA | 71 |
| 34 | NA | 2.4 | NA | 2.1 |
| 35 | NA | 209 | NA | NA |
| 36 | 11 | 18 | 6.5 | 17 |
| 37 | 85 | NA | 44 | NA |
| 38 | 7.2 | 8.3 | 2.8 | 8.5 |
| 39 | 3.6 | 5.5 | 2.2 | 6.3 |
| 40 | 1.7 | 2.0 | 0.56 | 2.1 |
| 41 | 3.5 | NA | 2.3 | NA |
| 42 | NA | 16 | NA | 14 |
| 43 | NA | 4.7 | NA | 5.3 |
| 44 | NA | 9.8 | NA | 10 |
| 45 | NA | 29 | NA | 28 |
| 46 | NA | 11 | NA | 9.2 |
| 47 | NA | 6.9 | NA | 5.1 |
| 48 | NA | 6.2 | NA | 5.6 |
| 49 | NA | 2.5 | NA | 2.3 |
| 50 | NA | 6.8 | NA | 7.0 |
| 51 | NA | 123 | NA | NA |
| 52 | NA | 910 | NA | NA |
| 53 | NA | 6.2 | NA | 5.3 |
| 54 | NA | 7.5 | NA | 6.0 |
| 55 | NA | 1.3 | NA | 0.96 |

TABLE 39-continued

PDE2 Ki's

| Ex # | Rhesus PDE2 Ki (nM) Lab A | Rhesus PDE2 Ki (nM) Lab B | Human PDE2 Ki (nM) Lab A | Human PDE2 Ki (nM) Lab B |
|---|---|---|---|---|
| 56 | NA | 36 | NA | 37 |
| 57 | 26 | 40 | 11 | 28 |
| 58 | 69 | NA | 49 | NA |
| 59 | 1143 | NA | 760 | NA |
| 60 | 278 | NA | 207 | NA |
| 61 | ~951 | NA | NA | NA |
| 62 | NA | 0.28 | NA | 0.27 |
| 63 | NA | NA | NA | 3.2 |
| 64 | NA | 0.39 | NA | 0.29 |
| 65 | NA | 0.076 | NA | 0.069 |
| 66 | NA | 12 | NA | 6.1 |
| 67 | NA | 0.32 | NA | 0.25 |
| 68 | NA | 11 | NA | 7.1 |
| 69 | NA | 0.27 | NA | 0.27 |
| 70 | NA | NA | NA | 4.1 |
| 71 | NA | 0.95 | NA | 0.75 |
| 72 | NA | NA | NA | 2.9 |
| 73 | NA | 0.25 | NA | 0.16 |
| 74 | NA | 0.15 | NA | 0.17 |
| 75 | NA | 0.79 | NA | 1.1 |
| 76 | NA | 0.21 | NA | 0.22 |
| 77 | NA | 0.084 | NA | 0.069 |
| 78 | NA | 0.14 | NA | 0.11 |
| 79 | NA | 0.054 | NA | 0.044 |
| 80 | NA | NA | NA | 25 |
| 81 | NA | 0.25 | NA | 0.29 |
| 82 | NA | NA | NA | 35 |
| 83 | NA | 1.1 | NA | 0.86 |
| 84 | NA | 1.0 | NA | 0.68 |
| 85 | NA | 0.30 | NA | 0.24 |
| 86 | NA | 0.91 | NA | 0.57 |
| 87 | NA | 0.40 | NA | 0.38 |
| 88 | NA | 0.31 | NA | 0.32 |
| 89 | NA | 0.30 | NA | 0.21 |
| 90 | NA | 2.3 | NA | 1.1 |
| 91 | NA | 0.18 | NA | 0.18 |
| 92 | NA | NA | NA | 8.4 |
| 93 | NA | 0.55 | NA | 0.42 |
| 94 | NA | 0.15 | NA | 0.14 |
| 95 | NA | 0.44 | NA | 0.39 |
| 96 | NA | 0.50 | NA | 0.32 |
| 97 | NA | 0.11 | NA | 0.090 |
| 98 | NA | NA | NA | 1.3 |
| 99 | NA | 0.38 | NA | 0.31 |
| 100 | NA | 1.1 | NA | 0.88 |
| 101 | NA | 0.35 | NA | 0.29 |
| 102 | NA | NA | NA | 9.9 |
| 103 | NA | 0.30 | NA | 0.28 |
| 104 | NA | NA | NA | 40 |
| 105 | NA | 1.6 | NA | 1.1 |
| 106 | NA | 6.2 | NA | 3.6 |
| 107 | NA | 0.12 | NA | 0.12 |
| 108 | NA | 0.18 | NA | 0.23 |
| 109 | NA | NA | NA | 8.0 |
| 110 | NA | NA | NA | 2.8 |
| 111 | NA | 0.14 | NA | 0.12 |
| 112 | NA | 1.1 | NA | 0.84 |
| 113 | NA | 0.055 | NA | 0.057 |
| 114 | NA | 0.71 | NA | 0.79 |
| 115 | NA | 0.32 | NA | 0.21 |
| 116 | NA | 0.16 | NA | 0.13 |
| 117 | NA | 0.025 | NA | 0.017 |
| 118 | NA | 0.44 | NA | 0.42 |
| 119 | NA | 0.036 | NA | 0.024 |
| 120 | NA | 0.28 | NA | 0.21 |
| 121 | NA | 0.31 | NA | 0.34 |
| 122 | NA | 0.37 | NA | 0.30 |
| 123 | NA | 0.61 | NA | 0.60 |
| 124 | NA | 0.70 | NA | 0.73 |
| 125 | NA | NA | NA | 2.4 |
| 126 | NA | 0.45 | NA | 0.30 |
| 127 | NA | 1.4 | NA | 0.81 |
| 128 | NA | 0.55 | NA | 0.50 |
| 129 | NA | 1.0 | NA | 0.55 |
| 130 | NA | 0.12 | NA | 0.071 |
| 131 | NA | NA | NA | 3.9 |
| 132 | NA | 0.059 | NA | 0.040 |
| 133 | NA | 0.60 | NA | 0.45 |
| 134 | NA | 0.050 | NA | 0.047 |
| 135 | NA | 0.72 | NA | 0.60 |
| 136 | NA | NA | NA | 1.9 |
| 137 | NA | 0.14 | NA | 0.073 |
| 138 | NA | 0.41 | NA | 0.19 |
| 139 | NA | 0.040 | NA | 0.064 |
| 140 | NA | 0.097 | NA | 0.070 |
| 141 | NA | 0.64 | NA | 0.56 |
| 142 | NA | 0.29 | NA | 0.19 |
| 143 | NA | 0.063 | NA | 0.068 |
| 144 | NA | 3.1 | NA | 1.7 |
| 145 | NA | 0.13 | NA | 0.11 |
| 146 | NA | NA | NA | 8.1 |
| 147 | NA | 0.54 | NA | 0.52 |
| 148 | NA | 3.3 | NA | 2.6 |
| 149 | NA | 0.46 | NA | 0.51 |
| 150 | NA | 0.12 | NA | 0.12 |
| 151 | NA | 0.79 | NA | 0.61 |
| 152 | NA | 0.97 | NA | 0.57 |
| 153 | NA | NA | NA | 3.0 |
| 154 | NA | 0.57 | NA | 0.55 |
| 155 | NA | NA | NA | 3.8 |
| 156 | NA | 0.47 | NA | 0.50 |
| 157 | NA | NA | NA | 12 |
| 158 | NA | NA | NA | 0.89 |
| 159 | NA | NA | NA | 2.3 |
| 160 | NA | NA | NA | 1.6 |
| 161 | NA | 1.9 | NA | 1.6 |
| 162 | NA | 0.63 | NA | 0.54 |
| 163 | NA | 0.070 | NA | 0.056 |
| 164 | NA | 2.0 | NA | 1.7 |
| 165 | NA | 0.28 | NA | 0.33 |
| 166 | NA | 0.91 | NA | 0.61 |
| 167 | NA | 0.18 | NA | 0.20 |
| 168 | NA | 8.1 | NA | 5.3 |
| 169 | NA | 0.20 | NA | 0.099 |
| 170 | NA | 11 | NA | 7.6 |
| 171 | NA | 0.24 | NA | 0.20 |
| 172 | NA | NA | NA | 2.2 |
| 173 | NA | 0.096 | NA | 0.063 |
| 174 | NA | NA | NA | 2.7 |
| 175 | NA | 0.32 | NA | 0.39 |
| 176 | NA | 0.28 | NA | 0.23 |
| 177 | NA | 0.058 | NA | 0.047 |
| 178 | NA | NA | NA | 1.1 |
| 179 | NA | 0.072 | NA | 0.072 |
| 180 | NA | NA | NA | 1.2 |
| 181 | NA | 0.11 | NA | 0.058 |
| 182 | NA | 0.38 | NA | 0.32 |
| 183 | NA | 0.082 | NA | 0.064 |
| 184 | NA | 0.24 | NA | 0.19 |
| 185 | NA | 0.16 | NA | 0.12 |
| 186 | NA | 0.14 | NA | 0.13 |
| 187 | NA | NA | NA | 19 |
| 188 | NA | 0.41 | NA | 0.35 |
| 189 | NA | 0.62 | NA | 0.35 |
| 190 | NA | NA | NA | 27 |
| 191 | NA | 0.42 | NA | 0.38 |
| 192 | NA | 0.42 | NA | 0.41 |
| 193 | NA | 0.41 | NA | 0.39 |
| 194 | NA | NA | NA | 6.1 |
| 195 | NA | 0.14 | NA | 0.17 |
| 196 | NA | 0.59 | NA | 0.31 |
| 197 | NA | NA | NA | 18 |
| 198 | NA | 0.068 | NA | 0.048 |
| 199 | NA | NA | NA | 1.1 |
| 200 | NA | 0.070 | NA | 0.041 |
| 201 | NA | NA | NA | 1.2 |
| 202 | NA | 0.058 | NA | 0.042 |
| 203 | NA | 0.74 | NA | 0.61 |

TABLE 39-continued

PDE2 Ki's

| Ex # | Rhesus PDE2 Ki (nM) Lab A | Rhesus PDE2 Ki (nM) Lab B | Human PDE2 Ki (nM) Lab A | Human PDE2 Ki (nM) Lab B |
|---|---|---|---|---|
| 204 | NA | NA | NA | 1.4 |
| 205 | NA | 0.072 | NA | 0.038 |
| 206 | NA | 0.51 | NA | 0.37 |
| 207 | NA | 0.043 | NA | 0.030 |
| 208 | NA | NA | NA | 20 |
| 209 | NA | 0.14 | NA | 0.077 |
| 210 | NA | NA | NA | 3.3 |
| 211 | NA | 0.070 | NA | 0.048 |
| 212 | NA | 0.91 | NA | 0.61 |
| 213 | NA | 0.075 | NA | 0.053 |
| 214 | NA | 0.050 | NA | 0.045 |
| 215 | NA | NA | NA | 0.98 |
| 216 | NA | 1.4 | NA | 1.1 |
| 217 | NA | 0.027 | NA | 0.016 |
| 218 | NA | 0.21 | NA | 0.16 |
| 219 | NA | 0.030 | NA | 0.022 |
| 220 | NA | 0.50 | NA | 0.32 |
| 221 | NA | 0.067 | NA | 0.046 |
| 222 | NA | 0.063 | NA | 0.044 |
| 223 | NA | NA | NA | 1.8 |
| 224 | NA | 0.23 | NA | 0.16 |
| 225 | NA | 0.40 | NA | 0.41 |
| 226 | NA | 0.26 | NA | 0.22 |
| 227 | NA | 12 | NA | 8.3 |
| 228 | NA | 210 | NA | NA |
| 229 | NA | 13 | NA | 9.6 |
| 230 | NA | 21 | NA | 13 |
| 231 | NA | 25 | NA | 18 |
| 232 | NA | 192 | NA | NA |
| 233 | NA | 132 | NA | NA |
| 234 | NA | 180 | NA | NA |
| 235 | NA | 1.5 | NA | 1.4 |
| 236 | NA | 5.0 | NA | 3.4 |
| 237 | NA | 494 | NA | NA |
| 238 | NA | 7.1 | NA | 5.8 |
| 239 | NA | 166 | NA | NA |
| 240 | NA | 11 | NA | 8.0 |
| 241 | NA | 199 | NA | NA |
| 242 | NA | 150 | NA | NA |
| 243 | NA | 191 | NA | NA |
| 244 | NA | 21 | NA | 21 |
| 245 | NA | 698 | NA | NA |
| 246 | NA | NA | NA | 408 |
| 247 | NA | NA | NA | >2955 |
| 248 | NA | NA | NA | 47 |
| 249 | NA | NA | NA | 841 |
| 250 | NA | 26 | NA | 27 |
| 251 | NA | 363 | NA | NA |
| 252 | NA | 68 | NA | 73 |
| 253 | NA | 120 | NA | NA |
| 254 | NA | 102 | NA | 121 |
| 255 | NA | 3.7 | NA | 2.4 |
| 256 | 166 | NA | 126 | NA |
| 257 | 0.96 | 1.5 | 0.68 | 2.0 |
| 258 | NA | 10 | NA | 9.7 |
| 259 | NA | 148 | NA | NA |
| 260 | NA | 26 | NA | 25 |
| 261 | NA | ~1401 | NA | NA |
| 262 | NA | 334 | NA | NA |
| 263 | NA | 5889 | NA | NA |
| 264 | NA | 600 | NA | NA |
| 265 | NA | 276 | NA | NA |
| 266 | NA | 14 | NA | 13 |
| 267 | NA | 448 | NA | NA |
| 268 | 8.0 | NA | 5.6 | NA |
| 269 | 139 | NA | 85 | NA |
| 270 | 6.0 | NA | 3.9 | NA |
| 271 | NA | NA | NA | 911 |
| 272 | NA | NA | NA | 43 |
| 273 | NA | 113 | NA | NA |
| 274 | NA | 3.2 | NA | 4.0 |
| 275 | NA | NA | NA | 416 |
| 276 | NA | NA | NA | 3.6 |
| 211 | NA | 235 | NA | NA |
| 278 | NA | 1.2 | NA | 1.6 |
| 279 | NA | 1.8 | NA | 1.9 |
| 280 | NA | 85 | NA | NA |
| 281 | NA | 1.2 | NA | 1.3 |
| 282 | NA | 51 | NA | 59 |
| 283 | NA | ~1508 | NA | NA |
| 284 | NA | 206 | NA | NA |
| 285 | NA | 232 | NA | NA |
| 286 | NA | 1.5 | NA | 2.2 |
| 287 | NA | 44 | NA | 38 |
| 288 | NA | 1.6 | NA | 2.4 |
| 289 | NA | NA | NA | 0.25 |
| 290 | NA | NA | NA | 0.26 |
| 291 | NA | NA | NA | 2.5 |
| 292 | NA | NA | NA | 137 |
| 293 | NA | 12 | NA | 10 |
| 294 | NA | NA | NA | 105 |
| 295 | NA | NA | NA | 168 |
| 296 | NA | 8.6 | NA | 7.3 |
| 297 | NA | 207 | NA | NA |
| 298 | NA | 5.0 | NA | 4.7 |
| 299 | NA | 21 | NA | 17 |
| 300 | NA | 101 | NA | NA |
| 301 | NA | NA | NA | 1.8 |
| 302 | NA | NA | NA | 3.7 |
| 303 | NA | 206 | NA | NA |
| 304 | NA | 43 | NA | 46 |
| 305 | NA | NA | NA | 1.9 |
| 306 | NA | NA | NA | 330 |
| 307 | NA | NA | NA | 10 |
| 308 | NA | NA | NA | 213 |
| 309 | NA | NA | NA | 2.7 |
| 310 | NA | NA | NA | 36 |
| 311 | NA | NA | NA | 4.9 |
| 312 | NA | NA | NA | 265 |
| 313 | NA | NA | NA | 2.2 |
| 314 | NA | NA | NA | 106 |
| 315 | NA | NA | NA | 629 |
| 316 | NA | NA | NA | 6.1 |
| 317 | NA | NA | NA | 326 |
| 318 | NA | NA | NA | 3.0 |
| 319 | NA | NA | NA | 590 |
| 320 | NA | NA | NA | 13 |
| 321 | NA | NA | NA | 145 |
| 322 | NA | NA | NA | 9.3 |
| 323 | NA | NA | NA | 304 |
| 324 | NA | NA | NA | 6.8 |
| 325 | NA | NA | NA | 529 |
| 326 | NA | NA | NA | 16 |
| 327 | NA | NA | NA | 382 |
| 328 | NA | NA | NA | 3.0 |
| 329 | NA | NA | NA | 136 |
| 330 | NA | NA | NA | 5.7 |
| 331 | NA | NA | NA | 346 |
| 332 | NA | NA | NA | 3.3 |
| 333 | NA | NA | NA | 134 |
| 334 | NA | NA | NA | 2.3 |
| 335 | NA | NA | NA | 137 |
| 336 | NA | NA | NA | 3.2 |
| 337 | NA | NA | NA | 2361 |
| 338 | NA | NA | NA | 373 |
| 339 | NA | NA | NA | 2.1 |
| 340 | NA | NA | NA | 0.58 |
| 341 | NA | NA | NA | 0.15 |
| 342 | NA | NA | NA | 0.10 |
| 343 | NA | NA | NA | 1.7 |
| 344 | NA | NA | NA | 6.3 |
| 345 | NA | NA | NA | 0.13 |
| 346 | NA | NA | NA | 6.5 |
| 347 | NA | NA | NA | 0.08 |
| 348 | NA | NA | NA | 0.03 |
| 349 | NA | NA | NA | 4.0 |
| 350 | NA | NA | NA | 0.14 |
| 351 | NA | NA | NA | 0.02 |

TABLE 39-continued

PDE2 Ki's

| Ex # | Rhesus PDE2 Ki (nM) Lab A | Rhesus PDE2 Ki (nM) Lab B | Human PDE2 Ki (nM) Lab A | Human PDE2 Ki (nM) Lab B |
|---|---|---|---|---|
| 352 | NA | NA | NA | 1.2 |
| 353 | NA | NA | NA | 0.05 |
| 354 | NA | NA | NA | 2.4 |
| 355 | NA | NA | NA | 284 |
| 356 | NA | NA | NA | 0.68 |
| 357 | NA | NA | NA | 19 |
| 358 | NA | NA | NA | 5.3 |
| 359 | NA | NA | NA | 0.33 |

(NA = Not available)

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of structural formula I:

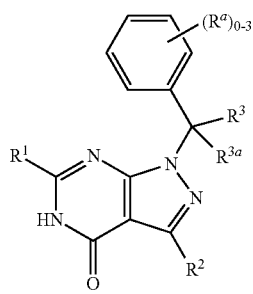

I or a pharmaceutically acceptable salt thereof, wherein:
$R^1$ represents OH, $OC_{1-6}$alkyl, $NR_2$, said alkyl optionally substituted with 1 to 3 groups of $R^a$,
R represents hydrogen, or $C_{1-6}$alkyl, or two R groups can be combined with the nitrogen to which they are attached to form a $C_{3-6}$ heterocycloalkyl, said alkyl and heterocycloalkyl optionally substituted with 1 to 3 groups of halogen, or $C_{1-6}$alkyl;
$R^2$ represents halo, $C_{1-6}$alkyl, $(CH_2)_nOR$, $C_{1-4}$haloalkyl, C(O)OR, $(CH_2)_nC_{4-10}$heterocyclyl, O—$(CH_2)_nC_{4-10}$heterocyclyl, $C(O)NH(CH_2CF_3)$, $C(O)NR_2$, $NR_2$, $NHSO_2R$, C(O)R, C(O)—N-linked morpholinyl, $NHC(O)CH_3$, $(CH_2)_nC(CF_3)OH$, $CH(CH_3)CH_2OH$, $CF_2CH_2OH$, said alkyl and heterocyclyl optionally substituted with 1 to 3 groups of $R^a$,
$R^3$ and $R^{3a}$ independently represent hydrogen, $C_{1-6}$alkyl, $C_{2-6}$alkenyl, or $C_{3-6}$cycloalkyl, or $R^3$ and $R^{3a}$ can combine with the carbon atom to which they are attached to form a $C_{3-6}$cycloalkyl, said alkyl and cycloalkyl optionally substituted with 1 to 3 groups of $R^a$,
$R^a$ is selected from the group consisting of halo, CN, $C_{1-6}$alkyl, $(CH_2)_nOR$, $(CH_2)_nC_{1-4}$haloalkyl, O—$C_{1-4}$haloalkyl, $SCF_3$, $SF_5$, $C_{6-10}$aryl, —$O(CH_2)_nN(R)_2$, $(CHR)_nN(R)_2$, $NHC(O)CH_3$, $OCH_2C_{6-10}$aryl, and $C_{3-6}$cycloalkyl, said cycloalkyl optionally substituted with 1 to 3 groups of $C_{1-6}$alkyl and $C_{1-4}$haloalkyl;
n represents 0, 1, 2, 3, or 4.

2. The compound according to claim 1 or a pharmaceutically acceptable salt thereof wherein $R^1$ is OH.

3. The compound according to claim 1 or a pharmaceutically acceptable salt thereof wherein $R^1$ is $NR_2$ selected from the group consisting of $N(CH_3)_2$, $NH_2$, and $NHCH_3$.

4. The compound according to claim 1 or a pharmaceutically acceptable salt thereof wherein $R^1$ is $OC_{1-6}$alkyl.

5. The compound according to claim 1 or a pharmaceutically acceptable salt thereof wherein $R^2$ is optionally substituted $C_{1-6}$alkyl selected from $CH_2OH$, $CH_2CH_2OH$, $CH_2F$, $CH_3$, $CF_3$, $CH_2CF_3$, $CHF_2$, $CH_2CN$, $(CH_2)_2F$, $CH_2OCH_2$phenyl, $CH_2OCH_3$, $CF_2CF_3$, and $CH(CH_3)CH_2OH$.

6. The compound according to claim 1 or a pharmaceutically acceptable salt thereof wherein $R^3$ and $R^{3a}$ independently represent hydrogen, $CH_3$, $CH(CH_3)_2$, $CH_2CH_3$, $C(CH_3)_3$, $CH_2CF_3$, cyclopropyl, cyclobutyl, cyclopentyl and cyclohexyl.

7. The compound according to claim 6 or a pharmaceutically acceptable salt thereof wherein one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, cyclopropyl, cyclobutyl, cyclopentyl and cyclohexyl.

8. The compound according to claim 1 wherein $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl.

9. The compound according to claim 1 or a pharmaceutically acceptable salt thereof wherein $R^a$ is selected from OH, halo, $(CH_2)_nCH_3$, $CH(CH_3)_2$, $C(CH_3)_3$, $(CH_2)_nOCH_3$, $OCH(CH_3)_2$, $CF_2CH_3$, $CH_2F$, $CHF_2$, $(CH_2)_nCF_3$, $CF_2CH_3$, $OCHF_2$, $OCF_3$, $SCF_3$, $SF_5$, $CH_2NH_2$, $(CH_2)_nN(CH_3)_2$, $CF_2CF_3$, cyclobutyl, cyclopropyl, phenyl, naphthyl, said groups where appropriate, optionally substituted with one to three groups of $R^b$.

10. The compound according to claim 1 represented by structural formula Ia:

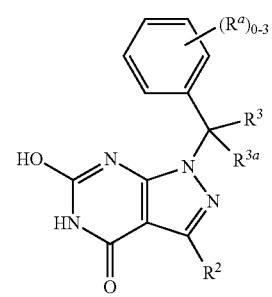

Ia or a pharmaceutically acceptable salt thereof.

11. The compound according to claim 10 or a pharmaceutically acceptable salt thereof wherein $R^2$ is optionally substituted $C_{1-6}$alkyl selected from $CH_2OH$, $CH_2CH_2OH$, $CH_2F$, $CH_3$, $CF_3$, $CH_2CF_3$, $CHF_2$, $CH_2CN$, $(CH_2)_2F$, $CH_2OCH_2$phenyl, $CH_2OCH_3$, $CF_2CF_3$, and $CH(CH_3)CH_2OH$, $R^3$ and $R^{3a}$ independently represent hydrogen, $CH_3$, $CH(CH_3)_2$, $CH_2CH_3$, $C(CH_3)_3$, $CH_2CF_3$, cyclopropyl, cyclobutyl, cyclopentyl and cyclohexyl, or $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl.

12. The compound according to claim 10 or a pharmaceutically acceptable salt thereof wherein $R^a$ on the phenyl ring of formula Ia is selected from chlorine, fluorine, $CH_3$, $CH(CH_3)_2$, $C(CH_3)_3$, $(CH_2)_nOCH_3$, $OCH(CH_3)_2$, $CF_2CH_3$, $CF_2CF_3$, $CH_2F$, $CHF_2$, $CF_3$, $OCHF_2$, $OCF_3$, $SF_5$, and cyclopropyl.

13. The compound according to claim 10 or a pharmaceutically acceptable salt thereof wherein $R^2$ is $CH_2OH$, $CH_2CH_2OH$, $CH_2F$, $CHF_2$, $CF_3$, or $CH_3$, one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, and cyclopropyl, or $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl, and the $R^a$ on the phenyl ring of formula Ia is selected from fluorine, $CH_3$, $CH(CH_3)_2$, $C(CH_3)_3$, $(CH_2)_nOCH_3$, $OC(CH_3)_2$, $CH(CH_3)F_2$, $CF_2CF_3$, $CH_2F$, $CHF_2$, $CF_3$, $OCHF_2$, $OCF_3$, $SF_5$, and cyclopropyl.

14. The compound according to claim 1 represented by structural formula Ib:

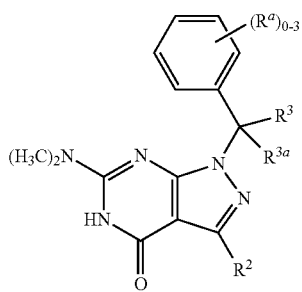

or a pharmaceutically acceptable salt thereof.

15. The compound according to claim 14 or a pharmaceutically acceptable salt thereof wherein $R^2$ is optionally substituted $C_{1-6}$alkyl selected from $CH_2OH$, $CH_2CH_2OH$, $CH_2F$, $CH_3$, $CF_3$, $CH_2CF_3$, $CHF_2$, $CH_2CN$, $(CH_2)_2F$, $CH_2OCH_2phenyl$, $CH_2OCH_3$, $CF_2CF_3$, and $CH(CH_3)CH_2OH$, $R^3$ and $R^{3a}$ independently represent hydrogen, $CH_3$, $CH(CH_3)_2$, $CH_2CH_3$, $C(CH_3)_3$, $CH_2CF_3$, cyclopropyl, cyclobutyl, cyclopentyl and cyclohexyl, or $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl.

16. The compound according to claim 14 or a pharmaceutically acceptable salt thereof wherein the $R^a$ on the phenyl ring of formula Ib is selected from chlorine, fluorine, $CH_3$, $CH(CH_3)_2$, $C(CH_3)_3$, $(CH_2)_nOCH_3$, $OC(CH_3)_2$, $CH(CH_3)F_2$, $CF_2CF_3$, $CH_2F$, $CHF_2$, $CF_3$, $OCHF_2$, $OCF_3$, $SF_5$, and cyclopropyl.

17. The compound according to claim 14 or a pharmaceutically acceptable salt thereof wherein $R^2$ is $CH_2OH$, $CH_2CH_2OH$, $CH_2F$, $CHF_2$, $CF_3$, or $CH_3$, one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, and cyclopropyl, or $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl, and the $R^a$ on the phenyl ring of formula Ib is selected from fluorine, $CH_3$, $CH(CH_3)_2$, $C(CH_3)_3$, $(CH_2)_nOCH_3$, $OC(CH_3)_2$, $CH(CH_3)F_2$, $CF_2CF_3$, $CH_2F$, $CHF_2$, $CF_3$, $OCHF_2$, $OCF_3$, $SF_5$, and cyclopropyl.

18. The compound according to claim 1 which is selected from the group consisting of:

(R)-1-(1-(3-Fluoro-4-(trifluoromethyl)phenyl)ethyl)-6-hydroxy-3-(hydroxymethyl)-1H-pyrazolo[3,4-d]pyrimidin-4(5H)-one,
(S)-1-(1-(3-Fluoro-4-(trifluoromethyl)phenyl)ethyl)-6-hydroxy-3-(hydroxymethyl)-1H-pyrazolo[3,4-d]pyrimidin-4(5H)-one,
(R)-6-Hydroxy-3-(hydroxymethyl)-1-((1-methylcyclopropyl)(4-(trifluoromethyl)-phenyl)methyl)-1H-pyrazolo[3,4-d]pyrimidin-4(5H)-one,
(S)-6-Hydroxy-3-(hydroxymethyl)-1-((1-methylcyclopropyl)(4-(trifluoromethyl)-phenyl)methyl)-1H-pyrazolo[3,4-d]pyrimidin-4(5H)-one,
6-Hydroxy-3-(hydroxymethyl)-1-(1-(4-(trifluoromethoxy)phenyl)ethyl)-1H-pyrazolo[3,4-d]pyrimidin-4(5H)-one,
1-(1-(4-Cyclopropylphenyl)ethyl)-6-hydroxy-3-(hydroxymethyl)-1H-pyrazolo[3,4-d]pyrimidin-4(5H)-one,
1-(1-(4-tert-Butylphenyl)ethyl)-6-hydroxy-3-(hydroxymethyl)-1H-pyrazolo[3,4-d]pyrimidin-4(5H)-one,
6-Hydroxy-3-(hydroxymethyl)-1-(1-p-tolylethyl)-1H-pyrazolo[3,4-d]pyrimidin-4(5H)-one,
6-Hydroxy-3-(hydroxymethyl)-1-[4-(trifluoromethyl)benzyl]-1,5-dihydro-4H-pyrazolo[3,4-d]pyrimidin-4-one,
(R)-(1-(3-Fluoro-4-(trifluoromethoxy-)phenyl)ethyl)-6-hydroxy-3-(hydroxymethyl)-1H-pyrazolo[3,4-d]pyrimidin-4(5H)-one,
(S)-(1-(3-Fluoro-4-(trifluoromethoxy)-phenyl)ethyl)-6-hydroxy-3-(hydroxymethyl)-1H-pyrazolo[3,4-d]pyrimidin-4(5H)-one,
(R)-6-Hydroxy-3-(hydroxymethyl)-1-(2-methyl-1-(4-(trifluoro-methyl)phenyl)propyl)-1H-pyrazolo[3,4-d]pyrimidin-4(5H)-one,
(S)-6-Hydroxy-3-(hydroxymethyl)-1-(2-methyl-1-(4-(trifluoromethyl)phenyl)propyl)-1H-pyrazolo[3,4-d]pyrimidin-4(5H)-one,
(R)-1-(Cyclopropyl(4-(trifluoromethyl)phenyl)methyl)-6-hydroxy-3-(hydroxymethyl)-1H-pyrazolo[3,4-d]pyrimidin-4(5H)-one,
(S)-1-(Cyclopropyl(4-(trifluoromethyl)phenyl)methyl)-6-hydroxy-3-(hydroxymethyl)-1H-pyrazolo[3,4-d]pyrimidin-4(5H)-one,
(R)-1-((3-Fluoro-4-(trifluoromethyl)phenyl)(1-methylcyclopropyl)methyl)-6-hydroxy-3-(hydroxymethyl)-1H-pyrazolo[3,4-d]pyrimidin-4(5H)-one,
(S)-1-((3-Fluoro-4-(trifluoromethyl)phenyl)(1-methylcyclopropyl)methyl)-6-hydroxy-3-(hydroxymethyl)-1H-pyrazolo[3,4-d]pyrimidin-4(5H)-one,
(R)-6-Hydroxy-3-(hydroxymethyl)-1-{1-[4-(trifluoromethyl)phenyl]ethyl}-1,5-dihydro-4H-pyrazolo[3,4-d]pyrimidin-4-one,
(S)-6-Hydroxy-3-(hydroxymethyl)-1-{1-[4-(trifluoromethyl)phenyl]ethyl}-1,5-dihydro-4H-pyrazolo[3,4-d]pyrimidin-4-one,
(R)-6-Hydroxy-3-(hydroxymethyl)-1-{1-[4-(pentafluorosulfanyl)phenyl]ethyl}-1,5-dihydro-4H-pyrazolo[3,4-d]pyrimidin-4-one,
(S)-6-Hydroxy-3-(hydroxymethyl)-1-{1-[4-(pentafluorosulfanyl)phenyl]ethyl}-1,5-dihydro-4H-pyrazolo[3,4-d]pyrimidin-4-one,
(R)-6-Hydroxy-3-(hydroxymethyl)-1-(3,3,3-trifluoro-1-(4-(trifluoromethyl)phenyl)propyl)-1H-pyrazolo[3,4-d]pyrimidin-4(5H)-one,
(S)-6-Hydroxy-3-(hydroxymethyl)-1-(3,3,3-trifluoro-1-(4-(trifluoromethyl)phenyl)propyl)-1H-pyrazolo[3,4-d]pyrimidin-4(5H)-one, (R)-1-(1-(3-Fluoro-4-(trifluoromethyl)phenyl)-2,2-dimethylpropyl)-6-hydroxy-3-(hydroxymethyl)-1H-pyrazolo[3,4-d]pyrimidin-4(5H)-one,
(S)-1-(1-(3-Fluoro-4-(trifluoromethyl)phenyl)-2,2-dimethylpropyl)-6-hydroxy-3-(hydroxymethyl)-1H-pyrazolo[3,4-d]pyrimidin-4(5H)-one,
6-Hydroxy-3-(hydroxymethyl)-1-(1-(4-(trifluoromethyl)phenyl)cyclobutyl)-1H-pyrazolo[3,4-d] pyrimidin-4(5H)-one,
(R)-1-(1-(3-Fluoro-4-(trifluoromethyl)phenyl)-2-methylpropyl)-6-hydroxy-3-(hydroxymethyl)-1H-pyrazolo[3,4-d]pyrimidin-4(5H)-one,
(S)-1-(1-(3-Fluoro-4-(trifluoromethyl)phenyl)-2-methylpropyl)-6-hydroxy-3-(hydroxymethyl)-1H-pyrazolo[3,4-d]pyrimidin-4(5H)-one,
(R)-1-(2,2-Dimethyl-1-(4-(trifluoromethyl)phenyl)propyl)-6-hydroxy-3-(hydroxymethyl)-1H-pyrazolo[3,4-d]pyrimidin-4(5H)-one,
(S)-1-(2,2-Dimethyl-1-(4-(trifluoromethyl)phenyl)propyl)-6-hydroxy-3-(hydroxymethyl)-1H-pyrazolo[3,4-d]pyrimidin-4(5H)-one,
(R)-6-Hydroxy-3-(hydroxymethyl)-1-(1-(4-(perfluoroethyl)phenyl)ethyl)-1H-pyrazolo[3,4-d]pyrimidin-4(5H)-one,
(S)-6-Hydroxy-3-(hydroxymethyl)-1-(1-(4-(perfluoroethyl)phenyl)ethyl)-1H-pyrazolo[3,4-d]pyrimidin-4(5H)-one,
1-(2-Fluoro-1-(4-(trifluoromethyl)phenyl)ethyl)-6-hydroxy-3-(hydroxymethyl)-1H-pyrazolo[3,4-d] pyrimidin-4(5H)-one,
(R)-(1-(3-Fluoro-4-(trifluoromethyl)phenyl)ethyl)-3-(fluoromethyl)-6-hydroxy-1H-pyrazolo[3,4-d]pyrimidin-4(5H)-one,
(S)-1-(1-(3-Fluoro-4-(trifluoromethyl)phenyl)ethyl)-3-(fluoromethyl)-6-hydroxy-1H-pyrazolo[3,4-d]pyrimidin-4(5H)-one,
3-(Fluoromethyl)-6-hydroxy-1-(1-(4-(trifluoromethoxy)phenyl)ethyl)-1H-pyrazolo[3,4-d]pyrimidin-4(5H)-one,
3-(Fluoromethyl)-6-hydroxy-1-(1-p-tolylethyl)-1H-pyrazolo[3,4-d]pyrimidin-4(5H)-one,
1-(1-(3-Fluoro-4-(trifluoromethoxy)phenyl)ethyl)-3-(fluoromethyl)-6-hydroxy-1H-pyrazolo[3,4-d]pyrimidin-4(5H)-one,
1-(Cyclopropyl(4-(trifluoromethyl)phenyl)methyl)-3-(fluoromethyl)-6-hydroxy-1H-pyrazolo[3,4-d]pyrimidin-4(5H)-one,
3-(Fluoromethyl)-6-hydroxy-1-(2-methyl-1-(4-(trifluoromethyl)phenyl)propyl)-1H-pyrazolo[3,4-d]pyrimidin-4(5H)-one,
3-(Fluoromethyl)-6-hydroxy-1-{1-[4-(trifluoromethyl)phenyl]ethyl}-1,5-dihydro-4H-pyrazolo[3,4-d]pyrimidin-4-one,
(R)-3-(Fluoromethyl)-6-hydroxy-1-(2-methyl-1-(4-(trifluoromethoxy)phenyl)propyl)-1H-pyrazolo[3,4-d]pyrimidin-4(5H)-one,
(S)-3-(Fluoromethyl)-6-hydroxy-1-(2-methyl-1-(4-(trifluoromethoxy)phenyl)propyl)-1H-pyrazolo[3,4-d]pyrimidin-4(5H)-one,
(R)-1-(Cyclopropyl(3-fluoro-4-(trifluoromethoxy)phenyl)methyl)-3-(fluoromethyl)-6-hydroxy-1H-pyrazolo[3,4-d]pyrimidin-4(5H)-one,
(S)-1-(Cyclopropyl(3-fluoro-4-(trifluoromethoxy)phenyl)methyl)-3-(fluoromethyl)-6-hydroxy-1H-pyrazolo[3,4-d]pyrimidin-4(5H)-one,
3-(Fluoromethyl)-6-hydroxy-1-(1-(4-(trifluoromethyl)phenyl)cyclobutyl)-1H-pyrazolo[3,4-d]pyrimidin-4(5H)-one,
(S)-1-(1-(4-tert-Butylphenyl)ethyl)-3-(fluoromethyl)-6-hydroxy-1H-pyrazolo[3,4-d]pyrimidin-4(5H)-one,
(S)-1-(Cyclopropyl(3-fluoro-4-(trifluoromethyl)phenyl)methyl)-3-(fluoromethyl)-6-hydroxy-1H-pyrazolo[3,4-d]pyrimidin-4(5H)-one,
(S)-1-(1-(4-tert-Butylphenyl)-2-methylpropyl)-3-(fluoromethyl)-6-hydroxy-1H-pyrazolo[3,4-d]pyrimidin-4(5H)-one,
(S)-3-(Fluoromethyl)-6-hydroxy-1-(1-(4-(pentafluorothio)phenyl)ethyl)-1H-pyrazolo[3,4-d]pyrimidin-4(5H)-one,
(R)-1-(2,2-Dimethyl-1-(4-(trifluoromethyl)phenyl)propyl)-3-(fluoromethyl)-6-hydroxy-1H-pyrazolo[3,4-d]pyrimidin-4(5H)-one,
(S)-1-(2,2-Dimethyl-1-(4-(trifluoromethyl)phenyl)propyl)-3-(fluoromethyl)-6-hydroxy-1H-pyrazolo[3,4-d]pyrimidin-4(5H)-one,
(R)-1-(1-(3-Fluoro-4-(trifluoromethoxy)phenyl)-2-methylpropyl)-3-(fluoromethyl)-6-hydroxy-1H-pyrazolo[3,4-d]pyrimidin-4(5H)-one,
(S)-1-(1-(3-Fluoro-4-(trifluoromethoxy)phenyl)-2-methylpropyl)-3-(fluoromethyl)-6-hydroxy-1H-pyrazolo[3,4-d]pyrimidin-4(5H)-one,
(R)-1-(1-(3-Fluoro-4-(trifluoromethyl)phenyl)-2-methylpropyl)-3-(fluoromethyl)-6-hydroxy-1H-pyrazolo[3,4-d]pyrimidin-4(5H)-one,
(S)-1-(1-(3-Fluoro-4-(trifluoromethyl)phenyl)-2-methylpropyl)-3-(fluoromethyl)-6-hydroxy-1H-pyrazolo[3,4-d]pyrimidin-4(5H)-one,
3-(Chloromethyl)-6-hydroxy-1-(1-p-tolylethyl)-1H-pyrazolo[3,4-d]pyrimidin-4(5H)-one,
6-Hydroxy-3-methyl-1-{1-[4-(trifluoromethyl)phenyl]ethyl}-1,5-dihydro-4H-pyrazolo[3,4-d]pyrimidin-4-one,
6-Methoxy-3-methyl-1-{1-[4-(trifluoromethyl)phenyl]ethyl}-1,5-dihydro-4H-pyrazolo[3,4-d]pyrimidin-4-one,
6-Hydroxy-3-methyl-1-{1-[4-(trifluoromethoxy)phenyl]ethyl}-1,5-dihydro-4H-pyrazolo[3,4-d]pyrimidin-4-one,
6-Hydroxy-3-methyl-1-[4-(trifluoromethyl)benzyl]-1,5-dihydro-4H-pyrazolo[3,4-d]pyrimidin-4-one,
(R)-1-(Cyclopropyl(4-(difluoromethyl)phenyl)methyl)-6-(dimethylamino)-3-(hydroxymethyl)-1H-pyrazolo[3,4-d]pyrimidin-4(5H)-one,
(S)-1-(Cyclopropyl(4-(difluoromethyl)phenyl)methyl)-6-(dimethylamino)-3-(hydroxymethyl)-1H-pyrazolo[3,4-d]pyrimidin-4(5H)-one,
(R)-6-(Dimethylamino)-3-(hydroxymethyl)-1-(2-methyl-1-(4-(trifluoromethyl)phenyl)propyl)-1H-pyrazolo[3,4-d]pyrimidin-4(5H)-one,
(S)-6-(Dimethylamino)-3-(hydroxymethyl)-1-(2-methyl-1-(4-(trifluoromethyl)phenyl)propyl)-1H-pyrazolo[3,4-d]pyrimidin-4(5H)-one,
(R)-1-(1-(4-tert-Butylphenyl)ethyl)-6-(dimethylamino)-3-(hydroxymethyl)-1H-pyrazolo[3,4-d]pyrimidin-4(5H)-one,
(S)-1-(1-(4-tert-Butylphenyl)ethyl)-6-(dimethylamino)-3-(hydroxymethyl)-1H-pyrazolo[3,4-d]pyrimidin-4(5H)-one,
(R)-6-(Dimethylamino)-1-(1-(3-fluoro-4-(trifluoromethyl)phenyl)ethyl)-3-(hydroxymethyl)-1H-pyrazolo[3,4-d]pyrimidin-4(5H)-one, (S)-6-(Dimethylamino)-1-(1-(3-fluoro-4-(trifluoromethyl)phenyl)ethyl)-3-(hydroxymethyl)-1H-pyrazolo[3,4-d]pyrimidin-4(5H)-one,
(R)-6-(Dimethylamino)-3-(hydroxymethyl)-1-(1-(4-(2,2,2-trifluoroethyl)phenyl)ethyl)-1H-pyrazolo[3,4-d]pyrimidin-4(5H)-one,
(S)-6-(Dimethylamino)-3-(hydroxymethyl)-1-(1-(4-(2,2,2-trifluoroethyl)phenyl)ethyl)-1H-pyrazolo[3,4-d]pyrimidin-4(5H)-one,
(R)-6-(Dimethylamino)-3-(hydroxymethyl)-1-(1-(4-(trifluoromethyl)phenyl)propyl)-1H-pyrazolo[3,4-d]pyrimidin-4(5H)-one,
(S)-6-(Dimethylamino)-3-(hydroxymethyl)-1-(1-(4-(trifluoromethyl)phenyl)propyl)-1H-pyrazolo[3,4-d]pyrimidin-4(5H)-one,
(R)-1-(Cyclopropyl(4-(trifluoromethyl)phenyl)methyl)-6-(dimethylamino)-3-(hydroxymethyl)-1H-pyrazolo[3,4-d]pyrimidin-4(5H)-one,
(S)-1-(Cyclopropyl(4-(trifluoromethyl)phenyl)methyl)-6-(dimethylamino)-3-(hydroxymethyl)-1H-pyrazolo[3,4-d]pyrimidin-4(5H)-one,
(R)-1-(Cyclopropyl(4-isopropylphenyl)methyl)-6-(dimethylamino)-3-(hydroxymethyl)-1H-pyrazolo[3,4-d]pyrimidin-4(5H)-one,
(S)-1-(Cyclopropyl(4-isopropylphenyl)methyl)-6-(dimethylamino)-3-(hydroxymethyl)-1H-pyrazolo[3,4-d]pyrimidin-4(5H)-one,
(R)-6-(Dimethylamino)-3-(hydroxymethyl)-1-(1-(4-isopropylphenyl)-2-methylpropyl)-1H-pyrazolo[3,4-d]pyrimidin-4(5H)-one,
(S)-6-(Dimethylamino)-3-(hydroxymethyl)-1-(1-(4-isopropylphenyl)-2-methylpropyl)-1H-pyrazolo[3,4-d]pyrimidin-4(5H)-one,
(R)-6-(Dimethylamino)-1-(1-(2-fluoro-4-(trifluoromethyl)phenyl)ethyl)-3-(hydroxymethyl)-1H-pyrazolo[3,4-d]pyrimidin-4(5H)-one,
(S)-6-(Dimethylamino)-1-(1-(2-fluoro-4-(trifluoromethyl)phenyl)ethyl)-3-(hydroxymethyl)-1H-pyrazolo[3,4-d]pyrimidin-4(5H)-one,
(R)-1-(1-(4-(Difluoromethyl)phenyl)ethyl)-6-(dimethylamino)-3-(hydroxymethyl)-1H-pyrazolo[3,4-d]pyrimidin-4(5H)-one,
(S)-1-(1-(4-(Difluoromethyl)phenyl)ethyl)-6-(dimethylamino)-3-(hydroxymethyl)-1H-pyrazolo[3,4-d]pyrimidin-4(5H)-one,
(R)-6-(Dimethylamino)-1-(1-(3-fluoro-4-(trifluoromethoxy)phenyl)ethyl)-3-(hydroxymethyl)-1H-pyrazolo[3,4-d]pyrimidin-4(5H)-one,
(S)-6-(Dimethylamino)-1-(1-(3-fluoro-4-(trifluoromethoxy)phenyl)ethyl)-3-(hydroxymethyl)-1H-pyrazolo[3,4-d]pyrimidin-4(5H)-one,
(R)-1-(Cyclopropyl(4-(2,2,2-trifluoroethyl)phenyl)methyl)-6-(dimethylamino)-3-(hydroxymethyl)-1H-pyrazolo[3,4-d]pyrimidin-4(5H)-one,
(S)-1-(Cyclopropyl(4-(2,2,2-trifluoroethyl)phenyl)methyl)-6-(dimethylamino)-3-(hydroxymethyl)-1H-pyrazolo[3,4-d]pyrimidin-4(5H)-one,
(R)-6-(Dimethylamino)-3-(hydroxymethyl)-1-(2-methyl-1-(4-(2,2,2-trifluoroethyl)phenyl)propyl)-1H-pyrazolo[3,4-d]pyrimidin-4(5H)-one,
(S)-6-(Dimethylamino)-3-(hydroxymethyl)-1-(2-methyl-1-(4-(2,2,2-trifluoroethyl)phenyl)propyl)-1H-pyrazolo[3,4-d]pyrimidin-4(5H)-one,
(R)-1-(1-(4-(Difluoromethyl)phenyl)-2-methylpropyl)-6-(dimethylamino)-3-(hydroxymethyl)-1H-pyrazolo[3,4-d]pyrimidin-4(5H)-one,
(S)-1-(1-(4-(Difluoromethyl)phenyl)-2-methylpropyl)-6-(dimethylamino)-3-(hydroxymethyl)-1H-pyrazolo[3,4-d]pyrimidin-4(5H)-one,
(R)-1-(1-(4-(Difluoromethyl)phenyl)propyl)-6-(dimethylamino)-3-(hydroxymethyl)-1H-pyrazolo[3,4-d]pyrimidin-4(5H)-one,
(S)-1-(1-(4-(Difluoromethyl)phenyl)propyl)-6-(dimethylamino)-3-(hydroxymethyl)-1H-pyrazolo[3,4-d]pyrimidin-4(5H)-one,
(R)-1-(Cyclopropyl(3-fluoro-4-(2,2,2-trifluoroethyl)phenyl)methyl)-6-(dimethylamino)-3-(hydroxymethyl)-1H-pyrazolo[3,4-d]pyrimidin-4(5H)-one,
(S)-1-(Cyclopropyl(3-fluoro-4-(2,2,2-trifluoroethyl)phenyl)methyl)-6-(dimethylamino)-3-(hydroxymethyl)-1H-pyrazolo[3,4-d]pyrimidin-4(5H)-one,
(R)-6-(Dimethylamino)-1-(1-(3-fluoro-4-(2,2,2-trifluoroethyl)phenyl)propyl)-3-(hydroxymethyl)-1H-pyrazolo[3,4-d]pyrimidin-4(5H)-one,
(S)-6-(Dimethylamino)-1-(1-(3-fluoro-4-(2,2,2-trifluoroethyl)phenyl)propyl)-3-(hydroxymethyl)-1H-pyrazolo[3,4-d]pyrimidin-4(5H)-one,
(R)-6-(Dimethylamino)-3-(hydroxymethyl)-1-(1-(4-(2,2,2-trifluoroethyl)phenyl)propyl)-1H-pyrazolo[3,4-d]pyrimidin-4(5H)-one,
(S)-6-(Dimethylamino)-3-(hydroxymethyl)-1-(1-(4-(2,2,2-trifluoroethyl)phenyl)propyl)-1H-pyrazolo[3,4-d]pyrimidin-4(5H)-one,
(R)-6-(Dimethylamino)-1-(1-(3-fluoro-4-(2,2,2-trifluoroethyl)phenyl)ethyl)-3-(hydroxymethyl)-1H-pyrazolo[3,4-d]pyrimidin-4(5H)-one,
(S)-6-(Dimethylamino)-1-(1-(3-fluoro-4-(2,2,2-trifluoroethyl)phenyl)ethyl)-3-(hydroxymethyl)-1H-pyrazolo[3,4-d]pyrimidin-4(5H)-one,
(R)-1-(1-(4-(1,1-Difluoroethyl)phenyl)ethyl)-6-(dimethylamino)-3-(hydroxymethyl)-1H-pyrazolo[3,4-d]pyrimidin-4(5H)-one,
(S)-1-(1-(4-(1,1-Difluoroethyl)phenyl)ethyl)-6-(dimethylamino)-3-(hydroxymethyl)-1H-pyrazolo[3,4-d]pyrimidin-4(5H)-one,
(R)-1-(1-(4-(Difluoromethyl)-3-fluorophenyl)ethyl)-6-(dimethylamino)-3-(hydroxymethyl)-1H-pyrazolo[3,4-d]pyrimidin-4(5H)-one,
(S)-1-(1-(4-(Difluoromethyl)-3-fluorophenyl)ethyl)-6-(dimethylamino)-3-(hydroxymethyl)-1H-pyrazolo[3,4-d]pyrimidin-4(5H)-one,
(R)-1-(1-(4-(1,1-Difluoroethyl)-3-fluorophenyl)ethyl)-6-(dimethylamino)-3-(hydroxymethyl)-1H-pyrazolo[3,4-d]pyrimidin-4(5H)-one,
(S)-1-(1-(4-(1,1-Difluoroethyl)-3-fluorophenyl)ethyl)-6-(dimethylamino)-3-(hydroxymethyl)-1H-pyrazolo[3,4-d]pyrimidin-4(5H)-one,
(R)-1-(1-(4-(1,1-Difluoroethyl)-2-fluorophenyl)ethyl)-6-(dimethylamino)-3-(hydroxymethyl)-1H-pyrazolo[3,4-d]pyrimidin-4(5H)-one,
(S)-1-(1-(4-(1,1-Difluoroethyl)-2-fluorophenyl)ethyl)-6-(dimethylamino)-3-(hydroxymethyl)-1H-pyrazolo[3,4-d]pyrimidin-4(5H)-one,
(R)-1-(1-(4-(1,1-Difluoroethyl)-2-fluorophenyl)propyl)-6-(dimethylamino)-3-(hydroxymethyl)-1H-pyrazolo[3,4-d]pyrimidin-4(5H)-one,
(S)-1-(1-(4-(1,1-Difluoroethyl)-2-fluorophenyl)propyl)-6-(dimethylamino)-3-(hydroxymethyl)-1H-pyrazolo[3,4-d]pyrimidin-4(5H)-one,
(R)-1-(1-(4-(1,1-Difluoroethyl)-3-fluorophenyl)propyl)-6-(dimethylamino)-3-(hydroxymethyl)-1H-pyrazolo[3,4-d]pyrimidin-4(5H)-one, (S)-1-(1-(4-(1,1-Difluoroethyl)-3-fluorophenyl)propyl)-6-(dimethylamino)-3-(hydroxymethyl)-1H-pyrazolo[3,4-d]pyrimidin-4(5H)-one,
(S)-1-(1-(4-(Difluoromethyl)-3-fluorophenyl)-2-methylpropyl)-6-(dimethylamino)-3-(hydroxymethyl)-1H-pyrazolo[3,4-d]pyrimidin-4(5H)-one,
(R)-1-(1-(4-(Difluoromethyl)-3-fluorophenyl)-2-methylpropyl)-6-(dimethylamino)-3-(hydroxymethyl)-1H-pyrazolo[3,4-d]pyrimidin-4(5H)-one,
(R)-1-(1-(4-(1,1-Difluoroethyl)-3-fluorophenyl)-2-methylpropyl)-6-(dimethylamino)-3-(hydroxymethyl)-1H-pyrazolo[3,4-d]pyrimidin-4(5H)-one,
(R)-1-(1-(4-(1,1-Difluoroethyl)-3-fluorophenyl)-2-methylpropyl)-6-(dimethylamino)-3-(hydroxymethyl)-1H-pyrazolo[3,4-d]pyrimidin-4(5H)-one,
(R)-1-(1-(4-(1,1-Difluoroethyl)-2-fluorophenyl)-2-methylpropyl)-6-(dimethylamino)-3-(hydroxymethyl)-1H-pyrazolo[3,4-d]pyrimidin-4(5H)-one,
(S)-1-(1-(4-(1,1-Difluoroethyl)-2-fluorophenyl)-2-methylpropyl)-6-(dimethylamino)-3-(hydroxymethyl)-1H-pyrazolo[3,4-d]pyrimidin-4(5H)-one,
(R)-1-(1-(4-(Difluoromethoxy)phenyl)-2-methylpropyl)-6-(dimethylamino)-3-(hydroxymethyl)-1H-pyrazolo[3,4-d]pyrimidin-4(5H)-one,
(S)-1-(1-(4-(Difluoromethoxy)phenyl)-2-methylpropyl)-6-(dimethylamino)-3-(hydroxymethyl)-1H-pyrazolo[3,4-d]pyrimidin-4(5H)-one,
(R)-1-(Cyclopropyl(4-(difluoromethoxy)-3-fluorophenyl)methyl)-6-(dimethylamino)-3-(hydroxymethyl)-1H-pyrazolo[3,4-d]pyrimidin-4(5H)-one,
(S)-1-(Cyclopropyl(4-(difluoromethoxy)-3-fluorophenyl)methyl)-6-(dimethylamino)-3-(hydroxymethyl)-1H-pyrazolo[3,4-d]pyrimidin-4(5H)-one,
(R)-1-(1-(4-(Difluoromethoxy)phenyl)propyl)-6-(dimethylamino)-3-(hydroxymethyl)-1H-pyrazolo[3,4-d]pyrimidin-4(5H)-one,
(S)-1-(1-(4-(Difluoromethoxy)phenyl)propyl)-6-(dimethylamino)-3-(hydroxymethyl)-1H-pyrazolo[3,4-d]pyrimidin-4(5H)-one,
(R)-1-(1-(4-(Difluoromethoxy)-3-fluorophenyl)propyl)-6-(dimethylamino)-3-(hydroxymethyl)-1H-pyrazolo[3,4-d]pyrimidin-4(5H)-one,
(S)-1-(1-(4-(Difluoromethoxy)-3-fluorophenyl)propyl)-6-(dimethylamino)-3-(hydroxymethyl)-1H-pyrazolo[3,4-d]pyrimidin-4(5H)-one,
(R)-1-(Cyclopropyl(4-(difluoromethoxy)phenyl)methyl)-6-(dimethylamino)-3-(hydroxymethyl)-1H-pyrazolo[3,4-d]pyrimidin-4(5H)-one,
(S)-1-(Cyclopropyl(4-(difluoromethoxy)phenyl)methyl)-6-(dimethylamino)-3-(hydroxymethyl)-1H-pyrazolo[3,4-d]pyrimidin-4(5H)-one,
(R)-6-(Dimethylamino)-1-(1-(2-fluoro-4-(trifluoromethyl)phenyl)propyl)-3-(hydroxymethyl)-1H-pyrazolo[3,4-d]pyrimidin-4(5H)-one,
(S)-6-(Dimethylamino)-1-(1-(2-fluoro-4-(trifluoromethyl)phenyl)propyl)-3-(hydroxymethyl)-1H-pyrazolo[3,4-d]pyrimidin-4(5H)-one,
(R)-6-(Dimethylamino)-1-(1-(2-fluoro-4-(trifluoromethyl)phenyl)-2-methylpropyl)-3-(hydroxymethyl)-1H-pyrazolo[3,4-d]pyrimidin-4(5H)-one,
(S)-6-(Dimethylamino)-1-(1-(2-fluoro-4-(trifluoromethyl)phenyl)-2-methylpropyl)-3-(hydroxymethyl)-1H-pyrazolo[3,4-d]pyrimidin-4(5H)-one,
(R)-1-(Cyclopropyl(2-fluoro-4-(trifluoromethyl)phenyl)methyl)-6-(dimethylamino)-3-(hydroxymethyl)-1H-pyrazolo[3,4-d]pyrimidin-4(5H)-one,
(S)-1-(Cyclopropyl(2-fluoro-4-(trifluoromethyl)phenyl)methyl)-6-(dimethylamino)-3-(hydroxymethyl)-1H-pyrazolo[3,4-d]pyrimidin-4(5H)-one,
(R)-1-(1-(4-(1,1-Difluoroethyl)phenyl)propyl)-6-(dimethylamino)-3-(hydroxymethyl)-1H-pyrazolo[3,4-d]pyrimidin-4(5H)-one,
(S)-1-(1-(4-(1,1-Difluoroethyl)phenyl)propyl)-6-(dimethylamino)-3-(hydroxymethyl)-1H-pyrazolo[3,4-d]pyrimidin-4(5H)-one,
(R)-1-(1-(4-(1,1-Difluoroethyl)phenyl)-2-methylpropyl)-6-(dimethylamino)-3-(hydroxymethyl)-1H-pyrazolo[3,4-d]pyrimidin-4(5H)-one,
(S)-1-(1-(4-(1,1-Difluoroethyl)phenyl)-2-methylpropyl)-6-(dimethylamino)-3-(hydroxymethyl)-1H-pyrazolo[3,4-d]pyrimidin-4(5H)-one,
(R)-1-(Cyclopropyl(4-(1,1-difluoroethyl)phenyl)methyl)-6-(dimethylamino)-3-(hydroxymethyl)-1H-pyrazolo[3,4-d]pyrimidin-4(5H)-one,
(S)-1-(Cyclopropyl(4-(1,1-difluoroethyl)phenyl)methyl)-6-(dimethylamino)-3-(hydroxymethyl)-1H-pyrazolo[3,4-d]pyrimidin-4(5H)-one,
(R)-6-(Dimethylamino)-1-(1-(3-fluoro-4-(trifluoromethyl)phenyl)-2-methylpropyl)-3-(hydroxymethyl)-1H-pyrazolo[3,4-d]pyrimidin-4(5H)-one,
(S)-6-(Dimethylamino)-1-(1-(3-fluoro-4-(trifluoromethyl)phenyl)-2-methylpropyl)-3-(hydroxymethyl)-1H-pyrazolo[3,4-d]pyrimidin-4(5H)-one,
(R)-6-(Dimethylamino)-1-(1-(3-fluoro-4-(trifluoromethyl)phenyl)propyl)-3-(hydroxymethyl)-1H-pyrazolo[3,4-d]pyrimidin-4(5H)-one,
(S)-6-(Dimethylamino)-1-(1-(3-fluoro-4-(trifluoromethyl)phenyl)propyl)-3-(hydroxymethyl)-1H-pyrazolo[3,4-d]pyrimidin-4(5H)-one,
(R)-1-(1-(4-(Difluoromethyl)-3-fluorophenyl)propyl)-6-(dimethylamino)-3-(hydroxymethyl)-1H-pyrazolo[3,4-d]pyrimidin-4(5H)-one,
(S)-1-(1-(4-(Difluoromethyl)-3-fluorophenyl)propyl)-6-(dimethylamino)-3-(hydroxymethyl)-1H-pyrazolo[3,4-d]pyrimidin-4(5H)-one,
(R)-6-(Dimethylamino)-3-(hydroxymethyl)-1-(1-(4-(trifluoromethoxy)phenyl)ethyl)-1H-pyrazolo[3,4-d]pyrimidin-4(5H)-one,
(S)-6-(Dimethylamino)-3-(hydroxymethyl)-1-(1-(4-(trifluoromethoxy)phenyl)ethyl)-1H-pyrazolo[3,4-d]pyrimidin-4(5H)-one,
(R)-1-(Cyclopropyl(3-fluoro-4-(trifluoromethyl)phenyl)methyl)-6-(dimethylamino)-3-(hydroxymethyl)-1H-pyrazolo[3,4-d]pyrimidin-4(5H)-one,
(S)-1-(Cyclopropyl(3-fluoro-4-(trifluoromethyl)phenyl)methyl)-6-(dimethylamino)-3-(hydroxymethyl)-1H-pyrazolo[3,4-d]pyrimidin-4(5H)-one,
(R)-1-(Cyclopropyl(4-(difluoromethyl)-3-fluorophenyl)methyl)-6-(dimethylamino)-3-(hydroxymethyl)-1H-pyrazolo[3,4-d]pyrimidin-4(5H)-one,
(S)-1-(Cyclopropyl(4-(difluoromethyl)-3-fluorophenyl)methyl)-6-(dimethylamino)-3-(hydroxymethyl)-1H-pyrazolo[3,4-d]pyrimidin-4(5H)-one,
(S)-6-(Dimethylamino)-3-(hydroxymethyl)-1-(1-(4-(trifluoromethyl)phenyl)ethyl)-1H-pyrazolo[3,4-d]pyrimidin-4(5H)-one,
6-[(3-Chloropropyl)amino]-3-(hydroxymethyl)-1-{(1S)-1-[4-(trifluoromethyl)-phenyl]ethyl}-1,5-dihydro-4H-pyrazolo[3,4-d]pyrimidin-4-one,
3-(Hydroxymethyl)-6-pyrrolidin-1-yl-1-{(1S)-1-[4-(trifluoromethyl)phenyl]ethyl}-1,5-dihydro-4H-pyrazolo[3,4-d]pyrimidin-4-one, 6-Amino-3-(hydroxymethyl)-1-{(1S)-1-[4-(trifluoromethyl)phenyl]ethyl}-1,5-dihydro-4H-pyrazolo[3,4-d]pyrimidin-4-one, (S)-6-(Azetidin-1-yl)-3-(hydroxymethyl)-1-(1-(4-(trifluoromethyl)phenyl)ethyl)-1,5-dihydro-4H-pyrazolo[3,4-d]pyrimidin-4-one, 6-(3,3-Difluoroazetidin-1-yl)-3-(hydroxymethyl)-1-{(1S)-1-[4-(trifluoromethyl)phenyl]ethyl}-1,5-dihydro-4H-pyrazolo[3,4-d]pyrimidin-4-one, 3-(Hydroxymethyl)-6-(3-methylazetidin-1-yl)-1-{(1S)-1-[4-(trifluoromethyl)phenyl]ethyl}-1,5-dihydro-4H-pyrazolo[3,4-d]pyrimidin-4-one, 6-(3-Fluoroazetidin-1-yl)-3-(hydroxymethyl)-1-{(1S)-1-[4-(trifluoromethyl)phenyl]ethyl}-1,5-dihydro-4H-pyrazolo[3,4-d]pyrimidin-4-one, (R)-6-(Dimethylamino)-3-(fluoromethyl)-1-(2-methyl-1-(4-(trifluoromethyl)phenyl)propyl)-1H-pyrazolo[3,4-d]pyrimidin-4(5H)-one, (S)-6-(Dimethylamino)-3-(fluoromethyl)-1-(2-methyl-1-(4-(trifluoromethyl)phenyl)propyl)-1H-pyrazolo[3,4-d]pyrimidin-4(5H)-one, (R)-6-(Dimethylamino)-3-(fluoromethyl)-1-(1-(4-(trifluoromethoxy)phenyl)ethyl)-1H-pyrazolo[3,4-d]pyrimidin-4(5H)-one, (S)-6-(Dimethylamino)-3-(fluoromethyl)-1-(1-(4-(trifluoromethoxy)phenyl)ethyl)-1H-pyrazolo[3,4-d]pyrimidin-4(5H)-one, (R)-6-(Dimethylamino)-1-(1-(3-fluoro-4-(trifluoromethoxy)phenyl)ethyl)-3-(fluoromethyl)-1H-pyrazolo[3,4-d]pyrimidin-4(5H)-one, (S)-6-(Dimethylamino)-1-(1-(3-fluoro-4-(trifluoromethoxy)phenyl)ethyl)-3-(fluoromethyl)-1H-pyrazolo[3,4-d]pyrimidin-4(5H)-one, (R)-6-(Dimethylamino)-1-(1-(3-fluoro-4-(trifluoromethyl)phenyl)ethyl)-3-(fluoromethyl)-1H-pyrazolo[3,4-d]pyrimidin-4(5H)-one, (S)-6-(Dimethylamino)-1-(1-(3-fluoro-4-(trifluoromethyl)phenyl)ethyl)-3-(fluoromethyl)-1H-pyrazolo[3,4-d]pyrimidin-4(5H)-one, (R)-1-(1-(4-tert-Butylphenyl)ethyl)-6-(dimethylamino)-3-(fluoromethyl)-1H-pyrazolo[3,4-d]pyrimidin-4(5H)-one, (S)-1-(1-(4-tert-Butylphenyl)ethyl)-6-(dimethylamino)-3-(fluoromethyl)-1H-pyrazolo[3,4-d]pyrimidin-4(5H)-one, (R)-6-(Dimethylamino)-3-(fluoromethyl)-1-(1-(4-(trifluoromethyl)phenyl)propyl)-1H-pyrazolo[3,4-d]pyrimidin-4(5H)-one, (S)-6-(Dimethylamino)-3-(fluoromethyl)-1-(1-(4-(trifluoromethyl)phenyl)propyl)-1H-pyrazolo[3,4-d]pyrimidin-4(5H)-one, (R)-6-(Dimethylamino)-3-(fluoromethyl)-1-(1-(4-(2,2,2-trifluoroethyl)phenyl)ethyl)-1H-pyrazolo[3,4-d]pyrimidin-4(5H)-one, (S)-6-(Dimethylamino)-3-(fluoromethyl)-1-(1-(4-(2,2,2-trifluoroethyl)phenyl)ethyl)-1H-pyrazolo[3,4-d]pyrimidin-4(5H)-one, (R)-6-(Dimethylamino)-3-(fluoromethyl)-1-(1-(4-isopropylphenyl)-2-methylpropyl)-1H-pyrazolo[3,4-d]pyrimidin-4(5H)-one, (S)-6-(Dimethylamino)-3-(fluoromethyl)-1-(1-(4-isopropylphenyl)-2-methylpropyl)-1H-pyrazolo[3,4-d]pyrimidin-4(5H)-one, (R)-1-(Cyclopropyl(4-(trifluoromethyl)phenyl)methyl)-6-(dimethylamino)-3-(fluoromethyl)-1H-pyrazolo[3,4-d]pyrimidin-4(5H)-one, (S)-1-(Cyclopropyl(4-(trifluoromethyl)phenyl)methyl)-6-(dimethylamino)-3-(fluoromethyl)-1H-pyrazolo[3,4-d]pyrimidin-4(5H)-one, (R)-1-(Cyclopropyl(3-fluoro-4-(trifluoromethyl)phenyl)methyl)-6-(dimethylamino)-3-(fluoromethyl)-1H-pyrazolo[3,4-d]pyrimidin-4(5H)-one, (S)-1-(Cyclopropyl(3-fluoro-4-(trifluoromethyl)phenyl)methyl)-6-(dimethylamino)-3-(fluoromethyl)-1H-pyrazolo[3,4-d]pyrimidin-4(5H)-one, (R–)-1-(Cyclopropyl(4-isopropylphenyl)methyl)-6-(dimethylamino)-3-(fluoromethyl)-1H-pyrazolo[3,4-d]pyrimidin-4(5H)-one, (S)-1-(Cyclopropyl(4-isopropylphenyl)methyl)-6-(dimethylamino)-3-(fluoromethyl)-1H-pyrazolo[3,4-d]pyrimidin-4(5H)-one, (R)-1-(1-(4-(Difluoromethoxy)phenyl)-2-methylpropyl)-6-(dimethylamino)-3-(fluoromethyl)-1H-pyrazolo[3,4-d]pyrimidin-4(5H)-one, (S)-1-(1-(4-(Difluoromethoxy)phenyl)-2-methylpropyl)-6-(dimethylamino)-3-(fluoromethyl)-1H-pyrazolo[3,4-d]pyrimidin-4(5H)-one, (R)-6-(Dimethylamino)-1-(1-(2-fluoro-4-(trifluoromethyl)phenyl)ethyl)-3-(fluoromethyl)-1H-pyrazolo[3,4-d]pyrimidin-4(5H)-one, (S)-6-(Dimethylamino)-1-(1-(2-fluoro-4-(trifluoromethyl)phenyl)ethyl)-3-(fluoromethyl)-1H-pyrazolo[3,4-d]pyrimidin-4(5H)-one, (R)-1-(Cyclopropyl(4-(difluoromethoxy)-3-fluorophenyl)methyl)-6-(dimethylamino)-3-(fluoromethyl)-1H-pyrazolo[3,4-d]pyrimidin-4(5H)-one, (S)-1-(Cyclopropyl(4-(difluoromethoxy)-3-fluorophenyl)methyl)-6-(dimethylamino)-3-(fluoromethyl)-1H-pyrazolo[3,4-d]pyrimidin-4(5H)-one, (R)-1-(1-(4-(Difluoromethyl)phenyl)ethyl)-6-(dimethylamino)-3-(fluoromethyl)-1H-pyrazolo[3,4-d]pyrimidin-4(5H)-one, (S)-1-(1-(4-(Difluoromethyl)phenyl)ethyl)-6-(dimethylamino)-3-(fluoromethyl)-1H-pyrazolo[3,4-d]pyrimidin-4(5H)-one, (R)-1-(Cyclopropyl(4-(2,2,2-trifluoroethyl)phenyl)methyl)-6-(dimethylamino)-3-(fluoromethyl)-1H-pyrazolo[3,4-d]pyrimidin-4(5H)-one, (S)-1-(Cyclopropyl(4-(2,2,2-trifluoroethyl)phenyl)methyl)-6-(dimethylamino)-3-(fluoromethyl)-1H-pyrazolo[3,4-d]pyrimidin-4(5H)-one, (R)-1-(1-(4-(1,1-Difluoroethyl)phenyl)ethyl)-6-(dimethylamino)-3-(fluoromethyl)-1H-pyrazolo[3,4-d]pyrimidin-4(5H)-one, (S)-1-(1-(4-(1,1-Difluoroethyl)phenyl)ethyl)-6-(dimethylamino)-3-(fluoromethyl)-1H-pyrazolo[3,4-d]pyrimidin-4(5H)-one, (R)-1-(1-(4-(Difluoromethyl)-3-fluorophenyl)ethyl)-6-(dimethylamino)-3-(fluoromethyl)-1H-pyrazolo[3,4-d]pyrimidin-4(5H)-one, (S)-1-(1-(4-(Difluoromethyl)-3-fluorophenyl)ethyl)-6-(dimethylamino)-3-(fluoromethyl)-1H-pyrazolo[3,4-d]pyrimidin-4(5H)-one, (R)-6-(Dimethylamino)-1-(1-(2-fluoro-4-(trifluoromethyl)phenyl)propyl)-3-(fluoromethyl)-1H-pyrazolo[3,4-d]pyrimidin-4(5H)-one, (S)-6-(Dimethylamino)-1-(1-(2-fluoro-4-(trifluoromethyl)phenyl)propyl)-3-(fluoromethyl)-1H-pyrazolo[3,4-d]pyrimidin-4(5H)-one, (R)-6-(Dimethylamino)-1-(1-(2-fluoro-4-(trifluoromethyl)phenyl)-2-methylpropyl)-3-(fluoromethyl)-1H-pyrazolo[3,4-d]pyrimidin-4(5H)-one, (S)-6-(Dimethylamino)-1-(1-(2-fluoro-4-(trifluoromethyl)phenyl)-2-methylpropyl)-3-(fluoromethyl)-1H-pyrazolo[3,4-d]pyrimidin-4(5H)-one,
(R)-1-(Cyclopropyl(2-fluoro-4-(trifluoromethyl)phenyl)methyl)-6-(dimethylamino)-3-(fluoromethyl)-1H-pyrazolo[3,4-d]pyrimidin-4(5H)-one,
(S)-1-(Cyclopropyl(2-fluoro-4-(trifluoromethyl)phenyl)methyl)-6-(dimethylamino)-3-(fluoromethyl)-1H-pyrazolo[3,4-d]pyrimidin-4(5H)-one,
(R)-1-(1-(4-(1,1-Difluoroethyl)phenyl)propyl)-6-(dimethylamino)-3-(fluoromethyl)-1H-pyrazolo[3,4-d]pyrimidin-4(5H)-one,
(S)-1-(1-(4-(1,1-Difluoroethyl)phenyl)propyl)-6-(dimethylamino)-3-(fluoromethyl)-1H-pyrazolo[3,4-d]pyrimidin-4(5H)-one,
(R)-1-(1-(4-(1,1-Difluoroethyl)phenyl)-2-methylpropyl)-6-(dimethylamino)-3-(fluoromethyl)-1H-pyrazolo[3,4-d]pyrimidin-4(5H)-one,
(S)-1-(1-(4-(1,1-Difluoroethyl)phenyl)-2-methylpropyl)-6-(dimethylamino)-3-(fluoromethyl)-1H-pyrazolo[3,4-d]pyrimidin-4(5H)-one,
(R)-1-(1-(4-(1,1-Difluoroethyl)-2-fluorophenyl)ethyl)-6-(dimethylamino)-3-(fluoromethyl)-1H-pyrazolo[3,4-d]pyrimidin-4(5H)-one,
(S)-1-(1-(4-(1,1-Difluoroethyl)-2-fluorophenyl)ethyl)-6-(dimethylamino)-3-(fluoromethyl)-1H-pyrazolo[3,4-d]pyrimidin-4(5H)-one,
(R)-1-(1-(4-(1,1-Difluoroethyl)-3-fluorophenyl)ethyl)-6-(dimethylamino)-3-(fluoromethyl)-1H-pyrazolo[3,4-d]pyrimidin-4(5H)-one,
(S)-1-(1-(4-(1,1-Difluoroethyl)-3-fluorophenyl)ethyl)-6-(dimethylamino)-3-(fluoromethyl)-1H-pyrazolo[3,4-d]pyrimidin-4(5H)-one,
(R)-1-(Cyclopropyl(4-(1,1-difluoroethyl)phenyl)methyl)-6-(dimethylamino)-3-(fluoromethyl)-1H-pyrazolo[3,4-d]pyrimidin-4(5H)-one,
(S)-1-(Cyclopropyl(4-(1,1-difluoroethyl)phenyl)methyl)-6-(dimethylamino)-3-(fluoromethyl)-1H-pyrazolo[3,4-d]pyrimidin-4(5H)-one,
(R)-1-(1-(4-(1,1-Difluoroethyl)-2-fluorophenyl)propyl)-6-(dimethylamino)-3-(fluoromethyl)-1H-pyrazolo[3,4-d]pyrimidin-4(5H)-one,
(S)-1-(1-(4-(1,1-Difluoroethyl)-2-fluorophenyl)propyl)-6-(dimethylamino)-3-(fluoromethyl)-1H-pyrazolo[3,4-d]pyrimidin-4(5H)-one,
(R)-1-(1-(4-(1,1-Difluoroethyl)-3-fluorophenyl)propyl)-6-(dimethylamino)-3-(fluoromethyl)-1H-pyrazolo[3,4-d]pyrimidin-4(5H)-one,
(S)-1-(1-(4-(1,1-Difluoroethyl)-3-fluorophenyl)propyl)-6-(dimethylamino)-3-(fluoromethyl)-1H-pyrazolo[3,4-d]pyrimidin-4(5H)-one,
(R)-1-(1-(4-(1,1-Difluoroethyl)-3-fluorophenyl)-2-methylpropyl)-6-(dimethylamino)-3-(fluoromethyl)-1H-pyrazolo[3,4-d]pyrimidin-4(5H)-one,
(S)-1-(1-(4-(1,1-Difluoroethyl)-3-fluorophenyl)-2-methylpropyl)-6-(dimethylamino)-3-(fluoromethyl)-1H-pyrazolo[3,4-d]pyrimidin-4(5H)-one,
(R)-6-(Dimethylamino)-1-(1-(3-fluoro-4-(trifluoromethyl)phenyl)-2-methylpropyl)-3-(fluoromethyl)-1H-pyrazolo[3,4-d]pyrimidin-4(5H)-one,
(S)-6-(Dimethylamino)-1-(1-(3-fluoro-4-(trifluoromethyl)phenyl)-2-methylpropyl)-3-(fluoromethyl)-1H-pyrazolo[3,4-d]pyrimidin-4(5H)-one,
(R)-6-(Dimethylamino)-1-(1-(3-fluoro-4-(trifluoromethyl)phenyl)propyl)-3-(fluoromethyl)-1H-pyrazolo[3,4-d]pyrimidin-4(5H)-one,
(S)-6-(Dimethylamino)-1-(1-(3-fluoro-4-(trifluoromethyl)phenyl)propyl)-3-(fluoromethyl)-1H-pyrazolo[3,4-d]pyrimidin-4(5H)-one,
(S)-6-(Dimethylamino)-3-(fluoromethyl)-1-(1-(4-(trifluoromethyl)phenyl)ethyl)-1H-pyrazolo[3,4-d]pyrimidin-4(5H)-one,
6-Azetidin-1-yl-3-(fluoromethyl)-1-{(1S)-1-[4-(trifluoromethyl)phenyl]ethyl}-1,5-dihydro-4H-pyrazolo[3,4-d]pyrimidin-4-one,
3-(Fluoromethyl)-6-pyrrolidin-1-yl-1-{(1S)-1-[4-(trifluoromethyl)phenyl]ethyl}-1,5-dihydro-4H-pyrazolo[3,4-d]pyrimidin-4-one,
(R)-1-(Cyclopropyl(4-(trifluoromethyl)phenyl)methyl)-6-hydroxy-3-(2,2,2-trifluoroethyl)-1H-pyrazolo[3,4-d]pyrimidin-4(5H)-one,
(S)-1-(Cyclopropyl(4-(trifluoromethyl)phenyl)methyl)-6-hydroxy-3-(2,2,2-trifluoroethyl)-1H-pyrazolo[3,4-d]pyrimidin-4(5H)-one,
1-(1-(3-Fluoro-4-(trifluoromethoxy)phenyl)ethyl)-6-hydroxy-3-(2,2,2-trifluoroethyl)-1H-pyrazolo[3,4-d]pyrimidin-4(5H)-one,
6-Hydroxy-3-(2,2,2-trifluoroethyl)-1-(1-(4-(trifluoromethoxy)phenyl)ethyl)-1H-pyrazolo[3,4-d]pyrimidin-4(5H)-one,
6-Hydroxy-3-(2,2,2-trifluoroethyl)-1-(1-(4-(pentafluorosulfanyl)phenyl)ethyl)-1H-pyrazolo[3,4-d]pyrimidin-4(5H)-one,
(R)-6-Hydroxy-1-(2-methyl-1-(4-(trifluoromethoxy)phenyl)propyl)-3-(2,2,2-trifluoroethyl)-1H-pyrazolo[3,4-d]pyrimidin-4(5H)-one,
(S)-6-Hydroxy-1-(2-methyl-1-(4-(trifluoromethoxy)phenyl)propyl)-3-(2,2,2-trifluoroethyl)-1H-pyrazolo[3,4-d]pyrimidin-4(5H)-one,
(R)-1-(1-(3-Fluoro-4-(trifluoromethyl)phenyl)ethyl)-6-hydroxy-3-(2,2,2-trifluoroethyl)-1H-pyrazolo[3,4-d]pyrimidin-4(5H)-one,
(S)-1-(1-(3-Fluoro-4-(trifluoromethyl)phenyl)ethyl)-6-hydroxy-3-(2,2,2-trifluoroethyl)-1H-pyrazolo[3,4-d]pyrimidin-4(5H)-one,
(R)-1-(1-(4-tert-Butylphenyl)ethyl)-6-hydroxy-3-(2,2,2-trifluoroethyl)-1H-pyrazolo[3,4-d]pyrimidin-4(5H)-one,
(S)-1-(1-(4-tert-Butylphenyl)ethyl)-6-hydroxy-3-(2,2,2-trifluoroethyl)-1H-pyrazolo[3,4-d]pyrimidin-4(5H)-one,
(R)-1-(Cyclopropyl(3-fluoro-4-(trifluoromethyl)phenyl)methyl)-6-hydroxy-3-(2,2,2-trifluoroethyl)-1H-pyrazolo[3,4-d]pyrimidin-4(5H)-one,
(S)-1-(Cyclopropyl(3-fluoro-4-(trifluoromethyl)phenyl)methyl)-6-hydroxy-3-(2,2,2-trifluoroethyl)-1H-pyrazolo[3,4-d]pyrimidin-4(5H)-one,
(R)-6-Hydroxy-1-(2-methyl-1-(4-(trifluoromethyl)phenyl)propyl)-3-(2,2,2-trifluoroethyl)-1H-pyrazolo[3,4-d]pyrimidin-4(5H)-one,
(S)-6-Hydroxy-1-(2-methyl-1-(4-(trifluoromethyl)phenyl)propyl)-3-(2,2,2-trifluoroethyl)-1H-pyrazolo[3,4-d]pyrimidin-4(5H)-one,
(R)-1-(Cyclopropyl(4-(trifluoromethoxy)phenyl)methyl)-6-hydroxy-3-(2,2,2-trifluoroethyl)-1H-pyrazolo[3,4-d]pyrimidin-4(5H)-one,
(S)-1-(Cyclopropyl(4-(trifluoromethoxy)phenyl)methyl)-6-hydroxy-3-(2,2,2-trifluoroethyl)-1H-pyrazolo[3,4-d]pyrimidin-4(5H)-one,
(R)-6-Hydroxy-1-((1-methylcyclopropyl)(4-(trifluoromethyl)phenyl)methyl)-3-(2,2,2-trifluoroethyl)-1H-pyrazolo[3,4-d]pyrimidin-4(5H)-one, (S)-6-Hydroxy-1-((1-methylcyclopropyl)(4-(trifluoromethyl)phenyl)methyl)-3-(2,2,2-trifluoroethyl)-1H-pyrazolo[3,4-d]pyrimidin-4(5H)-one,
(R)-1-(1-(3-Fluoro-4-(trifluoromethyl)phenyl)-2,2-dimethylpropyl)-6-hydroxy-3-(2,2,2-trifluoroethyl)-1H-pyrazolo[3,4-d]pyrimidin-4(5H)-one,
(S)-1-(1-(3-Fluoro-4-(trifluoromethyl)phenyl)-2,2-dimethylpropyl)-6-hydroxy-3-(2,2,2-trifluoroethyl)-1H-pyrazolo[3,4-d]pyrimidin-4(5H)-one,
(R)-1-((3-Fluoro-4-(trifluoromethyl)phenyl)(1-methylcyclopropyl)methyl)-6-hydroxy-3-(2,2,2-trifluoroethyl)-1H-pyrazolo[3,4-d]pyrimidin-4(5H)-one,
(S)-1-((3-Fluoro-4-(trifluoromethyl)phenyl)(1-methylcyclopropyl)methyl)-6-hydroxy-3-(2,2,2-trifluoroethyl)-1H-pyrazolo[3,4-d]pyrimidin-4(5H)-one,
(R)-1-((4-tert-Butylphenyl)(cyclopropyl)methyl)-6-hydroxy-3-(2,2,2-trifluoroethyl)-1H-pyrazolo[3,4-d]pyrimidin-4(5H)-one,
(S)-1-((4-tert-Butylphenyl)(cyclopropyl)methyl)-6-hydroxy-3-(2,2,2-trifluoroethyl)-1H-pyrazolo[3,4-d]pyrimidin-4(5H)-one,
(R)-1-(Cyclopropyl(3-fluoro-4-(trifluoromethoxy)phenyl)methyl)-6-hydroxy-3-(2,2,2-trifluoroethyl)-1H-pyrazolo[3,4-d]pyrimidin-4(5H)-one,
(S)-1-(Cyclopropyl(3-fluoro-4-(trifluoromethoxy)phenyl)methyl)-6-hydroxy-3-(2,2,2-trifluoroethyl)-1H-pyrazolo[3,4-d]pyrimidin-4(5H)-one,
(R)-6-Hydroxy-3-(trifluoromethyl)-1-(1-(4-(trifluoromethyl)phenyl)ethyl)-1H-pyrazolo[3,4-d]pyrimidin-4(5H)-one,
(S)-6-Hydroxy-3-(trifluoromethyl)-1-(1-(4-(trifluoromethyl)phenyl)ethyl)-1H-pyrazolo[3,4-d]pyrimidin-4(5H)-one,
(R)-6-Hydroxy-3-(2,2,2-trifluoroethyl)-1-{1-[4-(trifluoromethyl)phenyl]ethyl}-1,5-dihydro-4H-pyrazolo[3,4-d]pyrimidin-4-one,
(S)-6-Hydroxy-3-(2,2,2-trifluoroethyl)-1-{1-[4-(trifluoromethyl)phenyl]ethyl}-1,5-dihydro-4H-pyrazolo[3,4-d]pyrimidin-4-one,
(R)-1-(1-(3-Fluoro-4-(trifluoromethyl)phenyl)-2-methylpropyl)-6-hydroxy-3-(2,2,2-trifluoroethyl)-1H-pyrazolo[3,4-d]pyrimidin-4(5H)-one,
(S)-1-(1-(3-Fluoro-4-(trifluoromethyl)phenyl)-2-methylpropyl)-6-hydroxy-3-(2,2,2-trifluoroethyl)-1H-pyrazolo[3,4-d]pyrimidin-4(5H)-one,
(R)-1-(1-(4-tert-Butylphenyl)-2-methylpropyl)-6-hydroxy-3-(2,2,2-trifluoroethyl)-1H-pyrazolo[3,4-d]pyrimidin-4(5H)-one,
(S)-1-(1-(4-tert-Butylphenyl)-2-methylpropyl)-6-hydroxy-3-(2,2,2-trifluoroethyl)-1H-pyrazolo[3,4-d]pyrimidin-4(5H)-one,
(R)-1-(2,2-Dimethyl-1-(4-(trifluoromethyl)phenyl)propyl)-6-hydroxy-3-(2,2,2-trifluoroethyl)-1H-pyrazolo[3,4-d]pyrimidin-4(5H)-one,
(S)-1-(2,2-Dimethyl-1-(4-(trifluoromethyl)phenyl)propyl)-6-hydroxy-3-(2,2,2-trifluoroethyl)-1H-pyrazolo[3,4-d]pyrimidin-4(5H)-one,
(R)-1-(1-(3-Fluoro-4-(trifluoromethoxy)phenyl)-2-methylpropyl)-6-hydroxy-3-(2,2,2-trifluoroethyl)-1H-pyrazolo[3,4-d]pyrimidin-4(5H)-one,
(S)-1-(1-(3-Fluoro-4-(trifluoromethoxy)phenyl)-2-methylpropyl)-6-hydroxy-3-(2,2,2-trifluoroethyl)-1H-pyrazolo[3,4-d]pyrimidin-4(5H)-one,
(R)-6-Hydroxy-3-(perfluoroethyl)-1-(1-(4-(trifluoromethyl)phenyl)ethyl)-1H-pyrazolo[3,4-d]pyrimidin-4(5H)-one,
(S)-6-Hydroxy-3-(perfluoroethyl)-1-(1-(4-(trifluoromethyl)phenyl)ethyl)-1H-pyrazolo[3,4-d]pyrimidin-4(5H)-one,
3-Methyl-6-pyrrolidin-1-yl-1-{1-[4-(trifluoromethyl)phenyl]ethyl})-1,5-dihydro-4H-pyrazolo[3,4-d]pyrimidin-4-one,
3-Methyl-6-(methylamino)-1-(1-(4-(trifluoromethyl)phenyl)ethyl)-1,5-dihydro-4H-pyrazolo[3,4-d]pyrimidin-4-one,
6-(Dimethylamino)-3-methyl-1-{1-[4-(trifluoromethyl)phenyl]ethyl})-1,5-dihydro-4H-pyrazolo[3,4-d]pyrimidin-4-one,
(R)-3-(Difluoromethyl)-6-hydroxy-1-(3,3,3-trifluoro-1-(4-(trifluoromethyl)phenyl)propyl)-1H-pyrazolo[3,4-d]pyrimidin-4(5H)-one,
(S)-3-(Difluoromethyl)-6-hydroxy-1-(3,3,3-trifluoro-1-(4-(trifluoromethyl)phenyl)propyl)-1H-pyrazolo[3,4-d]pyrimidin-4(5H)-one,
(R)-3-(Difluoromethyl)-6-hydroxy-1-(1-(4-(trifluoromethoxy)phenyl)ethyl)-1H-pyrazolo[3,4-d]pyrimidin-4(5H)-one,
(S)-3-(Difluoromethyl)-6-hydroxy-1-(1-(4-(trifluoromethoxy)phenyl)ethyl)-1H-pyrazolo[3,4-d]pyrimidin-4(5H)-one,
(R)-1-(1-(4-Cyclopropylphenyl)ethyl)-3-(difluoromethyl)-6-hydroxy-1H-pyrazolo[3,4-d]pyrimidin-4(5H)-one,
(S)-1-(1-(4-Cyclopropylphenyl)ethyl)-3-(difluoromethyl)-6-hydroxy-1H-pyrazolo[3,4-d]pyrimidin-4(5H)-one,
(R)-3-(Difluoromethyl)-1-(1-(3-fluoro-4-(trifluoromethyl)phenyl)ethyl)-6-hydroxy-1H-pyrazolo[3,4-d]pyrimidin-4(5H)-one,
(S)-3-(Difluoromethyl)-1-(1-(3-fluoro-4-(trifluoromethyl)phenyl)ethyl)-6-hydroxy-1H-pyrazolo[3,4-d]pyrimidin-4(5H)-one,
(R)-1-(Cyclopropyl(4-(trifluoromethyl)phenyl)methyl)-3-(difluoromethyl)-6-hydroxy-1H-pyrazolo[3,4-d]pyrimidin-4(5H)-one,
(S)-1-(Cyclopropyl(4-(trifluoromethyl)phenyl)methyl)-3-(difluoromethyl)-6-hydroxy-1H-pyrazolo[3,4-d]pyrimidin-4(5H)-one,
(R)-3-(Difluoromethyl)-6-hydroxy-1-(2-methyl-1-(4-(trifluoromethyl)phenyl)propyl)-1H-pyrazolo[3,4-d]pyrimidin-4(5H)-one,
(S)-3-(Difluoromethyl)-6-hydroxy-1-(2-methyl-1-(4-(trifluoromethyl)phenyl)propyl)-1H-pyrazolo[3,4-d]pyrimidin-4(5H)-one,
(R)-3-(Difluoromethyl)-1-(2,2-dimethyl-1-(4-(trifluoromethyl)phenyl)propyl)-6-hydroxy-1H-pyrazolo[3,4-d]pyrimidin-4(5H)-one,
(S)-3-(Difluoromethyl)-1-(2,2-dimethyl-1-(4-(trifluoromethyl)phenyl)propyl)-6-hydroxy-1H-pyrazolo[3,4-d]pyrimidin-4(5H)-one,
(R)-3-(Difluoromethyl)-6-hydroxy-1-(1-(4-(trifluoromethyl)phenyl)propyl)-1H-pyrazolo[3,4-d]pyrimidin-4(5H)-one,
(S)-3-(Difluoromethyl)-6-hydroxy-1-(1-(4-(trifluoromethyl)phenyl)propyl)-1H-pyrazolo[3,4-d]pyrimidin-4(5H)-one,
(R)-3-(Difluoromethyl)-1-(1-(3-fluoro-4-(trifluoromethoxy)phenyl)ethyl)-6-hydroxy-H-pyrazolo[3,4-d]pyrimidin-4(5H)-one,
(S)-3-(Difluoromethyl)-1-(1-(3-fluoro-4-(trifluoromethoxy)phenyl)ethyl)-6-hydroxy-H-pyrazolo[3,4-d]pyrimidin-4(5H)-one, (S)-3-(Difluoromethyl)-6-(dimethylamino)-1-(1-(4-(trifluoromethyl)phenyl)ethyl)-1H-pyrazolo[3,4-d]pyrimidin-4(5H)-one, 6-Azetidin-1-yl-3-(difluoromethyl)-1-{(1S)-1-[4-(trifluoromethyl)phenyl]ethyl}-1,5-dihydro-4H-pyrazolo[3,4-d]pyrimidin-4-one, (R)-3-(2,2-Difluoroethyl)-6-hydroxy-1-(1-(4-(trifluoromethyl)phenyl)ethyl)-1H-pyrazolo[3,4-d]pyrimidin-4(5H)-one, (S)-3-(2,2-Difluoroethyl)-6-hydroxy-1-(1-(4-(trifluoromethyl)phenyl)ethyl)-1H-pyrazolo[3,4-d]pyrimidin-4(5H)-one, (S)-6-Hydroxy-3-(2-hydroxyethyl)-1-(1-(4-(trifluoromethyl)phenyl)ethyl)-1H-pyrazolo[3,4-d]pyrimidin-4(5H)-one, (R,S)-6-Hydroxy-3-(1-hydroxypropyl)-1-(1-(4-(trifluoromethyl)phenyl)ethyl)-1H-pyrazolo[3,4-d]pyrimidin-4(5H)-one, (R,R)-6-Hydroxy-3-(1-hydroxypropyl)-1-(1-(4-(trifluoromethyl)phenyl)ethyl)-1H-pyrazolo[3,4-d]pyrimidin-4(5H)-one, (S,S)-6-Hydroxy-3-(1-hydroxypropyl)-1-(1-(4-(trifluoromethyl)phenyl)ethyl)-1H-pyrazolo[3,4-d]pyrimidin-4(5H)-one, (S,R)-6-Hydroxy-3-(1-hydroxypropyl)-1-(1-(4-(trifluoromethyl)phenyl)ethyl)-1H-pyrazolo[3,4-d]pyrimidin-4(5H)-one, (R)-2-(1-(Cyclopropyl(4-(trifluoromethyl)phenyl)methyl)-6-hydroxy-4-oxo-4,5-dihydro-1H-pyrazolo[3,4-d]pyrimidin-3-yl)acetonitrile, (S)-2-(1-(Cyclopropyl(4-(trifluoromethyl)phenyl)methyl)-6-hydroxy-4-oxo-4,5-dihydro-1H-pyrazolo[3,4-d]pyrimidin-3-yl)acetonitrile, (S)-2-(6-Hydroxy-4-oxo-1-(1-(4-(trifluoromethyl)phenyl)ethyl)-4,5-dihydro-1H-pyrazolo[3,4-d]pyrimidin-3-yl)acetonitrile, (R)-2-(1-(1-(3-Fluoro-4-(trifluoromethoxy)phenyl)ethyl)-6-hydroxy-4-oxo-4,5-dihdro-1H-pyrazolo[3,4-d]pyrimidin-3-yl)acetonitrile, (S)-2-(1-(1-(3-Fluoro-4-(trifluoromethoxy)phenyl)ethyl)-6-hydroxy-4-oxo-4,5-dihydro-1H-pyrazolo[3,4-d]pyrimidin-3-yl)acetonitrile, (S)-3-(Hydroxymethyl)-6-(methylthio)-1-(1-(4-(trifluoromethyl)phenyl)ethyl)-1H-pyrazolo[3,4-d]pyrimidin-4(5H)-one, 6-Ethoxy-3-(hydroxymethyl)-1-{(1S)-1-[4-(trifluoromethyl)phenyl]ethyl}-1,5-dihydro-4H-pyrazolo[3,4-d]pyrimidin-4-one, (S)-3-((Benzyloxy)methyl)-6-hydroxy-1-(1-(4-(trifluoromethyl)phenyl)ethyl)-1,5-dihydro-4H-pyrazolo[3,4-d]pyrimidin-4-one, (S)-6-Hydroxy-3-(methoxymethyl)-1-(1-(4-(trifluoromethyl)phenyl)ethyl)-1,5-dihydro-4H-pyrazolo[3,4-d]pyrimidin-4-one, (R)-1-(1-(2-Fluoro-4-(trifluoromethyl)phenyl)ethyl)-6-hydroxy-3-(trifluoromethyl)-1H-pyrazolo[3,4-d]pyrimidin-4(5H)-one, (S)-1-(1-(2-Fluoro-4-(trifluoromethyl)phenyl)ethyl)-6-hydroxy-3-(trifluoromethyl)-1H-pyrazolo[3,4-d]pyrimidin-4(5H)-one, (R)-1-{1-[2-Fluoro-4-(trifluoromethoxy)phenyl]ethyl}-6-hydroxy-3-(trifluoromethyl)-1,5-dihydro-4H-pyrazolo[3,4-d]pyrimidin-4-one, (S)-1-{1-[2-Fluoro-4-(trifluoromethoxy)phenyl]ethyl}-6-hydroxy-3-(trifluoromethyl)-1,5-dihydro-4H-pyrazolo[3,4-d]pyrimidin-4-one, (R)-1-{1-[3-Fluoro-4-(trifluoromethoxy)phenyl]ethyl}-6-hydroxy-3-(trifluoromethyl)-1,5-dihydro-4H-pyrazolo[3,4-d]pyrimidin-4-one, (S)-1-{1-[3-Fluoro-4-(trifluoromethoxy)phenyl]ethyl}-6-hydroxy-3-(trifluoromethyl)-1,5-dihydro-4H-pyrazolo[3,4-d]pyrimidin-4-one, (R)-6-Hydroxy-1-{1-[4-(pentafluoro-lambda~6~-sulfanyl)phenyl]ethyl}-3-(trifluoromethyl)-1,5-dihydro-4H-pyrazolo[3,4-d]pyrimidin-4-one, (S)-6-Hydroxy-1-{1-[4-(pentafluoro-lambda~6~-sulfanyl)phenyl]ethyl}-3-(trifluoromethyl)-1,5-dihydro-4H-pyrazolo[3,4-d]pyrimidin-4-one, (R)-1-{1-[3-Fluoro-4-(trifluoromethyl)phenyl]ethyl}-6-hydroxy-3-(trifluoromethyl)-1,5-dihydro-4H-pyrazolo[3,4-d]pyrimidin-4-one, (S)-1-{1-[3-Fluoro-4-(trifluoromethyl)phenyl]ethyl}-6-hydroxy-3-(trifluoromethyl)-1,5-dihydro-4H-pyrazolo[3,4-d]pyrimidin-4-one, (R)-1-{1-[4-(Difluoromethoxy)phenyl]ethyl}-6-hydroxy-3-(trifluoromethyl)-1,5-dihydro-4H-pyrazolo[3,4-d]pyrimidin-4-one, (S)-1-{1-[4-(Difluoromethoxy)phenyl]ethyl}-6-hydroxy-3-(trifluoromethyl)-1,5-dihydro-4H-pyrazolo[3,4-d]pyrimidin-4-one, (R)-1-(1-(4-(1,1-Difluoroethyl)phenyl)ethyl)-6-hydroxy-3-(trifluoromethyl)-1H-pyrazolo[3,4-d]pyrimidin-4(5H)-one, (S)-1-(1-(4-(1,1-Difluoroethyl)phenyl)ethyl)-6-hydroxy-3-(trifluoromethyl)-1H-pyrazolo[3,4-d]pyrimidin-4(5H)-one, (R)-1-(1-(4-(2,2-Difluoroethyl)phenyl)ethyl)-6-hydroxy-3-(trifluoromethyl)-1H-pyrazolo[3,4-d]pyrimidin-4(5H)-one, (S)-1-(1-(4-(2,2-Difluoroethyl)phenyl)ethyl)-6-hydroxy-3-(trifluoromethyl)-1H-pyrazolo[3,4-d]pyrimidin-4(5H)-one, (R)-1-(1-(3-Chloro-4-(trifluoromethoxy)phenyl)ethyl)-6-hydroxy-3-(trifluoromethyl)-1H-pyrazolo[3,4-d]pyrimidin-4(5H)-one, (S)-1-(1-(3-Chloro-4-(trifluoromethoxy)phenyl)ethyl)-6-hydroxy-3-(trifluoromethyl)-1H-pyrazolo[3,4-d]pyrimidin-4(5H)-one, (R)-1-(1-(4-(Difluoromethoxy)-3-fluorophenyl)ethyl)-6-hydroxy-3-(trifluoromethyl)-1H-pyrazolo[3,4-d]pyrimidin-4(5H)-one, (S)-1-(1-(4-(Difluoromethoxy)-3-fluorophenyl)ethyl)-6-hydroxy-3-(trifluoromethyl)-1H-pyrazolo[3,4-d]pyrimidin-4(5H)-one (R)-1-(1-(3-Chloro-4-(difluoromethoxy)phenyl)ethyl)-6-hydroxy-3-(trifluoromethyl)-1H-pyrazolo[3,4-d]pyrimidin-4(5H)-one, (S)-1-(1-(3-Chloro-4-(difluoromethoxy)phenyl)ethyl)-6-hydroxy-3-(trifluoromethyl)-1H-pyrazolo[3,4-d]pyrimidin-4(5H)-one, (R)-1-(1-(3-Chloro-4-(trifluoromethyl)phenyl)ethyl)-6-hydroxy-3-(trifluoromethyl)-1H-pyrazolo[3,4-d]pyrimidin-4(5H)-one, (S)-1-(1-(3-Chloro-4-(trifluoromethyl)phenyl)ethyl)-6-hydroxy-3-(trifluoromethyl)-1H-pyrazolo[3,4-d]pyrimidin-4(5H)-one, (R)-6-Hydroxy-1-(1-(4-(trifluoromethoxy)phenyl)ethyl)-3-(trifluoromethyl)-1H-pyrazolo[3,4-d]pyrimidin-4(5H)-one, (S)-6-Hydroxy-1-(1-(4-(trifluoromethoxy)phenyl)ethyl)-3-(trifluoromethyl)-1H-pyrazolo[3,4-d]pyrimidin-4(5H)-one, (R)-6-Hydroxy-3-(trifluoromethyl)-1-(1-(4-(trifluoromethyl)phenyl)propyl)-1H-pyrazolo[3,4-d]pyrimidin-4(5H)-one, (S)-6-hydroxy-3-(trifluoromethyl)-1-(1-(4-(trifluoromethyl)phenyl)propyl)-1H-pyrazolo[3,4-d]pyrimidin-4(5H)-one, (R)-6-Hydroxy-1-(2-methyl-1-(4-(trifluoromethyl)phenyl)propyl)-3-(trifluoromethyl)-1H-pyrazolo[3,4-d]pyrimidin-4(5H)-one, (S)-6-Hydroxy-1-(2-methyl-1-(4-(trifluoromethyl)phenyl)propyl)-3-(trifluoromethyl)-1H-pyrazolo[3,4-d]pyrimidin-4(5H)-one, (R)-1-(Cyclopropyl(4-(trifluoromethyl)phenyl)methyl)-6-hydroxy-3-(trifluoromethyl)-1H-pyrazolo[3,4-d]pyrimidin-4(5H)-one, (S)-1-(Cyclopropyl(4-(trifluoromethyl)phenyl)methyl)-6-hydroxy-3-(trifluoromethyl)-1H-pyrazolo[3,4-d]pyrimidin-4(5H)-one, (R)-1-(2,2-Dimethyl-1-(4-(trifluoromethyl)phenyl)propyl)-6-hydroxy-3-(trifluoromethyl)-1H-pyrazolo[3,4-d]pyrimidin-4(5H)-one, (S)-1-(2,2-Dimethyl-1-(4-(trifluoromethyl)phenyl)propyl)-6-hydroxy-3-(trifluoromethyl)-1H-pyrazolo[3,4-d]pyrimidin-4(5H)-one, (S)-6-(Dimethylamino)-3-(trifluoromethyl)-1-(1-(4-(trifluoromethyl)phenyl)ethyl)-1H-pyrazolo[3,4-d]pyrimidin-4(5H)-one, (R)-1-(1-(4-(Difluoromethoxy)-3-fluorophenyl)propyl)-6-(dimethylamino)-3-(fluoromethyl)-1H-pyrazolo[3,4-d]pyrimidin-4(5H)-one, (S)-1-(1-(4-(Difluoromethoxy)-3-fluorophenyl)propyl)-6-(dimethylamino)-3-(fluoromethyl)-1H-pyrazolo[3,4-d]pyrimidin-4(5H)-one, (R)-1-(1-(4-(Difluoromethoxy)-2-fluorophenyl)propyl)-6-(dimethylamino)-3-(fluoromethyl)-1H-pyrazolo[3,4-d]pyrimidin-4(5H)-one, (S)-1-(1-(4-(Difluoromethoxy)-2-fluorophenyl)propyl)-6-(dimethylamino)-3-(fluoromethyl)-1H-pyrazolo[3,4-d]pyrimidin-4(5H)-one, (R)-1-(1-(4-(Difluoromethyl)-3-fluorophenyl)propyl)-6-(dimethylamino)-3-(fluoromethyl)-1H-pyrazolo[3,4-d]pyrimidin-4(5H)-one, (S)-1-(1-(4-(Difluoromethyl)-3-fluorophenyl)propyl)-6-(dimethylamino)-3-(fluoromethyl)-1H-pyrazolo[3,4-d]pyrimidin-4(5H)-one (R)-1-(1-(4-(Difluoromethyl)phenyl)propyl)-6-(dimethylamino)-3-(fluoromethyl)-1H-pyrazolo[3,4-d]pyrimidin-4(5H)-one, (S)-1-(1-(4-(Difluoromethyl)phenyl)propyl)-6-(dimethylamino)-3-(fluoromethyl)-1H-pyrazolo[3,4-d]pyrimidin-4(5H)-one, (R)-1-(1-(4-(difluoromethyl)-2-fluorophenyl)propyl)-6-(dimethylamino)-3-(fluoromethyl)-1H-pyrazolo[3,4-d]pyrimidin-4(5H)-one, (S)-1-(1-(4-(difluoromethyl)-2-fluorophenyl)propyl)-6-(dimethylamino)-3-(fluoromethyl)-1H-pyrazolo[3,4-d]pyrimidin-4(5H)-one, (R)-1-(Cyclopropyl(4-(1,1-difluoroethyl)-3-fluorophenyl)methyl)-6-(dimethylamino)-3-(hydroxymethyl)-1H-pyrazolo[3,4-d]pyrimidin-4(5H)-one, (S)-1-(Cyclopropyl(4-(1,1-difluoroethyl)-3-fluorophenyl)methyl)-6-(dimethylamino)-3-(hydroxymethyl)-1H-pyrazolo[3,4-d]pyrimidin-4(5H)-one, (R)-1-(Cyclopropyl(4-(1,1-difluoroethyl)-2-fluorophenyl)methyl)-6-(dimethylamino)-3-(hydroxymethyl)-1H-pyrazolo[3,4-d]pyrimidin-4(5H)-one, (S)-1-(Cyclopropyl(4-(1,1-difluoroethyl)-2-fluorophenyl)methyl)-6-(dimethylamino)-3-(hydroxymethyl)-1H-pyrazolo[3,4-d]pyrimidin-4(5H)-one, 6-Hydroxy-3-(trifluoromethyl)-1-(1-(4-(trifluoromethyl)phenyl)cyclopropyl)-1H-pyrazolo[3,4-d]pyrimidin-4(5H)-one, 6-Hydroxy-3-(trifluoromethyl)-1-(1-(4-(trifluoromethyl)phenyl)allyl)-1H-pyrazolo[3,4-d]pyrimidin-4(5H)-one, (R)-6-Amino-1-(1-(4-(1,1-difluoroethyl)phenyl)-2-methylpropyl)-3-(hydroxymethyl)-1H-pyrazolo[3,4-d]pyrimidin-4(5H)-one, (S)-6-Amino-1-(1-(4-(1,1-difluoroethyl)phenyl)-2-methylpropyl)-3-(hydroxymethyl)-1H-pyrazolo[3,4-d]pyrimidin-4(5H)-one, (R)-1-(1-(4-(1,1-Difluoroethyl)phenyl)-2-methylpropyl)-3-(hydroxymethyl)-6-(methylamino)-1H-pyrazolo[3,4-d]pyrimidin-4(5H)-one, (S)-1-(1-(4-(1,1-Difluoroethyl)phenyl)-2-methylpropyl)-3-(hydroxymethyl)-6-(methylamino)-1H-pyrazolo[3,4-d]pyrimidin-4(5H)-one, or a pharmaceutically acceptable salt thereof.

19. A pharmaceutical composition which comprises a pharmaceutically acceptable carrier and a compound of claim 1 or a pharmaceutically acceptable salt thereof.

\* \* \* \* \*

UNITED STATES PATENT AND TRADEMARK OFFICE
CERTIFICATE OF CORRECTION

PATENT NO. : 10,174,037 B2
APPLICATION NO. : 15/576351
DATED : January 8, 2019
INVENTOR(S) : Dong Ming Shen et al.

It is certified that error appears in the above-identified patent and that said Letters Patent is hereby corrected as shown below:

On the Title Page

In item (73), the Assignee:
Please replace "MERCK SHARP & DOHME CORP., Rahway, NJ"
With --MERCK SHARP & DOHME CORP., Rahway, NJ (US); MSD R & D (China) Co. LTD., Shanghai (CN)--.

Signed and Sealed this
Sixth Day of October, 2020

Andrei Iancu
*Director of the United States Patent and Trademark Office*